/ 
US007534593B2

(12) United States Patent
Corbett et al.

(10) Patent No.: US 7,534,593 B2
(45) Date of Patent: May 19, 2009

(54) CRYSTALS OF GLUCOKINASE AND METHODS OF GROWING THEM

(75) Inventors: Wendy Lea Corbett, Lebanon, NJ (US);
Robert Lewis Crowther, East Stroudsburg, PA (US); Pete William Dunten, Mountainview, PA (US); R. Ursula Kammlott, Fair Lawn, NJ (US); Christine Maria Lukacs, Millburn, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 644 days.

(21) Appl. No.: 10/816,708

(22) Filed: Apr. 2, 2004

(65) Prior Publication Data
US 2006/0141599 A1 Jun. 29, 2006

Related U.S. Application Data

(62) Division of application No. 10/318,308, filed on Dec. 12, 2002, now Pat. No. 6,911,545.

(60) Provisional application No. 60/341,988, filed on Dec. 19, 2001.

(51) Int. Cl.
*C12N 9/12* (2006.01)
*A61K 38/00* (2006.01)

(52) U.S. Cl. ..................................... 435/194; 424/94.5
(58) Field of Classification Search ........................ None
See application file for complete search history.

(56) References Cited

U.S. PATENT DOCUMENTS 6,320,050 B1   11/2001   Bizzarro et al.

FOREIGN PATENT DOCUMENTS

| WO | WO 00/58293 | 10/2000 |
| WO | WO 01/83465 A2 | 11/2001 |
| WO | WO 01/85706 A1 | 11/2001 |
| WO | WO 01/85707 A1 | 11/2001 |
| WO | WO 01/90301 A3 | 11/2001 |
| WO | WO 03/080585 | 3/2003 |

OTHER PUBLICATIONS

Giege et al. Crystallogenesis of Biological Macromolecules: Facts and Perspectives. Acta Cryst., (1994) D50: 339-350.*

(Continued)

*Primary Examiner*—Suzanne M. Noakes
*Assistant Examiner*—Alexander D Kim
(74) *Attorney, Agent, or Firm*—George W. Johnston; Dennis P. Tramaloni; Samuel H. Megerditchian

(57) ABSTRACT

Crystalline forms of mammalian Glucokinase, ideally human liver isozyme source, of sufficient size and quality to obtain structural data by X-ray crystallography are presented. Methods of growing such crystals are also disclosed.

4 Claims, 65 Drawing Sheets

OTHER PUBLICATIONS

Branden et al. Introduction to Protein Structure Second Edition, Garland Publishing Inc., New York, 1999, p. 374-375, 382.*
Drenth et al. Principles of X-ray Crystallography, Springer, New York, 1995.*
Kierzek et al., 2001, Biophys Chem 91:1-20.*
Wiencek, Ann Rev Biomed Eng, 1999, 1:505-534.*
Aleshin et al. Mar. 3, 2000, J. Mol. Biol, vol. 296, pp. 1001-1015.*
Aleshin et al., Structure 6, pp. 39-50, 1998.
Bennett, Jr. et al., J. Mol. Biol. vol. 140, pp. 183-209, 1978.
Ito et al., Structure 9, pp. 205-214, 2001.
Colowick, S. P., The Enzymes, vol. 9 (P. Boyer, ed.) Academic Press, New York, NY pp. 1-48, 1973.
Chipkin, S. R., et al., Joslin's Diabetes (C.R. Khan & G. C. Wier, eds.), Lea & Febiger, Philadelphia, PA, pp. 97-115, 1994.
Printz, R. G., et al., Ann. Rev. Nutrition, vol. 13, (R. E. Olson, D. M. Bier, & D. B. McCormick eds.) pp. 463-496, 1993.
Meglasson, M. D. et al., Amer. J. Physiol. vol. 246 pp. E1-E13, 1984.
Grupe, A., et al., Cell vol. 83, pp. 69-78, 1995.
Ferrie T. et al., FASB J. vol. 10, pp. 1213-1218, 1996.
Liang, Y. et al., Biochem. J. vol. 309, pp. 167-173, 1995.
Glaser, B. et al., New England J. Med. vol. 338, pp. 226-230, 1998.
Tsuge, et. al., Protein Science, vol. 11, pp. 2456-2463 (2002).
Mahalingam, et. al., vol. 48, pp. 1698-1705 (1999).
Aleshin Alexander E., et al., FEBS Letters, XP002253654, vol. 391, No. 1-2, pp. 9-10 (1996).
Aleshin Alexander E., et a., Journal of Molecular Biology, XP002253657, vol. 296, No. 4 pp. 1001-1015 (2000).
Tongleli Li, J. Biomaterials Sci. Polymer Edn., XP002918057, vol. 9, No. 4, pp. 327-344 (1998).
Xu, L.Z., et al., J. Biol. Chem., vol. 269, pp. 27458-27465 (1994).
Mulichak, A.M., et al., Nat. Struct. Biol., vol. 7, pp. 555-560 (1998).
Pilkis, S.J., et al., J. Biol. Chem., vol. 269, pp. 21925-21928 (1994).
Ysern, X, et al., J. Biol. Chem., vol. 264, pp. 7765-7767 (1989).
Qian-Cutone, J., et al., J. of Antibiotics, vol. 52, pp. 245-255 (1999).
Doliba, N., et al., Diabetes, vol. 50(2), pp. A359 (2001).
Maciej Kozak, et al, Acta Crystallographica, Section D: Biological Crystallography, vol. D57(4), pp. 586-588 (2001).
Alexander E. Aleshin, et al., J. Mol. Biol., vol. 282, pp. 345-357 (1998).
Diane E. Marotta, et al., Archives of Biochemistry and Biophysics, vol. 436, pp. 23-31 (2005).

* cited by examiner

Figure 2. The amino-acid sequence of the GST-GK fusion protein. The GST sequence was taken from GenBank entry U13852. Residue 229 of the fusion protein is the first residue of GK.

```
  1  MSPILGYWKI  KGLVQPTRLL  LEYLEEKYEE  HLYERDEGDK  WRNKKFELGL  EFPNLPYYID
 61  GDVKLTQSMA  IIRYIADKHN  MLGGCPKERA  EISMLEGAVL  DIRYGVSRIA  YSKDFETLKV
121  DFLSKLPEML  KMFEDRLCHK  TYLNGDHVTH  PDFMLYDALD  VVLYMDPMCL  DAFPKLVCFK
181  KRIEAIPQID  KYLKSSKYIA  WPLQGWQATF  GGGDHPPKSD  LIEGRGIHMP  RPRSQLPQPN
241  SQVEQILAEF  QLQEEDLKKV  MRRMQKEMDR  GLRLETHEEA  SVKMLPTYVR  STPEGSEVGD
301  FLSLDLGGTN  FRVMLVKVGE  GEEGQWSVKT  KHQMYSIPED  AMTGTAEMLF  DYISECISDF
361  LDKHQMKHKK  LPLGFTFSFP  VRHEDIDKGI  LLNWTKGFKA  SGAEGNNVVG  LLRDAIKRRG
421  DFEMDVVAMV  NDTVATMISC  YYEDHQCEVG  MIVGTGCNAC  YMEEMQNVEL  VEGDEGRMCV
481  NTEWGAFGDS  GELDEFLLEY  DRLVDESSAN  PGQQLYEKLI  GGKYMGELVR  LVLLRLVDEN
541  LLFHGEASEQ  LRTRGAFETR  FVSQVESDTG  DRKQIYNILS  TLGLRPSTTD  CDIVRRACES
601  VSTRAAHMCS  AGLAGVINRM  RESRSEDVMR  ITVGVDGSVY  KLHPSFKERF  HASVRRLTPS
661  CEITFIESEE  GSGRGAALVS  AVACKKACML  GQ
```

| Atom | Atom No. | Atom Type | A.A. Type | A.A.# | X | Y | Z | OCC | B |
|---|---|---|---|---|---|---|---|---|---|
| ATOM | 1 | CB | SER | 8 | -0.421 | 63.744 | 24.899 | 1.00 | 50.68 |
| ATOM | 2 | OG | SER | 8 | -0.752 | 63.605 | 23.524 | 1.00 | 50.85 |
| ATOM | 3 | C | SER | 8 | 1.865 | 64.216 | 24.094 | 1.00 | 50.72 |
| ATOM | 4 | O | SER | 8 | 2.308 | 63.644 | 23.102 | 1.00 | 51.79 |
| ATOM | 5 | N | SER | 8 | 1.473 | 63.793 | 26.507 | 1.00 | 50.36 |
| ATOM | 6 | CA | SER | 8 | 1.057 | 63.446 | 25.120 | 1.00 | 50.55 |
| ATOM | 7 | N | GLN | 9 | 2.041 | 65.515 | 24.314 | 1.00 | 49.84 |
| ATOM | 8 | CA | GLN | 9 | 2.831 | 66.312 | 23.385 | 1.00 | 48.95 |
| ATOM | 9 | CB | GLN | 9 | 2.983 | 67.745 | 23.895 | 1.00 | 49.08 |
| ATOM | 10 | CG | GLN | 9 | 3.676 | 68.686 | 22.925 | 1.00 | 50.25 |
| ATOM | 11 | CD | GLN | 9 | 3.206 | 70.127 | 23.085 | 1.00 | 51.06 |
| ATOM | 12 | OE1 | GLN | 9 | 2.037 | 70.433 | 22.846 | 1.00 | 51.38 |
| ATOM | 13 | NE2 | GLN | 9 | 4.112 | 71.017 | 23.499 | 1.00 | 51.44 |
| ATOM | 14 | C | GLN | 9 | 4.190 | 65.633 | 23.294 | 1.00 | 48.56 |
| ATOM | 15 | O | GLN | 9 | 4.884 | 65.741 | 22.285 | 1.00 | 48.75 |
| ATOM | 16 | N | VAL | 10 | 4.560 | 64.926 | 24.361 | 1.00 | 47.77 |
| ATOM | 17 | CA | VAL | 10 | 5.823 | 64.198 | 24.392 | 1.00 | 46.87 |
| ATOM | 18 | CB | VAL | 10 | 6.293 | 63.902 | 25.842 | 1.00 | 46.39 |
| ATOM | 19 | CG1 | VAL | 10 | 7.303 | 62.782 | 25.841 | 1.00 | 46.41 |
| ATOM | 20 | CG2 | VAL | 10 | 6.952 | 65.135 | 26.436 | 1.00 | 46.79 |
| ATOM | 21 | C | VAL | 10 | 5.616 | 62.885 | 23.653 | 1.00 | 46.17 |
| ATOM | 22 | O | VAL | 10 | 6.521 | 62.384 | 22.991 | 1.00 | 46.18 |
| ATOM | 23 | N | GLU | 11 | 4.423 | 62.317 | 23.768 | 1.00 | 45.28 |
| ATOM | 24 | CA | GLU | 11 | 4.159 | 61.071 | 23.069 | 1.00 | 45.19 |
| ATOM | 25 | CB | GLU | 11 | 2.905 | 60.393 | 23.616 | 1.00 | 45.21 |
| ATOM | 26 | CG | GLU | 11 | 3.105 | 59.709 | 24.967 | 1.00 | 46.05 |
| ATOM | 27 | CD | GLU | 11 | 4.224 | 58.664 | 24.957 | 1.00 | 46.30 |
| ATOM | 28 | OE1 | GLU | 11 | 4.350 | 57.918 | 23.948 | 1.00 | 46.28 |
| ATOM | 29 | OE2 | GLU | 11 | 4.963 | 58.583 | 25.972 | 1.00 | 45.66 |
| ATOM | 30 | C | GLU | 11 | 4.002 | 61.345 | 21.580 | 1.00 | 44.48 |
| ATOM | 31 | O | GLU | 11 | 4.068 | 60.430 | 20.755 | 1.00 | 44.48 |
| ATOM | 32 | N | GLN | 12 | 3.807 | 62.614 | 21.239 | 1.00 | 43.86 |
| ATOM | 33 | CA | GLN | 12 | 3.646 | 62.996 | 19.845 | 1.00 | 42.86 |
| ATOM | 34 | CB | GLN | 12 | 2.972 | 64.368 | 19.715 | 1.00 | 44.49 |
| ATOM | 35 | CG | GLN | 12 | 2.833 | 64.840 | 18.259 | 1.00 | 46.49 |
| ATOM | 36 | CD | GLN | 12 | 1.986 | 66.099 | 18.113 | 1.00 | 47.74 |
| ATOM | 37 | OE1 | GLN | 12 | 2.055 | 66.799 | 17.088 | 1.00 | 48.30 |
| ATOM | 38 | NE2 | GLN | 12 | 1.174 | 66.388 | 19.131 | 1.00 | 47.51 |
| ATOM | 39 | C | GLN | 12 | 5.014 | 63.023 | 19.192 | 1.00 | 41.14 |
| ATOM | 40 | O | GLN | 12 | 5.139 | 62.739 | 18.002 | 1.00 | 41.76 |
| ATOM | 41 | N | ILE | 13 | 6.038 | 63.360 | 19.971 | 1.00 | 38.51 |
| ATOM | 42 | CA | ILE | 13 | 7.398 | 63.388 | 19.450 | 1.00 | 36.48 |
| ATOM | 43 | CB | ILE | 13 | 8.274 | 64.351 | 20.261 | 1.00 | 35.85 |
| ATOM | 44 | CG2 | ILE | 13 | 9.731 | 64.228 | 19.827 | 1.00 | 35.71 |
| ATOM | 45 | CG1 | ILE | 13 | 7.740 | 65.777 | 20.079 | 1.00 | 35.77 |
| ATOM | 46 | CD1 | ILE | 13 | 8.584 | 66.867 | 20.710 | 1.00 | 35.91 |
| ATOM | 47 | C | ILE | 13 | 8.018 | 61.981 | 19.452 | 1.00 | 36.01 |
| ATOM | 48 | O | ILE | 13 | 8.572 | 61.528 | 18.442 | 1.00 | 35.99 |
| ATOM | 49 | N | LEU | 14 | 7.903 | 61.288 | 20.580 | 1.00 | 34.88 |
| ATOM | 50 | CA | LEU | 14 | 8.430 | 59.934 | 20.711 | 1.00 | 33.91 |
| ATOM | 51 | CB | LEU | 14 | 8.230 | 59.432 | 22.141 | 1.00 | 33.29 |
| ATOM | 52 | CG | LEU | 14 | 8.853 | 60.321 | 23.215 | 1.00 | 33.43 |
| ATOM | 53 | CD1 | LEU | 14 | 8.510 | 59.781 | 24.594 | 1.00 | 33.04 |

*FIG. 4A*

| | | | | | | | | |
|---|---|---|---|---|---|---|---|---|
| ATOM | 54 | CD2 | LEU | 14 | 10.354 | 60.398 | 23.001 | 1.00 33.04 |
| ATOM | 55 | C | LEU | 14 | 7.766 | 58.957 | 19.730 | 1.00 33.55 |
| ATOM | 56 | O | LEU | 14 | 8.208 | 57.812 | 19.578 | 1.00 33.21 |
| ATOM | 57 | N | ALA | 15 | 6.710 | 59.403 | 19.065 | 1.00 32.69 |
| ATOM | 58 | CA | ALA | 15 | 6.021 | 58.551 | 18.104 | 1.00 32.59 |
| ATOM | 59 | CB | ALA | 15 | 4.628 | 59.104 | 17.821 | 1.00 31.95 |
| ATOM | 60 | C | ALA | 15 | 6.838 | 58.449 | 16.808 | 1.00 32.79 |
| ATOM | 61 | O | ALA | 15 | 6.664 | 57.519 | 16.018 | 1.00 33.05 |
| ATOM | 62 | N | GLU | 16 | 7.746 | 59.395 | 16.599 | 1.00 32.33 |
| ATOM | 63 | CA | GLU | 16 | 8.575 | 59.369 | 15.403 | 1.00 32.74 |
| ATOM | 64 | CB | GLU | 16 | 9.566 | 60.531 | 15.401 | 1.00 34.23 |
| ATOM | 65 | CG | GLU | 16 | 8.950 | 61.910 | 15.298 | 1.00 38.39 |
| ATOM | 66 | CD | GLU | 16 | 10.017 | 62.998 | 15.162 | 1.00 41.11 |
| ATOM | 67 | OE1 | GLU | 16 | 10.445 | 63.269 | 14.012 | 1.00 40.68 |
| ATOM | 68 | OE2 | GLU | 16 | 10.438 | 63.562 | 16.212 | 1.00 42.77 |
| ATOM | 69 | C | GLU | 16 | 9.369 | 58.073 | 15.279 | 1.00 31.93 |
| ATOM | 70 | O | GLU | 16 | 9.570 | 57.568 | 14.179 | 1.00 33.41 |
| ATOM | 71 | N | PHE | 17 | 9.841 | 57.539 | 16.401 | 1.00 30.37 |
| ATOM | 72 | CA | PHE | 17 | 10.640 | 56.321 | 16.369 | 1.00 27.71 |
| ATOM | 73 | CB | PHE | 17 | 11.346 | 56.129 | 17.711 | 1.00 26.32 |
| ATOM | 74 | CG | PHE | 17 | 12.309 | 57.230 | 18.045 | 1.00 24.22 |
| ATOM | 75 | CD1 | PHE | 17 | 11.846 | 58.500 | 18.389 | 1.00 23.88 |
| ATOM | 76 | CD2 | PHE | 17 | 13.680 | 57.010 | 17.981 | 1.00 22.24 |
| ATOM | 77 | CE1 | PHE | 17 | 12.741 | 59.531 | 18.660 | 1.00 22.63 |
| ATOM | 78 | CE2 | PHE | 17 | 14.574 | 58.027 | 18.250 | 1.00 21.23 |
| ATOM | 79 | CZ | PHE | 17 | 14.105 | 59.291 | 18.589 | 1.00 22.01 |
| ATOM | 80 | C | PHE | 17 | 9.836 | 55.077 | 16.012 | 1.00 27.77 |
| ATOM | 81 | O | PHE | 17 | 10.400 | 54.004 | 15.802 | 1.00 27.38 |
| ATOM | 82 | N | GLN | 18 | 8.517 | 55.213 | 15.957 | 1.00 28.12 |
| ATOM | 83 | CA | GLN | 18 | 7.684 | 54.080 | 15.593 | 1.00 29.17 |
| ATOM | 84 | CB | GLN | 18 | 6.216 | 54.484 | 15.599 | 1.00 30.98 |
| ATOM | 85 | CG | GLN | 18 | 5.446 | 54.017 | 16.806 | 1.00 32.94 |
| ATOM | 86 | CD | GLN | 18 | 4.152 | 54.785 | 16.974 | 1.00 34.65 |
| ATOM | 87 | OE1 | GLN | 18 | 3.389 | 54.976 | 16.014 | 1.00 37.17 |
| ATOM | 88 | NE2 | GLN | 18 | 3.892 | 55.228 | 18.190 | 1.00 33.67 |
| ATOM | 89 | C | GLN | 18 | 8.068 | 53.602 | 14.193 | 1.00 28.97 |
| ATOM | 90 | O | GLN | 18 | 8.471 | 54.399 | 13.346 | 1.00 28.83 |
| ATOM | 91 | N | LEU | 19 | 7.931 | 52.298 | 13.971 | 1.00 29.02 |
| ATOM | 92 | CA | LEU | 19 | 8.235 | 51.659 | 12.704 | 1.00 29.94 |
| ATOM | 93 | CB | LEU | 19 | 9.641 | 51.069 | 12.749 | 1.00 29.78 |
| ATOM | 94 | CG | LEU | 19 | 10.782 | 51.813 | 12.037 | 1.00 30.77 |
| ATOM | 95 | CD1 | LEU | 19 | 10.886 | 53.251 | 12.477 | 1.00 30.67 |
| ATOM | 96 | CD2 | LEU | 19 | 12.083 | 51.087 | 12.339 | 1.00 32.05 |
| ATOM | 97 | C | LEU | 19 | 7.199 | 50.549 | 12.511 | 1.00 31.41 |
| ATOM | 98 | O | LEU | 19 | 7.288 | 49.484 | 13.137 | 1.00 31.35 |
| ATOM | 99 | N | GLN | 20 | 6.205 | 50.801 | 11.663 | 1.00 32.64 |
| ATOM | 100 | CA | GLN | 20 | 5.153 | 49.817 | 11.422 | 1.00 34.95 |
| ATOM | 101 | CB | GLN | 20 | 4.024 | 50.413 | 10.570 | 1.00 35.78 |
| ATOM | 102 | CG | GLN | 20 | 3.301 | 51.622 | 11.175 | 1.00 37.65 |
| ATOM | 103 | CD | GLN | 20 | 3.048 | 51.486 | 12.669 | 1.00 39.03 |
| ATOM | 104 | OE1 | GLN | 20 | 2.603 | 50.441 | 13.152 | 1.00 40.92 |
| ATOM | 105 | NE2 | GLN | 20 | 3.324 | 52.552 | 13.410 | 1.00 40.04 |
| ATOM | 106 | C | GLN | 20 | 5.692 | 48.568 | 10.730 | 1.00 35.83 |
| ATOM | 107 | O | GLN | 20 | 6.827 | 48.547 | 10.247 | 1.00 36.56 |
| ATOM | 108 | N | GLU | 21 | 4.864 | 47.531 | 10.681 | 1.00 36.52 |
| ATOM | 109 | CA | GLU | 21 | 5.240 | 46.279 | 10.062 | 1.00 37.80 |
| ATOM | 110 | CB | GLU | 21 | 4.024 | 45.357 | 9.998 | 1.00 39.22 |

*FIG. 4B*

| | | | | | | | | |
|---|---|---|---|---|---|---|---|---|
| ATOM | 111 | CG | GLU | 21 | 4.298 | 43.898 | 9.625 | 1.00 42.88 |
| ATOM | 112 | CD | GLU | 21 | 4.568 | 43.009 | 10.844 | 1.00 44.63 |
| ATOM | 113 | OE1 | GLU | 21 | 4.540 | 41.758 | 10.699 | 1.00 45.40 |
| ATOM | 114 | OE2 | GLU | 21 | 4.810 | 43.564 | 11.943 | 1.00 45.89 |
| ATOM | 115 | C | GLU | 21 | 5.770 | 46.549 | 8.654 | 1.00 38.20 |
| ATOM | 116 | O | GLU | 21 | 6.892 | 46.183 | 8.324 | 1.00 38.71 |
| ATOM | 117 | N | GLU | 22 | 4.972 | 47.208 | 7.826 | 1.00 38.54 |
| ATOM | 118 | CA | GLU | 22 | 5.386 | 47.478 | 6.457 | 1.00 39.08 |
| ATOM | 119 | CB | GLU | 22 | 4.308 | 48.267 | 5.703 | 1.00 40.61 |
| ATOM | 120 | CG | GLU | 22 | 3.123 | 47.406 | 5.313 | 1.00 43.51 |
| ATOM | 121 | CD | GLU | 22 | 3.556 | 46.039 | 4.773 | 1.00 45.80 |
| ATOM | 122 | OE1 | GLU | 22 | 4.243 | 45.999 | 3.719 | 1.00 46.20 |
| ATOM | 123 | OE2 | GLU | 22 | 3.215 | 45.007 | 5.414 | 1.00 46.87 |
| ATOM | 124 | C | GLU | 22 | 6.711 | 48.197 | 6.359 | 1.00 38.74 |
| ATOM | 125 | O | GLU | 22 | 7.482 | 47.954 | 5.423 | 1.00 39.26 |
| ATOM | 126 | N | ASP | 23 | 6.988 | 49.084 | 7.308 | 1.00 37.74 |
| ATOM | 127 | CA | ASP | 23 | 8.258 | 49.795 | 7.276 | 1.00 37.23 |
| ATOM | 128 | CB | ASP | 23 | 8.356 | 50.779 | 8.437 | 1.00 38.62 |
| ATOM | 129 | CG | ASP | 23 | 7.240 | 51.789 | 8.427 | 1.00 40.46 |
| ATOM | 130 | OD1 | ASP | 23 | 7.104 | 52.508 | 7.408 | 1.00 41.26 |
| ATOM | 131 | OD2 | ASP | 23 | 6.495 | 51.861 | 9.438 | 1.00 41.77 |
| ATOM | 132 | C | ASP | 23 | 9.371 | 48.760 | 7.382 | 1.00 35.54 |
| ATOM | 133 | O | ASP | 23 | 10.267 | 48.698 | 6.536 | 1.00 35.43 |
| ATOM | 134 | N | LEU | 24 | 9.294 | 47.937 | 8.420 | 1.00 33.31 |
| ATOM | 135 | CA | LEU | 24 | 10.288 | 46.910 | 8.631 | 1.00 32.04 |
| ATOM | 136 | CB | LEU | 24 | 9.898 | 46.062 | 9.842 | 1.00 31.35 |
| ATOM | 137 | CG | LEU | 24 | 9.920 | 46.801 | 11.196 | 1.00 31.20 |
| ATOM | 138 | CD1 | LEU | 24 | 9.710 | 45.815 | 12.343 | 1.00 29.48 |
| ATOM | 139 | CD2 | LEU | 24 | 11.253 | 47.526 | 11.367 | 1.00 31.51 |
| ATOM | 140 | C | LEU | 24 | 10.509 | 46.041 | 7.385 | 1.00 31.61 |
| ATOM | 141 | O | LEU | 24 | 11.645 | 45.723 | 7.049 | 1.00 31.67 |
| ATOM | 142 | N | LYS | 25 | 9.434 | 45.673 | 6.693 | 1.00 31.58 |
| ATOM | 143 | CA | LYS | 25 | 9.551 | 44.863 | 5.486 | 1.00 31.41 |
| ATOM | 144 | CB | LYS | 25 | 8.186 | 44.347 | 5.061 | 1.00 31.91 |
| ATOM | 145 | CG | LYS | 25 | 7.574 | 43.372 | 6.033 | 1.00 34.39 |
| ATOM | 146 | CD | LYS | 25 | 6.224 | 42.901 | 5.531 | 1.00 36.61 |
| ATOM | 147 | CE | LYS | 25 | 5.414 | 42.232 | 6.640 | 1.00 38.71 |
| ATOM | 148 | NZ | LYS | 25 | 3.978 | 42.086 | 6.235 | 1.00 39.39 |
| ATOM | 149 | C | LYS | 25 | 10.166 | 45.679 | 4.352 | 1.00 31.50 |
| ATOM | 150 | O | LYS | 25 | 10.969 | 45.170 | 3.568 | 1.00 30.92 |
| ATOM | 151 | N | LYS | 26 | 9.784 | 46.947 | 4.261 | 1.00 31.82 |
| ATOM | 152 | CA | LYS | 26 | 10.332 | 47.819 | 3.229 | 1.00 32.63 |
| ATOM | 153 | CB | LYS | 26 | 9.695 | 49.203 | 3.315 | 1.00 33.38 |
| ATOM | 154 | CG | LYS | 26 | 10.053 | 50.129 | 2.177 | 1.00 35.11 |
| ATOM | 155 | CD | LYS | 26 | 9.424 | 51.502 | 2.400 | 1.00 37.48 |
| ATOM | 156 | CE | LYS | 26 | 9.364 | 52.312 | 1.104 | 1.00 39.72 |
| ATOM | 157 | NZ | LYS | 26 | 8.706 | 53.645 | 1.307 | 1.00 42.62 |
| ATOM | 158 | C | LYS | 26 | 11.845 | 47.919 | 3.441 | 1.00 32.91 |
| ATOM | 159 | O | LYS | 26 | 12.614 | 48.012 | 2.479 | 1.00 32.90 |
| ATOM | 160 | N | VAL | 27 | 12.265 | 47.901 | 4.705 | 1.00 33.16 |
| ATOM | 161 | CA | VAL | 27 | 13.687 | 47.956 | 5.046 | 1.00 33.43 |
| ATOM | 162 | CB | VAL | 27 | 13.903 | 48.281 | 6.555 | 1.00 32.58 |
| ATOM | 163 | CG1 | VAL | 27 | 15.335 | 47.960 | 6.963 | 1.00 32.13 |
| ATOM | 164 | CG2 | VAL | 27 | 13.622 | 49.755 | 6.818 | 1.00 31.04 |
| ATOM | 165 | C | VAL | 27 | 14.305 | 46.586 | 4.727 | 1.00 33.90 |
| ATOM | 166 | O | VAL | 27 | 15.323 | 46.482 | 4.036 | 1.00 33.83 |
| ATOM | 167 | N | MSE | 28 | 13.668 | 45.536 | 5.223 | 1.00 34.26 |

*FIG. 4C*

| | | | | | | | | |
|---|---|---|---|---|---|---|---|---|
| ATOM | 168 | CA | MSE | 28 | 14.140 | 44.193 | 4.983 | 1.00 34.84 |
| ATOM | 169 | CB | MSE | 28 | 13.072 | 43.198 | 5.393 | 1.00 35.83 |
| ATOM | 170 | CG | MSE | 28 | 13.456 | 41.784 | 5.144 | 1.00 38.88 |
| ATOM | 171 | SE | MSE | 28 | 12.108 | 40.670 | 5.608 | 1.00 45.40 |
| ATOM | 172 | CE | MSE | 28 | 11.054 | 40.713 | 4.095 | 1.00 42.96 |
| ATOM | 173 | C | MSE | 28 | 14.465 | 44.016 | 3.505 | 1.00 35.32 |
| ATOM | 174 | O | MSE | 28 | 15.571 | 43.621 | 3.144 | 1.00 35.22 |
| ATOM | 175 | N | ARG | 29 | 13.495 | 44.331 | 2.655 | 1.00 36.22 |
| ATOM | 176 | CA | ARG | 29 | 13.665 | 44.191 | 1.218 | 1.00 36.59 |
| ATOM | 177 | CB | ARG | 29 | 12.352 | 44.520 | 0.509 | 1.00 37.37 |
| ATOM | 178 | CG | ARG | 29 | 11.223 | 43.542 | 0.827 | 1.00 38.96 |
| ATOM | 179 | CD | ARG | 29 | 9.913 | 43.960 | 0.152 | 1.00 40.89 |
| ATOM | 180 | NE | ARG | 29 | 8.760 | 43.281 | 0.744 | 1.00 42.88 |
| ATOM | 181 | CZ | ARG | 29 | 7.621 | 43.889 | 1.081 | 1.00 43.80 |
| ATOM | 182 | NH1 | ARG | 29 | 7.475 | 45.201 | 0.881 | 1.00 43.07 |
| ATOM | 183 | NH2 | ARG | 29 | 6.631 | 43.188 | 1.636 | 1.00 44.12 |
| ATOM | 184 | C | ARG | 29 | 14.814 | 45.008 | 0.625 | 1.00 36.30 |
| ATOM | 185 | O | ARG | 29 | 15.615 | 44.469 | -0.133 | 1.00 35.58 |
| ATOM | 186 | N | ARG | 30 | 14.906 | 46.296 | 0.948 | 1.00 36.85 |
| ATOM | 187 | CA | ARG | 30 | 16.008 | 47.091 | 0.410 | 1.00 38.41 |
| ATOM | 188 | CB | ARG | 30 | 15.944 | 48.543 | 0.894 | 1.00 39.31 |
| ATOM | 189 | CG | ARG | 30 | 14.676 | 49.285 | 0.513 | 1.00 41.96 |
| ATOM | 190 | CD | ARG | 30 | 14.742 | 50.763 | 0.933 | 1.00 44.07 |
| ATOM | 191 | NE | ARG | 30 | 13.415 | 51.384 | 0.995 | 1.00 45.48 |
| ATOM | 192 | CZ | ARG | 30 | 13.179 | 52.628 | 1.416 | 1.00 45.93 |
| ATOM | 193 | NH1 | ARG | 30 | 14.175 | 53.403 | 1.810 | 1.00 45.92 |
| ATOM | 194 | NH2 | ARG | 30 | 11.937 | 53.091 | 1.467 | 1.00 45.68 |
| ATOM | 195 | C | ARG | 30 | 17.338 | 46.461 | 0.843 | 1.00 39.05 |
| ATOM | 196 | O | ARG | 30 | 18.286 | 46.404 | 0.061 | 1.00 38.99 |
| ATOM | 197 | N | MSE | 31 | 17.408 | 45.999 | 2.092 | 1.00 39.11 |
| ATOM | 198 | CA | MSE | 31 | 18.615 | 45.348 | 2.596 | 1.00 38.96 |
| ATOM | 199 | CB | MSE | 31 | 18.374 | 44.784 | 4.002 | 1.00 40.43 |
| ATOM | 200 | CG | MSE | 31 | 19.512 | 43.922 | 4.599 | 1.00 42.62 |
| ATOM | 201 | SE | MSE | 31 | 21.083 | 44.819 | 5.027 | 1.00 48.46 |
| ATOM | 202 | CE | MSE | 31 | 20.438 | 45.988 | 6.389 | 1.00 45.46 |
| ATOM | 203 | C | MSE | 31 | 18.901 | 44.209 | 1.633 | 1.00 38.25 |
| ATOM | 204 | O | MSE | 31 | 19.973 | 44.132 | 1.038 | 1.00 38.18 |
| ATOM | 205 | N | GLN | 32 | 17.915 | 43.334 | 1.478 | 1.00 37.93 |
| ATOM | 206 | CA | GLN | 32 | 18.037 | 42.199 | 0.589 | 1.00 37.33 |
| ATOM | 207 | CB | GLN | 32 | 16.708 | 41.475 | 0.480 | 1.00 36.41 |
| ATOM | 208 | CG | GLN | 32 | 16.219 | 40.905 | 1.780 | 1.00 37.04 |
| ATOM | 209 | CD | GLN | 32 | 15.304 | 39.723 | 1.561 | 1.00 37.28 |
| ATOM | 210 | OE1 | GLN | 32 | 15.740 | 38.682 | 1.072 | 1.00 38.23 |
| ATOM | 211 | NE2 | GLN | 32 | 14.027 | 39.874 | 1.912 | 1.00 37.39 |
| ATOM | 212 | C | GLN | 32 | 18.475 | 42.641 | -0.791 | 1.00 37.81 |
| ATOM | 213 | O | GLN | 32 | 19.215 | 41.929 | -1.466 | 1.00 37.79 |
| ATOM | 214 | N | LYS | 33 | 18.019 | 43.819 | -1.205 | 1.00 38.80 |
| ATOM | 215 | CA | LYS | 33 | 18.362 | 44.345 | -2.516 | 1.00 39.85 |
| ATOM | 216 | CB | LYS | 33 | 17.525 | 45.588 | -2.830 | 1.00 40.63 |
| ATOM | 217 | CG | LYS | 33 | 17.591 | 45.992 | -4.298 | 1.00 42.21 |
| ATOM | 218 | CD | LYS | 33 | 16.924 | 47.336 | -4.561 | 1.00 43.78 |
| ATOM | 219 | CE | LYS | 33 | 17.160 | 47.803 | -6.006 | 1.00 44.42 |
| ATOM | 220 | NZ | LYS | 33 | 16.639 | 49.187 | -6.256 | 1.00 44.23 |
| ATOM | 221 | C | LYS | 33 | 19.843 | 44.695 | -2.574 | 1.00 40.37 |
| ATOM | 222 | O | LYS | 33 | 20.519 | 44.411 | -3.564 | 1.00 40.53 |
| ATOM | 223 | N | GLU | 34 | 20.331 | 45.312 | -1.500 | 1.00 40.59 |
| ATOM | 224 | CA | GLU | 34 | 21.730 | 45.712 | -1.378 | 1.00 40.95 |

*FIG. 4D*

| ATOM | 225 | CB | GLU | 34 | 21.912 | 46.641 | -0.179 | 1.00 | 41.24 |
| ATOM | 226 | CG | GLU | 34 | 21.229 | 47.956 | -0.359 | 1.00 | 41.42 |
| ATOM | 227 | CD | GLU | 34 | 21.476 | 48.506 | -1.741 | 1.00 | 42.21 |
| ATOM | 228 | OE1 | GLU | 34 | 22.650 | 48.810 | -2.063 | 1.00 | 42.30 |
| ATOM | 229 | OE2 | GLU | 34 | 20.493 | 48.613 | -2.507 | 1.00 | 43.29 |
| ATOM | 230 | C | GLU | 34 | 22.667 | 44.528 | -1.221 | 1.00 | 40.87 |
| ATOM | 231 | O | GLU | 34 | 23.770 | 44.527 | -1.767 | 1.00 | 41.06 |
| ATOM | 232 | N | MSE | 35 | 22.233 | 43.534 | -0.456 | 1.00 | 41.15 |
| ATOM | 233 | CA | MSE | 35 | 23.038 | 42.350 | -0.232 | 1.00 | 41.36 |
| ATOM | 234 | CB | MSE | 35 | 22.289 | 41.354 | 0.648 | 1.00 | 41.62 |
| ATOM | 235 | CG | MSE | 35 | 22.320 | 41.711 | 2.117 | 1.00 | 43.28 |
| ATOM | 236 | SE | MSE | 35 | 21.428 | 40.506 | 3.120 | 1.00 | 46.51 |
| ATOM | 237 | CE | MSE | 35 | 22.217 | 38.947 | 2.587 | 1.00 | 45.63 |
| ATOM | 238 | C | MSE | 35 | 23.376 | 41.701 | -1.554 | 1.00 | 41.91 |
| ATOM | 239 | O | MSE | 35 | 24.532 | 41.367 | -1.824 | 1.00 | 42.73 |
| ATOM | 240 | N | ASP | 36 | 22.367 | 41.533 | -2.395 | 1.00 | 42.15 |
| ATOM | 241 | CA | ASP | 36 | 22.593 | 40.898 | -3.675 | 1.00 | 41.96 |
| ATOM | 242 | CB | ASP | 36 | 21.264 | 40.633 | -4.369 | 1.00 | 43.56 |
| ATOM | 243 | CG | ASP | 36 | 21.446 | 39.947 | -5.699 | 1.00 | 45.91 |
| ATOM | 244 | OD1 | ASP | 36 | 21.821 | 40.652 | -6.675 | 1.00 | 46.71 |
| ATOM | 245 | OD2 | ASP | 36 | 21.232 | 38.707 | -5.754 | 1.00 | 46.76 |
| ATOM | 246 | C | ASP | 36 | 23.502 | 41.717 | -4.578 | 1.00 | 41.03 |
| ATOM | 247 | O | ASP | 36 | 24.406 | 41.178 | -5.217 | 1.00 | 40.61 |
| ATOM | 248 | N | ARG | 37 | 23.257 | 43.021 | -4.620 | 1.00 | 40.36 |
| ATOM | 249 | CA | ARG | 37 | 24.034 | 43.937 | -5.446 | 1.00 | 39.76 |
| ATOM | 250 | CB | ARG | 37 | 23.498 | 45.355 | -5.283 | 1.00 | 39.56 |
| ATOM | 251 | CG | ARG | 37 | 22.252 | 45.621 | -6.112 | 1.00 | 40.04 |
| ATOM | 252 | CD | ARG | 37 | 21.465 | 46.815 | -5.590 | 1.00 | 41.19 |
| ATOM | 253 | NE | ARG | 37 | 22.278 | 48.002 | -5.307 | 1.00 | 41.70 |
| ATOM | 254 | CZ | ARG | 37 | 22.938 | 48.711 | -6.221 | 1.00 | 42.38 |
| ATOM | 255 | NH1 | ARG | 37 | 22.899 | 48.362 | -7.505 | 1.00 | 42.59 |
| ATOM | 256 | NH2 | ARG | 37 | 23.615 | 49.792 | -5.851 | 1.00 | 41.94 |
| ATOM | 257 | C | ARG | 37 | 25.524 | 43.908 | -5.152 | 1.00 | 39.94 |
| ATOM | 258 | O | ARG | 37 | 26.335 | 43.732 | -6.059 | 1.00 | 40.39 |
| ATOM | 259 | N | GLY | 38 | 25.893 | 44.076 | -3.890 | 1.00 | 39.94 |
| ATOM | 260 | CA | GLY | 38 | 27.305 | 44.063 | -3.557 | 1.00 | 39.60 |
| ATOM | 261 | C | GLY | 38 | 27.933 | 42.689 | -3.699 | 1.00 | 39.23 |
| ATOM | 262 | O | GLY | 38 | 29.163 | 42.546 | -3.695 | 1.00 | 39.59 |
| ATOM | 263 | N | LEU | 39 | 27.087 | 41.677 | -3.834 | 1.00 | 38.16 |
| ATOM | 264 | CA | LEU | 39 | 27.545 | 40.307 | -3.960 | 1.00 | 37.65 |
| ATOM | 265 | CB | LEU | 39 | 26.428 | 39.376 | -3.495 | 1.00 | 35.76 |
| ATOM | 266 | CG | LEU | 39 | 26.821 | 38.029 | -2.900 | 1.00 | 34.52 |
| ATOM | 267 | CD1 | LEU | 39 | 27.899 | 38.248 | -1.857 | 1.00 | 33.52 |
| ATOM | 268 | CD2 | LEU | 39 | 25.606 | 37.348 | -2.284 | 1.00 | 32.44 |
| ATOM | 269 | C | LEU | 39 | 27.931 | 39.989 | -5.407 | 1.00 | 39.20 |
| ATOM | 270 | O | LEU | 39 | 28.594 | 38.980 | -5.681 | 1.00 | 39.88 |
| ATOM | 271 | N | ARG | 40 | 27.537 | 40.866 | -6.329 | 1.00 | 40.51 |
| ATOM | 272 | CA | ARG | 40 | 27.809 | 40.656 | -7.751 | 1.00 | 41.77 |
| ATOM | 273 | CB | ARG | 40 | 26.494 | 40.686 | -8.526 | 1.00 | 42.80 |
| ATOM | 274 | CG | ARG | 40 | 25.735 | 39.392 | -8.377 | 1.00 | 44.75 |
| ATOM | 275 | CD | ARG | 40 | 24.257 | 39.551 | -8.636 | 1.00 | 46.47 |
| ATOM | 276 | NE | ARG | 40 | 23.639 | 38.239 | -8.797 | 1.00 | 48.71 |
| ATOM | 277 | CZ | ARG | 40 | 22.331 | 38.034 | -8.890 | 1.00 | 50.01 |
| ATOM | 278 | NH1 | ARG | 40 | 21.497 | 39.064 | -8.831 | 1.00 | 51.43 |
| ATOM | 279 | NH2 | ARG | 40 | 21.861 | 36.804 | -9.060 | 1.00 | 50.46 |
| ATOM | 280 | C | ARG | 40 | 28.802 | 41.623 | -8.374 | 1.00 | 42.16 |
| ATOM | 281 | O | ARG | 40 | 28.783 | 42.819 | -8.097 | 1.00 | 42.42 |

*FIG. 4E*

| | | | | | | | | |
|---|---|---|---|---|---|---|---|---|
| ATOM | 282 | N | LEU | 41 | 29.650 | 41.087 | -9.247 | 1.00 42.03 |
| ATOM | 283 | CA | LEU | 41 | 30.689 | 41.864 | -9.902 | 1.00 42.00 |
| ATOM | 284 | CB | LEU | 41 | 31.307 | 41.044 | -11.041 | 1.00 42.00 |
| ATOM | 285 | CG | LEU | 41 | 32.577 | 41.650 | -11.660 | 1.00 41.78 |
| ATOM | 286 | CD1 | LEU | 41 | 33.638 | 41.836 | -10.583 | 1.00 40.20 |
| ATOM | 287 | CD2 | LEU | 41 | 33.087 | 40.747 | -12.773 | 1.00 41.95 |
| ATOM | 288 | C | LEU | 41 | 30.278 | 43.237 | -10.428 | 1.00 42.57 |
| ATOM | 289 | O | LEU | 41 | 30.920 | 44.243 | -10.110 | 1.00 42.64 |
| ATOM | 290 | N | GLU | 42 | 29.219 | 43.292 | -11.227 | 1.00 43.03 |
| ATOM | 291 | CA | GLU | 42 | 28.788 | 44.562 | -11.803 | 1.00 44.63 |
| ATOM | 292 | CB | GLU | 42 | 27.494 | 44.369 | -12.607 | 1.00 43.97 |
| ATOM | 293 | CG | GLU | 42 | 26.436 | 43.533 | -11.922 | 1.00 44.02 |
| ATOM | 294 | CD | GLU | 42 | 26.546 | 42.057 | -12.248 | 1.00 43.71 |
| ATOM | 295 | OE1 | GLU | 42 | 27.673 | 41.527 | -12.245 | 1.00 45.13 |
| ATOM | 296 | OE2 | GLU | 42 | 25.504 | 41.416 | -12.496 | 1.00 43.50 |
| ATOM | 297 | C | GLU | 42 | 28.616 | 45.714 | -10.805 | 1.00 46.21 |
| ATOM | 298 | O | GLU | 42 | 28.963 | 46.860 | -11.103 | 1.00 46.22 |
| ATOM | 299 | N | THR | 43 | 28.105 | 45.413 | -9.616 | 1.00 47.90 |
| ATOM | 300 | CA | THR | 43 | 27.873 | 46.443 | -8.608 | 1.00 49.10 |
| ATOM | 301 | CB | THR | 43 | 26.370 | 46.533 | -8.285 | 1.00 48.63 |
| ATOM | 302 | OG1 | THR | 43 | 25.772 | 45.242 | -8.465 | 1.00 47.66 |
| ATOM | 303 | CG2 | THR | 43 | 25.679 | 47.531 | -9.192 | 1.00 48.90 |
| ATOM | 304 | C | THR | 43 | 28.629 | 46.226 | -7.302 | 1.00 50.94 |
| ATOM | 305 | O | THR | 43 | 28.481 | 47.008 | -6.362 | 1.00 51.52 |
| ATOM | 306 | N | HIS | 44 | 29.456 | 45.185 | -7.249 | 1.00 52.58 |
| ATOM | 307 | CA | HIS | 44 | 30.204 | 44.854 | -6.037 | 1.00 53.89 |
| ATOM | 308 | CB | HIS | 44 | 31.210 | 43.727 | -6.311 | 1.00 54.68 |
| ATOM | 309 | CG | HIS | 44 | 32.552 | 44.208 | -6.775 | 1.00 55.77 |
| ATOM | 310 | CD2 | HIS | 44 | 33.748 | 44.257 | -6.139 | 1.00 55.82 |
| ATOM | 311 | ND1 | HIS | 44 | 32.758 | 44.772 | -8.017 | 1.00 56.36 |
| ATOM | 312 | CE1 | HIS | 44 | 34.020 | 45.146 | -8.125 | 1.00 56.30 |
| ATOM | 313 | NE2 | HIS | 44 | 34.643 | 44.845 | -6.999 | 1.00 56.06 |
| ATOM | 314 | C | HIS | 44 | 30.950 | 46.013 | -5.398 | 1.00 54.87 |
| ATOM | 315 | O | HIS | 44 | 30.823 | 46.254 | -4.199 | 1.00 55.06 |
| ATOM | 316 | N | GLU | 45 | 31.724 | 46.732 | -6.203 | 1.00 56.25 |
| ATOM | 317 | CA | GLU | 45 | 32.540 | 47.826 | -5.703 | 1.00 57.17 |
| ATOM | 318 | CB | GLU | 45 | 33.618 | 48.180 | -6.721 | 1.00 59.35 |
| ATOM | 319 | CG | GLU | 45 | 33.146 | 49.127 | -7.800 | 1.00 61.61 |
| ATOM | 320 | CD | GLU | 45 | 34.107 | 50.279 | -7.985 | 1.00 63.07 |
| ATOM | 321 | OE1 | GLU | 45 | 35.228 | 50.038 | -8.487 | 1.00 63.72 |
| ATOM | 322 | OE2 | GLU | 45 | 33.747 | 51.420 | -7.613 | 1.00 64.00 |
| ATOM | 323 | C | GLU | 45 | 31.762 | 49.074 | -5.356 | 1.00 56.66 |
| ATOM | 324 | O | GLU | 45 | 32.295 | 49.985 | -4.732 | 1.00 56.54 |
| ATOM | 325 | N | GLU | 46 | 30.508 | 49.135 | -5.772 | 1.00 56.24 |
| ATOM | 326 | CA | GLU | 46 | 29.708 | 50.306 | -5.456 | 1.00 56.37 |
| ATOM | 327 | CB | GLU | 46 | 29.542 | 51.157 | -6.704 | 1.00 57.92 |
| ATOM | 328 | CG | GLU | 46 | 30.881 | 51.645 | -7.212 | 1.00 60.77 |
| ATOM | 329 | CD | GLU | 46 | 30.782 | 52.400 | -8.515 | 1.00 62.28 |
| ATOM | 330 | OE1 | GLU | 46 | 30.566 | 51.762 | -9.571 | 1.00 62.25 |
| ATOM | 331 | OE2 | GLU | 46 | 30.914 | 53.641 | -8.474 | 1.00 63.95 |
| ATOM | 332 | C | GLU | 46 | 28.366 | 49.891 | -4.873 | 1.00 55.40 |
| ATOM | 333 | O | GLU | 46 | 27.309 | 50.123 | -5.457 | 1.00 55.75 |
| ATOM | 334 | N | ALA | 47 | 28.440 | 49.264 | -3.704 | 1.00 53.89 |
| ATOM | 335 | CA | ALA | 47 | 27.273 | 48.783 | -2.987 | 1.00 51.80 |
| ATOM | 336 | CB | ALA | 47 | 27.140 | 47.280 | -3.159 | 1.00 52.36 |
| ATOM | 337 | C | ALA | 47 | 27.470 | 49.111 | -1.524 | 1.00 49.98 |
| ATOM | 338 | O | ALA | 47 | 28.448 | 48.664 | -0.923 | 1.00 50.36 |

*FIG. 4F*

| ATOM | 339 | N | SER | 48 | 26.553 | 49.894 | -0.960 | 1.00 | 47.18 |
| ATOM | 340 | CA | SER | 48 | 26.630 | 50.267 | 0.444 | 1.00 | 44.70 |
| ATOM | 341 | CB | SER | 48 | 25.299 | 50.860 | 0.897 | 1.00 | 46.13 |
| ATOM | 342 | OG | SER | 48 | 24.243 | 49.927 | 0.720 | 1.00 | 47.87 |
| ATOM | 343 | C | SER | 48 | 26.965 | 49.041 | 1.287 | 1.00 | 42.45 |
| ATOM | 344 | O | SER | 48 | 27.841 | 49.082 | 2.147 | 1.00 | 42.01 |
| ATOM | 345 | N | VAL | 49 | 26.261 | 47.946 | 1.037 | 1.00 | 40.48 |
| ATOM | 346 | CA | VAL | 49 | 26.516 | 46.713 | 1.762 | 1.00 | 38.96 |
| ATOM | 347 | CB | VAL | 49 | 25.231 | 45.849 | 1.875 | 1.00 | 38.62 |
| ATOM | 348 | CG1 | VAL | 49 | 25.496 | 44.625 | 2.740 | 1.00 | 38.40 |
| ATOM | 349 | CG2 | VAL | 49 | 24.102 | 46.672 | 2.472 | 1.00 | 37.16 |
| ATOM | 350 | C | VAL | 49 | 27.572 | 45.997 | 0.929 | 1.00 | 37.97 |
| ATOM | 351 | O | VAL | 49 | 27.266 | 45.474 | -0.137 | 1.00 | 38.42 |
| ATOM | 352 | N | LYS | 50 | 28.810 | 45.982 | 1.422 | 1.00 | 36.51 |
| ATOM | 353 | CA | LYS | 50 | 29.937 | 45.385 | 0.703 | 1.00 | 34.95 |
| ATOM | 354 | CB | LYS | 50 | 31.250 | 45.843 | 1.334 | 1.00 | 35.51 |
| ATOM | 355 | CG | LYS | 50 | 31.574 | 47.322 | 1.091 | 1.00 | 36.68 |
| ATOM | 356 | CD | LYS | 50 | 30.676 | 48.249 | 1.913 | 1.00 | 39.05 |
| ATOM | 357 | CE | LYS | 50 | 30.865 | 48.018 | 3.419 | 1.00 | 39.54 |
| ATOM | 358 | NZ | LYS | 50 | 32.316 | 48.157 | 3.792 | 1.00 | 40.04 |
| ATOM | 359 | C | LYS | 50 | 30.012 | 43.879 | 0.482 | 1.00 | 33.72 |
| ATOM | 360 | O | LYS | 50 | 30.845 | 43.421 | -0.293 | 1.00 | 33.30 |
| ATOM | 361 | N | MSE | 51 | 29.171 | 43.100 | 1.147 | 1.00 | 33.02 |
| ATOM | 362 | CA | MSE | 51 | 29.209 | 41.647 | 0.967 | 1.00 | 32.08 |
| ATOM | 363 | CB | MSE | 51 | 28.291 | 41.257 | -0.190 | 1.00 | 34.01 |
| ATOM | 364 | CG | MSE | 51 | 26.867 | 41.744 | -0.025 | 1.00 | 36.03 |
| ATOM | 365 | SE | MSE | 51 | 26.148 | 41.146 | 1.529 | 1.00 | 40.73 |
| ATOM | 366 | CE | MSE | 51 | 25.558 | 39.411 | 1.085 | 1.00 | 37.98 |
| ATOM | 367 | C | MSE | 51 | 30.637 | 41.180 | 0.666 | 1.00 | 30.17 |
| ATOM | 368 | O | MSE | 51 | 30.928 | 40.723 | -0.437 | 1.00 | 30.22 |
| ATOM | 369 | N | LEU | 52 | 31.518 | 41.295 | 1.650 | 1.00 | 28.96 |
| ATOM | 370 | CA | LEU | 52 | 32.920 | 40.928 | 1.487 | 1.00 | 27.43 |
| ATOM | 371 | CB | LEU | 52 | 33.769 | 41.839 | 2.357 | 1.00 | 28.05 |
| ATOM | 372 | CG | LEU | 52 | 33.649 | 43.319 | 1.991 | 1.00 | 28.52 |
| ATOM | 373 | CD1 | LEU | 52 | 34.222 | 44.171 | 3.116 | 1.00 | 28.77 |
| ATOM | 374 | CD2 | LEU | 52 | 34.369 | 43.583 | 0.658 | 1.00 | 28.75 |
| ATOM | 375 | C | LEU | 52 | 33.273 | 39.482 | 1.803 | 1.00 | 26.61 |
| ATOM | 376 | O | LEU | 52 | 32.997 | 38.995 | 2.893 | 1.00 | 25.26 |
| ATOM | 377 | N | PRO | 53 | 33.911 | 38.774 | 0.844 | 1.00 | 27.04 |
| ATOM | 378 | CD | PRO | 53 | 34.270 | 39.142 | -0.540 | 1.00 | 25.69 |
| ATOM | 379 | CA | PRO | 53 | 34.264 | 37.375 | 1.133 | 1.00 | 27.99 |
| ATOM | 380 | CB | PRO | 53 | 34.807 | 36.864 | -0.204 | 1.00 | 26.92 |
| ATOM | 381 | CG | PRO | 53 | 34.184 | 37.825 | -1.241 | 1.00 | 25.77 |
| ATOM | 382 | C | PRO | 53 | 35.314 | 37.361 | 2.239 | 1.00 | 28.40 |
| ATOM | 383 | O | PRO | 53 | 36.152 | 38.271 | 2.317 | 1.00 | 28.36 |
| ATOM | 384 | N | THR | 54 | 35.255 | 36.329 | 3.080 | 1.00 | 29.46 |
| ATOM | 385 | CA | THR | 54 | 36.149 | 36.142 | 4.226 | 1.00 | 30.53 |
| ATOM | 386 | CB | THR | 54 | 35.317 | 35.951 | 5.502 | 1.00 | 29.48 |
| ATOM | 387 | OG1 | THR | 54 | 34.539 | 34.711 | 5.418 | 1.00 | 27.97 |
| ATOM | 388 | CG2 | THR | 54 | 34.324 | 37.084 | 5.659 | 1.00 | 29.42 |
| ATOM | 389 | C | THR | 54 | 37.018 | 34.884 | 4.071 | 1.00 | 31.60 |
| ATOM | 390 | O | THR | 54 | 37.657 | 34.423 | 5.025 | 1.00 | 32.25 |
| ATOM | 391 | N | TYR | 55 | 37.017 | 34.311 | 2.877 | 1.00 | 32.63 |
| ATOM | 392 | CA | TYR | 55 | 37.763 | 33.089 | 2.615 | 1.00 | 34.41 |
| ATOM | 393 | CB | TYR | 55 | 39.249 | 33.421 | 2.405 | 1.00 | 33.07 |
| ATOM | 394 | CG | TYR | 55 | 39.458 | 34.175 | 1.101 | 1.00 | 32.58 |
| ATOM | 395 | CD1 | TYR | 55 | 39.518 | 35.571 | 1.067 | 1.00 | 32.44 |

*FIG. 4G*

| ATOM | 396 | CE1 | TYR | 55 | 39.572 | 36.263 | -0.157 | 1.00 | 32.48 |
| ATOM | 397 | CD2 | TYR | 55 | 39.467 | 33.492 | -0.117 | 1.00 | 31.97 |
| ATOM | 398 | CE2 | TYR | 55 | 39.516 | 34.172 | -1.335 | 1.00 | 31.83 |
| ATOM | 399 | CZ | TYR | 55 | 39.566 | 35.548 | -1.351 | 1.00 | 32.18 |
| ATOM | 400 | OH | TYR | 55 | 39.575 | 36.200 | -2.568 | 1.00 | 32.67 |
| ATOM | 401 | C | TYR | 55 | 37.559 | 31.956 | 3.637 | 1.00 | 36.06 |
| ATOM | 402 | O | TYR | 55 | 38.314 | 30.991 | 3.665 | 1.00 | 37.61 |
| ATOM | 403 | N | VAL | 56 | 36.518 | 32.059 | 4.459 | 1.00 | 38.03 |
| ATOM | 404 | CA | VAL | 56 | 36.199 | 31.006 | 5.429 | 1.00 | 39.87 |
| ATOM | 405 | CB | VAL | 56 | 35.483 | 31.586 | 6.663 | 1.00 | 38.75 |
| ATOM | 406 | CG1 | VAL | 56 | 35.202 | 30.492 | 7.669 | 1.00 | 38.10 |
| ATOM | 407 | CG2 | VAL | 56 | 36.336 | 32.660 | 7.285 | 1.00 | 38.76 |
| ATOM | 408 | C | VAL | 56 | 35.249 | 30.032 | 4.706 | 1.00 | 42.20 |
| ATOM | 409 | O | VAL | 56 | 34.098 | 30.376 | 4.418 | 1.00 | 42.02 |
| ATOM | 410 | N | ARG | 57 | 35.718 | 28.821 | 4.414 | 1.00 | 44.49 |
| ATOM | 411 | CA | ARG | 57 | 34.896 | 27.860 | 3.676 | 1.00 | 47.07 |
| ATOM | 412 | CB | ARG | 57 | 35.688 | 27.288 | 2.499 | 1.00 | 48.02 |
| ATOM | 413 | CG | ARG | 57 | 36.209 | 28.310 | 1.508 | 1.00 | 49.08 |
| ATOM | 414 | CD | ARG | 57 | 36.558 | 27.626 | 0.185 | 1.00 | 49.69 |
| ATOM | 415 | NE | ARG | 57 | 37.239 | 28.528 | -0.737 | 1.00 | 49.50 |
| ATOM | 416 | CZ | ARG | 57 | 38.367 | 29.167 | -0.447 | 1.00 | 48.83 |
| ATOM | 417 | NH1 | ARG | 57 | 38.938 | 28.997 | 0.745 | 1.00 | 48.13 |
| ATOM | 418 | NH2 | ARG | 57 | 38.915 | 29.978 | -1.345 | 1.00 | 47.51 |
| ATOM | 419 | C | ARG | 57 | 34.311 | 26.695 | 4.449 | 1.00 | 48.57 |
| ATOM | 420 | O | ARG | 57 | 34.810 | 26.310 | 5.500 | 1.00 | 48.65 |
| ATOM | 421 | N | SER | 58 | 33.256 | 26.117 | 3.891 | 1.00 | 51.15 |
| ATOM | 422 | CA | SER | 58 | 32.589 | 24.973 | 4.501 | 1.00 | 54.78 |
| ATOM | 423 | CB | SER | 58 | 31.204 | 24.793 | 3.882 | 1.00 | 54.26 |
| ATOM | 424 | OG | SER | 58 | 31.258 | 24.980 | 2.475 | 1.00 | 54.39 |
| ATOM | 425 | C | SER | 58 | 33.419 | 23.708 | 4.295 | 1.00 | 57.39 |
| ATOM | 426 | O | SER | 58 | 33.097 | 22.645 | 4.823 | 1.00 | 57.47 |
| ATOM | 427 | N | THR | 59 | 34.484 | 23.840 | 3.510 | 1.00 | 60.71 |
| ATOM | 428 | CA | THR | 59 | 35.392 | 22.740 | 3.216 | 1.00 | 64.02 |
| ATOM | 429 | CB | THR | 59 | 35.886 | 22.823 | 1.758 | 1.00 | 63.73 |
| ATOM | 430 | OG1 | THR | 59 | 36.637 | 24.029 | 1.570 | 1.00 | 63.22 |
| ATOM | 431 | CG2 | THR | 59 | 34.704 | 22.843 | 0.801 | 1.00 | 63.87 |
| ATOM | 432 | C | THR | 59 | 36.571 | 22.880 | 4.176 | 1.00 | 67.10 |
| ATOM | 433 | O | THR | 59 | 37.554 | 23.562 | 3.884 | 1.00 | 67.44 |
| ATOM | 434 | N | PRO | 60 | 36.480 | 22.238 | 5.349 | 1.00 | 69.75 |
| ATOM | 435 | CD | PRO | 60 | 35.366 | 21.412 | 5.854 | 1.00 | 70.63 |
| ATOM | 436 | CA | PRO | 60 | 37.556 | 22.320 | 6.337 | 1.00 | 71.72 |
| ATOM | 437 | CB | PRO | 60 | 36.841 | 21.982 | 7.636 | 1.00 | 71.72 |
| ATOM | 438 | CG | PRO | 60 | 35.909 | 20.881 | 7.182 | 1.00 | 71.50 |
| ATOM | 439 | C | PRO | 60 | 38.709 | 21.370 | 6.056 | 1.00 | 73.48 |
| ATOM | 440 | O | PRO | 60 | 39.522 | 21.609 | 5.158 | 1.00 | 73.53 |
| ATOM | 441 | N | GLU | 61 | 38.754 | 20.287 | 6.830 | 1.00 | 75.48 |
| ATOM | 442 | CA | GLU | 61 | 39.808 | 19.283 | 6.731 | 1.00 | 76.98 |
| ATOM | 443 | CB | GLU | 61 | 39.969 | 18.788 | 5.289 | 1.00 | 78.43 |
| ATOM | 444 | CG | GLU | 61 | 40.806 | 17.516 | 5.161 | 1.00 | 80.68 |
| ATOM | 445 | CD | GLU | 61 | 42.177 | 17.744 | 4.530 | 1.00 | 81.88 |
| ATOM | 446 | OE1 | GLU | 61 | 42.993 | 18.498 | 5.100 | 1.00 | 82.28 |
| ATOM | 447 | OE2 | GLU | 61 | 42.442 | 17.156 | 3.458 | 1.00 | 82.68 |
| ATOM | 448 | C | GLU | 61 | 41.083 | 19.969 | 7.194 | 1.00 | 77.00 |
| ATOM | 449 | O | GLU | 61 | 41.942 | 20.327 | 6.389 | 1.00 | 77.10 |
| ATOM | 450 | N | GLY | 62 | 41.177 | 20.181 | 8.502 | 1.00 | 76.85 |
| ATOM | 451 | CA | GLY | 62 | 42.344 | 20.826 | 9.069 | 1.00 | 76.72 |
| ATOM | 452 | C | GLY | 62 | 42.415 | 20.539 | 10.555 | 1.00 | 76.65 |

*FIG. 4H*

```
ATOM  453  O    GLY  62   42.507  19.380  10.969  1.00  76.79
ATOM  454  N    SER  63   42.361  21.594  11.362  1.00  76.25
ATOM  455  CA   SER  63   42.417  21.458  12.814  1.00  75.06
ATOM  456  CB   SER  63   41.401  20.413  13.300  1.00  75.92
ATOM  457  OG   SER  63   41.350  20.363  14.718  1.00  76.69
ATOM  458  C    SER  63   43.818  21.062  13.259  1.00  73.60
ATOM  459  O    SER  63   44.090  19.899  13.561  1.00  73.10
ATOM  460  N    GLU  64   44.705  22.045  13.280  1.00  71.83
ATOM  461  CA   GLU  64   46.071  21.819  13.703  1.00  70.12
ATOM  462  CB   GLU  64   46.996  22.824  13.011  1.00  71.42
ATOM  463  CG   GLU  64   48.464  22.726  13.417  1.00  73.74
ATOM  464  CD   GLU  64   49.014  21.309  13.342  1.00  74.84
ATOM  465  OE1  GLU  64   48.623  20.466  14.187  1.00  75.26
ATOM  466  OE2  GLU  64   49.837  21.041  12.434  1.00  75.45
ATOM  467  C    GLU  64   46.136  21.971  15.221  1.00  67.97
ATOM  468  O    GLU  64   46.775  22.886  15.734  1.00  68.33
ATOM  469  N    VAL  65   45.448  21.076  15.927  1.00  65.13
ATOM  470  CA   VAL  65   45.400  21.067  17.391  1.00  62.32
ATOM  471  CB   VAL  65   45.335  19.621  17.918  1.00  62.48
ATOM  472  CG1  VAL  65   45.487  19.607  19.430  1.00  62.45
ATOM  473  CG2  VAL  65   44.011  18.975  17.508  1.00  62.79
ATOM  474  C    VAL  65   46.587  21.752  18.055  1.00  60.42
ATOM  475  O    VAL  65   47.703  21.708  17.540  1.00  60.54
ATOM  476  N    GLY  66   46.354  22.386  19.200  1.00  58.26
ATOM  477  CA   GLY  66   47.454  23.043  19.888  1.00  55.67
ATOM  478  C    GLY  66   47.081  24.174  20.823  1.00  53.42
ATOM  479  O    GLY  66   46.153  24.052  21.615  1.00  54.08
ATOM  480  N    ASP  67   47.832  25.267  20.739  1.00  51.06
ATOM  481  CA   ASP  67   47.614  26.460  21.549  1.00  48.67
ATOM  482  CB   ASP  67   48.617  26.531  22.703  1.00  49.14
ATOM  483  CG   ASP  67   48.381  25.462  23.751  1.00  49.34
ATOM  484  OD1  ASP  67   48.201  24.287  23.365  1.00  49.37
ATOM  485  OD2  ASP  67   48.386  25.791  24.956  1.00  49.62
ATOM  486  C    ASP  67   47.832  27.634  20.612  1.00  47.26
ATOM  487  O    ASP  67   48.786  27.635  19.827  1.00  47.44
ATOM  488  N    PHE  68   46.955  28.632  20.678  1.00  45.41
ATOM  489  CA   PHE  68   47.075  29.778  19.785  1.00  43.60
ATOM  490  CB   PHE  68   46.031  29.682  18.667  1.00  41.17
ATOM  491  CG   PHE  68   46.032  28.361  17.946  1.00  39.29
ATOM  492  CD1  PHE  68   45.621  27.199  18.592  1.00  38.55
ATOM  493  CD2  PHE  68   46.468  28.272  16.623  1.00  38.76
ATOM  494  CE1  PHE  68   45.647  25.966  17.934  1.00  38.24
ATOM  495  CE2  PHE  68   46.498  27.050  15.959  1.00  37.31
ATOM  496  CZ   PHE  68   46.086  25.893  16.619  1.00  37.76
ATOM  497  C    PHE  68   46.918  31.096  20.514  1.00  43.33
ATOM  498  O    PHE  68   46.395  31.147  21.621  1.00  43.27
ATOM  499  N    LEU  69   47.386  32.166  19.889  1.00  43.51
ATOM  500  CA   LEU  69   47.274  33.475  20.497  1.00  44.73
ATOM  501  CB   LEU  69   48.625  34.197  20.518  1.00  45.26
ATOM  502  CG   LEU  69   48.781  34.949  21.848  1.00  46.33
ATOM  503  CD1  LEU  69   49.166  33.928  22.932  1.00  46.09
ATOM  504  CD2  LEU  69   49.811  36.072  21.748  1.00  45.48
ATOM  505  C    LEU  69   46.275  34.278  19.681  1.00  45.37
ATOM  506  O    LEU  69   46.448  34.451  18.470  1.00  45.62
ATOM  507  N    SER  70   45.228  34.758  20.351  1.00  45.75
ATOM  508  CA   SER  70   44.177  35.528  19.697  1.00  44.98
ATOM  509  CB   SER  70   42.794  34.984  20.074  1.00  44.61
```

*FIG. 4I*

```
ATOM    510  OG   SER   70      42.697  33.589  19.844  1.00 44.25
ATOM    511  C    SER   70      44.250  36.978  20.109  1.00 44.92
ATOM    512  O    SER   70      44.451  37.289  21.277  1.00 44.67
ATOM    513  N    LEU   71      44.095  37.858  19.130  1.00 45.85
ATOM    514  CA   LEU   71      44.092  39.294  19.366  1.00 47.27
ATOM    515  CB   LEU   71      45.064  40.000  18.421  1.00 47.71
ATOM    516  CG   LEU   71      46.552  39.942  18.787  1.00 49.06
ATOM    517  CD1  LEU   71      47.008  38.497  19.039  1.00 49.69
ATOM    518  CD2  LEU   71      47.348  40.572  17.656  1.00 49.35
ATOM    519  C    LEU   71      42.668  39.752  19.082  1.00 47.94
ATOM    520  O    LEU   71      41.873  38.997  18.499  1.00 48.06
ATOM    521  N    ASP   72      42.333  40.976  19.479  1.00 48.20
ATOM    522  CA   ASP   72      40.985  41.451  19.244  1.00 48.67
ATOM    523  CB   ASP   72      40.043  40.807  20.262  1.00 48.71
ATOM    524  CG   ASP   72      38.668  41.420  20.243  1.00 49.13
ATOM    525  OD1  ASP   72      38.090  41.549  19.144  1.00 49.57
ATOM    526  OD2  ASP   72      38.168  41.777  21.331  1.00 50.11
ATOM    527  C    ASP   72      40.819  42.962  19.258  1.00 48.98
ATOM    528  O    ASP   72      40.247  43.530  20.187  1.00 48.82
ATOM    529  N    LEU   73      41.312  43.613  18.214  1.00 49.73
ATOM    530  CA   LEU   73      41.193  45.060  18.117  1.00 51.48
ATOM    531  CB   LEU   73      42.199  45.603  17.096  1.00 50.80
ATOM    532  CG   LEU   73      42.160  47.096  16.774  1.00 50.07
ATOM    533  CD1  LEU   73      42.358  47.902  18.045  1.00 50.10
ATOM    534  CD2  LEU   73      43.223  47.421  15.738  1.00 49.97
ATOM    535  C    LEU   73      39.764  45.392  17.687  1.00 52.93
ATOM    536  O    LEU   73      38.909  44.507  17.628  1.00 52.38
ATOM    537  N    GLY   74      39.504  46.665  17.401  1.00 54.88
ATOM    538  CA   GLY   74      38.177  47.068  16.983  1.00 56.88
ATOM    539  C    GLY   74      37.285  47.420  18.148  1.00 58.48
ATOM    540  O    GLY   74      36.476  48.348  18.071  1.00 58.31
ATOM    541  N    GLY   75      37.428  46.668  19.233  1.00 60.27
ATOM    542  CA   GLY   75      36.621  46.925  20.410  1.00 62.46
ATOM    543  C    GLY   75      37.020  48.230  21.074  1.00 63.75
ATOM    544  O    GLY   75      37.824  49.005  20.536  1.00 64.06
ATOM    545  N    THR   76      36.452  48.481  22.248  1.00 64.50
ATOM    546  CA   THR   76      36.759  49.697  22.991  1.00 65.42
ATOM    547  CB   THR   76      35.905  49.776  24.266  1.00 66.28
ATOM    548  OG1  THR   76      36.361  48.791  25.203  1.00 67.43
ATOM    549  CG2  THR   76      34.425  49.505  23.938  1.00 66.14
ATOM    550  C    THR   76      38.238  49.651  23.385  1.00 65.25
ATOM    551  O    THR   76      39.005  50.595  23.152  1.00 65.01
ATOM    552  N    ASN   77      38.622  48.528  23.980  1.00 64.74
ATOM    553  CA   ASN   77      39.987  48.309  24.412  1.00 64.17
ATOM    554  CB   ASN   77      40.015  47.966  25.903  1.00 65.44
ATOM    555  CG   ASN   77      39.346  49.027  26.765  1.00 66.47
ATOM    556  OD1  ASN   77      39.656  50.219  26.663  1.00 67.13
ATOM    557  ND2  ASN   77      38.431  48.596  27.629  1.00 66.65
ATOM    558  C    ASN   77      40.547  47.149  23.603  1.00 63.19
ATOM    559  O    ASN   77      39.795  46.303  23.120  1.00 62.58
ATOM    560  N    PHE   78      41.866  47.123  23.446  1.00 62.14
ATOM    561  CA   PHE   78      42.526  46.051  22.708  1.00 61.12
ATOM    562  CB   PHE   78      43.887  46.514  22.172  1.00 61.81
ATOM    563  CG   PHE   78      44.684  45.420  21.516  1.00 62.50
ATOM    564  CD1  PHE   78      44.347  44.956  20.245  1.00 62.81
ATOM    565  CD2  PHE   78      45.741  44.818  22.189  1.00 62.99
ATOM    566  CE1  PHE   78      45.051  43.899  19.655  1.00 62.72
```

*FIG. 4J*

| ATOM | 567 | CE2 | PHE | 78 | 46.450 | 43.763 | 21.607 | 1.00 | 63.38 |
|------|-----|-----|-----|----|--------|--------|--------|------|-------|
| ATOM | 568 | CZ  | PHE | 78 | 46.103 | 43.301 | 20.336 | 1.00 | 63.01 |
| ATOM | 569 | C   | PHE | 78 | 42.732 | 44.893 | 23.668 | 1.00 | 60.09 |
| ATOM | 570 | O   | PHE | 78 | 43.065 | 45.100 | 24.834 | 1.00 | 60.08 |
| ATOM | 571 | N   | ARG | 79 | 42.528 | 43.675 | 23.184 | 1.00 | 58.63 |
| ATOM | 572 | CA  | ARG | 79 | 42.706 | 42.504 | 24.025 | 1.00 | 57.40 |
| ATOM | 573 | CB  | ARG | 79 | 41.367 | 41.819 | 24.280 | 1.00 | 57.06 |
| ATOM | 574 | CG  | ARG | 79 | 41.481 | 40.637 | 25.222 | 1.00 | 57.49 |
| ATOM | 575 | CD  | ARG | 79 | 40.221 | 39.819 | 25.219 | 1.00 | 57.47 |
| ATOM | 576 | NE  | ARG | 79 | 39.062 | 40.646 | 25.504 | 1.00 | 57.16 |
| ATOM | 577 | CZ  | ARG | 79 | 37.818 | 40.266 | 25.267 | 1.00 | 57.69 |
| ATOM | 578 | NH1 | ARG | 79 | 37.586 | 39.071 | 24.738 | 1.00 | 57.38 |
| ATOM | 579 | NH2 | ARG | 79 | 36.812 | 41.080 | 25.555 | 1.00 | 58.45 |
| ATOM | 580 | C   | ARG | 79 | 43.663 | 41.522 | 23.368 | 1.00 | 56.71 |
| ATOM | 581 | O   | ARG | 79 | 43.926 | 41.619 | 22.170 | 1.00 | 57.24 |
| ATOM | 582 | N   | VAL | 80 | 44.180 | 40.590 | 24.167 | 1.00 | 55.50 |
| ATOM | 583 | CA  | VAL | 80 | 45.114 | 39.557 | 23.724 | 1.00 | 54.27 |
| ATOM | 584 | CB  | VAL | 80 | 46.576 | 39.947 | 23.996 | 1.00 | 54.31 |
| ATOM | 585 | CG1 | VAL | 80 | 47.491 | 38.779 | 23.674 | 1.00 | 54.49 |
| ATOM | 586 | CG2 | VAL | 80 | 46.960 | 41.158 | 23.166 | 1.00 | 54.39 |
| ATOM | 587 | C   | VAL | 80 | 44.806 | 38.327 | 24.555 | 1.00 | 54.04 |
| ATOM | 588 | O   | VAL | 80 | 44.517 | 38.447 | 25.738 | 1.00 | 53.31 |
| ATOM | 589 | N   | MSE | 81 | 44.881 | 37.144 | 23.957 | 1.00 | 54.52 |
| ATOM | 590 | CA  | MSE | 81 | 44.568 | 35.935 | 24.703 | 1.00 | 54.59 |
| ATOM | 591 | CB  | MSE | 81 | 43.053 | 35.804 | 24.828 | 1.00 | 57.08 |
| ATOM | 592 | CG  | MSE | 81 | 42.300 | 36.025 | 23.520 | 1.00 | 60.39 |
| ATOM | 593 | SE  | MSE | 81 | 40.534 | 36.437 | 23.792 | 1.00 | 65.62 |
| ATOM | 594 | CE  | MSE | 81 | 39.999 | 34.926 | 24.679 | 1.00 | 62.03 |
| ATOM | 595 | C   | MSE | 81 | 45.142 | 34.645 | 24.146 | 1.00 | 53.56 |
| ATOM | 596 | O   | MSE | 81 | 45.598 | 34.582 | 23.007 | 1.00 | 52.99 |
| ATOM | 597 | N   | LEU | 82 | 45.096 | 33.611 | 24.978 | 1.00 | 52.63 |
| ATOM | 598 | CA  | LEU | 82 | 45.602 | 32.292 | 24.638 | 1.00 | 51.86 |
| ATOM | 599 | CB  | LEU | 82 | 46.660 | 31.863 | 25.665 | 1.00 | 52.75 |
| ATOM | 600 | CG  | LEU | 82 | 47.261 | 30.455 | 25.542 | 1.00 | 53.22 |
| ATOM | 601 | CD1 | LEU | 82 | 48.562 | 30.521 | 24.736 | 1.00 | 52.42 |
| ATOM | 602 | CD2 | LEU | 82 | 47.523 | 29.882 | 26.937 | 1.00 | 53.00 |
| ATOM | 603 | C   | LEU | 82 | 44.461 | 31.286 | 24.650 | 1.00 | 51.18 |
| ATOM | 604 | O   | LEU | 82 | 43.718 | 31.186 | 25.632 | 1.00 | 51.20 |
| ATOM | 605 | N   | VAL | 83 | 44.333 | 30.535 | 23.563 | 1.00 | 50.58 |
| ATOM | 606 | CA  | VAL | 83 | 43.292 | 29.522 | 23.448 | 1.00 | 50.00 |
| ATOM | 607 | CB  | VAL | 83 | 42.274 | 29.887 | 22.362 | 1.00 | 49.63 |
| ATOM | 608 | CG1 | VAL | 83 | 41.213 | 28.794 | 22.262 | 1.00 | 49.26 |
| ATOM | 609 | CG2 | VAL | 83 | 41.660 | 31.244 | 22.670 | 1.00 | 48.32 |
| ATOM | 610 | C   | VAL | 83 | 43.914 | 28.187 | 23.080 | 1.00 | 50.53 |
| ATOM | 611 | O   | VAL | 83 | 44.759 | 28.122 | 22.192 | 1.00 | 50.93 |
| ATOM | 612 | N   | LYS | 84 | 43.496 | 27.127 | 23.763 | 1.00 | 51.05 |
| ATOM | 613 | CA  | LYS | 84 | 44.017 | 25.788 | 23.504 | 1.00 | 51.89 |
| ATOM | 614 | CB  | LYS | 84 | 44.338 | 25.061 | 24.826 | 1.00 | 51.79 |
| ATOM | 615 | CG  | LYS | 84 | 44.716 | 23.581 | 24.659 | 1.00 | 51.85 |
| ATOM | 616 | CD  | LYS | 84 | 44.951 | 22.870 | 26.009 | 1.00 | 51.58 |
| ATOM | 617 | CE  | LYS | 84 | 46.429 | 22.848 | 26.422 | 1.00 | 50.92 |
| ATOM | 618 | NZ  | LYS | 84 | 47.041 | 24.198 | 26.592 | 1.00 | 50.33 |
| ATOM | 619 | C   | LYS | 84 | 42.997 | 24.983 | 22.708 | 1.00 | 52.68 |
| ATOM | 620 | O   | LYS | 84 | 42.115 | 24.327 | 23.282 | 1.00 | 53.00 |
| ATOM | 621 | N   | VAL | 85 | 43.124 | 25.038 | 21.383 | 1.00 | 52.91 |
| ATOM | 622 | CA  | VAL | 85 | 42.224 | 24.319 | 20.488 | 1.00 | 52.70 |
| ATOM | 623 | CB  | VAL | 85 | 42.399 | 24.805 | 19.048 | 1.00 | 51.79 |

*FIG. 4K*

| | | | | | | | | |
|---|---|---|---|---|---|---|---|---|
| ATOM | 624 | CG1 | VAL | 85 | 41.302 | 24.232 | 18.176 | 1.00 52.19 |
| ATOM | 625 | CG2 | VAL | 85 | 42.389 | 26.319 | 19.017 | 1.00 51.59 |
| ATOM | 626 | C | VAL | 85 | 42.525 | 22.823 | 20.548 | 1.00 53.51 |
| ATOM | 627 | O | VAL | 85 | 43.637 | 22.389 | 20.243 | 1.00 53.87 |
| ATOM | 628 | N | GLY | 86 | 41.534 | 22.037 | 20.952 | 1.00 54.38 |
| ATOM | 629 | CA | GLY | 86 | 41.726 | 20.603 | 21.053 | 1.00 55.35 |
| ATOM | 630 | C | GLY | 86 | 40.901 | 19.810 | 20.060 | 1.00 56.21 |
| ATOM | 631 | O | GLY | 86 | 40.136 | 20.370 | 19.278 | 1.00 55.63 |
| ATOM | 632 | N | GLU | 87 | 41.050 | 18.493 | 20.106 | 1.00 57.81 |
| ATOM | 633 | CA | GLU | 87 | 40.339 | 17.611 | 19.195 | 1.00 59.64 |
| ATOM | 634 | CB | GLU | 87 | 41.290 | 16.529 | 18.673 | 1.00 60.88 |
| ATOM | 635 | CG | GLU | 87 | 40.680 | 15.648 | 17.611 | 1.00 62.26 |
| ATOM | 636 | CD | GLU | 87 | 40.215 | 16.457 | 16.423 | 1.00 63.21 |
| ATOM | 637 | OE1 | GLU | 87 | 41.072 | 16.931 | 15.644 | 1.00 63.20 |
| ATOM | 638 | OE2 | GLU | 87 | 38.989 | 16.631 | 16.278 | 1.00 64.58 |
| ATOM | 639 | C | GLU | 87 | 39.133 | 16.959 | 19.859 | 1.00 60.12 |
| ATOM | 640 | O | GLU | 87 | 39.271 | 16.187 | 20.810 | 1.00 60.00 |
| ATOM | 641 | N | GLY | 88 | 37.948 | 17.273 | 19.347 | 1.00 60.93 |
| ATOM | 642 | CA | GLY | 88 | 36.735 | 16.707 | 19.902 | 1.00 61.61 |
| ATOM | 643 | C | GLY | 88 | 35.840 | 16.120 | 18.833 | 1.00 62.11 |
| ATOM | 644 | O | GLY | 88 | 36.038 | 16.346 | 17.638 | 1.00 61.67 |
| ATOM | 645 | N | GLU | 89 | 34.845 | 15.363 | 19.274 | 1.00 62.79 |
| ATOM | 646 | CA | GLU | 89 | 33.898 | 14.724 | 18.372 | 1.00 63.90 |
| ATOM | 647 | CB | GLU | 89 | 32.782 | 14.089 | 19.203 | 1.00 63.50 |
| ATOM | 648 | CG | GLU | 89 | 33.304 | 13.137 | 20.275 | 1.00 62.64 |
| ATOM | 649 | CD | GLU | 89 | 32.214 | 12.623 | 21.203 | 1.00 62.46 |
| ATOM | 650 | OE1 | GLU | 89 | 32.510 | 11.728 | 22.019 | 1.00 62.39 |
| ATOM | 651 | OE2 | GLU | 89 | 31.064 | 13.110 | 21.128 | 1.00 62.11 |
| ATOM | 652 | C | GLU | 89 | 33.312 | 15.688 | 17.325 | 1.00 65.16 |
| ATOM | 653 | O | GLU | 89 | 32.975 | 16.837 | 17.634 | 1.00 64.98 |
| ATOM | 654 | N | GLU | 90 | 33.204 | 15.205 | 16.087 | 1.00 66.03 |
| ATOM | 655 | CA | GLU | 90 | 32.667 | 15.977 | 14.958 | 1.00 66.67 |
| ATOM | 656 | CB | GLU | 90 | 31.135 | 15.974 | 14.978 | 1.00 67.21 |
| ATOM | 657 | CG | GLU | 90 | 30.495 | 14.620 | 14.717 | 1.00 66.83 |
| ATOM | 658 | CD | GLU | 90 | 28.986 | 14.662 | 14.869 | 1.00 67.49 |
| ATOM | 659 | OE1 | GLU | 90 | 28.308 | 15.273 | 14.009 | 1.00 67.17 |
| ATOM | 660 | OE2 | GLU | 90 | 28.480 | 14.090 | 15.858 | 1.00 66.84 |
| ATOM | 661 | C | GLU | 90 | 33.149 | 17.421 | 14.871 | 1.00 66.91 |
| ATOM | 662 | O | GLU | 90 | 32.623 | 18.212 | 14.080 | 1.00 66.74 |
| ATOM | 663 | N | GLY | 91 | 34.149 | 17.769 | 15.671 | 1.00 67.05 |
| ATOM | 664 | CA | GLY | 91 | 34.649 | 19.126 | 15.628 | 1.00 67.38 |
| ATOM | 665 | C | GLY | 91 | 36.036 | 19.339 | 16.201 | 1.00 67.42 |
| ATOM | 666 | O | GLY | 91 | 37.025 | 18.797 | 15.708 | 1.00 68.24 |
| ATOM | 667 | N | GLN | 92 | 36.094 | 20.154 | 17.246 | 1.00 66.86 |
| ATOM | 668 | CA | GLN | 92 | 37.335 | 20.492 | 17.929 | 1.00 65.93 |
| ATOM | 669 | CB | GLN | 92 | 38.395 | 20.968 | 16.924 | 1.00 66.17 |
| ATOM | 670 | CG | GLN | 92 | 38.007 | 22.215 | 16.159 | 1.00 66.24 |
| ATOM | 671 | CD | GLN | 92 | 38.564 | 22.236 | 14.750 | 1.00 66.57 |
| ATOM | 672 | OE1 | GLN | 92 | 38.432 | 21.260 | 14.007 | 1.00 66.37 |
| ATOM | 673 | NE2 | GLN | 92 | 39.177 | 23.356 | 14.367 | 1.00 66.54 |
| ATOM | 674 | C | GLN | 92 | 36.999 | 21.605 | 18.920 | 1.00 65.21 |
| ATOM | 675 | O | GLN | 92 | 36.625 | 22.721 | 18.530 | 1.00 65.44 |
| ATOM | 676 | N | TRP | 93 | 37.111 | 21.278 | 20.204 | 1.00 63.62 |
| ATOM | 677 | CA | TRP | 93 | 36.820 | 22.227 | 21.261 | 1.00 61.61 |
| ATOM | 678 | CB | TRP | 93 | 36.859 | 21.540 | 22.626 | 1.00 62.77 |
| ATOM | 679 | CG | TRP | 93 | 38.050 | 20.641 | 22.857 | 1.00 63.86 |
| ATOM | 680 | CD2 | TRP | 93 | 39.213 | 20.943 | 23.637 | 1.00 64.17 |

*FIG. 4L*

| | | | | | | | | |
|---|---|---|---|---|---|---|---|---|
| ATOM | 681 | CE2 | TRP | 93 | 40.026 | 19.787 | 23.645 | 1.00 64.21 |
| ATOM | 682 | CE3 | TRP | 93 | 39.647 | 22.080 | 24.336 | 1.00 64.11 |
| ATOM | 683 | CD1 | TRP | 93 | 38.206 | 19.349 | 22.424 | 1.00 63.84 |
| ATOM | 684 | NE1 | TRP | 93 | 39.387 | 18.830 | 22.897 | 1.00 63.69 |
| ATOM | 685 | CZ2 | TRP | 93 | 41.246 | 19.731 | 24.324 | 1.00 64.43 |
| ATOM | 686 | CZ3 | TRP | 93 | 40.859 | 22.026 | 25.009 | 1.00 64.63 |
| ATOM | 687 | CH2 | TRP | 93 | 41.645 | 20.857 | 24.999 | 1.00 64.71 |
| ATOM | 688 | C | TRP | 93 | 37.784 | 23.393 | 21.248 | 1.00 59.53 |
| ATOM | 689 | O | TRP | 93 | 38.733 | 23.420 | 20.474 | 1.00 59.18 |
| ATOM | 690 | N | SER | 94 | 37.521 | 24.366 | 22.106 | 1.00 57.94 |
| ATOM | 691 | CA | SER | 94 | 38.353 | 25.549 | 22.207 | 1.00 56.46 |
| ATOM | 692 | CB | SER | 94 | 37.880 | 26.615 | 21.219 | 1.00 56.58 |
| ATOM | 693 | OG | SER | 94 | 36.504 | 26.899 | 21.412 | 1.00 56.78 |
| ATOM | 694 | C | SER | 94 | 38.185 | 26.050 | 23.624 | 1.00 55.56 |
| ATOM | 695 | O | SER | 94 | 37.142 | 25.822 | 24.237 | 1.00 55.36 |
| ATOM | 696 | N | VAL | 95 | 39.208 | 26.722 | 24.146 | 1.00 54.53 |
| ATOM | 697 | CA | VAL | 95 | 39.152 | 27.248 | 25.504 | 1.00 53.17 |
| ATOM | 698 | CB | VAL | 95 | 39.511 | 26.183 | 26.549 | 1.00 52.17 |
| ATOM | 699 | CG1 | VAL | 95 | 39.742 | 26.844 | 27.891 | 1.00 52.13 |
| ATOM | 700 | CG2 | VAL | 95 | 38.396 | 25.172 | 26.666 | 1.00 51.73 |
| ATOM | 701 | C | VAL | 95 | 40.099 | 28.399 | 25.719 | 1.00 52.74 |
| ATOM | 702 | O | VAL | 95 | 41.268 | 28.315 | 25.357 | 1.00 53.14 |
| ATOM | 703 | N | LYS | 96 | 39.587 | 29.469 | 26.318 | 1.00 52.63 |
| ATOM | 704 | CA | LYS | 96 | 40.402 | 30.637 | 26.629 | 1.00 52.93 |
| ATOM | 705 | CB | LYS | 96 | 39.513 | 31.849 | 26.932 | 1.00 53.25 |
| ATOM | 706 | CG | LYS | 96 | 40.277 | 33.129 | 27.231 | 1.00 53.79 |
| ATOM | 707 | CD | LYS | 96 | 39.910 | 33.706 | 28.595 | 1.00 54.80 |
| ATOM | 708 | CE | LYS | 96 | 38.427 | 34.102 | 28.682 | 1.00 55.69 |
| ATOM | 709 | NZ | LYS | 96 | 38.027 | 35.162 | 27.696 | 1.00 55.59 |
| ATOM | 710 | C | LYS | 96 | 41.154 | 30.218 | 27.882 | 1.00 52.96 |
| ATOM | 711 | O | LYS | 96 | 40.546 | 29.733 | 28.834 | 1.00 52.93 |
| ATOM | 712 | N | THR | 97 | 42.470 | 30.384 | 27.886 | 1.00 53.38 |
| ATOM | 713 | CA | THR | 97 | 43.253 | 29.980 | 29.050 | 1.00 53.93 |
| ATOM | 714 | CB | THR | 97 | 44.238 | 28.850 | 28.684 | 1.00 53.99 |
| ATOM | 715 | OG1 | THR | 97 | 43.512 | 27.736 | 28.151 | 1.00 52.99 |
| ATOM | 716 | CG2 | THR | 97 | 44.998 | 28.394 | 29.918 | 1.00 55.29 |
| ATOM | 717 | C | THR | 97 | 44.036 | 31.132 | 29.670 | 1.00 53.82 |
| ATOM | 718 | O | THR | 97 | 44.330 | 31.123 | 30.866 | 1.00 53.34 |
| ATOM | 719 | N | LYS | 98 | 44.373 | 32.117 | 28.848 | 1.00 53.85 |
| ATOM | 720 | CA | LYS | 98 | 45.115 | 33.276 | 29.315 | 1.00 54.60 |
| ATOM | 721 | CB | LYS | 98 | 46.627 | 33.096 | 29.087 | 1.00 55.51 |
| ATOM | 722 | CG | LYS | 98 | 47.220 | 31.809 | 29.652 | 1.00 56.78 |
| ATOM | 723 | CD | LYS | 98 | 47.074 | 31.733 | 31.162 | 1.00 58.23 |
| ATOM | 724 | CE | LYS | 98 | 47.553 | 30.389 | 31.713 | 1.00 58.82 |
| ATOM | 725 | NZ | LYS | 98 | 47.404 | 30.320 | 33.201 | 1.00 58.98 |
| ATOM | 726 | C | LYS | 98 | 44.644 | 34.479 | 28.518 | 1.00 54.54 |
| ATOM | 727 | O | LYS | 98 | 44.323 | 34.360 | 27.329 | 1.00 54.79 |
| ATOM | 728 | N | HIS | 99 | 44.590 | 35.632 | 29.173 | 1.00 54.03 |
| ATOM | 729 | CA | HIS | 99 | 44.193 | 36.853 | 28.496 | 1.00 54.03 |
| ATOM | 730 | CB | HIS | 99 | 42.720 | 36.793 | 28.052 | 1.00 55.02 |
| ATOM | 731 | CG | HIS | 99 | 41.732 | 36.872 | 29.172 | 1.00 55.71 |
| ATOM | 732 | CD2 | HIS | 99 | 40.682 | 37.704 | 29.373 | 1.00 55.66 |
| ATOM | 733 | ND1 | HIS | 99 | 41.739 | 35.999 | 30.239 | 1.00 56.19 |
| ATOM | 734 | CE1 | HIS | 99 | 40.736 | 36.288 | 31.049 | 1.00 56.30 |
| ATOM | 735 | NE2 | HIS | 99 | 40.080 | 37.319 | 30.546 | 1.00 56.72 |
| ATOM | 736 | C | HIS | 99 | 44.445 | 38.082 | 29.351 | 1.00 53.46 |
| ATOM | 737 | O | HIS | 99 | 44.526 | 38.007 | 30.577 | 1.00 53.47 |

*FIG. 4M*

| | | | | | | | | |
|---|---|---|---|---|---|---|---|---|
| ATOM | 738 | N | GLN | 100 | 44.583 | 39.214 | 28.683 | 1.00 52.94 |
| ATOM | 739 | CA | GLN | 100 | 44.841 | 40.468 | 29.349 | 1.00 53.34 |
| ATOM | 740 | CB | GLN | 100 | 46.354 | 40.649 | 29.513 | 1.00 53.39 |
| ATOM | 741 | CG | GLN | 100 | 46.790 | 42.001 | 30.055 | 1.00 54.26 |
| ATOM | 742 | CD | GLN | 100 | 46.168 | 42.345 | 31.394 | 1.00 54.43 |
| ATOM | 743 | OE1 | GLN | 100 | 46.349 | 41.629 | 32.384 | 1.00 55.27 |
| ATOM | 744 | NE2 | GLN | 100 | 45.433 | 43.452 | 31.432 | 1.00 53.60 |
| ATOM | 745 | C | GLN | 100 | 44.243 | 41.567 | 28.481 | 1.00 53.43 |
| ATOM | 746 | O | GLN | 100 | 44.416 | 41.569 | 27.260 | 1.00 53.75 |
| ATOM | 747 | N | THR | 101 | 43.527 | 42.493 | 29.105 | 1.00 52.90 |
| ATOM | 748 | CA | THR | 101 | 42.905 | 43.576 | 28.367 | 1.00 53.12 |
| ATOM | 749 | CB | THR | 101 | 41.495 | 43.826 | 28.894 | 1.00 52.52 |
| ATOM | 750 | OG1 | THR | 101 | 40.789 | 42.582 | 28.925 | 1.00 52.85 |
| ATOM | 751 | CG2 | THR | 101 | 40.752 | 44.808 | 27.999 | 1.00 52.23 |
| ATOM | 752 | C | THR | 101 | 43.731 | 44.845 | 28.499 | 1.00 53.61 |
| ATOM | 753 | O | THR | 101 | 44.285 | 45.108 | 29.563 | 1.00 53.95 |
| ATOM | 754 | N | TYR | 102 | 43.809 | 45.628 | 27.422 | 1.00 54.10 |
| ATOM | 755 | CA | TYR | 102 | 44.585 | 46.869 | 27.422 | 1.00 55.36 |
| ATOM | 756 | CB | TYR | 102 | 45.878 | 46.708 | 26.608 | 1.00 54.89 |
| ATOM | 757 | CG | TYR | 102 | 46.788 | 45.569 | 27.015 | 1.00 54.25 |
| ATOM | 758 | CD1 | TYR | 102 | 46.382 | 44.241 | 26.888 | 1.00 54.08 |
| ATOM | 759 | CE1 | TYR | 102 | 47.227 | 43.197 | 27.226 | 1.00 53.44 |
| ATOM | 760 | CD2 | TYR | 102 | 48.069 | 45.822 | 27.497 | 1.00 53.79 |
| ATOM | 761 | CE2 | TYR | 102 | 48.922 | 44.785 | 27.840 | 1.00 53.76 |
| ATOM | 762 | CZ | TYR | 102 | 48.498 | 43.475 | 27.701 | 1.00 53.85 |
| ATOM | 763 | OH | TYR | 102 | 49.355 | 42.442 | 28.021 | 1.00 54.03 |
| ATOM | 764 | C | TYR | 102 | 43.813 | 48.041 | 26.822 | 1.00 56.65 |
| ATOM | 765 | O | TYR | 102 | 43.173 | 47.899 | 25.781 | 1.00 56.91 |
| ATOM | 766 | N | SER | 103 | 43.891 | 49.203 | 27.462 | 1.00 58.50 |
| ATOM | 767 | CA | SER | 103 | 43.217 | 50.385 | 26.938 | 1.00 60.94 |
| ATOM | 768 | CB | SER | 103 | 42.997 | 51.411 | 28.049 | 1.00 61.09 |
| ATOM | 769 | OG | SER | 103 | 44.231 | 51.829 | 28.602 | 1.00 62.50 |
| ATOM | 770 | C | SER | 103 | 44.090 | 50.985 | 25.833 | 1.00 62.31 |
| ATOM | 771 | O | SER | 103 | 45.293 | 50.729 | 25.771 | 1.00 62.27 |
| ATOM | 772 | N | ALA | 104 | 43.487 | 51.783 | 24.960 | 1.00 64.47 |
| ATOM | 773 | CA | ALA | 104 | 44.226 | 52.386 | 23.856 | 1.00 67.01 |
| ATOM | 774 | CB | ALA | 104 | 43.516 | 52.093 | 22.526 | 1.00 67.01 |
| ATOM | 775 | C | ALA | 104 | 44.410 | 53.888 | 24.025 | 1.00 68.66 |
| ATOM | 776 | O | ALA | 104 | 43.458 | 54.658 | 23.902 | 1.00 69.01 |
| ATOM | 777 | N | PRO | 105 | 45.648 | 54.327 | 24.305 | 1.00 70.09 |
| ATOM | 778 | CD | PRO | 105 | 46.878 | 53.522 | 24.397 | 1.00 70.06 |
| ATOM | 779 | CA | PRO | 105 | 45.946 | 55.751 | 24.485 | 1.00 71.25 |
| ATOM | 780 | CB | PRO | 105 | 47.443 | 55.748 | 24.783 | 1.00 70.79 |
| ATOM | 781 | CG | PRO | 105 | 47.929 | 54.535 | 24.046 | 1.00 70.54 |
| ATOM | 782 | C | PRO | 105 | 45.592 | 56.586 | 23.251 | 1.00 72.81 |
| ATOM | 783 | O | PRO | 105 | 45.837 | 56.170 | 22.117 | 1.00 73.09 |
| ATOM | 784 | N | GLU | 106 | 45.012 | 57.762 | 23.479 | 1.00 74.39 |
| ATOM | 785 | CA | GLU | 106 | 44.619 | 58.652 | 22.391 | 1.00 76.25 |
| ATOM | 786 | CB | GLU | 106 | 43.991 | 59.921 | 22.950 | 1.00 76.77 |
| ATOM | 787 | CG | GLU | 106 | 42.702 | 59.673 | 23.680 | 1.00 78.35 |
| ATOM | 788 | CD | GLU | 106 | 42.397 | 60.775 | 24.657 | 1.00 79.28 |
| ATOM | 789 | OE1 | GLU | 106 | 42.239 | 61.934 | 24.214 | 1.00 79.74 |
| ATOM | 790 | OE2 | GLU | 106 | 42.326 | 60.478 | 25.871 | 1.00 80.03 |
| ATOM | 791 | C | GLU | 106 | 45.784 | 59.028 | 21.494 | 1.00 77.33 |
| ATOM | 792 | O | GLU | 106 | 45.600 | 59.262 | 20.300 | 1.00 77.48 |
| ATOM | 793 | N | ASP | 107 | 46.980 | 59.104 | 22.068 | 1.00 78.72 |
| ATOM | 794 | CA | ASP | 107 | 48.161 | 59.440 | 21.284 | 1.00 80.10 |

*FIG. 4N*

| | | | | | | | | |
|---|---|---|---|---|---|---|---|---|
| ATOM | 795 | CB | ASP | 107 | 49.431 | 59.316 | 22.134 | 1.00 80.44 |
| ATOM | 796 | CG | ASP | 107 | 49.965 | 57.889 | 22.185 | 1.00 81.03 |
| ATOM | 797 | OD1 | ASP | 107 | 49.198 | 56.976 | 22.569 | 1.00 81.42 |
| ATOM | 798 | OD2 | ASP | 107 | 51.151 | 57.682 | 21.839 | 1.00 80.86 |
| ATOM | 799 | C | ASP | 107 | 48.212 | 58.424 | 20.151 | 1.00 80.92 |
| ATOM | 800 | O | ASP | 107 | 48.724 | 58.703 | 19.065 | 1.00 81.29 |
| ATOM | 801 | N | ALA | 108 | 47.670 | 57.241 | 20.428 | 1.00 81.68 |
| ATOM | 802 | CA | ALA | 108 | 47.628 | 56.151 | 19.463 | 1.00 82.45 |
| ATOM | 803 | CB | ALA | 108 | 47.605 | 54.813 | 20.200 | 1.00 82.45 |
| ATOM | 804 | C | ALA | 108 | 46.406 | 56.275 | 18.553 | 1.00 82.91 |
| ATOM | 805 | O | ALA | 108 | 46.536 | 56.351 | 17.331 | 1.00 82.98 |
| ATOM | 806 | N | MSE | 109 | 45.221 | 56.303 | 19.157 | 1.00 83.41 |
| ATOM | 807 | CA | MSE | 109 | 43.974 | 56.414 | 18.407 | 1.00 83.78 |
| ATOM | 808 | CB | MSE | 109 | 42.787 | 56.519 | 19.368 | 1.00 85.45 |
| ATOM | 809 | CG | MSE | 109 | 41.581 | 55.678 | 18.972 | 1.00 87.01 |
| ATOM | 810 | SE | MSE | 109 | 41.933 | 53.898 | 19.096 | 1.00 90.12 |
| ATOM | 811 | CE | MSE | 109 | 42.665 | 53.581 | 17.453 | 1.00 88.95 |
| ATOM | 812 | C | MSE | 109 | 43.992 | 57.633 | 17.494 | 1.00 83.17 |
| ATOM | 813 | O | MSE | 109 | 43.235 | 57.710 | 16.527 | 1.00 83.19 |
| ATOM | 814 | N | THR | 110 | 44.854 | 58.590 | 17.820 | 1.00 82.51 |
| ATOM | 815 | CA | THR | 110 | 44.986 | 59.815 | 17.040 | 1.00 82.00 |
| ATOM | 816 | CB | THR | 110 | 45.289 | 61.022 | 17.949 | 1.00 82.44 |
| ATOM | 817 | OG1 | THR | 110 | 44.302 | 61.103 | 18.986 | 1.00 83.00 |
| ATOM | 818 | CG2 | THR | 110 | 45.283 | 62.313 | 17.142 | 1.00 82.69 |
| ATOM | 819 | C | THR | 110 | 46.150 | 59.640 | 16.082 | 1.00 81.25 |
| ATOM | 820 | O | THR | 110 | 46.127 | 60.123 | 14.949 | 1.00 80.95 |
| ATOM | 821 | N | GLY | 111 | 47.168 | 58.933 | 16.559 | 1.00 80.84 |
| ATOM | 822 | CA | GLY | 111 | 48.358 | 58.691 | 15.768 | 1.00 80.12 |
| ATOM | 823 | C | GLY | 111 | 48.121 | 57.986 | 14.450 | 1.00 79.53 |
| ATOM | 824 | O | GLY | 111 | 47.018 | 57.531 | 14.148 | 1.00 79.54 |
| ATOM | 825 | N | THR | 112 | 49.181 | 57.904 | 13.658 | 1.00 78.87 |
| ATOM | 826 | CA | THR | 112 | 49.129 | 57.254 | 12.360 | 1.00 78.09 |
| ATOM | 827 | CB | THR | 112 | 50.427 | 57.553 | 11.561 | 1.00 78.67 |
| ATOM | 828 | OG1 | THR | 112 | 50.329 | 57.001 | 10.240 | 1.00 79.18 |
| ATOM | 829 | CG2 | THR | 112 | 51.644 | 56.956 | 12.279 | 1.00 78.48 |
| ATOM | 830 | C | THR | 112 | 48.992 | 55.748 | 12.579 | 1.00 77.09 |
| ATOM | 831 | O | THR | 112 | 49.231 | 55.254 | 13.685 | 1.00 76.48 |
| ATOM | 832 | N | ALA | 113 | 48.601 | 55.027 | 11.529 | 1.00 76.26 |
| ATOM | 833 | CA | ALA | 113 | 48.443 | 53.573 | 11.603 | 1.00 75.60 |
| ATOM | 834 | CB | ALA | 113 | 48.184 | 53.001 | 10.208 | 1.00 76.00 |
| ATOM | 835 | C | ALA | 113 | 49.711 | 52.965 | 12.191 | 1.00 74.65 |
| ATOM | 836 | O | ALA | 113 | 49.665 | 52.006 | 12.968 | 1.00 74.58 |
| ATOM | 837 | N | GLU | 114 | 50.845 | 53.538 | 11.803 | 1.00 73.24 |
| ATOM | 838 | CA | GLU | 114 | 52.139 | 53.088 | 12.288 | 1.00 71.57 |
| ATOM | 839 | CB | GLU | 114 | 53.246 | 53.971 | 11.700 | 1.00 72.34 |
| ATOM | 840 | CG | GLU | 114 | 53.130 | 54.167 | 10.188 | 1.00 71.64 |
| ATOM | 841 | CD | GLU | 114 | 53.325 | 52.877 | 9.401 | 1.00 72.49 |
| ATOM | 842 | OE1 | GLU | 114 | 53.192 | 51.781 | 9.994 | 1.00 72.24 |
| ATOM | 843 | OE2 | GLU | 114 | 53.600 | 52.960 | 8.183 | 1.00 71.83 |
| ATOM | 844 | C | GLU | 114 | 52.085 | 53.233 | 13.801 | 1.00 70.37 |
| ATOM | 845 | O | GLU | 114 | 52.297 | 52.266 | 14.537 | 1.00 69.92 |
| ATOM | 846 | N | MET | 115 | 51.778 | 54.450 | 14.246 | 1.00 68.75 |
| ATOM | 847 | CA | MET | 115 | 51.657 | 54.760 | 15.669 | 1.00 66.97 |
| ATOM | 848 | CB | MET | 115 | 51.013 | 56.140 | 15.866 | 1.00 67.15 |
| ATOM | 849 | CG | MET | 115 | 51.999 | 57.277 | 16.040 | 1.00 66.94 |
| ATOM | 850 | SD | MET | 115 | 53.203 | 56.869 | 17.320 | 1.00 67.61 |
| ATOM | 851 | CE | MET | 115 | 52.137 | 56.732 | 18.788 | 1.00 66.65 |

*FIG. 40*

| | | | | | | | | | |
|---|---|---|---|---|---|---|---|---|---|
| ATOM | 852 | C | MET | 115 | 50.799 | 53.718 | 16.374 | 1.00 | 65.81 |
| ATOM | 853 | O | MET | 115 | 51.266 | 53.010 | 17.275 | 1.00 | 65.94 |
| ATOM | 854 | N | LEU | 116 | 49.542 | 53.635 | 15.940 | 1.00 | 63.70 |
| ATOM | 855 | CA | LEU | 116 | 48.561 | 52.711 | 16.504 | 1.00 | 61.63 |
| ATOM | 856 | CB | LEU | 116 | 47.287 | 52.720 | 15.650 | 1.00 | 60.89 |
| ATOM | 857 | CG | LEU | 116 | 45.948 | 52.226 | 16.205 | 1.00 | 59.42 |
| ATOM | 858 | CD1 | LEU | 116 | 44.953 | 52.182 | 15.051 | 1.00 | 58.84 |
| ATOM | 859 | CD2 | LEU | 116 | 46.081 | 50.858 | 16.847 | 1.00 | 58.86 |
| ATOM | 860 | C | LEU | 116 | 49.083 | 51.285 | 16.613 | 1.00 | 60.35 |
| ATOM | 861 | O | LEU | 116 | 48.977 | 50.665 | 17.667 | 1.00 | 60.48 |
| ATOM | 862 | N | PHE | 117 | 49.641 | 50.756 | 15.531 | 1.00 | 59.14 |
| ATOM | 863 | CA | PHE | 117 | 50.138 | 49.391 | 15.580 | 1.00 | 58.14 |
| ATOM | 864 | CB | PHE | 117 | 50.298 | 48.819 | 14.173 | 1.00 | 57.03 |
| ATOM | 865 | CG | PHE | 117 | 49.055 | 48.144 | 13.669 | 1.00 | 56.22 |
| ATOM | 866 | CD1 | PHE | 117 | 48.005 | 48.889 | 13.143 | 1.00 | 55.49 |
| ATOM | 867 | CD2 | PHE | 117 | 48.909 | 46.763 | 13.783 | 1.00 | 55.59 |
| ATOM | 868 | CE1 | PHE | 117 | 46.830 | 48.270 | 12.741 | 1.00 | 55.25 |
| ATOM | 869 | CE2 | PHE | 117 | 47.736 | 46.134 | 13.384 | 1.00 | 55.20 |
| ATOM | 870 | CZ | PHE | 117 | 46.695 | 46.887 | 12.862 | 1.00 | 55.23 |
| ATOM | 871 | C | PHE | 117 | 51.415 | 49.204 | 16.382 | 1.00 | 57.89 |
| ATOM | 872 | O | PHE | 117 | 51.799 | 48.073 | 16.690 | 1.00 | 57.80 |
| ATOM | 873 | N | ALA | 118 | 52.078 | 50.303 | 16.725 | 1.00 | 57.35 |
| ATOM | 874 | CA | ALA | 118 | 53.275 | 50.193 | 17.537 | 1.00 | 56.79 |
| ATOM | 875 | CB | ALA | 118 | 54.004 | 51.533 | 17.594 | 1.00 | 56.42 |
| ATOM | 876 | C | ALA | 118 | 52.747 | 49.792 | 18.922 | 1.00 | 56.46 |
| ATOM | 877 | O | ALA | 118 | 53.220 | 48.829 | 19.536 | 1.00 | 56.68 |
| ATOM | 878 | N | ALA | 119 | 51.733 | 50.515 | 19.391 | 1.00 | 55.57 |
| ATOM | 879 | CA | ALA | 119 | 51.142 | 50.226 | 20.693 | 1.00 | 55.05 |
| ATOM | 880 | CB | ALA | 119 | 49.931 | 51.135 | 20.952 | 1.00 | 53.91 |
| ATOM | 881 | C | ALA | 119 | 50.719 | 48.769 | 20.763 | 1.00 | 54.96 |
| ATOM | 882 | O | ALA | 119 | 51.090 | 48.052 | 21.698 | 1.00 | 54.94 |
| ATOM | 883 | N | ILE | 120 | 49.948 | 48.338 | 19.763 | 1.00 | 55.10 |
| ATOM | 884 | CA | ILE | 120 | 49.443 | 46.969 | 19.715 | 1.00 | 55.51 |
| ATOM | 885 | CB | ILE | 120 | 48.679 | 46.679 | 18.397 | 1.00 | 54.45 |
| ATOM | 886 | CG2 | ILE | 120 | 47.922 | 45.363 | 18.525 | 1.00 | 53.30 |
| ATOM | 887 | CG1 | ILE | 120 | 47.688 | 47.808 | 18.089 | 1.00 | 53.32 |
| ATOM | 888 | CD1 | ILE | 120 | 46.871 | 47.581 | 16.820 | 1.00 | 51.70 |
| ATOM | 889 | C | ILE | 120 | 50.575 | 45.957 | 19.846 | 1.00 | 56.57 |
| ATOM | 890 | O | ILE | 120 | 50.477 | 45.006 | 20.632 | 1.00 | 56.52 |
| ATOM | 891 | N | SER | 121 | 51.645 | 46.169 | 19.076 | 1.00 | 57.78 |
| ATOM | 892 | CA | SER | 121 | 52.814 | 45.284 | 19.093 | 1.00 | 58.54 |
| ATOM | 893 | CB | SER | 121 | 53.844 | 45.730 | 18.045 | 1.00 | 58.96 |
| ATOM | 894 | OG | SER | 121 | 53.377 | 45.507 | 16.720 | 1.00 | 59.32 |
| ATOM | 895 | C | SER | 121 | 53.457 | 45.280 | 20.473 | 1.00 | 58.74 |
| ATOM | 896 | O | SER | 121 | 54.007 | 44.265 | 20.918 | 1.00 | 57.56 |
| ATOM | 897 | N | GLU | 122 | 53.379 | 46.422 | 21.151 | 1.00 | 59.50 |
| ATOM | 898 | CA | GLU | 122 | 53.947 | 46.529 | 22.484 | 1.00 | 60.44 |
| ATOM | 899 | CB | GLU | 122 | 54.003 | 47.986 | 22.941 | 1.00 | 60.60 |
| ATOM | 900 | CG | GLU | 122 | 55.104 | 48.241 | 23.952 | 1.00 | 60.45 |
| ATOM | 901 | CD | GLU | 122 | 54.706 | 49.252 | 25.003 | 1.00 | 61.76 |
| ATOM | 902 | OE1 | GLU | 122 | 54.152 | 50.312 | 24.630 | 1.00 | 61.92 |
| ATOM | 903 | OE2 | GLU | 122 | 54.950 | 48.986 | 26.202 | 1.00 | 62.20 |
| ATOM | 904 | C | GLU | 122 | 53.091 | 45.725 | 23.452 | 1.00 | 60.63 |
| ATOM | 905 | O | GLU | 122 | 53.565 | 44.761 | 24.048 | 1.00 | 60.82 |
| ATOM | 906 | N | CYS | 123 | 51.831 | 46.120 | 23.605 | 1.00 | 60.96 |
| ATOM | 907 | CA | CYS | 123 | 50.936 | 45.410 | 24.510 | 1.00 | 61.79 |
| ATOM | 908 | CB | CYS | 123 | 49.481 | 45.840 | 24.278 | 1.00 | 61.63 |

*FIG. 4P*

| ATOM | 909 | SG | CYS | 123 | 49.191 | 47.636 | 24.439 | 1.00 | 62.83 |
|------|-----|-----|-----|-----|--------|--------|--------|------|-------|
| ATOM | 910 | C | CYS | 123 | 51.107 | 43.922 | 24.233 | 1.00 | 61.90 |
| ATOM | 911 | O | CYS | 123 | 51.028 | 43.095 | 25.147 | 1.00 | 61.89 |
| ATOM | 912 | N | ILE | 124 | 51.350 | 43.588 | 22.966 | 1.00 | 62.36 |
| ATOM | 913 | CA | ILE | 124 | 51.561 | 42.197 | 22.588 | 1.00 | 62.79 |
| ATOM | 914 | CB | ILE | 124 | 52.033 | 42.061 | 21.109 | 1.00 | 62.52 |
| ATOM | 915 | CG2 | ILE | 124 | 52.618 | 40.676 | 20.877 | 1.00 | 61.07 |
| ATOM | 916 | CG1 | ILE | 124 | 50.866 | 42.280 | 20.138 | 1.00 | 61.53 |
| ATOM | 917 | CD1 | ILE | 124 | 50.016 | 41.038 | 19.888 | 1.00 | 61.77 |
| ATOM | 918 | C | ILE | 124 | 52.673 | 41.706 | 23.499 | 1.00 | 62.76 |
| ATOM | 919 | O | ILE | 124 | 52.475 | 40.807 | 24.320 | 1.00 | 62.23 |
| ATOM | 920 | N | SER | 125 | 53.839 | 42.327 | 23.347 | 1.00 | 63.43 |
| ATOM | 921 | CA | SER | 125 | 55.020 | 42.002 | 24.138 | 1.00 | 64.63 |
| ATOM | 922 | CB | SER | 125 | 56.062 | 43.117 | 23.986 | 1.00 | 65.05 |
| ATOM | 923 | OG | SER | 125 | 57.324 | 42.745 | 24.523 | 1.00 | 67.01 |
| ATOM | 924 | C | SER | 125 | 54.646 | 41.840 | 25.610 | 1.00 | 64.32 |
| ATOM | 925 | O | SER | 125 | 54.886 | 40.794 | 26.219 | 1.00 | 64.46 |
| ATOM | 926 | N | ASP | 126 | 54.047 | 42.884 | 26.169 | 1.00 | 64.43 |
| ATOM | 927 | CA | ASP | 126 | 53.626 | 42.894 | 27.562 | 1.00 | 64.86 |
| ATOM | 928 | CB | ASP | 126 | 52.660 | 44.060 | 27.788 | 1.00 | 64.95 |
| ATOM | 929 | CG | ASP | 126 | 52.390 | 44.323 | 29.253 | 1.00 | 65.38 |
| ATOM | 930 | OD1 | ASP | 126 | 51.952 | 43.389 | 29.955 | 1.00 | 65.74 |
| ATOM | 931 | OD2 | ASP | 126 | 52.613 | 45.467 | 29.706 | 1.00 | 65.92 |
| ATOM | 932 | C | ASP | 126 | 52.968 | 41.572 | 27.980 | 1.00 | 64.65 |
| ATOM | 933 | O | ASP | 126 | 53.424 | 40.918 | 28.924 | 1.00 | 64.28 |
| ATOM | 934 | N | PHE | 127 | 51.902 | 41.189 | 27.274 | 1.00 | 64.96 |
| ATOM | 935 | CA | PHE | 127 | 51.177 | 39.948 | 27.565 | 1.00 | 65.21 |
| ATOM | 936 | CB | PHE | 127 | 50.145 | 39.657 | 26.468 | 1.00 | 64.22 |
| ATOM | 937 | CG | PHE | 127 | 49.569 | 38.258 | 26.525 | 1.00 | 63.67 |
| ATOM | 938 | CD1 | PHE | 127 | 48.774 | 37.857 | 27.594 | 1.00 | 63.64 |
| ATOM | 939 | CD2 | PHE | 127 | 49.830 | 37.343 | 25.512 | 1.00 | 63.42 |
| ATOM | 940 | CE1 | PHE | 127 | 48.247 | 36.564 | 27.652 | 1.00 | 63.40 |
| ATOM | 941 | CE2 | PHE | 127 | 49.308 | 36.051 | 25.560 | 1.00 | 63.55 |
| ATOM | 942 | CZ | PHE | 127 | 48.516 | 35.661 | 26.632 | 1.00 | 63.49 |
| ATOM | 943 | C | PHE | 127 | 52.154 | 38.791 | 27.631 | 1.00 | 65.83 |
| ATOM | 944 | O | PHE | 127 | 52.195 | 38.030 | 28.600 | 1.00 | 65.71 |
| ATOM | 945 | N | LEU | 128 | 52.931 | 38.684 | 26.562 | 1.00 | 66.57 |
| ATOM | 946 | CA | LEU | 128 | 53.942 | 37.656 | 26.387 | 1.00 | 67.52 |
| ATOM | 947 | CB | LEU | 128 | 54.773 | 38.022 | 25.166 | 1.00 | 67.64 |
| ATOM | 948 | CG | LEU | 128 | 53.926 | 38.452 | 23.969 | 1.00 | 67.42 |
| ATOM | 949 | CD1 | LEU | 128 | 54.819 | 39.108 | 22.941 | 1.00 | 67.90 |
| ATOM | 950 | CD2 | LEU | 128 | 53.195 | 37.251 | 23.387 | 1.00 | 67.65 |
| ATOM | 951 | C | LEU | 128 | 54.850 | 37.502 | 27.609 | 1.00 | 68.09 |
| ATOM | 952 | O | LEU | 128 | 54.829 | 36.468 | 28.285 | 1.00 | 67.92 |
| ATOM | 953 | N | ASP | 129 | 55.654 | 38.530 | 27.878 | 1.00 | 68.62 |
| ATOM | 954 | CA | ASP | 129 | 56.565 | 38.514 | 29.018 | 1.00 | 69.22 |
| ATOM | 955 | CB | ASP | 129 | 57.135 | 39.907 | 29.287 | 1.00 | 68.93 |
| ATOM | 956 | CG | ASP | 129 | 58.115 | 40.342 | 28.239 | 1.00 | 68.90 |
| ATOM | 957 | OD1 | ASP | 129 | 59.100 | 39.606 | 28.011 | 1.00 | 69.12 |
| ATOM | 958 | OD2 | ASP | 129 | 57.900 | 41.423 | 27.650 | 1.00 | 69.22 |
| ATOM | 959 | C | ASP | 129 | 55.843 | 38.059 | 30.267 | 1.00 | 69.59 |
| ATOM | 960 | O | ASP | 129 | 56.063 | 36.956 | 30.761 | 1.00 | 69.41 |
| ATOM | 961 | N | LYS | 130 | 54.973 | 38.940 | 30.753 | 1.00 | 70.10 |
| ATOM | 962 | CA | LYS | 130 | 54.190 | 38.733 | 31.958 | 1.00 | 70.67 |
| ATOM | 963 | CB | LYS | 130 | 53.285 | 39.946 | 32.159 | 1.00 | 70.80 |
| ATOM | 964 | CG | LYS | 130 | 54.076 | 41.252 | 32.052 | 1.00 | 70.54 |
| ATOM | 965 | CD | LYS | 130 | 53.218 | 42.479 | 32.266 | 1.00 | 70.22 |

FIG. 4Q

```
ATOM    966  CE   LYS 130      54.021  43.746  32.011  1.00 70.07
ATOM    967  NZ   LYS 130      53.204  44.977  32.195  1.00 69.69
ATOM    968  C    LYS 130      53.394  37.441  31.982  1.00 71.17
ATOM    969  O    LYS 130      52.381  37.331  32.673  1.00 70.99
ATOM    970  N    HIS 131      53.883  36.468  31.221  1.00 72.01
ATOM    971  CA   HIS 131      53.301  35.139  31.125  1.00 73.44
ATOM    972  CB   HIS 131      52.313  35.065  29.965  1.00 73.00
ATOM    973  CG   HIS 131      50.881  35.076  30.397  1.00 72.93
ATOM    974  CD2  HIS 131      49.960  34.085  30.454  1.00 72.73
ATOM    975  ND1  HIS 131      50.256  36.210  30.869  1.00 72.87
ATOM    976  CE1  HIS 131      49.010  35.917  31.196  1.00 73.01
ATOM    977  NE2  HIS 131      48.806  34.634  30.954  1.00 73.04
ATOM    978  C    HIS 131      54.424  34.124  30.908  1.00 74.61
ATOM    979  O    HIS 131      54.419  33.049  31.514  1.00 74.70
ATOM    980  N    GLN 132      55.374  34.502  30.046  1.00 76.14
ATOM    981  CA   GLN 132      56.566  33.727  29.658  1.00 77.30
ATOM    982  CB   GLN 132      56.536  32.293  30.218  1.00 77.68
ATOM    983  CG   GLN 132      55.424  31.387  29.676  1.00 78.41
ATOM    984  CD   GLN 132      55.823  30.611  28.436  1.00 78.88
ATOM    985  OE1  GLN 132      56.016  31.179  27.356  1.00 78.50
ATOM    986  NE2  GLN 132      55.951  29.294  28.587  1.00 79.41
ATOM    987  C    GLN 132      56.673  33.682  28.134  1.00 77.86
ATOM    988  O    GLN 132      57.769  33.638  27.574  1.00 77.91
ATOM    989  N    MSE 133      55.520  33.703  27.472  1.00 78.39
ATOM    990  CA   MSE 133      55.450  33.662  26.017  1.00 78.88
ATOM    991  CB   MSE 133      53.989  33.684  25.551  1.00 80.96
ATOM    992  CG   MSE 133      53.278  32.347  25.586  1.00 83.34
ATOM    993  SE   MSE 133      51.991  32.273  26.846  1.00 87.09
ATOM    994  CE   MSE 133      52.168  30.521  27.421  1.00 84.33
ATOM    995  C    MSE 133      56.174  34.812  25.333  1.00 77.90
ATOM    996  O    MSE 133      55.552  35.548  24.567  1.00 78.34
ATOM    997  N    LYS 134      57.470  34.973  25.587  1.00 75.97
ATOM    998  CA   LYS 134      58.225  36.053  24.949  1.00 73.96
ATOM    999  CB   LYS 134      58.976  36.879  25.997  1.00 73.14
ATOM   1000  CG   LYS 134      59.676  38.125  25.454  1.00 72.28
ATOM   1001  CD   LYS 134      58.697  39.250  25.141  1.00 70.99
ATOM   1002  CE   LYS 134      59.415  40.586  24.935  1.00 70.06
ATOM   1003  NZ   LYS 134      60.234  40.640  23.687  1.00 69.46
ATOM   1004  C    LYS 134      59.211  35.443  23.964  1.00 72.94
ATOM   1005  O    LYS 134      59.727  36.123  23.077  1.00 72.63
ATOM   1006  N    HIS 135      59.457  34.148  24.132  1.00 72.28
ATOM   1007  CA   HIS 135      60.377  33.411  23.275  1.00 71.52
ATOM   1008  CB   HIS 135      61.359  32.584  24.119  1.00 71.15
ATOM   1009  CG   HIS 135      60.719  31.448  24.859  1.00 70.88
ATOM   1010  CD2  HIS 135      60.908  30.109  24.773  1.00 70.87
ATOM   1011  ND1  HIS 135      59.750  31.635  25.822  1.00 70.81
ATOM   1012  CE1  HIS 135      59.370  30.462  26.298  1.00 70.56
ATOM   1013  NE2  HIS 135      60.057  29.519  25.678  1.00 70.85
ATOM   1014  C    HIS 135      59.584  32.482  22.365  1.00 71.26
ATOM   1015  O    HIS 135      60.152  31.818  21.499  1.00 71.53
ATOM   1016  N    LYS 136      58.272  32.434  22.574  1.00 70.85
ATOM   1017  CA   LYS 136      57.393  31.590  21.766  1.00 70.33
ATOM   1018  CB   LYS 136      56.077  31.329  22.508  1.00 69.64
ATOM   1019  CG   LYS 136      56.225  30.694  23.886  1.00 68.45
ATOM   1020  CD   LYS 136      56.740  29.271  23.783  1.00 68.01
ATOM   1021  CE   LYS 136      56.698  28.560  25.128  1.00 67.56
ATOM   1022  NZ   LYS 136      55.303  28.356  25.623  1.00 66.87
```

*FIG. 4R*

| ATOM | 1023 | C | LYS | 136 | 57.088 | 32.296 | 20.443 | 1.00 | 70.46 |
|---|---|---|---|---|---|---|---|---|---|
| ATOM | 1024 | O | LYS | 136 | 57.100 | 33.530 | 20.371 | 1.00 | 70.94 |
| ATOM | 1025 | N | LYS | 137 | 56.828 | 31.519 | 19.396 | 1.00 | 70.16 |
| ATOM | 1026 | CA | LYS | 137 | 56.505 | 32.096 | 18.096 | 1.00 | 69.80 |
| ATOM | 1027 | CB | LYS | 137 | 57.505 | 31.642 | 17.023 | 1.00 | 71.09 |
| ATOM | 1028 | CG | LYS | 137 | 57.602 | 30.132 | 16.801 | 1.00 | 71.73 |
| ATOM | 1029 | CD | LYS | 137 | 58.567 | 29.840 | 15.654 | 1.00 | 72.44 |
| ATOM | 1030 | CE | LYS | 137 | 58.915 | 28.363 | 15.545 | 1.00 | 72.39 |
| ATOM | 1031 | NZ | LYS | 137 | 59.919 | 28.136 | 14.463 | 1.00 | 72.59 |
| ATOM | 1032 | C | LYS | 137 | 55.097 | 31.685 | 17.702 | 1.00 | 68.73 |
| ATOM | 1033 | O | LYS | 137 | 54.799 | 31.476 | 16.524 | 1.00 | 69.92 |
| ATOM | 1034 | N | LEU | 138 | 54.243 | 31.579 | 18.716 | 1.00 | 66.57 |
| ATOM | 1035 | CA | LEU | 138 | 52.841 | 31.193 | 18.586 | 1.00 | 63.82 |
| ATOM | 1036 | CB | LEU | 138 | 52.057 | 31.788 | 19.748 | 1.00 | 63.11 |
| ATOM | 1037 | CG | LEU | 138 | 52.364 | 31.145 | 21.092 | 1.00 | 62.89 |
| ATOM | 1038 | CD1 | LEU | 138 | 51.924 | 32.068 | 22.220 | 1.00 | 62.68 |
| ATOM | 1039 | CD2 | LEU | 138 | 51.669 | 29.786 | 21.150 | 1.00 | 61.80 |
| ATOM | 1040 | C | LEU | 138 | 52.114 | 31.553 | 17.294 | 1.00 | 62.26 |
| ATOM | 1041 | O | LEU | 138 | 52.416 | 32.566 | 16.647 | 1.00 | 62.54 |
| ATOM | 1042 | N | PRO | 139 | 51.149 | 30.708 | 16.894 | 1.00 | 60.11 |
| ATOM | 1043 | CD | PRO | 139 | 50.841 | 29.394 | 17.489 | 1.00 | 59.82 |
| ATOM | 1044 | CA | PRO | 139 | 50.356 | 30.937 | 15.682 | 1.00 | 57.91 |
| ATOM | 1045 | CB | PRO | 139 | 49.761 | 29.564 | 15.398 | 1.00 | 58.05 |
| ATOM | 1046 | CG | PRO | 139 | 49.573 | 28.999 | 16.772 | 1.00 | 59.12 |
| ATOM | 1047 | C | PRO | 139 | 49.302 | 31.968 | 16.101 | 1.00 | 55.89 |
| ATOM | 1048 | O | PRO | 139 | 48.469 | 31.693 | 16.973 | 1.00 | 55.71 |
| ATOM | 1049 | N | LEU | 140 | 49.358 | 33.154 | 15.501 | 1.00 | 53.40 |
| ATOM | 1050 | CA | LEU | 140 | 48.440 | 34.237 | 15.850 | 1.00 | 50.78 |
| ATOM | 1051 | CB | LEU | 140 | 49.195 | 35.576 | 15.834 | 1.00 | 49.87 |
| ATOM | 1052 | CG | LEU | 140 | 48.452 | 36.893 | 16.091 | 1.00 | 49.01 |
| ATOM | 1053 | CD1 | LEU | 140 | 49.414 | 37.933 | 16.646 | 1.00 | 48.17 |
| ATOM | 1054 | CD2 | LEU | 140 | 47.825 | 37.389 | 14.801 | 1.00 | 48.88 |
| ATOM | 1055 | C | LEU | 140 | 47.169 | 34.359 | 15.018 | 1.00 | 49.13 |
| ATOM | 1056 | O | LEU | 140 | 47.211 | 34.368 | 13.785 | 1.00 | 49.12 |
| ATOM | 1057 | N | GLY | 141 | 46.040 | 34.441 | 15.722 | 1.00 | 46.93 |
| ATOM | 1058 | CA | GLY | 141 | 44.743 | 34.613 | 15.086 | 1.00 | 43.70 |
| ATOM | 1059 | C | GLY | 141 | 44.324 | 36.041 | 15.402 | 1.00 | 41.11 |
| ATOM | 1060 | O | GLY | 141 | 44.277 | 36.414 | 16.569 | 1.00 | 41.46 |
| ATOM | 1061 | N | PHE | 142 | 44.018 | 36.842 | 14.388 | 1.00 | 38.27 |
| ATOM | 1062 | CA | PHE | 142 | 43.659 | 38.232 | 14.629 | 1.00 | 36.42 |
| ATOM | 1063 | CB | PHE | 142 | 44.648 | 39.118 | 13.882 | 1.00 | 34.58 |
| ATOM | 1064 | CG | PHE | 142 | 44.403 | 40.593 | 14.037 | 1.00 | 33.28 |
| ATOM | 1065 | CD1 | PHE | 142 | 43.941 | 41.124 | 15.229 | 1.00 | 32.86 |
| ATOM | 1066 | CD2 | PHE | 142 | 44.702 | 41.465 | 12.992 | 1.00 | 32.75 |
| ATOM | 1067 | CE1 | PHE | 142 | 43.784 | 42.505 | 15.375 | 1.00 | 32.95 |
| ATOM | 1068 | CE2 | PHE | 142 | 44.551 | 42.845 | 13.125 | 1.00 | 31.57 |
| ATOM | 1069 | CZ | PHE | 142 | 44.094 | 43.365 | 14.313 | 1.00 | 32.24 |
| ATOM | 1070 | C | PHE | 142 | 42.224 | 38.652 | 14.300 | 1.00 | 36.83 |
| ATOM | 1071 | O | PHE | 142 | 41.843 | 38.801 | 13.124 | 1.00 | 36.76 |
| ATOM | 1072 | N | THR | 143 | 41.423 | 38.848 | 15.347 | 1.00 | 35.96 |
| ATOM | 1073 | CA | THR | 143 | 40.047 | 39.288 | 15.156 | 1.00 | 34.35 |
| ATOM | 1074 | CB | THR | 143 | 39.179 | 38.997 | 16.373 | 1.00 | 33.98 |
| ATOM | 1075 | OG1 | THR | 143 | 38.947 | 37.586 | 16.472 | 1.00 | 33.45 |
| ATOM | 1076 | CG2 | THR | 143 | 37.854 | 39.750 | 16.255 | 1.00 | 33.35 |
| ATOM | 1077 | C | THR | 143 | 40.081 | 40.793 | 14.964 | 1.00 | 33.92 |
| ATOM | 1078 | O | THR | 143 | 40.190 | 41.544 | 15.928 | 1.00 | 34.30 |
| ATOM | 1079 | N | PHE | 144 | 40.009 | 41.227 | 13.716 | 1.00 | 33.00 |

*FIG. 4S*

| ATOM | 1080 | CA  | PHE | 144 | 40.029 | 42.649 | 13.383 | 1.00 | 31.69 |
| ATOM | 1081 | CB  | PHE | 144 | 40.891 | 42.842 | 12.132 | 1.00 | 29.18 |
| ATOM | 1082 | CG  | PHE | 144 | 41.189 | 44.264 | 11.807 | 1.00 | 26.95 |
| ATOM | 1083 | CD1 | PHE | 144 | 41.727 | 45.108 | 12.763 | 1.00 | 26.21 |
| ATOM | 1084 | CD2 | PHE | 144 | 40.956 | 44.755 | 10.533 | 1.00 | 25.39 |
| ATOM | 1085 | CE1 | PHE | 144 | 42.026 | 46.428 | 12.450 | 1.00 | 26.79 |
| ATOM | 1086 | CE2 | PHE | 144 | 41.250 | 46.070 | 10.212 | 1.00 | 25.46 |
| ATOM | 1087 | CZ  | PHE | 144 | 41.785 | 46.910 | 11.167 | 1.00 | 25.80 |
| ATOM | 1088 | C   | PHE | 144 | 38.562 | 42.981 | 13.112 | 1.00 | 32.02 |
| ATOM | 1089 | O   | PHE | 144 | 37.929 | 42.280 | 12.333 | 1.00 | 33.96 |
| ATOM | 1090 | N   | SER | 145 | 38.025 | 44.027 | 13.744 | 1.00 | 32.29 |
| ATOM | 1091 | CA  | SER | 145 | 36.602 | 44.387 | 13.600 | 1.00 | 31.56 |
| ATOM | 1092 | CB  | SER | 145 | 35.993 | 44.689 | 14.968 | 1.00 | 31.79 |
| ATOM | 1093 | OG  | SER | 145 | 35.997 | 43.539 | 15.790 | 1.00 | 33.15 |
| ATOM | 1094 | C   | SER | 145 | 36.271 | 45.546 | 12.679 | 1.00 | 30.95 |
| ATOM | 1095 | O   | SER | 145 | 35.601 | 46.508 | 13.082 | 1.00 | 30.63 |
| ATOM | 1096 | N   | PHE | 146 | 36.723 | 45.456 | 11.439 | 1.00 | 30.27 |
| ATOM | 1097 | CA  | PHE | 146 | 36.452 | 46.513 | 10.489 | 1.00 | 29.49 |
| ATOM | 1098 | CB  | PHE | 146 | 37.573 | 47.541 | 10.535 | 1.00 | 29.01 |
| ATOM | 1099 | CG  | PHE | 146 | 37.848 | 48.054 | 11.908 | 1.00 | 27.96 |
| ATOM | 1100 | CD1 | PHE | 146 | 38.654 | 47.336 | 12.775 | 1.00 | 28.87 |
| ATOM | 1101 | CD2 | PHE | 146 | 37.245 | 49.221 | 12.359 | 1.00 | 27.88 |
| ATOM | 1102 | CE1 | PHE | 146 | 38.852 | 47.777 | 14.078 | 1.00 | 29.72 |
| ATOM | 1103 | CE2 | PHE | 146 | 37.434 | 49.670 | 13.659 | 1.00 | 26.92 |
| ATOM | 1104 | CZ  | PHE | 146 | 38.232 | 48.955 | 14.520 | 1.00 | 28.49 |
| ATOM | 1105 | C   | PHE | 146 | 36.318 | 45.937 | 9.093  | 1.00 | 29.49 |
| ATOM | 1106 | O   | PHE | 146 | 36.668 | 44.778 | 8.846  | 1.00 | 29.56 |
| ATOM | 1107 | N   | PRO | 147 | 35.805 | 46.738 | 8.152  | 1.00 | 29.02 |
| ATOM | 1108 | CD  | PRO | 147 | 35.452 | 48.167 | 8.211  | 1.00 | 28.09 |
| ATOM | 1109 | CA  | PRO | 147 | 35.662 | 46.212 | 6.798  | 1.00 | 30.12 |
| ATOM | 1110 | CB  | PRO | 147 | 34.852 | 47.309 | 6.099  | 1.00 | 28.65 |
| ATOM | 1111 | CG  | PRO | 147 | 35.377 | 48.540 | 6.749  | 1.00 | 28.13 |
| ATOM | 1112 | C   | PRO | 147 | 37.047 | 45.969 | 6.179  | 1.00 | 30.89 |
| ATOM | 1113 | O   | PRO | 147 | 37.938 | 46.821 | 6.263  | 1.00 | 32.17 |
| ATOM | 1114 | N   | VAL | 148 | 37.221 | 44.807 | 5.557  | 1.00 | 31.62 |
| ATOM | 1115 | CA  | VAL | 148 | 38.499 | 44.453 | 4.957  | 1.00 | 32.00 |
| ATOM | 1116 | CB  | VAL | 148 | 39.399 | 43.733 | 6.002  | 1.00 | 32.44 |
| ATOM | 1117 | CG1 | VAL | 148 | 40.471 | 42.940 | 5.311  | 1.00 | 33.36 |
| ATOM | 1118 | CG2 | VAL | 148 | 40.035 | 44.758 | 6.934  | 1.00 | 32.04 |
| ATOM | 1119 | C   | VAL | 148 | 38.351 | 43.557 | 3.733  | 1.00 | 31.54 |
| ATOM | 1120 | O   | VAL | 148 | 37.937 | 42.402 | 3.858  | 1.00 | 30.91 |
| ATOM | 1121 | N   | ALA | 149 | 38.688 | 44.091 | 2.560  | 1.00 | 31.66 |
| ATOM | 1122 | CA  | ALA | 149 | 38.610 | 43.316 | 1.324  | 1.00 | 32.33 |
| ATOM | 1123 | CB  | ALA | 149 | 38.834 | 44.213 | 0.120  | 1.00 | 31.16 |
| ATOM | 1124 | C   | ALA | 149 | 39.723 | 42.288 | 1.428  | 1.00 | 33.43 |
| ATOM | 1125 | O   | ALA | 149 | 40.882 | 42.653 | 1.431  | 1.00 | 35.59 |
| ATOM | 1126 | N   | HIS | 150 | 39.387 | 41.008 | 1.535  | 1.00 | 33.73 |
| ATOM | 1127 | CA  | HIS | 150 | 40.410 | 39.980 | 1.666  | 1.00 | 33.88 |
| ATOM | 1128 | CB  | HIS | 150 | 39.868 | 38.780 | 2.450  | 1.00 | 34.82 |
| ATOM | 1129 | CG  | HIS | 150 | 39.879 | 38.961 | 3.933  | 1.00 | 35.58 |
| ATOM | 1130 | CD2 | HIS | 150 | 40.344 | 38.162 | 4.921  | 1.00 | 36.49 |
| ATOM | 1131 | ND1 | HIS | 150 | 39.329 | 40.061 | 4.555  | 1.00 | 36.45 |
| ATOM | 1132 | CE1 | HIS | 150 | 39.454 | 39.930 | 5.865  | 1.00 | 36.79 |
| ATOM | 1133 | NE2 | HIS | 150 | 40.067 | 38.786 | 6.114  | 1.00 | 36.38 |
| ATOM | 1134 | C   | HIS | 150 | 40.960 | 39.442 | 0.353  | 1.00 | 34.39 |
| ATOM | 1135 | O   | HIS | 150 | 40.245 | 39.364 | -0.655 | 1.00 | 34.56 |
| ATOM | 1136 | N   | ALA | 151 | 42.239 | 39.068 | 0.380  | 1.00 | 34.73 |

*FIG. 4T*

| | | | | | | | | |
|---|---|---|---|---|---|---|---|---|
| ATOM | 1137 | CA | ALA | 151 | 42.898 | 38.440 | -0.762 | 1.00 34.53 |
| ATOM | 1138 | CB | ALA | 151 | 44.334 | 38.949 | -0.919 | 1.00 34.86 |
| ATOM | 1139 | C | ALA | 151 | 42.894 | 36.968 | -0.338 | 1.00 34.46 |
| ATOM | 1140 | O | ALA | 151 | 42.734 | 36.065 | -1.161 | 1.00 34.16 |
| ATOM | 1141 | N | ASP | 152 | 43.050 | 36.754 | 0.970 | 1.00 34.36 |
| ATOM | 1142 | CA | ASP | 152 | 43.045 | 35.422 | 1.562 | 1.00 35.45 |
| ATOM | 1143 | CB | ASP | 152 | 44.335 | 34.687 | 1.214 | 1.00 37.69 |
| ATOM | 1144 | CG | ASP | 152 | 44.233 | 33.185 | 1.431 | 1.00 40.20 |
| ATOM | 1145 | OD1 | ASP | 152 | 43.219 | 32.717 | 2.007 | 1.00 40.73 |
| ATOM | 1146 | OD2 | ASP | 152 | 45.177 | 32.464 | 1.018 | 1.00 42.29 |
| ATOM | 1147 | C | ASP | 152 | 42.901 | 35.549 | 3.088 | 1.00 35.53 |
| ATOM | 1148 | O | ASP | 152 | 43.048 | 36.642 | 3.642 | 1.00 35.08 |
| ATOM | 1149 | N | ILE | 153 | 42.627 | 34.433 | 3.762 | 1.00 35.49 |
| ATOM | 1150 | CA | ILE | 153 | 42.436 | 34.427 | 5.213 | 1.00 35.75 |
| ATOM | 1151 | CB | ILE | 153 | 42.258 | 32.984 | 5.754 | 1.00 35.32 |
| ATOM | 1152 | CG2 | ILE | 153 | 43.609 | 32.316 | 5.937 | 1.00 34.16 |
| ATOM | 1153 | CG1 | ILE | 153 | 41.593 | 33.022 | 7.130 | 1.00 35.44 |
| ATOM | 1154 | CD1 | ILE | 153 | 40.225 | 33.697 | 7.131 | 1.00 36.43 |
| ATOM | 1155 | C | ILE | 153 | 43.571 | 35.079 | 6.011 | 1.00 36.77 |
| ATOM | 1156 | O | ILE | 153 | 43.450 | 35.278 | 7.229 | 1.00 36.40 |
| ATOM | 1157 | N | ASP | 154 | 44.665 | 35.411 | 5.332 | 1.00 37.10 |
| ATOM | 1158 | CA | ASP | 154 | 45.815 | 36.003 | 6.000 | 1.00 37.27 |
| ATOM | 1159 | CB | ASP | 154 | 46.982 | 35.013 | 5.991 | 1.00 38.98 |
| ATOM | 1160 | CG | ASP | 154 | 47.795 | 35.079 | 4.703 | 1.00 41.58 |
| ATOM | 1161 | OD1 | ASP | 154 | 47.215 | 34.890 | 3.605 | 1.00 42.46 |
| ATOM | 1162 | OD2 | ASP | 154 | 49.022 | 35.331 | 4.789 | 1.00 42.65 |
| ATOM | 1163 | C | ASP | 154 | 46.233 | 37.287 | 5.307 | 1.00 36.74 |
| ATOM | 1164 | O | ASP | 154 | 47.360 | 37.751 | 5.471 | 1.00 37.07 |
| ATOM | 1165 | N | ALA | 155 | 45.328 | 37.865 | 4.531 | 1.00 35.91 |
| ATOM | 1166 | CA | ALA | 155 | 45.650 | 39.093 | 3.830 | 1.00 36.20 |
| ATOM | 1167 | CB | ALA | 155 | 46.522 | 38.771 | 2.621 | 1.00 36.22 |
| ATOM | 1168 | C | ALA | 155 | 44.412 | 39.864 | 3.387 | 1.00 36.20 |
| ATOM | 1169 | O | ALA | 155 | 43.490 | 39.289 | 2.820 | 1.00 36.87 |
| ATOM | 1170 | N | GLY | 156 | 44.402 | 41.168 | 3.642 | 1.00 36.26 |
| ATOM | 1171 | CA | GLY | 156 | 43.279 | 41.997 | 3.245 | 1.00 37.08 |
| ATOM | 1172 | C | GLY | 156 | 43.481 | 43.446 | 3.647 | 1.00 38.10 |
| ATOM | 1173 | O | GLY | 156 | 44.027 | 43.727 | 4.711 | 1.00 38.52 |
| ATOM | 1174 | N | ILE | 157 | 43.052 | 44.377 | 2.805 | 1.00 39.16 |
| ATOM | 1175 | CA | ILE | 157 | 43.203 | 45.789 | 3.125 | 1.00 41.42 |
| ATOM | 1176 | CB | ILE | 157 | 43.389 | 46.646 | 1.842 | 1.00 42.84 |
| ATOM | 1177 | CG2 | ILE | 157 | 44.844 | 46.550 | 1.349 | 1.00 44.32 |
| ATOM | 1178 | CG1 | ILE | 157 | 42.399 | 46.193 | 0.761 | 1.00 43.93 |
| ATOM | 1179 | CD1 | ILE | 157 | 42.630 | 46.838 | -0.615 | 1.00 44.55 |
| ATOM | 1180 | C | ILE | 157 | 42.010 | 46.331 | 3.921 | 1.00 42.26 |
| ATOM | 1181 | O | ILE | 157 | 40.864 | 45.912 | 3.732 | 1.00 42.28 |
| ATOM | 1182 | N | LEU | 158 | 42.300 | 47.259 | 4.824 | 1.00 42.54 |
| ATOM | 1183 | CA | LEU | 158 | 41.283 | 47.873 | 5.648 | 1.00 43.22 |
| ATOM | 1184 | CB | LEU | 158 | 41.928 | 48.504 | 6.884 | 1.00 44.12 |
| ATOM | 1185 | CG | LEU | 158 | 41.090 | 49.514 | 7.670 | 1.00 44.84 |
| ATOM | 1186 | CD1 | LEU | 158 | 40.020 | 48.782 | 8.472 | 1.00 45.23 |
| ATOM | 1187 | CD2 | LEU | 158 | 42.006 | 50.320 | 8.590 | 1.00 45.09 |
| ATOM | 1188 | C | LEU | 158 | 40.548 | 48.947 | 4.855 | 1.00 43.56 |
| ATOM | 1189 | O | LEU | 158 | 40.984 | 50.099 | 4.801 | 1.00 43.77 |
| ATOM | 1190 | N | LEU | 159 | 39.434 | 48.569 | 4.239 | 1.00 43.40 |
| ATOM | 1191 | CA | LEU | 159 | 38.634 | 49.508 | 3.465 | 1.00 43.01 |
| ATOM | 1192 | CB | LEU | 159 | 37.238 | 48.935 | 3.280 | 1.00 43.36 |
| ATOM | 1193 | CG | LEU | 159 | 37.279 | 47.599 | 2.539 | 1.00 43.44 |

*FIG. 4U*

```
ATOM   1194  CD1  LEU  159    36.020  46.808   2.829  1.00 44.00
ATOM   1195  CD2  LEU  159    37.443  47.857   1.050  1.00 42.93
ATOM   1196  C    LEU  159    38.564  50.879   4.139  1.00 42.62
ATOM   1197  O    LEU  159    38.745  51.905   3.488  1.00 43.03
ATOM   1198  N    ASN  160    38.297  50.902   5.440  1.00 42.20
ATOM   1199  CA   ASN  160    38.243  52.169   6.170  1.00 41.99
ATOM   1200  CB   ASN  160    37.347  53.197   5.447  1.00 42.23
ATOM   1201  CG   ASN  160    35.913  52.733   5.295  1.00 43.38
ATOM   1202  OD1  ASN  160    35.225  53.102   4.334  1.00 42.38
ATOM   1203  ND2  ASN  160    35.444  51.934   6.250  1.00 44.48
ATOM   1204  C    ASN  160    37.813  51.988   7.616  1.00 41.13
ATOM   1205  O    ASN  160    37.359  50.913   8.011  1.00 41.17
ATOM   1206  N    TRP  161    37.980  53.043   8.403  1.00 40.24
ATOM   1207  CA   TRP  161    37.652  53.004   9.824  1.00 39.69
ATOM   1208  CB   TRP  161    38.522  54.003  10.602  1.00 39.33
ATOM   1209  CG   TRP  161    39.987  53.640  10.769  1.00 39.07
ATOM   1210  CD2  TRP  161    40.527  52.469  11.411  1.00 38.63
ATOM   1211  CE2  TRP  161    41.931  52.616  11.438  1.00 38.27
ATOM   1212  CE3  TRP  161    39.960  51.317  11.972  1.00 38.43
ATOM   1213  CD1  TRP  161    41.060  54.417  10.436  1.00 38.40
ATOM   1214  NE1  TRP  161    42.228  53.812  10.840  1.00 38.42
ATOM   1215  CZ2  TRP  161    42.778  51.659  12.000  1.00 38.26
ATOM   1216  CZ3  TRP  161    40.809  50.357  12.538  1.00 38.07
ATOM   1217  CH2  TRP  161    42.200  50.540  12.545  1.00 38.37
ATOM   1218  C    TRP  161    36.196  53.301  10.150  1.00 39.07
ATOM   1219  O    TRP  161    35.578  54.193   9.562  1.00 39.38
ATOM   1220  N    THR  162    35.668  52.555  11.114  1.00 38.45
ATOM   1221  CA   THR  162    34.302  52.734  11.593  1.00 38.37
ATOM   1222  CB   THR  162    33.381  51.600  11.125  1.00 37.71
ATOM   1223  OG1  THR  162    33.926  50.338  11.548  1.00 37.02
ATOM   1224  CG2  THR  162    33.226  51.635   9.617  1.00 36.52
ATOM   1225  C    THR  162    34.357  52.702  13.121  1.00 38.24
ATOM   1226  O    THR  162    35.405  52.443  13.703  1.00 37.86
ATOM   1227  N    LYS  163    33.231  52.968  13.770  1.00 38.99
ATOM   1228  CA   LYS  163    33.192  52.941  15.222  1.00 39.72
ATOM   1229  CB   LYS  163    33.510  51.528  15.728  1.00 38.16
ATOM   1230  CG   LYS  163    32.467  50.487  15.311  1.00 36.62
ATOM   1231  CD   LYS  163    32.727  49.108  15.918  1.00 34.66
ATOM   1232  CE   LYS  163    33.829  48.349  15.195  1.00 33.22
ATOM   1233  NZ   LYS  163    34.068  47.031  15.850  1.00 32.19
ATOM   1234  C    LYS  163    34.142  53.956  15.848  1.00 40.71
ATOM   1235  O    LYS  163    34.690  53.723  16.931  1.00 40.69
ATOM   1236  N    GLY  164    34.338  55.076  15.156  1.00 41.81
ATOM   1237  CA   GLY  164    35.187  56.139  15.672  1.00 43.90
ATOM   1238  C    GLY  164    36.685  56.031  15.463  1.00 45.41
ATOM   1239  O    GLY  164    37.375  57.055  15.381  1.00 45.25
ATOM   1240  N    PHE  165    37.190  54.802  15.397  1.00 47.06
ATOM   1241  CA   PHE  165    38.613  54.560  15.197  1.00 48.70
ATOM   1242  CB   PHE  165    38.852  53.117  14.767  1.00 47.20
ATOM   1243  CG   PHE  165    39.290  52.222  15.870  1.00 45.64
ATOM   1244  CD1  PHE  165    38.443  51.937  16.929  1.00 45.87
ATOM   1245  CD2  PHE  165    40.544  51.632  15.833  1.00 45.19
ATOM   1246  CE1  PHE  165    38.840  51.064  17.945  1.00 46.28
ATOM   1247  CE2  PHE  165    40.952  50.763  16.834  1.00 45.80
ATOM   1248  CZ   PHE  165    40.098  50.475  17.896  1.00 45.96
ATOM   1249  C    PHE  165    39.250  55.471  14.154  1.00 50.94
ATOM   1250  O    PHE  165    38.633  55.823  13.143  1.00 50.36
```

*FIG. 4V*

| | | | | | | | | |
|---|---|---|---|---|---|---|---|---|
| ATOM | 1251 | N | LYS | 166 | 40.500 | 55.838 | 14.415 | 1.00 53.77 |
| ATOM | 1252 | CA | LYS | 166 | 41.275 | 56.680 | 13.514 | 1.00 56.56 |
| ATOM | 1253 | CB | LYS | 166 | 41.050 | 58.170 | 13.822 | 1.00 56.16 |
| ATOM | 1254 | CG | LYS | 166 | 39.720 | 58.697 | 13.290 | 1.00 56.44 |
| ATOM | 1255 | CD | LYS | 166 | 39.524 | 58.320 | 11.812 | 1.00 56.54 |
| ATOM | 1256 | CE | LYS | 166 | 38.131 | 58.694 | 11.305 | 1.00 56.74 |
| ATOM | 1257 | NZ | LYS | 166 | 37.863 | 58.198 | 9.922 | 1.00 56.86 |
| ATOM | 1258 | C | LYS | 166 | 42.751 | 56.322 | 13.640 | 1.00 58.33 |
| ATOM | 1259 | O | LYS | 166 | 43.180 | 55.747 | 14.651 | 1.00 58.69 |
| ATOM | 1260 | N | ALA | 167 | 43.510 | 56.647 | 12.597 | 1.00 59.76 |
| ATOM | 1261 | CA | ALA | 167 | 44.943 | 56.375 | 12.543 | 1.00 61.43 |
| ATOM | 1262 | CB | ALA | 167 | 45.220 | 54.901 | 12.834 | 1.00 60.92 |
| ATOM | 1263 | C | ALA | 167 | 45.401 | 56.725 | 11.137 | 1.00 62.76 |
| ATOM | 1264 | O | ALA | 167 | 45.147 | 55.967 | 10.197 | 1.00 63.38 |
| ATOM | 1265 | N | SER | 168 | 46.066 | 57.872 | 10.999 | 1.00 63.98 |
| ATOM | 1266 | CA | SER | 168 | 46.556 | 58.345 | 9.704 | 1.00 64.43 |
| ATOM | 1267 | CB | SER | 168 | 47.636 | 59.414 | 9.903 | 1.00 64.96 |
| ATOM | 1268 | OG | SER | 168 | 47.130 | 60.546 | 10.594 | 1.00 65.76 |
| ATOM | 1269 | C | SER | 168 | 47.115 | 57.216 | 8.846 | 1.00 64.59 |
| ATOM | 1270 | O | SER | 168 | 47.805 | 56.322 | 9.347 | 1.00 64.35 |
| ATOM | 1271 | N | GLY | 169 | 46.800 | 57.260 | 7.553 | 1.00 64.75 |
| ATOM | 1272 | CA | GLY | 169 | 47.280 | 56.245 | 6.632 | 1.00 65.55 |
| ATOM | 1273 | C | GLY | 169 | 47.158 | 54.821 | 7.142 | 1.00 65.88 |
| ATOM | 1274 | O | GLY | 169 | 48.151 | 54.097 | 7.255 | 1.00 65.72 |
| ATOM | 1275 | N | ALA | 170 | 45.936 | 54.416 | 7.465 | 1.00 66.32 |
| ATOM | 1276 | CA | ALA | 170 | 45.699 | 53.065 | 7.947 | 1.00 66.82 |
| ATOM | 1277 | CB | ALA | 170 | 44.930 | 53.100 | 9.256 | 1.00 66.65 |
| ATOM | 1278 | C | ALA | 170 | 44.890 | 52.346 | 6.879 | 1.00 67.02 |
| ATOM | 1279 | O | ALA | 170 | 45.209 | 51.226 | 6.477 | 1.00 67.31 |
| ATOM | 1280 | N | GLU | 171 | 43.847 | 53.017 | 6.410 | 1.00 66.85 |
| ATOM | 1281 | CA | GLU | 171 | 42.979 | 52.463 | 5.387 | 1.00 66.80 |
| ATOM | 1282 | CB | GLU | 171 | 41.705 | 53.292 | 5.287 | 1.00 67.90 |
| ATOM | 1283 | CG | GLU | 171 | 41.958 | 54.783 | 5.279 | 1.00 69.27 |
| ATOM | 1284 | CD | GLU | 171 | 40.850 | 55.552 | 4.590 | 1.00 70.17 |
| ATOM | 1285 | OE1 | GLU | 171 | 40.789 | 55.506 | 3.340 | 1.00 70.45 |
| ATOM | 1286 | OE2 | GLU | 171 | 40.038 | 56.191 | 5.296 | 1.00 70.67 |
| ATOM | 1287 | C | GLU | 171 | 43.666 | 52.427 | 4.032 | 1.00 65.92 |
| ATOM | 1288 | O | GLU | 171 | 44.469 | 53.301 | 3.711 | 1.00 66.22 |
| ATOM | 1289 | N | GLY | 172 | 43.339 | 51.408 | 3.242 | 1.00 64.69 |
| ATOM | 1290 | CA | GLY | 172 | 43.922 | 51.265 | 1.925 | 1.00 62.79 |
| ATOM | 1291 | C | GLY | 172 | 45.096 | 50.312 | 1.882 | 1.00 61.61 |
| ATOM | 1292 | O | GLY | 172 | 45.493 | 49.884 | 0.805 | 1.00 61.59 |
| ATOM | 1293 | N | ASN | 173 | 45.643 | 49.965 | 3.045 | 1.00 60.93 |
| ATOM | 1294 | CA | ASN | 173 | 46.800 | 49.065 | 3.115 | 1.00 60.42 |
| ATOM | 1295 | CB | ASN | 173 | 47.922 | 49.722 | 3.913 | 1.00 61.72 |
| ATOM | 1296 | CG | ASN | 173 | 48.035 | 51.201 | 3.631 | 1.00 62.78 |
| ATOM | 1297 | OD1 | ASN | 173 | 48.367 | 51.605 | 2.515 | 1.00 63.29 |
| ATOM | 1298 | ND2 | ASN | 173 | 47.741 | 52.024 | 4.637 | 1.00 63.06 |
| ATOM | 1299 | C | ASN | 173 | 46.463 | 47.747 | 3.771 | 1.00 59.26 |
| ATOM | 1300 | O | ASN | 173 | 45.440 | 47.624 | 4.430 | 1.00 59.57 |
| ATOM | 1301 | N | ASN | 174 | 47.336 | 46.763 | 3.598 | 1.00 58.79 |
| ATOM | 1302 | CA | ASN | 174 | 47.126 | 45.447 | 4.196 | 1.00 58.46 |
| ATOM | 1303 | CB | ASN | 174 | 48.264 | 44.495 | 3.793 | 1.00 57.45 |
| ATOM | 1304 | CG | ASN | 174 | 48.104 | 43.093 | 4.375 | 1.00 57.22 |
| ATOM | 1305 | OD1 | ASN | 174 | 48.757 | 42.144 | 3.924 | 1.00 56.21 |
| ATOM | 1306 | ND2 | ASN | 174 | 47.245 | 42.957 | 5.382 | 1.00 56.76 |
| ATOM | 1307 | C | ASN | 174 | 47.083 | 45.615 | 5.712 | 1.00 58.42 |

*FIG. 4W*

| | | | | | | | | | |
|---|---|---|---|---|---|---|---|---|---|
| ATOM | 1308 | O | ASN | 174 | 47.927 | 46.302 | 6.281 | 1.00 | 59.03 |
| ATOM | 1309 | N | VAL | 175 | 46.091 | 45.008 | 6.359 | 1.00 | 58.23 |
| ATOM | 1310 | CA | VAL | 175 | 45.966 | 45.106 | 7.809 | 1.00 | 57.79 |
| ATOM | 1311 | CB | VAL | 175 | 44.544 | 44.765 | 8.295 | 1.00 | 57.69 |
| ATOM | 1312 | CG1 | VAL | 175 | 44.461 | 44.933 | 9.807 | 1.00 | 56.81 |
| ATOM | 1313 | CG2 | VAL | 175 | 43.531 | 45.665 | 7.603 | 1.00 | 57.69 |
| ATOM | 1314 | C | VAL | 175 | 46.944 | 44.150 | 8.470 | 1.00 | 57.62 |
| ATOM | 1315 | O | VAL | 175 | 47.734 | 44.560 | 9.319 | 1.00 | 57.89 |
| ATOM | 1316 | N | VAL | 176 | 46.896 | 42.878 | 8.086 | 1.00 | 57.24 |
| ATOM | 1317 | CA | VAL | 176 | 47.818 | 41.904 | 8.660 | 1.00 | 57.25 |
| ATOM | 1318 | CB | VAL | 176 | 47.638 | 40.501 | 8.037 | 1.00 | 57.27 |
| ATOM | 1319 | CG1 | VAL | 176 | 48.597 | 39.511 | 8.701 | 1.00 | 56.21 |
| ATOM | 1320 | CG2 | VAL | 176 | 46.196 | 40.035 | 8.199 | 1.00 | 56.28 |
| ATOM | 1321 | C | VAL | 176 | 49.232 | 42.396 | 8.362 | 1.00 | 57.38 |
| ATOM | 1322 | O | VAL | 176 | 50.212 | 41.911 | 8.926 | 1.00 | 57.30 |
| ATOM | 1323 | N | GLY | 177 | 49.319 | 43.374 | 7.467 | 1.00 | 57.41 |
| ATOM | 1324 | CA | GLY | 177 | 50.605 | 43.939 | 7.103 | 1.00 | 57.60 |
| ATOM | 1325 | C | GLY | 177 | 51.135 | 44.878 | 8.170 | 1.00 | 57.50 |
| ATOM | 1326 | O | GLY | 177 | 52.171 | 44.605 | 8.781 | 1.00 | 58.09 |
| ATOM | 1327 | N | LEU | 178 | 50.425 | 45.982 | 8.396 | 1.00 | 56.68 |
| ATOM | 1328 | CA | LEU | 178 | 50.837 | 46.959 | 9.396 | 1.00 | 55.42 |
| ATOM | 1329 | CB | LEU | 178 | 49.710 | 47.968 | 9.646 | 1.00 | 55.02 |
| ATOM | 1330 | CG | LEU | 178 | 49.394 | 48.906 | 8.466 | 1.00 | 54.15 |
| ATOM | 1331 | CD1 | LEU | 178 | 48.158 | 49.743 | 8.766 | 1.00 | 53.80 |
| ATOM | 1332 | CD2 | LEU | 178 | 50.588 | 49.815 | 8.197 | 1.00 | 54.17 |
| ATOM | 1333 | C | LEU | 178 | 51.247 | 46.279 | 10.701 | 1.00 | 54.84 |
| ATOM | 1334 | O | LEU | 178 | 52.177 | 46.717 | 11.375 | 1.00 | 55.07 |
| ATOM | 1335 | N | LEU | 179 | 50.575 | 45.192 | 11.050 | 1.00 | 53.85 |
| ATOM | 1336 | CA | LEU | 179 | 50.917 | 44.491 | 12.274 | 1.00 | 53.57 |
| ATOM | 1337 | CB | LEU | 179 | 49.882 | 43.409 | 12.582 | 1.00 | 52.75 |
| ATOM | 1338 | CG | LEU | 179 | 50.099 | 42.671 | 13.907 | 1.00 | 52.23 |
| ATOM | 1339 | CD1 | LEU | 179 | 49.689 | 43.580 | 15.056 | 1.00 | 51.63 |
| ATOM | 1340 | CD2 | LEU | 179 | 49.286 | 41.381 | 13.935 | 1.00 | 51.34 |
| ATOM | 1341 | C | LEU | 179 | 52.286 | 43.845 | 12.128 | 1.00 | 54.26 |
| ATOM | 1342 | O | LEU | 179 | 53.070 | 43.796 | 13.075 | 1.00 | 54.60 |
| ATOM | 1343 | N | ARG | 180 | 52.576 | 43.343 | 10.932 | 1.00 | 54.59 |
| ATOM | 1344 | CA | ARG | 180 | 53.855 | 42.679 | 10.688 | 1.00 | 54.08 |
| ATOM | 1345 | CB | ARG | 180 | 53.824 | 41.911 | 9.357 | 1.00 | 52.59 |
| ATOM | 1346 | CG | ARG | 180 | 53.273 | 40.498 | 9.515 | 1.00 | 50.37 |
| ATOM | 1347 | CD | ARG | 180 | 53.276 | 39.702 | 8.223 | 1.00 | 47.24 |
| ATOM | 1348 | NE | ARG | 180 | 52.610 | 38.420 | 8.425 | 1.00 | 45.06 |
| ATOM | 1349 | CZ | ARG | 180 | 51.979 | 37.754 | 7.462 | 1.00 | 43.97 |
| ATOM | 1350 | NH1 | ARG | 180 | 51.935 | 38.256 | 6.226 | 1.00 | 42.53 |
| ATOM | 1351 | NH2 | ARG | 180 | 51.366 | 36.601 | 7.735 | 1.00 | 42.95 |
| ATOM | 1352 | C | ARG | 180 | 55.059 | 43.605 | 10.732 | 1.00 | 54.76 |
| ATOM | 1353 | O | ARG | 180 | 56.009 | 43.343 | 11.473 | 1.00 | 54.65 |
| ATOM | 1354 | N | ASP | 181 | 55.036 | 44.681 | 9.951 | 1.00 | 55.34 |
| ATOM | 1355 | CA | ASP | 181 | 56.169 | 45.593 | 9.972 | 1.00 | 56.60 |
| ATOM | 1356 | CB | ASP | 181 | 56.266 | 46.386 | 8.649 | 1.00 | 56.43 |
| ATOM | 1357 | CG | ASP | 181 | 55.132 | 47.382 | 8.448 | 1.00 | 55.64 |
| ATOM | 1358 | OD1 | ASP | 181 | 54.658 | 47.483 | 7.294 | 1.00 | 55.20 |
| ATOM | 1359 | OD2 | ASP | 181 | 54.734 | 48.076 | 9.416 | 1.00 | 55.23 |
| ATOM | 1360 | C | ASP | 181 | 56.115 | 46.514 | 11.199 | 1.00 | 57.64 |
| ATOM | 1361 | O | ASP | 181 | 56.510 | 47.685 | 11.153 | 1.00 | 57.96 |
| ATOM | 1362 | N | ALA | 182 | 55.634 | 45.947 | 12.303 | 1.00 | 57.87 |
| ATOM | 1363 | CA | ALA | 182 | 55.524 | 46.646 | 13.577 | 1.00 | 57.84 |
| ATOM | 1364 | CB | ALA | 182 | 54.078 | 47.048 | 13.836 | 1.00 | 58.19 |

*FIG. 4X*

| ATOM | 1365 | C | ALA | 182 | 56.013 | 45.683 | 14.657 | 1.00 | 57.83 |
|------|------|-----|-----|-----|--------|--------|--------|------|-------|
| ATOM | 1366 | O | ALA | 182 | 56.681 | 46.094 | 15.611 | 1.00 | 58.32 |
| ATOM | 1367 | N | ILE | 183 | 55.669 | 44.404 | 14.505 | 1.00 | 57.35 |
| ATOM | 1368 | CA | ILE | 183 | 56.109 | 43.381 | 15.448 | 1.00 | 57.40 |
| ATOM | 1369 | CB | ILE | 183 | 55.374 | 42.036 | 15.233 | 1.00 | 56.09 |
| ATOM | 1370 | CG2 | ILE | 183 | 56.025 | 40.932 | 16.074 | 1.00 | 55.25 |
| ATOM | 1371 | CG1 | ILE | 183 | 53.904 | 42.174 | 15.628 | 1.00 | 55.30 |
| ATOM | 1372 | CD1 | ILE | 183 | 53.115 | 40.881 | 15.505 | 1.00 | 54.14 |
| ATOM | 1373 | C | ILE | 183 | 57.600 | 43.164 | 15.199 | 1.00 | 58.51 |
| ATOM | 1374 | O | ILE | 183 | 58.294 | 42.531 | 16.002 | 1.00 | 59.24 |
| ATOM | 1375 | N | LYS | 184 | 58.093 | 43.689 | 14.077 | 1.00 | 59.04 |
| ATOM | 1376 | CA | LYS | 184 | 59.508 | 43.550 | 13.757 | 1.00 | 59.19 |
| ATOM | 1377 | CB | LYS | 184 | 59.719 | 43.243 | 12.268 | 1.00 | 59.15 |
| ATOM | 1378 | CG | LYS | 184 | 59.356 | 44.354 | 11.310 | 1.00 | 58.36 |
| ATOM | 1379 | CD | LYS | 184 | 59.566 | 43.897 | 9.868 | 1.00 | 58.59 |
| ATOM | 1380 | CE | LYS | 184 | 58.637 | 42.735 | 9.500 | 1.00 | 59.26 |
| ATOM | 1381 | NZ | LYS | 184 | 58.751 | 42.306 | 8.067 | 1.00 | 59.63 |
| ATOM | 1382 | C | LYS | 184 | 60.270 | 44.806 | 14.155 | 1.00 | 59.27 |
| ATOM | 1383 | O | LYS | 184 | 61.382 | 44.705 | 14.667 | 1.00 | 59.28 |
| ATOM | 1384 | N | ARG | 185 | 59.695 | 45.984 | 13.923 | 1.00 | 59.21 |
| ATOM | 1385 | CA | ARG | 185 | 60.383 | 47.211 | 14.331 | 1.00 | 59.69 |
| ATOM | 1386 | CB | ARG | 185 | 59.545 | 48.458 | 14.060 | 1.00 | 59.70 |
| ATOM | 1387 | CG | ARG | 185 | 59.278 | 48.772 | 12.610 | 1.00 | 60.85 |
| ATOM | 1388 | CD | ARG | 185 | 59.138 | 50.280 | 12.443 | 1.00 | 60.89 |
| ATOM | 1389 | NE | ARG | 185 | 58.121 | 50.628 | 11.459 | 1.00 | 62.26 |
| ATOM | 1390 | CZ | ARG | 185 | 56.819 | 50.403 | 11.620 | 1.00 | 61.84 |
| ATOM | 1391 | NH1 | ARG | 185 | 56.372 | 49.828 | 12.731 | 1.00 | 61.22 |
| ATOM | 1392 | NH2 | ARG | 185 | 55.966 | 50.754 | 10.666 | 1.00 | 62.23 |
| ATOM | 1393 | C | ARG | 185 | 60.574 | 47.104 | 15.836 | 1.00 | 60.41 |
| ATOM | 1394 | O | ARG | 185 | 61.630 | 47.430 | 16.384 | 1.00 | 60.45 |
| ATOM | 1395 | N | ARG | 186 | 59.518 | 46.633 | 16.489 | 1.00 | 61.07 |
| ATOM | 1396 | CA | ARG | 186 | 59.489 | 46.460 | 17.933 | 1.00 | 61.42 |
| ATOM | 1397 | CB | ARG | 186 | 58.066 | 46.055 | 18.358 | 1.00 | 61.16 |
| ATOM | 1398 | CG | ARG | 186 | 57.666 | 46.433 | 19.786 | 1.00 | 61.08 |
| ATOM | 1399 | CD | ARG | 186 | 58.249 | 45.473 | 20.828 | 1.00 | 60.87 |
| ATOM | 1400 | NE | ARG | 186 | 57.917 | 45.894 | 22.188 | 1.00 | 61.44 |
| ATOM | 1401 | CZ | ARG | 186 | 58.294 | 45.246 | 23.288 | 1.00 | 60.67 |
| ATOM | 1402 | NH1 | ARG | 186 | 59.024 | 44.133 | 23.201 | 1.00 | 60.28 |
| ATOM | 1403 | NH2 | ARG | 186 | 57.942 | 45.712 | 24.481 | 1.00 | 61.46 |
| ATOM | 1404 | C | ARG | 186 | 60.516 | 45.399 | 18.344 | 1.00 | 61.85 |
| ATOM | 1405 | O | ARG | 186 | 60.980 | 44.610 | 17.514 | 1.00 | 62.16 |
| ATOM | 1406 | N | GLY | 187 | 60.873 | 45.401 | 19.628 | 1.00 | 62.07 |
| ATOM | 1407 | CA | GLY | 187 | 61.843 | 44.455 | 20.157 | 1.00 | 62.22 |
| ATOM | 1408 | C | GLY | 187 | 61.591 | 43.017 | 19.754 | 1.00 | 62.50 |
| ATOM | 1409 | O | GLY | 187 | 60.541 | 42.692 | 19.202 | 1.00 | 62.37 |
| ATOM | 1410 | N | ASP | 188 | 62.556 | 42.148 | 20.036 | 1.00 | 63.08 |
| ATOM | 1411 | CA | ASP | 188 | 62.414 | 40.746 | 19.684 | 1.00 | 62.67 |
| ATOM | 1412 | CB | ASP | 188 | 63.465 | 39.873 | 20.373 | 1.00 | 61.80 |
| ATOM | 1413 | CG | ASP | 188 | 63.027 | 38.409 | 20.468 | 1.00 | 60.64 |
| ATOM | 1414 | OD1 | ASP | 188 | 62.125 | 38.107 | 21.289 | 1.00 | 60.77 |
| ATOM | 1415 | OD2 | ASP | 188 | 63.565 | 37.563 | 19.715 | 1.00 | 60.43 |
| ATOM | 1416 | C | ASP | 188 | 61.047 | 40.193 | 20.022 | 1.00 | 63.58 |
| ATOM | 1417 | O | ASP | 188 | 60.441 | 40.539 | 21.044 | 1.00 | 62.69 |
| ATOM | 1418 | N | PHE | 189 | 60.599 | 39.309 | 19.138 | 1.00 | 64.49 |
| ATOM | 1419 | CA | PHE | 189 | 59.327 | 38.632 | 19.249 | 1.00 | 64.75 |
| ATOM | 1420 | CB | PHE | 189 | 58.233 | 39.629 | 19.598 | 1.00 | 64.84 |
| ATOM | 1421 | CG | PHE | 189 | 56.886 | 39.010 | 19.689 | 1.00 | 65.46 |

*FIG. 4Y*

| ATOM | 1422 | CD1 | PHE | 189 | 56.707 | 37.824 | 20.402 | 1.00 | 65.54 |
| --- | --- | --- | --- | --- | --- | --- | --- | --- | --- |
| ATOM | 1423 | CD2 | PHE | 189 | 55.795 | 39.592 | 19.052 | 1.00 | 65.28 |
| ATOM | 1424 | CE1 | PHE | 189 | 55.455 | 37.224 | 20.481 | 1.00 | 65.61 |
| ATOM | 1425 | CE2 | PHE | 189 | 54.542 | 39.007 | 19.122 | 1.00 | 65.71 |
| ATOM | 1426 | CZ | PHE | 189 | 54.369 | 37.819 | 19.839 | 1.00 | 65.57 |
| ATOM | 1427 | C | PHE | 189 | 59.018 | 37.952 | 17.919 | 1.00 | 65.33 |
| ATOM | 1428 | O | PHE | 189 | 58.921 | 38.609 | 16.881 | 1.00 | 64.91 |
| ATOM | 1429 | N | GLU | 190 | 58.879 | 36.631 | 17.956 | 1.00 | 66.13 |
| ATOM | 1430 | CA | GLU | 190 | 58.584 | 35.854 | 16.752 | 1.00 | 66.57 |
| ATOM | 1431 | CB | GLU | 190 | 59.387 | 34.545 | 16.755 | 1.00 | 66.34 |
| ATOM | 1432 | CG | GLU | 190 | 60.778 | 34.649 | 17.389 | 1.00 | 64.66 |
| ATOM | 1433 | CD | GLU | 190 | 61.908 | 34.356 | 16.411 | 1.00 | 64.02 |
| ATOM | 1434 | OE1 | GLU | 190 | 63.054 | 34.161 | 16.874 | 1.00 | 63.09 |
| ATOM | 1435 | OE2 | GLU | 190 | 61.658 | 34.327 | 15.186 | 1.00 | 63.04 |
| ATOM | 1436 | C | GLU | 190 | 57.093 | 35.528 | 16.745 | 1.00 | 67.09 |
| ATOM | 1437 | O | GLU | 190 | 56.609 | 34.828 | 17.638 | 1.00 | 67.36 |
| ATOM | 1438 | N | MSE | 191 | 56.367 | 36.030 | 15.747 | 1.00 | 67.05 |
| ATOM | 1439 | CA | MSE | 191 | 54.928 | 35.775 | 15.666 | 1.00 | 66.65 |
| ATOM | 1440 | CB | MSE | 191 | 54.164 | 36.920 | 16.347 | 1.00 | 69.47 |
| ATOM | 1441 | CG | MSE | 191 | 52.867 | 36.492 | 17.037 | 1.00 | 72.30 |
| ATOM | 1442 | SE | MSE | 191 | 53.120 | 35.293 | 18.409 | 1.00 | 78.56 |
| ATOM | 1443 | CE | MSE | 191 | 51.941 | 35.893 | 19.581 | 1.00 | 75.88 |
| ATOM | 1444 | C | MSE | 191 | 54.412 | 35.590 | 14.230 | 1.00 | 64.85 |
| ATOM | 1445 | O | MSE | 191 | 54.399 | 36.538 | 13.435 | 1.00 | 64.30 |
| ATOM | 1446 | N | ASP | 192 | 53.977 | 34.368 | 13.910 | 1.00 | 62.82 |
| ATOM | 1447 | CA | ASP | 192 | 53.449 | 34.051 | 12.580 | 1.00 | 60.76 |
| ATOM | 1448 | CB | ASP | 192 | 53.774 | 32.607 | 12.207 | 1.00 | 61.24 |
| ATOM | 1449 | CG | ASP | 192 | 55.210 | 32.427 | 11.792 | 1.00 | 61.76 |
| ATOM | 1450 | OD1 | ASP | 192 | 55.684 | 33.219 | 10.947 | 1.00 | 62.45 |
| ATOM | 1451 | OD2 | ASP | 192 | 55.863 | 31.492 | 12.299 | 1.00 | 62.32 |
| ATOM | 1452 | C | ASP | 192 | 51.942 | 34.266 | 12.459 | 1.00 | 59.03 |
| ATOM | 1453 | O | ASP | 192 | 51.143 | 33.375 | 12.767 | 1.00 | 58.37 |
| ATOM | 1454 | N | VAL | 193 | 51.567 | 35.453 | 11.991 | 1.00 | 57.00 |
| ATOM | 1455 | CA | VAL | 193 | 50.167 | 35.818 | 11.818 | 1.00 | 54.85 |
| ATOM | 1456 | CB | VAL | 193 | 50.034 | 37.305 | 11.454 | 1.00 | 55.09 |
| ATOM | 1457 | CG1 | VAL | 193 | 48.568 | 37.712 | 11.448 | 1.00 | 54.84 |
| ATOM | 1458 | CG2 | VAL | 193 | 50.826 | 38.146 | 12.441 | 1.00 | 54.87 |
| ATOM | 1459 | C | VAL | 193 | 49.473 | 34.977 | 10.746 | 1.00 | 53.19 |
| ATOM | 1460 | O | VAL | 193 | 49.500 | 35.303 | 9.555 | 1.00 | 52.03 |
| ATOM | 1461 | N | VAL | 194 | 48.854 | 33.894 | 11.205 | 1.00 | 51.82 |
| ATOM | 1462 | CA | VAL | 194 | 48.126 | 32.949 | 10.367 | 1.00 | 50.66 |
| ATOM | 1463 | CB | VAL | 194 | 47.841 | 31.644 | 11.174 | 1.00 | 51.08 |
| ATOM | 1464 | CG1 | VAL | 194 | 46.686 | 30.860 | 10.554 | 1.00 | 52.09 |
| ATOM | 1465 | CG2 | VAL | 194 | 49.091 | 30.778 | 11.211 | 1.00 | 51.33 |
| ATOM | 1466 | C | VAL | 194 | 46.798 | 33.498 | 9.808 | 1.00 | 49.99 |
| ATOM | 1467 | O | VAL | 194 | 46.677 | 33.726 | 8.602 | 1.00 | 49.40 |
| ATOM | 1468 | N | ALA | 195 | 45.813 | 33.723 | 10.683 | 1.00 | 48.93 |
| ATOM | 1469 | CA | ALA | 195 | 44.499 | 34.193 | 10.251 | 1.00 | 47.60 |
| ATOM | 1470 | CB | ALA | 195 | 43.467 | 33.123 | 10.572 | 1.00 | 47.58 |
| ATOM | 1471 | C | ALA | 195 | 43.992 | 35.546 | 10.760 | 1.00 | 46.68 |
| ATOM | 1472 | O | ALA | 195 | 44.344 | 35.996 | 11.851 | 1.00 | 46.16 |
| ATOM | 1473 | N | MSE | 196 | 43.157 | 36.182 | 9.940 | 1.00 | 45.43 |
| ATOM | 1474 | CA | MSE | 196 | 42.521 | 37.459 | 10.279 | 1.00 | 44.60 |
| ATOM | 1475 | CB | MSE | 196 | 43.079 | 38.623 | 9.451 | 1.00 | 45.32 |
| ATOM | 1476 | CG | MSE | 196 | 42.329 | 39.925 | 9.716 | 1.00 | 47.29 |
| ATOM | 1477 | SE | MSE | 196 | 42.937 | 41.426 | 8.852 | 1.00 | 53.21 |
| ATOM | 1478 | CE | MSE | 196 | 44.264 | 41.920 | 9.982 | 1.00 | 51.44 |

*FIG. 4Z*

| ATOM | 1479 | C   | MSE | 196 | 41.019 | 37.333 | 10.002 | 1.00 | 43.09 |
| ---- | ---- | --- | --- | --- | ------ | ------ | ------ | ---- | ----- |
| ATOM | 1480 | O   | MSE | 196 | 40.610 | 36.973 |  8.892 | 1.00 | 43.71 |
| ATOM | 1481 | N   | VAL | 197 | 40.190 | 37.631 | 10.996 | 1.00 | 40.47 |
| ATOM | 1482 | CA  | VAL | 197 | 38.751 | 37.514 | 10.799 | 1.00 | 37.00 |
| ATOM | 1483 | CB  | VAL | 197 | 38.240 | 36.228 | 11.458 | 1.00 | 37.31 |
| ATOM | 1484 | CG1 | VAL | 197 | 38.840 | 35.004 | 10.766 | 1.00 | 36.64 |
| ATOM | 1485 | CG2 | VAL | 197 | 38.643 | 36.217 | 12.914 | 1.00 | 36.88 |
| ATOM | 1486 | C   | VAL | 197 | 37.991 | 38.710 | 11.354 | 1.00 | 35.22 |
| ATOM | 1487 | O   | VAL | 197 | 38.561 | 39.544 | 12.057 | 1.00 | 35.21 |
| ATOM | 1488 | N   | ASN | 198 | 36.708 | 38.801 | 11.015 | 1.00 | 33.39 |
| ATOM | 1489 | CA  | ASN | 198 | 35.830 | 39.883 | 11.491 | 1.00 | 30.23 |
| ATOM | 1490 | CB  | ASN | 198 | 34.740 | 40.175 | 10.446 | 1.00 | 30.65 |
| ATOM | 1491 | CG  | ASN | 198 | 33.801 | 41.309 | 10.852 | 1.00 | 31.35 |
| ATOM | 1492 | OD1 | ASN | 198 | 32.907 | 41.128 | 11.686 | 1.00 | 32.70 |
| ATOM | 1493 | ND2 | ASN | 198 | 33.997 | 42.486 | 10.251 | 1.00 | 30.53 |
| ATOM | 1494 | C   | ASN | 198 | 35.217 | 39.356 | 12.780 | 1.00 | 28.41 |
| ATOM | 1495 | O   | ASN | 198 | 35.052 | 38.143 | 12.937 | 1.00 | 26.14 |
| ATOM | 1496 | N   | ASP | 199 | 34.892 | 40.252 | 13.711 | 1.00 | 27.77 |
| ATOM | 1497 | CA  | ASP | 199 | 34.325 | 39.816 | 14.990 | 1.00 | 26.87 |
| ATOM | 1498 | CB  | ASP | 199 | 34.156 | 41.007 | 15.945 | 1.00 | 26.75 |
| ATOM | 1499 | CG  | ASP | 199 | 33.254 | 42.097 | 15.396 | 1.00 | 26.24 |
| ATOM | 1500 | OD1 | ASP | 199 | 33.221 | 42.292 | 14.167 | 1.00 | 26.90 |
| ATOM | 1501 | OD2 | ASP | 199 | 32.587 | 42.777 | 16.205 | 1.00 | 26.19 |
| ATOM | 1502 | C   | ASP | 199 | 33.027 | 39.034 | 14.843 | 1.00 | 26.43 |
| ATOM | 1503 | O   | ASP | 199 | 32.715 | 38.188 | 15.684 | 1.00 | 27.02 |
| ATOM | 1504 | N   | THR | 200 | 32.291 | 39.292 | 13.763 | 1.00 | 25.45 |
| ATOM | 1505 | CA  | THR | 200 | 31.050 | 38.585 | 13.510 | 1.00 | 25.65 |
| ATOM | 1506 | CB  | THR | 200 | 30.261 | 39.193 | 12.339 | 1.00 | 25.75 |
| ATOM | 1507 | OG1 | THR | 200 | 31.008 | 39.044 | 11.130 | 1.00 | 26.04 |
| ATOM | 1508 | CG2 | THR | 200 | 30.002 | 40.672 | 12.573 | 1.00 | 26.48 |
| ATOM | 1509 | C   | THR | 200 | 31.383 | 37.155 | 13.143 | 1.00 | 26.96 |
| ATOM | 1510 | O   | THR | 200 | 30.832 | 36.211 | 13.712 | 1.00 | 27.62 |
| ATOM | 1511 | N   | VAL | 201 | 32.295 | 36.990 | 12.189 | 1.00 | 28.07 |
| ATOM | 1512 | CA  | VAL | 201 | 32.695 | 35.654 | 11.742 | 1.00 | 28.50 |
| ATOM | 1513 | CB  | VAL | 201 | 33.785 | 35.726 | 10.665 | 1.00 | 29.26 |
| ATOM | 1514 | CG1 | VAL | 201 | 34.056 | 34.332 | 10.123 | 1.00 | 31.22 |
| ATOM | 1515 | CG2 | VAL | 201 | 33.370 | 36.684 |  9.546 | 1.00 | 27.90 |
| ATOM | 1516 | C   | VAL | 201 | 33.231 | 34.818 | 12.901 | 1.00 | 29.16 |
| ATOM | 1517 | O   | VAL | 201 | 32.816 | 33.676 | 13.101 | 1.00 | 29.44 |
| ATOM | 1518 | N   | ALA | 202 | 34.156 | 35.395 | 13.663 | 1.00 | 30.31 |
| ATOM | 1519 | CA  | ALA | 202 | 34.752 | 34.710 | 14.812 | 1.00 | 32.23 |
| ATOM | 1520 | CB  | ALA | 202 | 35.591 | 35.705 | 15.643 | 1.00 | 31.72 |
| ATOM | 1521 | C   | ALA | 202 | 33.688 | 34.070 | 15.696 | 1.00 | 33.37 |
| ATOM | 1522 | O   | ALA | 202 | 33.789 | 32.894 | 16.073 | 1.00 | 34.14 |
| ATOM | 1523 | N   | THR | 203 | 32.667 | 34.858 | 16.019 | 1.00 | 34.41 |
| ATOM | 1524 | CA  | THR | 203 | 31.566 | 34.422 | 16.870 | 1.00 | 35.37 |
| ATOM | 1525 | CB  | THR | 203 | 30.614 | 35.604 | 17.117 | 1.00 | 36.27 |
| ATOM | 1526 | OG1 | THR | 203 | 31.370 | 36.708 | 17.645 | 1.00 | 37.04 |
| ATOM | 1527 | CG2 | THR | 203 | 29.500 | 35.213 | 18.090 | 1.00 | 35.19 |
| ATOM | 1528 | C   | THR | 203 | 30.800 | 33.260 | 16.242 | 1.00 | 36.08 |
| ATOM | 1529 | O   | THR | 203 | 30.538 | 32.241 | 16.891 | 1.00 | 35.34 |
| ATOM | 1530 | N   | MSE | 204 | 30.433 | 33.415 | 14.978 | 1.00 | 36.89 |
| ATOM | 1531 | CA  | MSE | 204 | 29.722 | 32.348 | 14.299 | 1.00 | 37.94 |
| ATOM | 1532 | CB  | MSE | 204 | 29.582 | 32.665 | 12.811 | 1.00 | 39.76 |
| ATOM | 1533 | CG  | MSE | 204 | 29.065 | 31.504 | 11.954 | 1.00 | 40.74 |
| ATOM | 1534 | SE  | MSE | 204 | 29.135 | 31.967 | 10.181 | 1.00 | 45.75 |
| ATOM | 1535 | CE  | MSE | 204 | 30.643 | 31.057 |  9.627 | 1.00 | 45.26 |

*FIG. 4AA*

| | | | | | | | | |
|---|---|---|---|---|---|---|---|---|
| ATOM | 1536 | C | MSE | 204 | 30.531 | 31.075 | 14.465 | 1.00 38.36 |
| ATOM | 1537 | O | MSE | 204 | 30.024 | 30.064 | 14.954 | 1.00 37.86 |
| ATOM | 1538 | N | ILE | 205 | 31.798 | 31.148 | 14.061 | 1.00 38.79 |
| ATOM | 1539 | CA | ILE | 205 | 32.696 | 30.008 | 14.137 | 1.00 40.09 |
| ATOM | 1540 | CB | ILE | 205 | 34.178 | 30.451 | 13.981 | 1.00 39.81 |
| ATOM | 1541 | CG2 | ILE | 205 | 35.098 | 29.240 | 14.072 | 1.00 39.47 |
| ATOM | 1542 | CG1 | ILE | 205 | 34.398 | 31.112 | 12.616 | 1.00 39.46 |
| ATOM | 1543 | CD1 | ILE | 205 | 34.250 | 30.158 | 11.425 | 1.00 39.34 |
| ATOM | 1544 | C | ILE | 205 | 32.527 | 29.215 | 15.440 | 1.00 41.34 |
| ATOM | 1545 | O | ILE | 205 | 32.121 | 28.050 | 15.408 | 1.00 41.41 |
| ATOM | 1546 | N | SER | 206 | 32.812 | 29.830 | 16.584 | 1.00 42.01 |
| ATOM | 1547 | CA | SER | 206 | 32.683 | 29.112 | 17.849 | 1.00 43.71 |
| ATOM | 1548 | CB | SER | 206 | 32.999 | 30.038 | 19.013 | 1.00 43.57 |
| ATOM | 1549 | OG | SER | 206 | 32.149 | 31.163 | 18.971 | 1.00 44.54 |
| ATOM | 1550 | C | SER | 206 | 31.306 | 28.494 | 18.056 | 1.00 44.83 |
| ATOM | 1551 | O | SER | 206 | 31.185 | 27.304 | 18.364 | 1.00 45.40 |
| ATOM | 1552 | N | CYS | 207 | 30.260 | 29.291 | 17.894 | 1.00 46.32 |
| ATOM | 1553 | CA | CYS | 207 | 28.912 | 28.764 | 18.079 | 1.00 48.14 |
| ATOM | 1554 | CB | CYS | 207 | 27.869 | 29.842 | 17.780 | 1.00 46.74 |
| ATOM | 1555 | SG | CYS | 207 | 27.946 | 31.264 | 18.883 | 1.00 42.50 |
| ATOM | 1556 | C | CYS | 207 | 28.666 | 27.551 | 17.186 | 1.00 50.79 |
| ATOM | 1557 | O | CYS | 207 | 27.715 | 26.799 | 17.403 | 1.00 50.97 |
| ATOM | 1558 | N | TYR | 208 | 29.533 | 27.361 | 16.190 | 1.00 53.91 |
| ATOM | 1559 | CA | TYR | 208 | 29.418 | 26.243 | 15.247 | 1.00 56.61 |
| ATOM | 1560 | CB | TYR | 208 | 30.350 | 26.458 | 14.045 | 1.00 56.96 |
| ATOM | 1561 | CG | TYR | 208 | 30.370 | 25.303 | 13.062 | 1.00 57.29 |
| ATOM | 1562 | CD1 | TYR | 208 | 29.307 | 25.090 | 12.182 | 1.00 57.54 |
| ATOM | 1563 | CE1 | TYR | 208 | 29.319 | 24.026 | 11.280 | 1.00 57.47 |
| ATOM | 1564 | CD2 | TYR | 208 | 31.448 | 24.418 | 13.019 | 1.00 57.54 |
| ATOM | 1565 | CE2 | TYR | 208 | 31.468 | 23.350 | 12.125 | 1.00 57.60 |
| ATOM | 1566 | CZ | TYR | 208 | 30.404 | 23.163 | 11.258 | 1.00 57.47 |
| ATOM | 1567 | OH | TYR | 208 | 30.435 | 22.126 | 10.360 | 1.00 57.71 |
| ATOM | 1568 | C | TYR | 208 | 29.705 | 24.867 | 15.854 | 1.00 58.12 |
| ATOM | 1569 | O | TYR | 208 | 28.874 | 23.960 | 15.773 | 1.00 58.61 |
| ATOM | 1570 | N | TYR | 209 | 30.876 | 24.699 | 16.459 | 1.00 59.77 |
| ATOM | 1571 | CA | TYR | 209 | 31.198 | 23.399 | 17.028 | 1.00 61.36 |
| ATOM | 1572 | CB | TYR | 209 | 32.619 | 23.394 | 17.581 | 1.00 63.23 |
| ATOM | 1573 | CG | TYR | 209 | 33.648 | 23.401 | 16.472 | 1.00 65.26 |
| ATOM | 1574 | CD1 | TYR | 209 | 34.058 | 24.595 | 15.876 | 1.00 66.13 |
| ATOM | 1575 | CE1 | TYR | 209 | 34.959 | 24.594 | 14.807 | 1.00 67.31 |
| ATOM | 1576 | CD2 | TYR | 209 | 34.165 | 22.206 | 15.973 | 1.00 65.88 |
| ATOM | 1577 | CE2 | TYR | 209 | 35.062 | 22.193 | 14.906 | 1.00 66.79 |
| ATOM | 1578 | CZ | TYR | 209 | 35.457 | 23.386 | 14.328 | 1.00 67.37 |
| ATOM | 1579 | OH | TYR | 209 | 36.350 | 23.370 | 13.277 | 1.00 67.62 |
| ATOM | 1580 | C | TYR | 209 | 30.206 | 22.965 | 18.083 | 1.00 61.32 |
| ATOM | 1581 | O | TYR | 209 | 30.048 | 21.771 | 18.336 | 1.00 61.19 |
| ATOM | 1582 | N | GLU | 210 | 29.523 | 23.938 | 18.680 | 1.00 61.63 |
| ATOM | 1583 | CA | GLU | 210 | 28.524 | 23.658 | 19.701 | 1.00 61.05 |
| ATOM | 1584 | CB | GLU | 210 | 28.444 | 24.808 | 20.706 | 1.00 62.29 |
| ATOM | 1585 | CG | GLU | 210 | 27.539 | 24.499 | 21.884 | 1.00 65.45 |
| ATOM | 1586 | CD | GLU | 210 | 27.716 | 25.463 | 23.050 | 1.00 67.38 |
| ATOM | 1587 | OE1 | GLU | 210 | 28.865 | 25.609 | 23.535 | 1.00 68.93 |
| ATOM | 1588 | OE2 | GLU | 210 | 26.707 | 26.065 | 23.488 | 1.00 67.92 |
| ATOM | 1589 | C | GLU | 210 | 27.175 | 23.459 | 19.026 | 1.00 60.04 |
| ATOM | 1590 | O | GLU | 210 | 26.255 | 22.901 | 19.618 | 1.00 59.93 |
| ATOM | 1591 | N | ASP | 211 | 27.073 | 23.920 | 17.780 | 1.00 58.82 |
| ATOM | 1592 | CA | ASP | 211 | 25.849 | 23.797 | 16.984 | 1.00 57.80 |

FIG. 4BB

| | | | | | | | | |
|---|---|---|---|---|---|---|---|---|
| ATOM | 1593 | CB | ASP | 211 | 24.804 | 24.824 | 17.441 | 1.00 58.16 |
| ATOM | 1594 | CG | ASP | 211 | 23.504 | 24.730 | 16.653 | 1.00 58.25 |
| ATOM | 1595 | OD1 | ASP | 211 | 22.490 | 25.299 | 17.111 | 1.00 57.88 |
| ATOM | 1596 | OD2 | ASP | 211 | 23.495 | 24.096 | 15.572 | 1.00 58.65 |
| ATOM | 1597 | C | ASP | 211 | 26.173 | 23.993 | 15.503 | 1.00 56.54 |
| ATOM | 1598 | O | ASP | 211 | 26.351 | 25.116 | 15.037 | 1.00 56.17 |
| ATOM | 1599 | N | HIS | 212 | 26.234 | 22.884 | 14.773 | 1.00 55.81 |
| ATOM | 1600 | CA | HIS | 212 | 26.577 | 22.884 | 13.351 | 1.00 55.26 |
| ATOM | 1601 | CB | HIS | 212 | 26.699 | 21.442 | 12.852 | 1.00 57.87 |
| ATOM | 1602 | CG | HIS | 212 | 27.816 | 20.678 | 13.493 | 1.00 61.52 |
| ATOM | 1603 | CD2 | HIS | 212 | 27.815 | 19.527 | 14.205 | 1.00 62.63 |
| ATOM | 1604 | ND1 | HIS | 212 | 29.127 | 21.110 | 13.460 | 1.00 62.80 |
| ATOM | 1605 | CE1 | HIS | 212 | 29.884 | 20.258 | 14.127 | 1.00 63.70 |
| ATOM | 1606 | NE2 | HIS | 212 | 29.114 | 19.288 | 14.590 | 1.00 63.71 |
| ATOM | 1607 | C | HIS | 212 | 25.665 | 23.656 | 12.412 | 1.00 53.29 |
| ATOM | 1608 | O | HIS | 212 | 26.014 | 23.883 | 11.251 | 1.00 52.77 |
| ATOM | 1609 | N | GLN | 213 | 24.496 | 24.058 | 12.895 | 1.00 51.08 |
| ATOM | 1610 | CA | GLN | 213 | 23.579 | 24.790 | 12.037 | 1.00 48.22 |
| ATOM | 1611 | CB | GLN | 213 | 22.135 | 24.347 | 12.298 | 1.00 49.39 |
| ATOM | 1612 | CG | GLN | 213 | 21.957 | 22.839 | 12.130 | 1.00 50.76 |
| ATOM | 1613 | CD | GLN | 213 | 20.507 | 22.410 | 11.965 | 1.00 51.82 |
| ATOM | 1614 | OE1 | GLN | 213 | 19.653 | 22.721 | 12.803 | 1.00 52.48 |
| ATOM | 1615 | NE2 | GLN | 213 | 20.223 | 21.679 | 10.883 | 1.00 51.72 |
| ATOM | 1616 | C | GLN | 213 | 23.746 | 26.289 | 12.202 | 1.00 45.19 |
| ATOM | 1617 | O | GLN | 213 | 22.978 | 27.077 | 11.654 | 1.00 45.00 |
| ATOM | 1618 | N | CYS | 214 | 24.759 | 26.686 | 12.957 | 1.00 41.87 |
| ATOM | 1619 | CA | CYS | 214 | 25.015 | 28.105 | 13.122 | 1.00 39.08 |
| ATOM | 1620 | CB | CYS | 214 | 25.907 | 28.386 | 14.332 | 1.00 39.18 |
| ATOM | 1621 | SG | CYS | 214 | 26.281 | 30.175 | 14.542 | 1.00 40.32 |
| ATOM | 1622 | C | CYS | 214 | 25.743 | 28.530 | 11.859 | 1.00 36.43 |
| ATOM | 1623 | O | CYS | 214 | 26.915 | 28.214 | 11.689 | 1.00 36.06 |
| ATOM | 1624 | N | GLU | 215 | 25.046 | 29.223 | 10.967 | 1.00 33.00 |
| ATOM | 1625 | CA | GLU | 215 | 25.664 | 29.672 | 9.736 | 1.00 30.60 |
| ATOM | 1626 | CB | GLU | 215 | 25.056 | 28.960 | 8.541 | 1.00 31.95 |
| ATOM | 1627 | CG | GLU | 215 | 25.289 | 27.466 | 8.561 | 1.00 33.57 |
| ATOM | 1628 | CD | GLU | 215 | 24.973 | 26.827 | 7.233 | 1.00 35.80 |
| ATOM | 1629 | OE1 | GLU | 215 | 25.719 | 27.094 | 6.264 | 1.00 37.32 |
| ATOM | 1630 | OE2 | GLU | 215 | 23.978 | 26.064 | 7.156 | 1.00 37.21 |
| ATOM | 1631 | C | GLU | 215 | 25.518 | 31.162 | 9.563 | 1.00 28.84 |
| ATOM | 1632 | O | GLU | 215 | 25.665 | 31.687 | 8.459 | 1.00 28.39 |
| ATOM | 1633 | N | VAL | 216 | 25.243 | 31.847 | 10.669 | 1.00 26.45 |
| ATOM | 1634 | CA | VAL | 216 | 25.083 | 33.291 | 10.648 | 1.00 23.67 |
| ATOM | 1635 | CB | VAL | 216 | 23.589 | 33.706 | 10.607 | 1.00 23.44 |
| ATOM | 1636 | CG1 | VAL | 216 | 23.485 | 35.214 | 10.492 | 1.00 22.72 |
| ATOM | 1637 | CG2 | VAL | 216 | 22.875 | 33.031 | 9.449 | 1.00 22.30 |
| ATOM | 1638 | C | VAL | 216 | 25.671 | 33.858 | 11.921 | 1.00 22.20 |
| ATOM | 1639 | O | VAL | 216 | 25.444 | 33.328 | 13.006 | 1.00 22.86 |
| ATOM | 1640 | N | GLY | 217 | 26.423 | 34.939 | 11.793 | 1.00 21.40 |
| ATOM | 1641 | CA | GLY | 217 | 26.997 | 35.554 | 12.965 | 1.00 21.14 |
| ATOM | 1642 | C | GLY | 217 | 26.524 | 36.994 | 13.022 | 1.00 22.30 |
| ATOM | 1643 | O | GLY | 217 | 26.432 | 37.677 | 11.983 | 1.00 22.05 |
| ATOM | 1644 | N | MSE | 218 | 26.201 | 37.454 | 14.228 | 1.00 23.03 |
| ATOM | 1645 | CA | MSE | 218 | 25.748 | 38.815 | 14.414 | 1.00 23.03 |
| ATOM | 1646 | CB | MSE | 218 | 24.208 | 38.880 | 14.445 | 1.00 25.98 |
| ATOM | 1647 | CG | MSE | 218 | 23.647 | 40.306 | 14.646 | 1.00 28.99 |
| ATOM | 1648 | SE | MSE | 218 | 21.806 | 40.486 | 14.543 | 1.00 35.34 |
| ATOM | 1649 | CE | MSE | 218 | 21.273 | 39.804 | 16.207 | 1.00 31.95 |

*FIG. 4CC*

| | | | | | | | | |
|---|---|---|---|---|---|---|---|---|
| ATOM | 1650 | C | MSE | 218 | 26.320 | 39.405 | 15.694 | 1.00 21.99 |
| ATOM | 1651 | O | MSE | 218 | 26.425 | 38.738 | 16.724 | 1.00 22.34 |
| ATOM | 1652 | N | ILE | 219 | 26.694 | 40.670 | 15.606 | 1.00 21.28 |
| ATOM | 1653 | CA | ILE | 219 | 27.240 | 41.402 | 16.720 | 1.00 20.85 |
| ATOM | 1654 | CB | ILE | 219 | 28.702 | 41.840 | 16.449 | 1.00 20.74 |
| ATOM | 1655 | CG2 | ILE | 219 | 29.164 | 42.757 | 17.558 | 1.00 19.65 |
| ATOM | 1656 | CG1 | ILE | 219 | 29.623 | 40.627 | 16.335 | 1.00 19.32 |
| ATOM | 1657 | CD1 | ILE | 219 | 29.656 | 39.770 | 17.596 | 1.00 20.63 |
| ATOM | 1658 | C | ILE | 219 | 26.413 | 42.676 | 16.838 | 1.00 21.47 |
| ATOM | 1659 | O | ILE | 219 | 26.297 | 43.431 | 15.868 | 1.00 21.30 |
| ATOM | 1660 | N | VAL | 220 | 25.823 | 42.908 | 18.003 | 1.00 21.91 |
| ATOM | 1661 | CA | VAL | 220 | 25.059 | 44.135 | 18.224 | 1.00 22.49 |
| ATOM | 1662 | CB | VAL | 220 | 23.563 | 43.873 | 18.479 | 1.00 22.04 |
| ATOM | 1663 | CG1 | VAL | 220 | 22.815 | 45.183 | 18.425 | 1.00 21.50 |
| ATOM | 1664 | CG2 | VAL | 220 | 23.007 | 42.901 | 17.463 | 1.00 22.03 |
| ATOM | 1665 | C | VAL | 220 | 25.650 | 44.775 | 19.477 | 1.00 23.27 |
| ATOM | 1666 | O | VAL | 220 | 25.095 | 44.642 | 20.575 | 1.00 23.94 |
| ATOM | 1667 | N | GLY | 221 | 26.795 | 45.436 | 19.312 | 1.00 22.78 |
| ATOM | 1668 | CA | GLY | 221 | 27.448 | 46.063 | 20.443 | 1.00 22.86 |
| ATOM | 1669 | C | GLY | 221 | 27.728 | 47.509 | 20.138 | 1.00 23.75 |
| ATOM | 1670 | O | GLY | 221 | 26.816 | 48.264 | 19.828 | 1.00 25.09 |
| ATOM | 1671 | N | THR | 222 | 28.988 | 47.906 | 20.233 | 1.00 24.06 |
| ATOM | 1672 | CA | THR | 222 | 29.375 | 49.277 | 19.939 | 1.00 24.06 |
| ATOM | 1673 | CB | THR | 222 | 30.893 | 49.423 | 19.960 | 1.00 24.59 |
| ATOM | 1674 | OG1 | THR | 222 | 31.377 | 49.051 | 21.258 | 1.00 26.00 |
| ATOM | 1675 | CG2 | THR | 222 | 31.299 | 50.860 | 19.640 | 1.00 24.67 |
| ATOM | 1676 | C | THR | 222 | 28.888 | 49.530 | 18.533 | 1.00 24.09 |
| ATOM | 1677 | O | THR | 222 | 28.248 | 50.530 | 18.259 | 1.00 24.72 |
| ATOM | 1678 | N | GLY | 223 | 29.211 | 48.597 | 17.646 | 1.00 24.40 |
| ATOM | 1679 | CA | GLY | 223 | 28.790 | 48.686 | 16.262 | 1.00 24.65 |
| ATOM | 1680 | C | GLY | 223 | 27.797 | 47.560 | 16.020 | 1.00 25.05 |
| ATOM | 1681 | O | GLY | 223 | 27.478 | 46.779 | 16.936 | 1.00 25.80 |
| ATOM | 1682 | N | CYS | 224 | 27.298 | 47.453 | 14.798 | 1.00 24.73 |
| ATOM | 1683 | CA | CYS | 224 | 26.338 | 46.405 | 14.504 | 1.00 24.18 |
| ATOM | 1684 | CB | CYS | 224 | 24.928 | 46.958 | 14.682 | 1.00 24.47 |
| ATOM | 1685 | SG | CYS | 224 | 23.640 | 45.925 | 13.998 | 1.00 25.11 |
| ATOM | 1686 | C | CYS | 224 | 26.550 | 45.895 | 13.085 | 1.00 23.65 |
| ATOM | 1687 | O | CYS | 224 | 26.618 | 46.683 | 12.144 | 1.00 24.07 |
| ATOM | 1688 | N | ASN | 225 | 26.650 | 44.578 | 12.941 | 1.00 23.06 |
| ATOM | 1689 | CA | ASN | 225 | 26.883 | 43.963 | 11.638 | 1.00 23.27 |
| ATOM | 1690 | CB | ASN | 225 | 28.346 | 44.230 | 11.210 | 1.00 26.15 |
| ATOM | 1691 | CG | ASN | 225 | 28.831 | 43.296 | 10.098 | 1.00 27.94 |
| ATOM | 1692 | OD1 | ASN | 225 | 28.271 | 43.265 | 8.997 | 1.00 29.23 |
| ATOM | 1693 | ND2 | ASN | 225 | 29.878 | 42.524 | 10.393 | 1.00 28.62 |
| ATOM | 1694 | C | ASN | 225 | 26.603 | 42.459 | 11.740 | 1.00 21.80 |
| ATOM | 1695 | O | ASN | 225 | 26.291 | 41.954 | 12.827 | 1.00 20.54 |
| ATOM | 1696 | N | ALA | 226 | 26.709 | 41.759 | 10.610 | 1.00 19.99 |
| ATOM | 1697 | CA | ALA | 226 | 26.478 | 40.322 | 10.566 | 1.00 19.47 |
| ATOM | 1698 | CB | ALA | 226 | 24.994 | 40.032 | 10.443 | 1.00 20.99 |
| ATOM | 1699 | C | ALA | 226 | 27.194 | 39.723 | 9.378 | 1.00 18.72 |
| ATOM | 1700 | O | ALA | 226 | 27.529 | 40.428 | 8.415 | 1.00 17.97 |
| ATOM | 1701 | N | CYS | 227 | 27.404 | 38.415 | 9.439 | 1.00 18.36 |
| ATOM | 1702 | CA | CYS | 227 | 28.077 | 37.675 | 8.368 | 1.00 19.35 |
| ATOM | 1703 | CB | CYS | 227 | 29.523 | 37.396 | 8.751 | 1.00 18.42 |
| ATOM | 1704 | SG | CYS | 227 | 29.556 | 36.326 | 10.207 | 1.00 20.13 |
| ATOM | 1705 | C | CYS | 227 | 27.331 | 36.352 | 8.291 | 1.00 19.81 |
| ATOM | 1706 | O | CYS | 227 | 26.702 | 35.951 | 9.280 | 1.00 20.62 |

*FIG. 4DD*

| | | | | | | | | |
|---|---|---|---|---|---|---|---|---|
| ATOM | 1707 | N | TYR | 228 | 27.402 | 35.668 | 7.148 | 1.00 20.49 |
| ATOM | 1708 | CA | TYR | 228 | 26.705 | 34.384 | 6.989 | 1.00 20.56 |
| ATOM | 1709 | CB | TYR | 228 | 25.242 | 34.633 | 6.624 | 1.00 17.90 |
| ATOM | 1710 | CG | TYR | 228 | 25.096 | 35.134 | 5.204 | 1.00 15.65 |
| ATOM | 1711 | CD1 | TYR | 228 | 24.922 | 34.249 | 4.145 | 1.00 15.81 |
| ATOM | 1712 | CE1 | TYR | 228 | 24.885 | 34.701 | 2.823 | 1.00 15.89 |
| ATOM | 1713 | CD2 | TYR | 228 | 25.221 | 36.483 | 4.913 | 1.00 15.28 |
| ATOM | 1714 | CE2 | TYR | 228 | 25.186 | 36.949 | 3.601 | 1.00 16.08 |
| ATOM | 1715 | CZ | TYR | 228 | 25.022 | 36.051 | 2.564 | 1.00 16.76 |
| ATOM | 1716 | OH | TYR | 228 | 25.033 | 36.505 | 1.263 | 1.00 18.93 |
| ATOM | 1717 | C | TYR | 228 | 27.345 | 33.539 | 5.887 | 1.00 22.19 |
| ATOM | 1718 | O | TYR | 228 | 28.174 | 34.024 | 5.112 | 1.00 21.49 |
| ATOM | 1719 | N | MSE | 229 | 26.928 | 32.278 | 5.808 | 1.00 24.74 |
| ATOM | 1720 | CA | MSE | 229 | 27.438 | 31.349 | 4.808 | 1.00 26.69 |
| ATOM | 1721 | CB | MSE | 229 | 27.342 | 29.918 | 5.339 | 1.00 28.61 |
| ATOM | 1722 | CG | MSE | 229 | 28.167 | 29.637 | 6.598 | 1.00 32.37 |
| ATOM | 1723 | SE | MSE | 229 | 29.987 | 30.056 | 6.460 | 1.00 41.17 |
| ATOM | 1724 | CE | MSE | 229 | 30.544 | 28.874 | 5.098 | 1.00 36.30 |
| ATOM | 1725 | C | MSE | 229 | 26.663 | 31.470 | 3.481 | 1.00 27.83 |
| ATOM | 1726 | O | MSE | 229 | 25.535 | 30.994 | 3.363 | 1.00 28.02 |
| ATOM | 1727 | N | GLU | 230 | 27.282 | 32.109 | 2.492 | 1.00 29.19 |
| ATOM | 1728 | CA | GLU | 230 | 26.688 | 32.296 | 1.172 | 1.00 29.81 |
| ATOM | 1729 | CB | GLU | 230 | 27.165 | 33.623 | 0.577 | 1.00 30.83 |
| ATOM | 1730 | CG | GLU | 230 | 26.685 | 33.922 | -0.843 | 1.00 32.33 |
| ATOM | 1731 | CD | GLU | 230 | 25.173 | 33.825 | -0.989 | 1.00 34.04 |
| ATOM | 1732 | OE1 | GLU | 230 | 24.663 | 32.698 | -1.222 | 1.00 34.43 |
| ATOM | 1733 | OE2 | GLU | 230 | 24.497 | 34.878 | -0.858 | 1.00 33.65 |
| ATOM | 1734 | C | GLU | 230 | 27.127 | 31.143 | 0.282 | 1.00 30.91 |
| ATOM | 1735 | O | GLU | 230 | 27.958 | 30.319 | 0.685 | 1.00 30.80 |
| ATOM | 1736 | N | GLU | 231 | 26.562 | 31.078 | -0.923 | 1.00 32.47 |
| ATOM | 1737 | CA | GLU | 231 | 26.885 | 30.024 | -1.883 | 1.00 34.04 |
| ATOM | 1738 | CB | GLU | 231 | 25.668 | 29.696 | -2.745 | 1.00 34.21 |
| ATOM | 1739 | CG | GLU | 231 | 24.408 | 29.396 | -1.979 | 1.00 34.89 |
| ATOM | 1740 | CD | GLU | 231 | 24.452 | 28.054 | -1.296 | 1.00 36.36 |
| ATOM | 1741 | OE1 | GLU | 231 | 24.745 | 27.064 | -2.002 | 1.00 36.80 |
| ATOM | 1742 | OE2 | GLU | 231 | 24.182 | 27.981 | -0.067 | 1.00 36.72 |
| ATOM | 1743 | C | GLU | 231 | 27.997 | 30.550 | -2.777 | 1.00 35.65 |
| ATOM | 1744 | O | GLU | 231 | 27.889 | 31.663 | -3.304 | 1.00 35.42 |
| ATOM | 1745 | N | MSE | 232 | 29.060 | 29.758 | -2.952 | 1.00 37.13 |
| ATOM | 1746 | CA | MSE | 232 | 30.188 | 30.181 | -3.780 | 1.00 38.19 |
| ATOM | 1747 | CB | MSE | 232 | 31.191 | 29.036 | -3.935 | 1.00 41.27 |
| ATOM | 1748 | CG | MSE | 232 | 32.195 | 28.912 | -2.765 | 1.00 45.40 |
| ATOM | 1749 | SE | MSE | 232 | 33.237 | 30.431 | -2.467 | 1.00 52.07 |
| ATOM | 1750 | CE | MSE | 232 | 34.286 | 30.483 | -3.969 | 1.00 48.20 |
| ATOM | 1751 | C | MSE | 232 | 29.694 | 30.664 | -5.137 | 1.00 38.02 |
| ATOM | 1752 | O | MSE | 232 | 30.179 | 31.656 | -5.678 | 1.00 36.84 |
| ATOM | 1753 | N | GLN | 233 | 28.698 | 29.970 | -5.668 | 1.00 38.35 |
| ATOM | 1754 | CA | GLN | 233 | 28.110 | 30.331 | -6.948 | 1.00 38.79 |
| ATOM | 1755 | CB | GLN | 233 | 26.954 | 29.373 | -7.257 | 1.00 40.19 |
| ATOM | 1756 | CG | GLN | 233 | 25.658 | 30.041 | -7.672 | 1.00 41.80 |
| ATOM | 1757 | CD | GLN | 233 | 24.460 | 29.119 | -7.510 | 1.00 43.22 |
| ATOM | 1758 | OE1 | GLN | 233 | 24.226 | 28.582 | -6.424 | 1.00 44.27 |
| ATOM | 1759 | NE2 | GLN | 233 | 23.688 | 28.936 | -8.586 | 1.00 43.87 |
| ATOM | 1760 | C | GLN | 233 | 27.615 | 31.777 | -6.936 | 1.00 38.45 |
| ATOM | 1761 | O | GLN | 233 | 27.495 | 32.407 | -7.984 | 1.00 39.07 |
| ATOM | 1762 | N | ASN | 234 | 27.329 | 32.313 | -5.753 | 1.00 37.79 |
| ATOM | 1763 | CA | ASN | 234 | 26.840 | 33.687 | -5.668 | 1.00 36.56 |

FIG. 4EE

```
ATOM  1764  CB   ASN  234    25.657  33.771   -4.706  1.00  37.03
ATOM  1765  CG   ASN  234    24.505  32.864   -5.119  1.00  36.83
ATOM  1766  OD1  ASN  234    24.152  32.793   -6.299  1.00  36.50
ATOM  1767  ND2  ASN  234    23.910  32.173   -4.146  1.00  36.25
ATOM  1768  C    ASN  234    27.919  34.676   -5.250  1.00  35.71
ATOM  1769  O    ASN  234    27.712  35.890   -5.301  1.00  35.11
ATOM  1770  N    VAL  235    29.069  34.156   -4.837  1.00  35.22
ATOM  1771  CA   VAL  235    30.177  35.009   -4.439  1.00  34.85
ATOM  1772  CB   VAL  235    31.056  34.321   -3.384  1.00  34.01
ATOM  1773  CG1  VAL  235    31.949  35.343   -2.717  1.00  32.35
ATOM  1774  CG2  VAL  235    30.185  33.576   -2.376  1.00  32.63
ATOM  1775  C    VAL  235    30.999  35.209   -5.706  1.00  35.79
ATOM  1776  O    VAL  235    32.011  34.548   -5.910  1.00  35.65
ATOM  1777  N    GLU  236    30.556  36.125   -6.556  1.00  37.55
ATOM  1778  CA   GLU  236    31.220  36.383   -7.830  1.00  39.52
ATOM  1779  CB   GLU  236    30.337  37.284   -8.701  1.00  39.67
ATOM  1780  CG   GLU  236    29.242  36.539   -9.448  1.00  41.02
ATOM  1781  CD   GLU  236    28.214  37.467  -10.072  1.00  42.58
ATOM  1782  OE1  GLU  236    28.607  38.529  -10.630  1.00  42.67
ATOM  1783  OE2  GLU  236    27.009  37.121  -10.011  1.00  43.02
ATOM  1784  C    GLU  236    32.631  36.961   -7.782  1.00  40.97
ATOM  1785  O    GLU  236    33.328  36.967   -8.803  1.00  42.27
ATOM  1786  N    LEU  237    33.064  37.457   -6.628  1.00  41.32
ATOM  1787  CA   LEU  237    34.408  38.017   -6.538  1.00  41.63
ATOM  1788  CB   LEU  237    34.438  39.163   -5.537  1.00  41.68
ATOM  1789  CG   LEU  237    33.545  40.367   -5.820  1.00  42.50
ATOM  1790  CD1  LEU  237    33.630  41.301   -4.623  1.00  44.17
ATOM  1791  CD2  LEU  237    33.984  41.101   -7.085  1.00  42.46
ATOM  1792  C    LEU  237    35.454  36.970   -6.148  1.00  42.43
ATOM  1793  O    LEU  237    36.636  37.294   -6.010  1.00  42.30
ATOM  1794  N    VAL  238    35.019  35.724   -5.967  1.00  42.96
ATOM  1795  CA   VAL  238    35.922  34.629   -5.606  1.00  43.89
ATOM  1796  CB   VAL  238    35.917  34.380   -4.097  1.00  42.33
ATOM  1797  CG1  VAL  238    36.722  33.136   -3.769  1.00  41.32
ATOM  1798  CG2  VAL  238    36.503  35.578   -3.385  1.00  42.74
ATOM  1799  C    VAL  238    35.520  33.337   -6.313  1.00  45.65
ATOM  1800  O    VAL  238    34.755  32.555   -5.770  1.00  46.15
ATOM  1801  N    GLU  239    36.069  33.116   -7.510  1.00  47.60
ATOM  1802  CA   GLU  239    35.769  31.947   -8.346  1.00  48.96
ATOM  1803  CB   GLU  239    36.819  31.793   -9.448  1.00  51.17
ATOM  1804  CG   GLU  239    37.000  33.026  -10.290  1.00  53.95
ATOM  1805  CD   GLU  239    37.817  34.066   -9.570  1.00  56.27
ATOM  1806  OE1  GLU  239    39.070  33.982   -9.637  1.00  58.40
ATOM  1807  OE2  GLU  239    37.211  34.950   -8.918  1.00  57.25
ATOM  1808  C    GLU  239    35.599  30.594   -7.675  1.00  48.87
ATOM  1809  O    GLU  239    36.272  30.274   -6.701  1.00  48.25
ATOM  1810  N    GLY  240    34.705  29.797   -8.252  1.00  49.09
ATOM  1811  CA   GLY  240    34.412  28.469   -7.750  1.00  50.05
ATOM  1812  C    GLY  240    32.967  28.418   -7.296  1.00  51.04
ATOM  1813  O    GLY  240    32.482  29.379   -6.712  1.00  52.00
ATOM  1814  N    ASP  241    32.259  27.332   -7.580  1.00  51.38
ATOM  1815  CA   ASP  241    30.882  27.214   -7.127  1.00  52.10
ATOM  1816  CB   ASP  241    29.963  26.766   -8.252  1.00  52.95
ATOM  1817  CG   ASP  241    30.186  27.534   -9.529  1.00  53.84
ATOM  1818  OD1  ASP  241    30.046  28.779   -9.522  1.00  53.20
ATOM  1819  OD2  ASP  241    30.496  26.875  -10.546  1.00  53.97
ATOM  1820  C    ASP  241    30.924  26.122   -6.083  1.00  52.90
```

*FIG. 4FF*

```
ATOM  1821  O    ASP  241      29.898  25.563  -5.701  1.00  53.59
ATOM  1822  N    GLU  242      32.131  25.816  -5.626  1.00  53.45
ATOM  1823  CA   GLU  242      32.325  24.760  -4.646  1.00  53.65
ATOM  1824  CB   GLU  242      33.785  24.299  -4.670  1.00  55.19
ATOM  1825  CG   GLU  242      34.056  23.062  -3.826  1.00  57.57
ATOM  1826  CD   GLU  242      35.527  22.672  -3.811  1.00  58.85
ATOM  1827  OE1  GLU  242      36.063  22.340  -4.893  1.00  59.63
ATOM  1828  OE2  GLU  242      36.143  22.701  -2.717  1.00  59.85
ATOM  1829  C    GLU  242      31.933  25.159  -3.229  1.00  52.66
ATOM  1830  O    GLU  242      32.469  26.113  -2.661  1.00  53.15
ATOM  1831  N    GLY  243      30.987  24.418  -2.665  1.00  51.11
ATOM  1832  CA   GLY  243      30.545  24.673  -1.305  1.00  48.74
ATOM  1833  C    GLY  243      30.200  26.110  -0.967  1.00  46.87
ATOM  1834  O    GLY  243      29.879  26.917  -1.850  1.00  46.49
ATOM  1835  N    ARG  244      30.288  26.421   0.326  1.00  44.89
ATOM  1836  CA   ARG  244      29.967  27.748   0.838  1.00  43.27
ATOM  1837  CB   ARG  244      28.852  27.639   1.873  1.00  42.24
ATOM  1838  CG   ARG  244      27.571  27.040   1.339  1.00  42.16
ATOM  1839  CD   ARG  244      26.442  27.153   2.356  1.00  41.35
ATOM  1840  NE   ARG  244      25.254  26.425   1.925  1.00  39.30
ATOM  1841  CZ   ARG  244      24.702  25.446   2.630  1.00  39.15
ATOM  1842  NH1  ARG  244      25.236  25.085   3.794  1.00  38.10
ATOM  1843  NH2  ARG  244      23.627  24.821   2.168  1.00  38.77
ATOM  1844  C    ARG  244      31.121  28.524   1.465  1.00  42.34
ATOM  1845  O    ARG  244      32.089  27.945   1.958  1.00  41.77
ATOM  1846  N    MSE  245      30.990  29.849   1.446  1.00  42.07
ATOM  1847  CA   MSE  245      31.977  30.745   2.042  1.00  41.32
ATOM  1848  CB   MSE  245      32.846  31.391   0.974  1.00  42.25
ATOM  1849  CG   MSE  245      33.870  32.345   1.566  1.00  44.07
ATOM  1850  SE   MSE  245      34.884  33.206   0.332  1.00  47.16
ATOM  1851  CE   MSE  245      36.149  31.909  -0.005  1.00  44.40
ATOM  1852  C    MSE  245      31.324  31.863   2.863  1.00  40.37
ATOM  1853  O    MSE  245      30.525  32.644   2.338  1.00  40.13
ATOM  1854  N    CYS  246      31.664  31.940   4.148  1.00  38.95
ATOM  1855  CA   CYS  246      31.125  32.990   5.001  1.00  37.00
ATOM  1856  CB   CYS  246      31.794  32.953   6.376  1.00  37.69
ATOM  1857  SG   CYS  246      31.231  34.229   7.567  1.00  38.96
ATOM  1858  C    CYS  246      31.422  34.320   4.311  1.00  35.82
ATOM  1859  O    CYS  246      32.484  34.497   3.706  1.00  34.54
ATOM  1860  N    VAL  247      30.466  35.240   4.388  1.00  34.51
ATOM  1861  CA   VAL  247      30.591  36.566   3.782  1.00  32.46
ATOM  1862  CB   VAL  247      29.609  36.751   2.588  1.00  32.34
ATOM  1863  CG1  VAL  247      29.709  38.170   2.038  1.00  31.78
ATOM  1864  CG2  VAL  247      29.930  35.750   1.486  1.00  32.04
ATOM  1865  C    VAL  247      30.239  37.580   4.863  1.00  32.03
ATOM  1866  O    VAL  247      29.291  37.377   5.628  1.00  33.28
ATOM  1867  N    ASN  248      31.011  38.657   4.931  1.00  29.34
ATOM  1868  CA   ASN  248      30.792  39.699   5.917  1.00  27.36
ATOM  1869  CB   ASN  248      32.147  40.219   6.401  1.00  28.42
ATOM  1870  CG   ASN  248      32.031  41.471   7.253  1.00  29.34
ATOM  1871  OD1  ASN  248      30.975  41.774   7.816  1.00  29.82
ATOM  1872  ND2  ASN  248      33.141  42.201   7.374  1.00  29.54
ATOM  1873  C    ASN  248      29.983  40.798   5.257  1.00  27.10
ATOM  1874  O    ASN  248      30.531  41.618   4.503  1.00  26.98
ATOM  1875  N    THR  249      28.679  40.823   5.544  1.00  26.01
ATOM  1876  CA   THR  249      27.778  41.809   4.937  1.00  23.85
ATOM  1877  CB   THR  249      26.325  41.634   5.424  1.00  23.81
```

*FIG. 4GG*

```
ATOM   1878  OG1  THR  249     26.228  42.100   6.775  1.00  25.10
ATOM   1879  CG2  THR  249     25.899  40.156   5.380  1.00  22.15
ATOM   1880  C    THR  249     28.208  43.226   5.270  1.00  24.20
ATOM   1881  O    THR  249     28.023  44.143   4.467  1.00  23.38
ATOM   1882  N    GLU  250     28.777  43.406   6.462  1.00  24.31
ATOM   1883  CA   GLU  250     29.219  44.733   6.891  1.00  23.61
ATOM   1884  CB   GLU  250     30.446  45.145   6.060  1.00  23.87
ATOM   1885  CG   GLU  250     31.242  46.362   6.571  1.00  25.94
ATOM   1886  CD   GLU  250     32.237  46.041   7.700  1.00  25.83
ATOM   1887  OE1  GLU  250     32.728  44.893   7.813  1.00  25.67
ATOM   1888  OE2  GLU  250     32.552  46.960   8.473  1.00  26.46
ATOM   1889  C    GLU  250     28.003  45.624   6.589  1.00  23.30
ATOM   1890  O    GLU  250     28.110  46.648   5.896  1.00  23.33
ATOM   1891  N    TRP  251     26.841  45.208   7.096  1.00  22.28
ATOM   1892  CA   TRP  251     25.609  45.940   6.840  1.00  22.36
ATOM   1893  CB   TRP  251     24.376  45.077   7.133  1.00  20.65
ATOM   1894  CG   TRP  251     24.133  44.726   8.543  1.00  18.29
ATOM   1895  CD2  TRP  251     23.308  43.648   9.016  1.00  16.51
ATOM   1896  CE2  TRP  251     23.279  43.725  10.424  1.00  15.08
ATOM   1897  CE3  TRP  251     22.589  42.635   8.384  1.00  16.17
ATOM   1898  CD1  TRP  251     24.565  45.395   9.652  1.00  17.71
ATOM   1899  NE1  TRP  251     24.051  44.795  10.795  1.00  17.10
ATOM   1900  CZ2  TRP  251     22.567  42.830  11.201  1.00  14.23
ATOM   1901  CZ3  TRP  251     21.872  41.737   9.171  1.00  15.72
ATOM   1902  CH2  TRP  251     21.869  41.842  10.559  1.00  14.23
ATOM   1903  C    TRP  251     25.445  47.283   7.523  1.00  23.49
ATOM   1904  O    TRP  251     24.541  48.044   7.167  1.00  23.95
ATOM   1905  N    GLY  252     26.302  47.579   8.500  1.00  24.44
ATOM   1906  CA   GLY  252     26.214  48.857   9.179  1.00  25.17
ATOM   1907  C    GLY  252     26.195  49.979   8.152  1.00  26.19
ATOM   1908  O    GLY  252     25.715  51.086   8.429  1.00  26.19
ATOM   1909  N    ALA  253     26.714  49.675   6.960  1.00  26.83
ATOM   1910  CA   ALA  253     26.791  50.622   5.851  1.00  27.86
ATOM   1911  CB   ALA  253     27.822  50.148   4.851  1.00  27.90
ATOM   1912  C    ALA  253     25.448  50.834   5.144  1.00  28.52
ATOM   1913  O    ALA  253     25.249  51.834   4.448  1.00  27.73
ATOM   1914  N    PHE  254     24.536  49.884   5.314  1.00  30.23
ATOM   1915  CA   PHE  254     23.224  49.974   4.696  1.00  31.42
ATOM   1916  CB   PHE  254     22.289  48.947   5.314  1.00  31.71
ATOM   1917  CG   PHE  254     20.899  48.995   4.768  1.00  31.90
ATOM   1918  CD1  PHE  254     20.655  48.736   3.429  1.00  31.47
ATOM   1919  CD2  PHE  254     19.824  49.273   5.600  1.00  32.95
ATOM   1920  CE1  PHE  254     19.367  48.746   2.927  1.00  31.38
ATOM   1921  CE2  PHE  254     18.518  49.285   5.096  1.00  32.69
ATOM   1922  CZ   PHE  254     18.295  49.021   3.763  1.00  31.47
ATOM   1923  C    PHE  254     22.664  51.367   4.928  1.00  32.56
ATOM   1924  O    PHE  254     22.638  51.839   6.064  1.00  33.19
ATOM   1925  N    GLY  255     22.227  52.017   3.849  1.00  33.62
ATOM   1926  CA   GLY  255     21.674  53.354   3.947  1.00  34.98
ATOM   1927  C    GLY  255     22.673  54.429   3.565  1.00  36.85
ATOM   1928  O    GLY  255     22.317  55.604   3.424  1.00  36.70
ATOM   1929  N    ASP  256     23.932  54.038   3.395  1.00  38.95
ATOM   1930  CA   ASP  256     24.966  55.000   3.038  1.00  41.47
ATOM   1931  CB   ASP  256     26.349  54.347   3.088  1.00  41.77
ATOM   1932  CG   ASP  256     26.880  54.224   4.502  1.00  42.36
ATOM   1933  OD1  ASP  256     26.573  55.120   5.322  1.00  43.08
ATOM   1934  OD2  ASP  256     27.617  53.251   4.791  1.00  42.28
```

*FIG. 4HH*

```
ATOM   1935  C    ASP  256     24.744  55.636   1.666  1.00 43.10
ATOM   1936  O    ASP  256     25.489  56.533   1.261  1.00 44.08
ATOM   1937  N    SER  257     23.729  55.171   0.946  1.00 44.19
ATOM   1938  CA   SER  257     23.427  55.738  -0.363  1.00 45.32
ATOM   1939  CB   SER  257     23.714  54.713  -1.467  1.00 45.78
ATOM   1940  OG   SER  257     22.845  53.601  -1.375  1.00 46.48
ATOM   1941  C    SER  257     21.967  56.204  -0.423  1.00 45.41
ATOM   1942  O    SER  257     21.378  56.316  -1.501  1.00 46.14
ATOM   1943  N    GLY  258     21.393  56.466   0.751  1.00 45.52
ATOM   1944  CA   GLY  258     20.018  56.933   0.835  1.00 45.22
ATOM   1945  C    GLY  258     18.922  55.896   1.042  1.00 45.11
ATOM   1946  O    GLY  258     17.745  56.253   1.068  1.00 45.45
ATOM   1947  N    GLU  259     19.284  54.627   1.205  1.00 44.67
ATOM   1948  CA   GLU  259     18.288  53.572   1.380  1.00 44.04
ATOM   1949  CB   GLU  259     18.954  52.187   1.415  1.00 44.23
ATOM   1950  CG   GLU  259     19.952  51.916   0.295  1.00 44.88
ATOM   1951  CD   GLU  259     21.318  52.552   0.548  1.00 45.53
ATOM   1952  OE1  GLU  259     21.381  53.785   0.753  1.00 44.98
ATOM   1953  OE2  GLU  259     22.335  51.817   0.537  1.00 45.95
ATOM   1954  C    GLU  259     17.462  53.749   2.647  1.00 43.91
ATOM   1955  O    GLU  259     16.461  53.061   2.836  1.00 43.49
ATOM   1956  N    LEU  260     17.875  54.661   3.520  1.00 43.87
ATOM   1957  CA   LEU  260     17.143  54.865   4.765  1.00 44.40
ATOM   1958  CB   LEU  260     18.023  54.513   5.967  1.00 44.36
ATOM   1959  CG   LEU  260     18.398  53.041   6.153  1.00 44.87
ATOM   1960  CD1  LEU  260     19.315  52.879   7.369  1.00 44.30
ATOM   1961  CD2  LEU  260     17.127  52.216   6.307  1.00 44.88
ATOM   1962  C    LEU  260     16.632  56.282   4.932  1.00 44.59
ATOM   1963  O    LEU  260     15.744  56.534   5.749  1.00 44.72
ATOM   1964  N    ASP  261     17.200  57.202   4.161  1.00 44.48
ATOM   1965  CA   ASP  261     16.821  58.608   4.234  1.00 44.18
ATOM   1966  CB   ASP  261     16.813  59.224   2.841  1.00 44.99
ATOM   1967  CG   ASP  261     18.192  59.310   2.247  1.00 46.23
ATOM   1968  OD1  ASP  261     19.165  58.994   2.980  1.00 46.42
ATOM   1969  OD2  ASP  261     18.296  59.697   1.055  1.00 46.79
ATOM   1970  C    ASP  261     15.482  58.885   4.892  1.00 43.00
ATOM   1971  O    ASP  261     15.415  59.592   5.898  1.00 42.63
ATOM   1972  N    GLU  262     14.424  58.317   4.320  1.00 41.88
ATOM   1973  CA   GLU  262     13.070  58.525   4.810  1.00 41.00
ATOM   1974  CB   GLU  262     12.088  57.744   3.940  1.00 41.65
ATOM   1975  CG   GLU  262     12.249  56.254   3.999  1.00 43.54
ATOM   1976  CD   GLU  262     11.359  55.562   2.996  1.00 45.44
ATOM   1977  OE1  GLU  262     11.715  55.561   1.800  1.00 47.21
ATOM   1978  OE2  GLU  262     10.296  55.031   3.391  1.00 47.29
ATOM   1979  C    GLU  262     12.830  58.211   6.286  1.00 39.99
ATOM   1980  O    GLU  262     11.997  58.852   6.918  1.00 40.22
ATOM   1981  N    PHE  263     13.545  57.238   6.845  1.00 38.83
ATOM   1982  CA   PHE  263     13.360  56.908   8.258  1.00 37.00
ATOM   1983  CB   PHE  263     13.684  55.430   8.512  1.00 34.37
ATOM   1984  CG   PHE  263     12.828  54.476   7.717  1.00 32.41
ATOM   1985  CD1  PHE  263     13.366  53.753   6.660  1.00 30.67
ATOM   1986  CD2  PHE  263     11.474  54.317   8.012  1.00 30.95
ATOM   1987  CE1  PHE  263     12.567  52.886   5.909  1.00 29.82
ATOM   1988  CE2  PHE  263     10.667  53.450   7.261  1.00 28.87
ATOM   1989  CZ   PHE  263     11.214  52.737   6.213  1.00 29.09
ATOM   1990  C    PHE  263     14.197  57.797   9.190  1.00 36.78
ATOM   1991  O    PHE  263     13.809  58.041  10.327  1.00 37.58
```

*FIG. 4II*

| ATOM | 1992 | N | LEU | 264 | 15.328 | 58.301 | 8.712 | 1.00 | 36.72 |
|---|---|---|---|---|---|---|---|---|---|
| ATOM | 1993 | CA | LEU | 264 | 16.193 | 59.142 | 9.542 | 1.00 | 37.11 |
| ATOM | 1994 | CB | LEU | 264 | 17.389 | 59.638 | 8.725 | 1.00 | 36.98 |
| ATOM | 1995 | CG | LEU | 264 | 18.131 | 58.621 | 7.852 | 1.00 | 36.59 |
| ATOM | 1996 | CD1 | LEU | 264 | 19.233 | 59.346 | 7.077 | 1.00 | 35.39 |
| ATOM | 1997 | CD2 | LEU | 264 | 18.701 | 57.503 | 8.717 | 1.00 | 35.46 |
| ATOM | 1998 | C | LEU | 264 | 15.482 | 60.350 | 10.158 | 1.00 | 37.28 |
| ATOM | 1999 | O | LEU | 264 | 14.879 | 61.148 | 9.451 | 1.00 | 38.03 |
| ATOM | 2000 | N | LEU | 265 | 15.574 | 60.480 | 11.479 | 1.00 | 37.63 |
| ATOM | 2001 | CA | LEU | 265 | 14.965 | 61.585 | 12.215 | 1.00 | 37.33 |
| ATOM | 2002 | CB | LEU | 265 | 14.380 | 61.070 | 13.527 | 1.00 | 36.25 |
| ATOM | 2003 | CG | LEU | 265 | 13.529 | 59.807 | 13.417 | 1.00 | 35.76 |
| ATOM | 2004 | CD1 | LEU | 265 | 13.157 | 59.295 | 14.808 | 1.00 | 35.17 |
| ATOM | 2005 | CD2 | LEU | 265 | 12.292 | 60.120 | 12.598 | 1.00 | 35.59 |
| ATOM | 2006 | C | LEU | 265 | 16.054 | 62.613 | 12.521 | 1.00 | 38.22 |
| ATOM | 2007 | O | LEU | 265 | 17.239 | 62.285 | 12.486 | 1.00 | 38.34 |
| ATOM | 2008 | N | GLU | 266 | 15.653 | 63.844 | 12.832 | 1.00 | 39.22 |
| ATOM | 2009 | CA | GLU | 266 | 16.599 | 64.922 | 13.137 | 1.00 | 40.56 |
| ATOM | 2010 | CB | GLU | 266 | 15.874 | 66.101 | 13.813 | 1.00 | 41.82 |
| ATOM | 2011 | CG | GLU | 266 | 15.277 | 65.777 | 15.196 | 1.00 | 44.28 |
| ATOM | 2012 | CD | GLU | 266 | 14.612 | 66.974 | 15.886 | 1.00 | 44.95 |
| ATOM | 2013 | OE1 | GLU | 266 | 13.543 | 67.432 | 15.410 | 1.00 | 45.08 |
| ATOM | 2014 | OE2 | GLU | 266 | 15.163 | 67.452 | 16.910 | 1.00 | 45.53 |
| ATOM | 2015 | C | GLU | 266 | 17.733 | 64.435 | 14.036 | 1.00 | 40.54 |
| ATOM | 2016 | O | GLU | 266 | 18.910 | 64.657 | 13.750 | 1.00 | 40.69 |
| ATOM | 2017 | N | TYR | 267 | 17.366 | 63.760 | 15.121 | 1.00 | 40.61 |
| ATOM | 2018 | CA | TYR | 267 | 18.342 | 63.234 | 16.062 | 1.00 | 40.30 |
| ATOM | 2019 | CB | TYR | 267 | 17.639 | 62.364 | 17.110 | 1.00 | 39.44 |
| ATOM | 2020 | CG | TYR | 267 | 16.216 | 62.784 | 17.423 | 1.00 | 38.98 |
| ATOM | 2021 | CD1 | TYR | 267 | 15.134 | 61.967 | 17.066 | 1.00 | 38.66 |
| ATOM | 2022 | CE1 | TYR | 267 | 13.813 | 62.342 | 17.349 | 1.00 | 38.28 |
| ATOM | 2023 | CD2 | TYR | 267 | 15.943 | 63.995 | 18.075 | 1.00 | 38.72 |
| ATOM | 2024 | CE2 | TYR | 267 | 14.619 | 64.381 | 18.364 | 1.00 | 38.45 |
| ATOM | 2025 | CZ | TYR | 267 | 13.564 | 63.548 | 17.996 | 1.00 | 38.30 |
| ATOM | 2026 | OH | TYR | 267 | 12.267 | 63.923 | 18.251 | 1.00 | 37.22 |
| ATOM | 2027 | C | TYR | 267 | 19.381 | 62.403 | 15.296 | 1.00 | 40.27 |
| ATOM | 2028 | O | TYR | 267 | 20.580 | 62.469 | 15.579 | 1.00 | 40.14 |
| ATOM | 2029 | N | ASP | 268 | 18.909 | 61.626 | 14.324 | 1.00 | 40.61 |
| ATOM | 2030 | CA | ASP | 268 | 19.781 | 60.790 | 13.511 | 1.00 | 40.87 |
| ATOM | 2031 | CB | ASP | 268 | 18.946 | 59.920 | 12.566 | 1.00 | 39.36 |
| ATOM | 2032 | CG | ASP | 268 | 18.183 | 58.843 | 13.301 | 1.00 | 38.52 |
| ATOM | 2033 | OD1 | ASP | 268 | 18.819 | 58.118 | 14.082 | 1.00 | 39.79 |
| ATOM | 2034 | OD2 | ASP | 268 | 16.961 | 58.711 | 13.110 | 1.00 | 36.13 |
| ATOM | 2035 | C | ASP | 268 | 20.764 | 61.643 | 12.712 | 1.00 | 41.97 |
| ATOM | 2036 | O | ASP | 268 | 21.956 | 61.339 | 12.667 | 1.00 | 42.91 |
| ATOM | 2037 | N | ARG | 269 | 20.266 | 62.710 | 12.090 | 1.00 | 42.73 |
| ATOM | 2038 | CA | ARG | 269 | 21.113 | 63.606 | 11.310 | 1.00 | 43.23 |
| ATOM | 2039 | CB | ARG | 269 | 20.302 | 64.793 | 10.786 | 1.00 | 45.34 |
| ATOM | 2040 | CG | ARG | 269 | 18.923 | 64.464 | 10.223 | 1.00 | 47.46 |
| ATOM | 2041 | CD | ARG | 269 | 19.000 | 63.819 | 8.864 | 1.00 | 49.22 |
| ATOM | 2042 | NE | ARG | 269 | 17.667 | 63.552 | 8.337 | 1.00 | 52.67 |
| ATOM | 2043 | CZ | ARG | 269 | 17.426 | 62.969 | 7.165 | 1.00 | 54.63 |
| ATOM | 2044 | NH1 | ARG | 269 | 18.436 | 62.591 | 6.386 | 1.00 | 55.41 |
| ATOM | 2045 | NH2 | ARG | 269 | 16.173 | 62.747 | 6.775 | 1.00 | 55.38 |
| ATOM | 2046 | C | ARG | 269 | 22.204 | 64.150 | 12.231 | 1.00 | 42.99 |
| ATOM | 2047 | O | ARG | 269 | 23.400 | 63.999 | 11.977 | 1.00 | 43.63 |
| ATOM | 2048 | N | LEU | 270 | 21.777 | 64.796 | 13.305 | 1.00 | 41.99 |

*FIG. 4JJ*

```
ATOM   2049  CA   LEU  270      22.702  65.372  14.261  1.00  41.33
ATOM   2050  CB   LEU  270      21.924  65.812  15.502  1.00  41.15
ATOM   2051  CG   LEU  270      21.004  67.002  15.217  1.00  40.34
ATOM   2052  CD1  LEU  270      19.964  67.182  16.307  1.00  39.94
ATOM   2053  CD2  LEU  270      21.879  68.237  15.084  1.00  40.26
ATOM   2054  C    LEU  270      23.828  64.406  14.635  1.00  41.26
ATOM   2055  O    LEU  270      25.009  64.762  14.553  1.00  41.76
ATOM   2056  N    VAL  271      23.462  63.188  15.030  1.00  40.24
ATOM   2057  CA   VAL  271      24.443  62.177  15.415  1.00  40.08
ATOM   2058  CB   VAL  271      23.776  60.838  15.730  1.00  40.42
ATOM   2059  CG1  VAL  271      24.846  59.800  16.050  1.00  39.86
ATOM   2060  CG2  VAL  271      22.796  61.000  16.891  1.00  40.86
ATOM   2061  C    VAL  271      25.477  61.903  14.329  1.00  40.51
ATOM   2062  O    VAL  271      26.676  61.832  14.595  1.00  40.15
ATOM   2063  N    ASP  272      24.998  61.730  13.103  1.00  40.78
ATOM   2064  CA   ASP  272      25.866  61.447  11.977  1.00  40.36
ATOM   2065  CB   ASP  272      25.038  61.344  10.695  1.00  39.16
ATOM   2066  CG   ASP  272      25.792  60.670   9.553  1.00  38.09
ATOM   2067  OD1  ASP  272      26.821  60.000   9.807  1.00  36.54
ATOM   2068  OD2  ASP  272      25.335  60.798   8.394  1.00  37.12
ATOM   2069  C    ASP  272      26.901  62.544  11.849  1.00  40.88
ATOM   2070  O    ASP  272      28.099  62.297  11.953  1.00  40.75
ATOM   2071  N    GLU  273      26.429  63.763  11.638  1.00  41.96
ATOM   2072  CA   GLU  273      27.321  64.896  11.477  1.00  43.14
ATOM   2073  CB   GLU  273      26.501  66.170  11.470  1.00  44.13
ATOM   2074  CG   GLU  273      25.576  66.214  10.272  1.00  46.73
ATOM   2075  CD   GLU  273      24.629  67.388  10.308  1.00  48.40
ATOM   2076  OE1  GLU  273      25.047  68.455  10.828  1.00  49.15
ATOM   2077  OE2  GLU  273      23.482  67.241   9.811  1.00  48.64
ATOM   2078  C    GLU  273      28.428  64.968  12.517  1.00  43.48
ATOM   2079  O    GLU  273      29.575  65.279  12.187  1.00  43.59
ATOM   2080  N    SER  274      28.095  64.666  13.767  1.00  44.05
ATOM   2081  CA   SER  274      29.089  64.702  14.837  1.00  44.54
ATOM   2082  CB   SER  274      28.421  64.568  16.205  1.00  45.39
ATOM   2083  OG   SER  274      27.496  65.611  16.424  1.00  48.14
ATOM   2084  C    SER  274      30.106  63.582  14.694  1.00  44.23
ATOM   2085  O    SER  274      31.292  63.783  14.931  1.00  44.76
ATOM   2086  N    SER  275      29.632  62.400  14.318  1.00  43.84
ATOM   2087  CA   SER  275      30.489  61.227  14.162  1.00  43.42
ATOM   2088  CB   SER  275      29.754  60.139  13.392  1.00  43.28
ATOM   2089  OG   SER  275      29.758  60.444  12.010  1.00  42.94
ATOM   2090  C    SER  275      31.789  61.535  13.426  1.00  43.34
ATOM   2091  O    SER  275      31.914  62.552  12.738  1.00  43.76
ATOM   2092  N    ALA  276      32.756  60.639  13.570  1.00  42.68
ATOM   2093  CA   ALA  276      34.034  60.805  12.906  1.00  42.98
ATOM   2094  CB   ALA  276      35.108  60.015  13.639  1.00  42.92
ATOM   2095  C    ALA  276      33.930  60.319  11.465  1.00  43.23
ATOM   2096  O    ALA  276      34.936  60.277  10.751  1.00  44.60
ATOM   2097  N    ASN  277      32.722  59.949  11.039  1.00  42.10
ATOM   2098  CA   ASN  277      32.517  59.447   9.691  1.00  40.87
ATOM   2099  CB   ASN  277      32.615  57.927   9.685  1.00  41.63
ATOM   2100  CG   ASN  277      31.654  57.283  10.659  1.00  42.64
ATOM   2101  OD1  ASN  277      30.670  57.898  11.067  1.00  43.50
ATOM   2102  ND2  ASN  277      31.925  56.033  11.029  1.00  42.98
ATOM   2103  C    ASN  277      31.178  59.865   9.104  1.00  40.57
ATOM   2104  O    ASN  277      30.430  59.039   8.579  1.00  39.89
ATOM   2105  N    PRO  278      30.868  61.163   9.163  1.00  40.83
```

*FIG. 4KK*

```
ATOM  2106  CD   PRO  278    31.783  62.282   9.451  1.00 40.90
ATOM  2107  CA   PRO  278    29.600  61.657   8.623  1.00 40.71
ATOM  2108  CB   PRO  278    29.807  63.175   8.579  1.00 40.88
ATOM  2109  CG   PRO  278    31.303  63.326   8.474  1.00 41.27
ATOM  2110  C    PRO  278    29.239  61.074   7.258  1.00 40.60
ATOM  2111  O    PRO  278    29.949  61.284   6.270  1.00 40.71
ATOM  2112  N    GLY  279    28.131  60.338   7.216  1.00 40.34
ATOM  2113  CA   GLY  279    27.676  59.747   5.971  1.00 39.10
ATOM  2114  C    GLY  279    27.904  58.252   5.828  1.00 38.94
ATOM  2115  O    GLY  279    27.315  57.635   4.952  1.00 39.74
ATOM  2116  N    GLN  280    28.735  57.660   6.683  1.00 38.66
ATOM  2117  CA   GLN  280    29.049  56.230   6.605  1.00 37.75
ATOM  2118  CB   GLN  280    30.563  56.043   6.513  1.00 37.97
ATOM  2119  CG   GLN  280    31.243  56.954   5.509  1.00 39.85
ATOM  2120  CD   GLN  280    32.743  57.046   5.730  1.00 40.76
ATOM  2121  OE1  GLN  280    33.465  56.058   5.587  1.00 41.39
ATOM  2122  NE2  GLN  280    33.220  58.240   6.083  1.00 41.57
ATOM  2123  C    GLN  280    28.553  55.455   7.817  1.00 36.99
ATOM  2124  O    GLN  280    28.645  55.939   8.941  1.00 37.89
ATOM  2125  N    GLN  281    28.054  54.242   7.592  1.00 35.75
ATOM  2126  CA   GLN  281    27.572  53.401   8.681  1.00 34.04
ATOM  2127  CB   GLN  281    28.590  53.404   9.829  1.00 33.35
ATOM  2128  CG   GLN  281    29.971  52.951   9.447  1.00 33.09
ATOM  2129  CD   GLN  281    29.967  51.576   8.800  1.00 34.44
ATOM  2130  OE1  GLN  281    29.917  51.451   7.572  1.00 33.95
ATOM  2131  NE2  GLN  281    30.000  50.529   9.630 -1.00 34.63
ATOM  2132  C    GLN  281    26.210  53.831   9.237  1.00 33.42
ATOM  2133  O    GLN  281    25.895  53.530  10.390  1.00 34.87
ATOM  2134  N    LEU  282    25.395  54.511   8.436  1.00 31.53
ATOM  2135  CA   LEU  282    24.098  54.992   8.913  1.00 29.87
ATOM  2136  CB   LEU  282    23.345  55.685   7.777  1.00 30.15
ATOM  2137  CG   LEU  282    24.030  56.871   7.085  1.00 30.41
ATOM  2138  CD1  LEU  282    22.963  57.741   6.435  1.00 29.82
ATOM  2139  CD2  LEU  282    24.815  57.699   8.097  1.00 30.66
ATOM  2140  C    LEU  282    23.191  53.949   9.578  1.00 28.70
ATOM  2141  O    LEU  282    22.716  54.153  10.698  1.00 28.78
ATOM  2142  N    TYR  283    22.935  52.841   8.894  1.00 27.35
ATOM  2143  CA   TYR  283    22.095  51.793   9.461  1.00 26.53
ATOM  2144  CB   TYR  283    22.233  50.511   8.633  1.00 24.41
ATOM  2145  CG   TYR  283    21.420  49.338   9.143  1.00 22.90
ATOM  2146  CD1  TYR  283    20.021  49.413   9.210  1.00 21.94
ATOM  2147  CE1  TYR  283    19.257  48.318   9.609  1.00 20.96
ATOM  2148  CD2  TYR  283    22.038  48.129   9.503  1.00 21.53
ATOM  2149  CE2  TYR  283    21.279  47.030   9.907  1.00 20.87
ATOM  2150  CZ   TYR  283    19.886  47.140   9.950  1.00 21.33
ATOM  2151  OH   TYR  283    19.105  46.068  10.310  1.00 23.85
ATOM  2152  C    TYR  283    22.567  51.532  10.891  1.00 27.12
ATOM  2153  O    TYR  283    21.783  51.521  11.841  1.00 28.95
ATOM  2154  N    GLU  284    23.869  51.352  11.035  1.00 26.60
ATOM  2155  CA   GLU  284    24.486  51.072  12.317  1.00 26.43
ATOM  2156  CB   GLU  284    25.982  50.905  12.108  1.00 27.03
ATOM  2157  CG   GLU  284    26.763  50.680  13.375  1.00 27.21
ATOM  2158  CD   GLU  284    28.224  50.492  13.082  1.00 27.57
ATOM  2159  OE1  GLU  284    28.897  51.506  12.734  1.00 27.02
ATOM  2160  OE2  GLU  284    28.670  49.319  13.185  1.00 26.30
ATOM  2161  C    GLU  284    24.249  52.133  13.381  1.00 26.81
ATOM  2162  O    GLU  284    24.197  51.826  14.582  1.00 26.06
```

*FIG. 4LL*

| | | | | | | | | |
|---|---|---|---|---|---|---|---|---|
| ATOM | 2163 | N | LYS | 285 | 24.134 | 53.384 | 12.940 | 1.00 27.07 |
| ATOM | 2164 | CA | LYS | 285 | 23.926 | 54.502 | 13.860 | 1.00 27.39 |
| ATOM | 2165 | CB | LYS | 285 | 24.339 | 55.825 | 13.186 | 1.00 25.99 |
| ATOM | 2166 | CG | LYS | 285 | 25.840 | 56.012 | 13.132 | 1.00 24.13 |
| ATOM | 2167 | CD | LYS | 285 | 26.235 | 57.110 | 12.179 | 1.00 23.29 |
| ATOM | 2168 | CE | LYS | 285 | 27.755 | 57.193 | 12.052 | 1.00 22.03 |
| ATOM | 2169 | NZ | LYS | 285 | 28.142 | 58.198 | 11.027 | 1.00 21.72 |
| ATOM | 2170 | C | LYS | 285 | 22.488 | 54.595 | 14.368 | 1.00 28.05 |
| ATOM | 2171 | O | LYS | 285 | 22.086 | 55.615 | 14.941 | 1.00 28.61 |
| ATOM | 2172 | N | LEU | 286 | 21.717 | 53.535 | 14.144 | 1.00 27.60 |
| ATOM | 2173 | CA | LEU | 286 | 20.335 | 53.488 | 14.599 | 1.00 27.30 |
| ATOM | 2174 | CB | LEU | 286 | 19.399 | 53.157 | 13.435 | 1.00 28.57 |
| ATOM | 2175 | CG | LEU | 286 | 19.375 | 54.167 | 12.279 | 1.00 30.25 |
| ATOM | 2176 | CD1 | LEU | 286 | 18.480 | 53.647 | 11.139 | 1.00 29.98 |
| ATOM | 2177 | CD2 | LEU | 286 | 18.863 | 55.507 | 12.780 | 1.00 29.35 |
| ATOM | 2178 | C | LEU | 286 | 20.260 | 52.381 | 15.632 | 1.00 27.01 |
| ATOM | 2179 | O | LEU | 286 | 19.296 | 52.294 | 16.399 | 1.00 27.55 |
| ATOM | 2180 | N | ILE | 287 | 21.306 | 51.554 | 15.645 | 1.00 26.00 |
| ATOM | 2181 | CA | ILE | 287 | 21.415 | 50.399 | 16.532 | 1.00 24.38 |
| ATOM | 2182 | CB | ILE | 287 | 21.551 | 49.141 | 15.715 | 1.00 23.92 |
| ATOM | 2183 | CG2 | ILE | 287 | 21.470 | 47.919 | 16.628 | 1.00 22.70 |
| ATOM | 2184 | CG1 | ILE | 287 | 20.510 | 49.158 | 14.597 | 1.00 22.87 |
| ATOM | 2185 | CD1 | ILE | 287 | 20.676 | 48.042 | 13.607 | 1.00 22.79 |
| ATOM | 2186 | C | ILE | 287 | 22.639 | 50.444 | 17.433 | 1.00 24.65 |
| ATOM | 2187 | O | ILE | 287 | 22.550 | 50.255 | 18.644 | 1.00 23.54 |
| ATOM | 2188 | N | GLY | 288 | 23.791 | 50.668 | 16.810 | 1.00 25.94 |
| ATOM | 2189 | CA | GLY | 288 | 25.060 | 50.714 | 17.519 | 1.00 26.86 |
| ATOM | 2190 | C | GLY | 288 | 25.081 | 51.266 | 18.927 | 1.00 27.76 |
| ATOM | 2191 | O | GLY | 288 | 24.697 | 52.412 | 19.164 | 1.00 28.19 |
| ATOM | 2192 | N | GLY | 289 | 25.554 | 50.445 | 19.860 | 1.00 28.95 |
| ATOM | 2193 | CA | GLY | 289 | 25.656 | 50.856 | 21.249 | 1.00 30.64 |
| ATOM | 2194 | C | GLY | 289 | 26.632 | 52.007 | 21.407 | 1.00 31.92 |
| ATOM | 2195 | O | GLY | 289 | 26.930 | 52.442 | 22.509 | 1.00 32.56 |
| ATOM | 2196 | N | LYS | 290 | 27.133 | 52.504 | 20.291 | 1.00 32.83 |
| ATOM | 2197 | CA | LYS | 290 | 28.067 | 53.607 | 20.296 | 1.00 33.99 |
| ATOM | 2198 | CB | LYS | 290 | 29.104 | 53.373 | 19.191 | 1.00 35.04 |
| ATOM | 2199 | CG | LYS | 290 | 29.858 | 54.598 | 18.665 | 1.00 36.71 |
| ATOM | 2200 | CD | LYS | 290 | 31.032 | 54.996 | 19.551 | 1.00 38.80 |
| ATOM | 2201 | CE | LYS | 290 | 31.936 | 56.011 | 18.839 | 1.00 39.77 |
| ATOM | 2202 | NZ | LYS | 290 | 32.864 | 56.707 | 19.787 | 1.00 41.04 |
| ATOM | 2203 | C | LYS | 290 | 27.278 | 54.880 | 20.035 | 1.00 34.58 |
| ATOM | 2204 | O | LYS | 290 | 27.810 | 55.984 | 20.138 | 1.00 35.79 |
| ATOM | 2205 | N | TYR | 291 | 26.001 | 54.734 | 19.708 | 1.00 33.80 |
| ATOM | 2206 | CA | TYR | 291 | 25.196 | 55.907 | 19.406 | 1.00 33.61 |
| ATOM | 2207 | CB | TYR | 291 | 25.010 | 56.046 | 17.892 | 1.00 33.22 |
| ATOM | 2208 | CG | TYR | 291 | 26.256 | 55.752 | 17.084 | 1.00 33.77 |
| ATOM | 2209 | CD1 | TYR | 291 | 26.659 | 54.435 | 16.838 | 1.00 34.23 |
| ATOM | 2210 | CE1 | TYR | 291 | 27.789 | 54.155 | 16.065 | 1.00 34.17 |
| ATOM | 2211 | CD2 | TYR | 291 | 27.021 | 56.783 | 16.542 | 1.00 33.61 |
| ATOM | 2212 | CE2 | TYR | 291 | 28.150 | 56.515 | 15.773 | 1.00 33.54 |
| ATOM | 2213 | CZ | TYR | 291 | 28.528 | 55.200 | 15.532 | 1.00 33.76 |
| ATOM | 2214 | OH | TYR | 291 | 29.620 | 54.928 | 14.729 | 1.00 34.36 |
| ATOM | 2215 | C | TYR | 291 | 23.836 | 55.874 | 20.070 | 1.00 33.11 |
| ATOM | 2216 | O | TYR | 291 | 23.069 | 56.828 | 19.975 | 1.00 32.86 |
| ATOM | 2217 | N | MSE | 292 | 23.521 | 54.773 | 20.737 | 1.00 33.27 |
| ATOM | 2218 | CA | MSE | 292 | 22.230 | 54.699 | 21.389 | 1.00 33.18 |
| ATOM | 2219 | CB | MSE | 292 | 22.066 | 53.349 | 22.062 | 1.00 33.77 |

*FIG. 4MM*

```
ATOM   2220  CG   MSE  292      20.639  52.975  22.314  1.00 35.15
ATOM   2221  SE   MSE  292      20.564  51.230  22.803  1.00 41.54
ATOM   2222  CE   MSE  292      20.269  50.385  21.171  1.00 35.91
ATOM   2223  C    MSE  292      22.148  55.818  22.423  1.00 32.97
ATOM   2224  O    MSE  292      21.227  56.637  22.400  1.00 33.49
ATOM   2225  N    GLY  293      23.131  55.861  23.315  1.00 32.96
ATOM   2226  CA   GLY  293      23.151  56.892  24.334  1.00 32.25
ATOM   2227  C    GLY  293      23.067  58.290  23.750  1.00 32.18
ATOM   2228  O    GLY  293      22.307  59.126  24.241  1.00 33.24
ATOM   2229  N    GLU  294      23.835  58.560  22.702  1.00 31.47
ATOM   2230  CA   GLU  294      23.809  59.883  22.096  1.00 31.38
ATOM   2231  CB   GLU  294      24.875  59.971  21.008  1.00 33.29
ATOM   2232  CG   GLU  294      24.986  61.321  20.304  1.00 34.67
ATOM   2233  CD   GLU  294      25.227  62.474  21.257  1.00 35.80
ATOM   2234  OE1  GLU  294      25.708  62.244  22.389  1.00 36.49
ATOM   2235  OE2  GLU  294      24.946  63.623  20.858  1.00 37.16
ATOM   2236  C    GLU  294      22.428  60.192  21.521  1.00 30.62
ATOM   2237  O    GLU  294      21.919  61.305  21.664  1.00 30.94
ATOM   2238  N    LEU  295      21.818  59.204  20.878  1.00 29.56
ATOM   2239  CA   LEU  295      20.495  59.392  20.303  1.00 29.24
ATOM   2240  CB   LEU  295      20.030  58.112  19.589  1.00 27.27
ATOM   2241  CG   LEU  295      20.389  58.007  18.099  1.00 25.46
ATOM   2242  CD1  LEU  295      19.979  56.668  17.522  1.00 21.87
ATOM   2243  CD2  LEU  295      19.677  59.136  17.352  1.00 25.71
ATOM   2244  C    LEU  295      19.497  59.787  21.388  1.00 29.98
ATOM   2245  O    LEU  295      18.587  60.573  21.156  1.00 30.19
ATOM   2246  N    VAL  296      19.665  59.250  22.585  1.00 31.23
ATOM   2247  CA   VAL  296      18.745  59.590  23.657  1.00 32.87
ATOM   2248  CB   VAL  296      18.890  58.623  24.831  1.00 32.48
ATOM   2249  CG1  VAL  296      17.827  58.899  25.868  1.00 32.99
ATOM   2250  CG2  VAL  296      18.762  57.198  24.323  1.00 33.56
ATOM   2251  C    VAL  296      19.020  61.025  24.122  1.00 33.74
ATOM   2252  O    VAL  296      18.086  61.778  24.431  1.00 33.68
ATOM   2253  N    ARG  297      20.296  61.409  24.145  1.00 34.02
ATOM   2254  CA   ARG  297      20.659  62.757  24.563  1.00 35.34
ATOM   2255  CB   ARG  297      22.147  63.008  24.342  1.00 34.89
ATOM   2256  CG   ARG  297      22.940  63.279  25.609  1.00 35.27
ATOM   2257  CD   ARG  297      23.791  64.525  25.454  1.00 35.98
ATOM   2258  NE   ARG  297      24.226  64.700  24.074  1.00 37.11
ATOM   2259  CZ   ARG  297      24.476  65.878  23.513  1.00 37.43
ATOM   2260  NH1  ARG  297      24.348  66.994  24.226  1.00 38.45
ATOM   2261  NH2  ARG  297      24.809  65.944  22.229  1.00 36.61
ATOM   2262  C    ARG  297      19.870  63.766  23.747  1.00 36.07
ATOM   2263  O    ARG  297      19.103  64.574  24.285  1.00 36.76
ATOM   2264  N    LEU  298      20.063  63.699  22.437  1.00 36.93
ATOM   2265  CA   LEU  298      19.407  64.596  21.500  1.00 37.55
ATOM   2266  CB   LEU  298      19.768  64.178  20.077  1.00 37.28
ATOM   2267  CG   LEU  298      21.272  64.065  19.816  1.00 36.13
ATOM   2268  CD1  LEU  298      21.478  63.784  18.341  1.00 36.85
ATOM   2269  CD2  LEU  298      21.991  65.356  20.218  1.00 35.02
ATOM   2270  C    LEU  298      17.892  64.633  21.670  1.00 38.53
ATOM   2271  O    LEU  298      17.276  65.708  21.618  1.00 38.44
ATOM   2272  N    VAL  299      17.289  63.462  21.866  1.00 39.23
ATOM   2273  CA   VAL  299      15.839  63.389  22.054  1.00 40.08
ATOM   2274  CB   VAL  299      15.349  61.932  22.110  1.00 39.44
ATOM   2275  CG1  VAL  299      13.844  61.892  22.385  1.00 37.91
ATOM   2276  CG2  VAL  299      15.676  61.240  20.802  1.00 38.72
```

*FIG. 4NN*

| | | | | | | | | | |
|---|---|---|---|---|---|---|---|---|---|
| ATOM | 2277 | C | VAL | 299 | 15.435 | 64.087 | 23.350 | 1.00 | 40.94 |
| ATOM | 2278 | O | VAL | 299 | 14.321 | 64.612 | 23.461 | 1.00 | 41.66 |
| ATOM | 2279 | N | LEU | 300 | 16.337 | 64.091 | 24.328 | 1.00 | 41.41 |
| ATOM | 2280 | CA | LEU | 300 | 16.043 | 64.737 | 25.600 | 1.00 | 42.31 |
| ATOM | 2281 | CB | LEU | 300 | 16.973 | 64.224 | 26.713 | 1.00 | 41.48 |
| ATOM | 2282 | CG | LEU | 300 | 16.943 | 62.766 | 27.206 | 1.00 | 40.38 |
| ATOM | 2283 | CD1 | LEU | 300 | 17.677 | 62.711 | 28.545 | 1.00 | 40.14 |
| ATOM | 2284 | CD2 | LEU | 300 | 15.517 | 62.251 | 27.380 | 1.00 | 38.74 |
| ATOM | 2285 | C | LEU | 300 | 16.204 | 66.251 | 25.444 | 1.00 | 43.44 |
| ATOM | 2286 | O | LEU | 300 | 15.304 | 67.020 | 25.806 | 1.00 | 43.84 |
| ATOM | 2287 | N | LEU | 301 | 17.346 | 66.675 | 24.898 | 1.00 | 43.90 |
| ATOM | 2288 | CA | LEU | 301 | 17.603 | 68.100 | 24.707 | 1.00 | 43.85 |
| ATOM | 2289 | CB | LEU | 301 | 18.895 | 68.335 | 23.919 | 1.00 | 43.20 |
| ATOM | 2290 | CG | LEU | 301 | 20.211 | 67.969 | 24.613 | 1.00 | 43.48 |
| ATOM | 2291 | CD1 | LEU | 301 | 21.385 | 68.372 | 23.730 | 1.00 | 43.37 |
| ATOM | 2292 | CD2 | LEU | 301 | 20.307 | 68.675 | 25.955 | 1.00 | 43.71 |
| ATOM | 2293 | C | LEU | 301 | 16.444 | 68.738 | 23.969 | 1.00 | 44.11 |
| ATOM | 2294 | O | LEU | 301 | 16.068 | 69.875 | 24.254 | 1.00 | 44.38 |
| ATOM | 2295 | N | ARG | 302 | 15.863 | 68.007 | 23.025 | 1.00 | 44.45 |
| ATOM | 2296 | CA | ARG | 302 | 14.753 | 68.571 | 22.280 | 1.00 | 45.04 |
| ATOM | 2297 | CB | ARG | 302 | 14.296 | 67.660 | 21.148 | 1.00 | 45.49 |
| ATOM | 2298 | CG | ARG | 302 | 13.082 | 68.256 | 20.468 | 1.00 | 45.91 |
| ATOM | 2299 | CD | ARG | 302 | 12.391 | 67.327 | 19.514 | 1.00 | 46.45 |
| ATOM | 2300 | NE | ARG | 302 | 11.194 | 67.985 | 19.007 | 1.00 | 47.37 |
| ATOM | 2301 | CZ | ARG | 302 | 10.423 | 67.503 | 18.043 | 1.00 | 48.12 |
| ATOM | 2302 | NH1 | ARG | 302 | 10.719 | 66.344 | 17.466 | 1.00 | 48.80 |
| ATOM | 2303 | NH2 | ARG | 302 | 9.357 | 68.190 | 17.657 | 1.00 | 47.77 |
| ATOM | 2304 | C | ARG | 302 | 13.577 | 68.807 | 23.196 | 1.00 | 45.13 |
| ATOM | 2305 | O | ARG | 302 | 12.982 | 69.885 | 23.198 | 1.00 | 45.57 |
| ATOM | 2306 | N | LEU | 303 | 13.228 | 67.787 | 23.966 | 1.00 | 45.14 |
| ATOM | 2307 | CA | LEU | 303 | 12.113 | 67.918 | 24.883 | 1.00 | 45.18 |
| ATOM | 2308 | CB | LEU | 303 | 11.952 | 66.624 | 25.695 | 1.00 | 44.02 |
| ATOM | 2309 | CG | LEU | 303 | 11.495 | 65.427 | 24.846 | 1.00 | 42.43 |
| ATOM | 2310 | CD1 | LEU | 303 | 11.365 | 64.162 | 25.690 | 1.00 | 41.06 |
| ATOM | 2311 | CD2 | LEU | 303 | 10.154 | 65.784 | 24.207 | 1.00 | 41.96 |
| ATOM | 2312 | C | LEU | 303 | 12.359 | 69.133 | 25.783 | 1.00 | 45.83 |
| ATOM | 2313 | O | LEU | 303 | 11.444 | 69.919 | 26.044 | 1.00 | 45.85 |
| ATOM | 2314 | N | VAL | 304 | 13.599 | 69.302 | 26.232 | 1.00 | 46.44 |
| ATOM | 2315 | CA | VAL | 304 | 13.943 | 70.440 | 27.085 | 1.00 | 47.76 |
| ATOM | 2316 | CB | VAL | 304 | 15.443 | 70.426 | 27.496 | 1.00 | 47.79 |
| ATOM | 2317 | CG1 | VAL | 304 | 15.866 | 71.815 | 27.996 | 1.00 | 46.89 |
| ATOM | 2318 | CG2 | VAL | 304 | 15.678 | 69.386 | 28.581 | 1.00 | 47.81 |
| ATOM | 2319 | C | VAL | 304 | 13.666 | 71.764 | 26.371 | 1.00 | 48.44 |
| ATOM | 2320 | O | VAL | 304 | 12.899 | 72.596 | 26.861 | 1.00 | 48.95 |
| ATOM | 2321 | N | ASP | 305 | 14.297 | 71.946 | 25.212 | 1.00 | 48.52 |
| ATOM | 2322 | CA | ASP | 305 | 14.143 | 73.165 | 24.432 | 1.00 | 48.31 |
| ATOM | 2323 | CB | ASP | 305 | 14.968 | 73.067 | 23.143 | 1.00 | 49.45 |
| ATOM | 2324 | CG | ASP | 305 | 16.441 | 72.715 | 23.412 | 1.00 | 51.00 |
| ATOM | 2325 | OD1 | ASP | 305 | 17.056 | 73.323 | 24.317 | 1.00 | 50.99 |
| ATOM | 2326 | OD2 | ASP | 305 | 16.994 | 71.834 | 22.715 | 1.00 | 51.84 |
| ATOM | 2327 | C | ASP | 305 | 12.677 | 73.460 | 24.122 | 1.00 | 47.77 |
| ATOM | 2328 | O | ASP | 305 | 12.341 | 74.541 | 23.641 | 1.00 | 48.22 |
| ATOM | 2329 | N | GLU | 306 | 11.799 | 72.505 | 24.407 | 1.00 | 46.84 |
| ATOM | 2330 | CA | GLU | 306 | 10.378 | 72.713 | 24.176 | 1.00 | 46.34 |
| ATOM | 2331 | CB | GLU | 306 | 9.831 | 71.683 | 23.184 | 1.00 | 46.20 |
| ATOM | 2332 | CG | GLU | 306 | 9.866 | 72.216 | 21.761 | 1.00 | 48.15 |
| ATOM | 2333 | CD | GLU | 306 | 9.571 | 71.175 | 20.692 | 1.00 | 49.26 |

FIG. 400

```
ATOM   2334  OE1 GLU  306       8.514  70.499  20.768  1.00 50.03
ATOM   2335  OE2 GLU  306      10.398  71.049  19.759  1.00 49.62
ATOM   2336  C   GLU  306       9.635  72.661  25.493  1.00 45.99
ATOM   2337  O   GLU  306       8.459  72.331  25.550  1.00 45.90
ATOM   2338  N   ASN  307      10.350  72.997  26.560  1.00 46.00
ATOM   2339  CA  ASN  307       9.787  73.029  27.902  1.00 45.60
ATOM   2340  CB  ASN  307       9.033  74.342  28.094  1.00 46.42
ATOM   2341  CG  ASN  307       9.971  75.531  28.224  1.00 46.98
ATOM   2342  OD1 ASN  307      10.435  75.849  29.321  1.00 47.63
ATOM   2343  ND2 ASN  307      10.273  76.181  27.102  1.00 46.93
ATOM   2344  C   ASN  307       8.886  71.853  28.246  1.00 45.05
ATOM   2345  O   ASN  307       7.812  72.029  28.829  1.00 45.19
ATOM   2346  N   LEU  308       9.336  70.650  27.900  1.00 44.24
ATOM   2347  CA  LEU  308       8.575  69.439  28.180  1.00 43.28
ATOM   2348  CB  LEU  308       8.376  68.637  26.893  1.00 43.27
ATOM   2349  CG  LEU  308       7.070  68.825  26.115  1.00 44.09
ATOM   2350  CD1 LEU  308       6.765  70.294  25.935  1.00 44.22
ATOM   2351  CD2 LEU  308       7.182  68.139  24.760  1.00 43.94
ATOM   2352  C   LEU  308       9.287  68.570  29.205  1.00 42.96
ATOM   2353  O   LEU  308       8.688  67.660  29.775  1.00 42.27
ATOM   2354  N   LEU  309      10.560  68.868  29.448  1.00 43.49
ATOM   2355  CA  LEU  309      11.368  68.077  30.371  1.00 44.85
ATOM   2356  CB  LEU  309      12.030  66.936  29.581  1.00 43.53
ATOM   2357  CG  LEU  309      12.958  65.925  30.254  1.00 42.07
ATOM   2358  CD1 LEU  309      12.235  65.226  31.390  1.00 40.83
ATOM   2359  CD2 LEU  309      13.416  64.913  29.212  1.00 42.11
ATOM   2360  C   LEU  309      12.436  68.900  31.108  1.00 46.21
ATOM   2361  O   LEU  309      13.074  69.777  30.518  1.00 46.04
ATOM   2362  N   PHE  310      12.625  68.601  32.397  1.00 47.92
ATOM   2363  CA  PHE  310      13.608  69.293  33.238  1.00 49.25
ATOM   2364  CB  PHE  310      15.013  69.093  32.666  1.00 48.20
ATOM   2365  CG  PHE  310      15.438  67.650  32.590  1.00 47.06
ATOM   2366  CD1 PHE  310      16.338  67.228  31.615  1.00 46.24
ATOM   2367  CD2 PHE  310      14.947  66.715  33.497  1.00 46.63
ATOM   2368  CE1 PHE  310      16.740  65.903  31.540  1.00 45.74
ATOM   2369  CE2 PHE  310      15.344  65.385  33.433  1.00 46.27
ATOM   2370  CZ  PHE  310      16.243  64.978  32.451  1.00 45.93
ATOM   2371  C   PHE  310      13.292  70.785  33.345  1.00 51.16
ATOM   2372  O   PHE  310      14.185  71.616  33.561  1.00 50.84
ATOM   2373  N   HIS  311      12.009  71.109  33.183  1.00 53.40
ATOM   2374  CA  HIS  311      11.529  72.482  33.262  1.00 55.80
ATOM   2375  CB  HIS  311      11.744  73.012  34.683  1.00 57.57
ATOM   2376  CG  HIS  311      11.212  72.098  35.745  1.00 59.78
ATOM   2377  CD2 HIS  311      11.848  71.363  36.689  1.00 60.29
ATOM   2378  ND1 HIS  311       9.867  71.815  35.879  1.00 60.36
ATOM   2379  CE1 HIS  311       9.699  70.944  36.860  1.00 60.99
ATOM   2380  NE2 HIS  311      10.885  70.654  37.368  1.00 60.85
ATOM   2381  C   HIS  311      12.214  73.384  32.236  1.00 56.24
ATOM   2382  O   HIS  311      12.288  74.608  32.415  1.00 56.87
ATOM   2383  N   GLY  312      12.705  72.772  31.159  1.00 55.96
ATOM   2384  CA  GLY  312      13.366  73.522  30.109  1.00 55.87
ATOM   2385  C   GLY  312      14.820  73.804  30.420  1.00 56.16
ATOM   2386  O   GLY  312      15.563  74.264  29.562  1.00 56.58
ATOM   2387  N   GLU  313      15.235  73.519  31.646  1.00 56.52
ATOM   2388  CA  GLU  313      16.612  73.765  32.048  1.00 57.69
ATOM   2389  CB  GLU  313      16.621  74.379  33.447  1.00 59.84
ATOM   2390  CG  GLU  313      15.849  75.698  33.515  1.00 63.16
```

FIG. 4PP

```
ATOM   2391  CD   GLU  313      15.388  76.061  34.925  1.00 65.16
ATOM   2392  OE1  GLU  313      14.554  75.315  35.503  1.00 66.01
ATOM   2393  OE2  GLU  313      15.858  77.096  35.455  1.00 66.34
ATOM   2394  C    GLU  313      17.439  72.484  32.011  1.00 57.06
ATOM   2395  O    GLU  313      17.155  71.529  32.728  1.00 57.01
ATOM   2396  N    ALA  314      18.463  72.472  31.169  1.00 56.56
ATOM   2397  CA   ALA  314      19.316  71.305  31.029  1.00 56.76
ATOM   2398  CB   ALA  314      19.454  70.939  29.557  1.00 56.47
ATOM   2399  C    ALA  314      20.699  71.490  31.643  1.00 56.94
ATOM   2400  O    ALA  314      21.310  72.558  31.527  1.00 57.46
ATOM   2401  N    SER  315      21.183  70.422  32.276  1.00 56.73
ATOM   2402  CA   SER  315      22.487  70.383  32.932  1.00 56.15
ATOM   2403  CB   SER  315      22.666  69.029  33.624  1.00 56.44
ATOM   2404  OG   SER  315      23.981  68.868  34.130  1.00 57.39
ATOM   2405  C    SER  315      23.673  70.627  32.003  1.00 56.00
ATOM   2406  O    SER  315      23.595  70.416  30.793  1.00 55.42
ATOM   2407  N    GLU  316      24.776  71.070  32.598  1.00 56.67
ATOM   2408  CA   GLU  316      26.012  71.346  31.875  1.00 57.46
ATOM   2409  CB   GLU  316      27.111  71.754  32.860  1.00 58.71
ATOM   2410  CG   GLU  316      28.458  72.050  32.206  1.00 60.34
ATOM   2411  CD   GLU  316      28.442  73.343  31.406  1.00 61.64
ATOM   2412  OE1  GLU  316      28.288  74.420  32.031  1.00 62.41
ATOM   2413  OE2  GLU  316      28.574  73.280  30.160  1.00 61.76
ATOM   2414  C    GLU  316      26.442  70.078  31.161  1.00 57.35
ATOM   2415  O    GLU  316      26.770  70.088  29.972  1.00 57.68
ATOM   2416  N    GLN  317      26.439  68.988  31.920  1.00 56.84
ATOM   2417  CA   GLN  317      26.817  67.677  31.427  1.00 56.23
ATOM   2418  CB   GLN  317      26.760  66.669  32.580  1.00 55.93
ATOM   2419  CG   GLN  317      27.504  67.113  33.840  1.00 55.46
ATOM   2420  CD   GLN  317      27.063  66.355  35.085  1.00 55.01
ATOM   2421  OE1  GLN  317      27.246  65.140  35.194  1.00 54.83
ATOM   2422  NE2  GLN  317      26.468  67.074  36.029  1.00 54.68
ATOM   2423  C    GLN  317      25.902  67.210  30.290  1.00 56.37
ATOM   2424  O    GLN  317      26.376  66.634  29.312  1.00 56.16
ATOM   2425  N    LEU  318      24.599  67.476  30.412  1.00 56.41
ATOM   2426  CA   LEU  318      23.616  67.043  29.413  1.00 56.48
ATOM   2427  CB   LEU  318      22.190  67.333  29.890  1.00 55.59
ATOM   2428  CG   LEU  318      21.084  66.700  29.034  1.00 54.71
ATOM   2429  CD1  LEU  318      21.090  65.191  29.231  1.00 53.88
ATOM   2430  CD2  LEU  318      19.731  67.268  29.422  1.00 54.28
ATOM   2431  C    LEU  318      23.784  67.621  28.017  1.00 56.99
ATOM   2432  O    LEU  318      23.692  66.893  27.029  1.00 57.21
ATOM   2433  N    ARG  319      24.011  68.924  27.919  1.00 57.16
ATOM   2434  CA   ARG  319      24.177  69.530  26.606  1.00 57.68
ATOM   2435  CB   ARG  319      23.870  71.026  26.690  1.00 59.32
ATOM   2436  CG   ARG  319      22.420  71.284  27.105  1.00 62.20
ATOM   2437  CD   ARG  319      22.125  72.743  27.401  1.00 64.53
ATOM   2438  NE   ARG  319      20.758  72.927  27.892  1.00 66.89
ATOM   2439  CZ   ARG  319      20.297  74.055  28.433  1.00 68.29
ATOM   2440  NH1  ARG  319      21.096  75.112  28.555  1.00 68.30
ATOM   2441  NH2  ARG  319      19.034  74.127  28.851  1.00 68.25
ATOM   2442  C    ARG  319      25.587  69.278  26.081  1.00 57.09
ATOM   2443  O    ARG  319      26.049  69.951  25.160  1.00 57.05
ATOM   2444  N    THR  320      26.246  68.277  26.667  1.00 56.25
ATOM   2445  CA   THR  320      27.612  67.888  26.318  1.00 55.15
ATOM   2446  CB   THR  320      28.478  67.836  27.589  1.00 54.85
ATOM   2447  OG1  THR  320      28.601  69.158  28.133  1.00 54.94
```

*FIG. 4QQ*

```
ATOM   2448  CG2 THR   320      29.854  67.262  27.287  1.00 54.63
ATOM   2449  C   THR   320      27.689  66.524  25.613  1.00 55.04
ATOM   2450  O   THR   320      27.476  65.480  26.229  1.00 55.13
ATOM   2451  N   ARG   321      28.017  66.536  24.326  1.00 54.38
ATOM   2452  CA  ARG   321      28.106  65.304  23.545  1.00 54.36
ATOM   2453  CB  ARG   321      28.841  65.586  22.236  1.00 56.05
ATOM   2454  CG  ARG   321      28.153  66.651  21.402  1.00 59.03
ATOM   2455  CD  ARG   321      28.943  67.013  20.156  1.00 61.60
ATOM   2456  NE  ARG   321      28.331  68.123  19.426  1.00 63.68
ATOM   2457  CZ  ARG   321      28.909  68.753  18.406  1.00 65.43
ATOM   2458  NH1 ARG   321      30.119  68.381  17.997  1.00 65.83
ATOM   2459  NH2 ARG   321      28.280  69.750  17.792  1.00 65.76
ATOM   2460  C   ARG   321      28.765  64.123  24.262  1.00 52.97
ATOM   2461  O   ARG   321      29.885  64.234  24.758  1.00 53.13
ATOM   2462  N   GLY   322      28.056  62.996  24.316  1.00 51.39
ATOM   2463  CA  GLY   322      28.592  61.802  24.950  1.00 49.22
ATOM   2464  C   GLY   322      28.198  61.609  26.402  1.00 48.17
ATOM   2465  O   GLY   322      28.450  60.550  26.986  1.00 48.17
ATOM   2466  N   ALA   323      27.574  62.627  26.988  1.00 46.66
ATOM   2467  CA  ALA   323      27.150  62.573  28.385  1.00 44.99
ATOM   2468  CB  ALA   323      26.462  63.861  28.761  1.00 45.87
ATOM   2469  C   ALA   323      26.224  61.403  28.676  1.00 43.43
ATOM   2470  O   ALA   323      26.514  60.562  29.530  1.00 43.02
ATOM   2471  N   PHE   324      25.094  61.361  27.981  1.00 41.61
ATOM   2472  CA  PHE   324      24.147  60.282  28.185  1.00 40.44
ATOM   2473  CB  PHE   324      22.797  60.631  27.564  1.00 38.94
ATOM   2474  CG  PHE   324      21.644  59.988  28.262  1.00 38.08
ATOM   2475  CD1 PHE   324      21.047  60.613  29.360  1.00 37.48
ATOM   2476  CD2 PHE   324      21.185  58.733  27.860  1.00 36.96
ATOM   2477  CE1 PHE   324      20.010  59.998  30.050  1.00 37.11
ATOM   2478  CE2 PHE   324      20.146  58.105  28.542  1.00 37.79
ATOM   2479  CZ  PHE   324      19.555  58.739  29.643  1.00 37.73
ATOM   2480  C   PHE   324      24.721  59.033  27.525  1.00 40.11
ATOM   2481  O   PHE   324      24.785  58.937  26.289  1.00 40.76
ATOM   2482  N   GLU   325      25.129  58.072  28.350  1.00 39.06
ATOM   2483  CA  GLU   325      25.740  56.851  27.844  1.00 37.85
ATOM   2484  CB  GLU   325      26.846  56.418  28.781  1.00 38.17
ATOM   2485  CG  GLU   325      27.790  57.528  29.085  1.00 40.68
ATOM   2486  CD  GLU   325      28.922  57.075  29.951  1.00 42.47
ATOM   2487  OE1 GLU   325      28.653  56.608  31.086  1.00 44.06
ATOM   2488  OE2 GLU   325      30.080  57.181  29.490  1.00 44.51
ATOM   2489  C   GLU   325      24.799  55.693  27.641  1.00 36.60
ATOM   2490  O   GLU   325      23.903  55.445  28.447  1.00 37.31
ATOM   2491  N   THR   326      25.019  54.968  26.554  1.00 35.30
ATOM   2492  CA  THR   326      24.193  53.816  26.245  1.00 33.37
ATOM   2493  CB  THR   326      24.875  52.921  25.207  1.00 31.58
ATOM   2494  OG1 THR   326      24.934  53.617  23.956  1.00 29.82
ATOM   2495  CG2 THR   326      24.113  51.619  25.041  1.00 29.94
ATOM   2496  C   THR   326      23.951  53.016  27.515  1.00 33.05
ATOM   2497  O   THR   326      22.846  52.528  27.742  1.00 33.99
ATOM   2498  N   ARG   327      24.981  52.902  28.349  1.00 32.29
ATOM   2499  CA  ARG   327      24.859  52.148  29.588  1.00 31.76
ATOM   2500  CB  ARG   327      26.146  52.245  30.417  1.00 33.30
ATOM   2501  CG  ARG   327      26.226  51.162  31.485  1.00 36.71
ATOM   2502  CD  ARG   327      27.596  51.043  32.177  1.00 38.88
ATOM   2503  NE  ARG   327      27.795  52.024  33.249  1.00 40.62
ATOM   2504  CZ  ARG   327      28.274  53.255  33.069  1.00 41.13
```

*FIG. 4RR*

| ATOM | 2505 | NH1 | ARG | 327 | 28.615 | 53.670 | 31.846 | 1.00 | 40.49 |
|------|------|-----|-----|-----|--------|--------|--------|------|-------|
| ATOM | 2506 | NH2 | ARG | 327 | 28.393 | 54.078 | 34.113 | 1.00 | 40.82 |
| ATOM | 2507 | C | ARG | 327 | 23.681 | 52.691 | 30.387 | 1.00 | 30.62 |
| ATOM | 2508 | O | ARG | 327 | 22.888 | 51.930 | 30.940 | 1.00 | 29.96 |
| ATOM | 2509 | N | PHE | 328 | 23.559 | 54.014 | 30.425 | 1.00 | 29.60 |
| ATOM | 2510 | CA | PHE | 328 | 22.479 | 54.660 | 31.154 | 1.00 | 28.70 |
| ATOM | 2511 | CB | PHE | 328 | 22.632 | 56.176 | 31.069 | 1.00 | 28.03 |
| ATOM | 2512 | CG | PHE | 328 | 23.903 | 56.684 | 31.686 | 1.00 | 27.73 |
| ATOM | 2513 | CD1 | PHE | 328 | 24.337 | 57.975 | 31.439 | 1.00 | 27.37 |
| ATOM | 2514 | CD2 | PHE | 328 | 24.678 | 55.857 | 32.505 | 1.00 | 28.92 |
| ATOM | 2515 | CE1 | PHE | 328 | 25.526 | 58.437 | 31.992 | 1.00 | 28.75 |
| ATOM | 2516 | CE2 | PHE | 328 | 25.871 | 56.305 | 33.069 | 1.00 | 28.74 |
| ATOM | 2517 | CZ | PHE | 328 | 26.298 | 57.599 | 32.812 | 1.00 | 28.68 |
| ATOM | 2518 | C | PHE | 328 | 21.135 | 54.226 | 30.590 | 1.00 | 29.06 |
| ATOM | 2519 | O | PHE | 328 | 20.189 | 53.953 | 31.351 | 1.00 | 29.59 |
| ATOM | 2520 | N | VAL | 329 | 21.057 | 54.154 | 29.257 | 1.00 | 28.40 |
| ATOM | 2521 | CA | VAL | 329 | 19.830 | 53.735 | 28.587 | 1.00 | 26.44 |
| ATOM | 2522 | CB | VAL | 329 | 20.040 | 53.552 | 27.059 | 1.00 | 25.14 |
| ATOM | 2523 | CG1 | VAL | 329 | 18.737 | 53.107 | 26.387 | 1.00 | 22.55 |
| ATOM | 2524 | CG2 | VAL | 329 | 20.542 | 54.841 | 26.444 | 1.00 | 23.05 |
| ATOM | 2525 | C | VAL | 329 | 19.388 | 52.399 | 29.166 | 1.00 | 27.98 |
| ATOM | 2526 | O | VAL | 329 | 18.240 | 52.239 | 29.576 | 1.00 | 27.88 |
| ATOM | 2527 | N | SER | 330 | 20.308 | 51.442 | 29.219 | 1.00 | 28.76 |
| ATOM | 2528 | CA | SER | 330 | 19.966 | 50.117 | 29.718 | 1.00 | 30.08 |
| ATOM | 2529 | CB | SER | 330 | 21.136 | 49.171 | 29.534 | 1.00 | 30.45 |
| ATOM | 2530 | OG | SER | 330 | 20.720 | 47.852 | 29.822 | 1.00 | 31.92 |
| ATOM | 2531 | C | SER | 330 | 19.534 | 50.107 | 31.172 | 1.00 | 31.40 |
| ATOM | 2532 | O | SER | 330 | 18.690 | 49.298 | 31.577 | 1.00 | 31.74 |
| ATOM | 2533 | N | GLN | 331 | 20.118 | 50.993 | 31.972 | 1.00 | 32.45 |
| ATOM | 2534 | CA | GLN | 331 | 19.745 | 51.061 | 33.381 | 1.00 | 33.16 |
| ATOM | 2535 | CB | GLN | 331 | 20.668 | 51.992 | 34.151 | 1.00 | 33.58 |
| ATOM | 2536 | CG | GLN | 331 | 22.093 | 51.540 | 34.194 | 1.00 | 35.83 |
| ATOM | 2537 | CD | GLN | 331 | 22.947 | 52.534 | 34.919 | 1.00 | 37.72 |
| ATOM | 2538 | OE1 | GLN | 331 | 22.626 | 52.927 | 36.043 | 1.00 | 39.62 |
| ATOM | 2539 | NE2 | GLN | 331 | 24.042 | 52.958 | 34.291 | 1.00 | 38.98 |
| ATOM | 2540 | C | GLN | 331 | 18.327 | 51.591 | 33.482 | 1.00 | 33.78 |
| ATOM | 2541 | O | GLN | 331 | 17.428 | 50.881 | 33.938 | 1.00 | 34.06 |
| ATOM | 2542 | N | VAL | 332 | 18.129 | 52.835 | 33.038 | 1.00 | 33.77 |
| ATOM | 2543 | CA | VAL | 332 | 16.808 | 53.457 | 33.097 | 1.00 | 33.65 |
| ATOM | 2544 | CB | VAL | 332 | 16.760 | 54.791 | 32.282 | 1.00 | 32.19 |
| ATOM | 2545 | CG1 | VAL | 332 | 17.279 | 54.584 | 30.905 | 1.00 | 33.04 |
| ATOM | 2546 | CG2 | VAL | 332 | 15.340 | 55.312 | 32.215 | 1.00 | 31.67 |
| ATOM | 2547 | C | VAL | 332 | 15.695 | 52.505 | 32.638 | 1.00 | 34.20 |
| ATOM | 2548 | O | VAL | 332 | 14.571 | 52.566 | 33.139 | 1.00 | 34.51 |
| ATOM | 2549 | N | GLU | 333 | 16.001 | 51.607 | 31.711 | 1.00 | 34.30 |
| ATOM | 2550 | CA | GLU | 333 | 14.981 | 50.676 | 31.258 | 1.00 | 34.92 |
| ATOM | 2551 | CB | GLU | 333 | 15.210 | 50.289 | 29.795 | 1.00 | 34.40 |
| ATOM | 2552 | CG | GLU | 333 | 14.893 | 51.413 | 28.837 | 1.00 | 33.07 |
| ATOM | 2553 | CD | GLU | 333 | 14.806 | 50.956 | 27.409 | 1.00 | 31.80 |
| ATOM | 2554 | OE1 | GLU | 333 | 13.983 | 50.060 | 27.114 | 1.00 | 31.65 |
| ATOM | 2555 | OE2 | GLU | 333 | 15.561 | 51.504 | 26.581 | 1.00 | 31.72 |
| ATOM | 2556 | C | GLU | 333 | 14.949 | 49.438 | 32.135 | 1.00 | 35.76 |
| ATOM | 2557 | O | GLU | 333 | 14.163 | 48.520 | 31.911 | 1.00 | 35.73 |
| ATOM | 2558 | N | SER | 334 | 15.814 | 49.419 | 33.138 | 1.00 | 36.91 |
| ATOM | 2559 | CA | SER | 334 | 15.876 | 48.307 | 34.071 | 1.00 | 38.13 |
| ATOM | 2560 | CB | SER | 334 | 17.328 | 47.934 | 34.346 | 1.00 | 39.38 |
| ATOM | 2561 | OG | SER | 334 | 17.460 | 46.524 | 34.468 | 1.00 | 41.52 |

FIG. 4SS

```
ATOM   2562  C    SER  334      15.201  48.747  35.362  1.00  37.93
ATOM   2563  O    SER  334      15.053  47.973  36.306  1.00  38.63
ATOM   2564  N    ASP  335      14.807  50.014  35.385  1.00  38.51
ATOM   2565  CA   ASP  335      14.133  50.619  36.521  1.00  38.59
ATOM   2566  CB   ASP  335      13.776  52.061  36.173  1.00  39.10
ATOM   2567  CG   ASP  335      13.346  52.864  37.373  1.00  39.89
ATOM   2568  OD1  ASP  335      12.278  52.547  37.950  1.00  40.30
ATOM   2569  OD2  ASP  335      14.079  53.816  37.737  1.00  39.90
ATOM   2570  C    ASP  335      12.876  49.809  36.840  1.00  39.11
ATOM   2571  O    ASP  335      12.241  49.249  35.945  1.00  39.03
ATOM   2572  N    THR  336      12.517  49.768  38.119  1.00  39.68
ATOM   2573  CA   THR  336      11.372  48.999  38.605  1.00  39.94
ATOM   2574  CB   THR  336      11.773  48.297  39.896  1.00  39.68
ATOM   2575  OG1  THR  336      12.901  47.464  39.630  1.00  40.95
ATOM   2576  CG2  THR  336      10.650  47.452  40.426  1.00  39.84
ATOM   2577  C    THR  336      10.043  49.735  38.853  1.00  40.52
ATOM   2578  O    THR  336       8.984  49.108  38.931  1.00  40.91
ATOM   2579  N    GLY  337      10.085  51.054  38.970  1.00  40.80
ATOM   2580  CA   GLY  337       8.870  51.804  39.234  1.00  41.83
ATOM   2581  C    GLY  337       9.307  52.948  40.112  1.00  42.60
ATOM   2582  O    GLY  337       8.990  54.105  39.865  1.00  43.33
ATOM   2583  N    ASP  338      10.043  52.604  41.156  1.00  43.47
ATOM   2584  CA   ASP  338      10.606  53.589  42.059  1.00  44.40
ATOM   2585  CB   ASP  338      11.354  52.868  43.175  1.00  44.83
ATOM   2586  CG   ASP  338      12.303  51.808  42.637  1.00  45.34
ATOM   2587  OD1  ASP  338      11.879  51.032  41.751  1.00  46.12
ATOM   2588  OD2  ASP  338      13.465  51.742  43.087  1.00  45.59
ATOM   2589  C    ASP  338      11.597  54.296  41.142  1.00  44.84
ATOM   2590  O    ASP  338      12.605  53.709  40.756  1.00  45.53
ATOM   2591  N    ARG  339      11.310  55.533  40.763  1.00  44.81
ATOM   2592  CA   ARG  339      12.208  56.256  39.874  1.00  45.11
ATOM   2593  CB   ARG  339      11.702  57.687  39.654  1.00  45.72
ATOM   2594  CG   ARG  339      10.466  57.799  38.783  1.00  46.11
ATOM   2595  CD   ARG  339       9.201  57.413  39.521  1.00  46.99
ATOM   2596  NE   ARG  339       8.041  57.492  38.633  1.00  47.58
ATOM   2597  CZ   ARG  339       6.780  57.326  39.017  1.00  47.30
ATOM   2598  NH1  ARG  339       6.492  57.068  40.287  1.00  47.38
ATOM   2599  NH2  ARG  339       5.806  57.413  38.123  1.00  47.44
ATOM   2600  C    ARG  339      13.637  56.295  40.419  1.00  44.98
ATOM   2601  O    ARG  339      14.466  57.084  39.960  1.00  44.83
ATOM   2602  N    LYS  340      13.922  55.441  41.394  1.00  44.75
ATOM   2603  CA   LYS  340      15.238  55.394  42.001  1.00  45.05
ATOM   2604  CB   LYS  340      15.341  54.179  42.917  1.00  46.19
ATOM   2605  CG   LYS  340      14.358  54.250  44.081  1.00  47.87
ATOM   2606  CD   LYS  340      14.598  53.154  45.094  1.00  49.25
ATOM   2607  CE   LYS  340      13.365  52.949  45.957  1.00  50.44
ATOM   2608  NZ   LYS  340      13.353  51.589  46.598  1.00  51.78
ATOM   2609  C    LYS  340      16.398  55.422  41.014  1.00  44.66
ATOM   2610  O    LYS  340      17.186  56.372  41.026  1.00  44.90
ATOM   2611  N    GLN  341      16.509  54.408  40.155  1.00  43.94
ATOM   2612  CA   GLN  341      17.603  54.362  39.174  1.00  42.93
ATOM   2613  CB   GLN  341      17.598  53.028  38.435  1.00  45.04
ATOM   2614  CG   GLN  341      18.035  51.860  39.289  1.00  48.03
ATOM   2615  CD   GLN  341      18.758  50.801  38.482  1.00  49.69
ATOM   2616  OE1  GLN  341      19.731  51.101  37.779  1.00  50.67
ATOM   2617  NE2  GLN  341      18.297  49.556  38.581  1.00  50.43
ATOM   2618  C    GLN  341      17.616  55.497  38.146  1.00  40.93
```

*FIG. 4TT*

```
ATOM   2619  O    GLN  341      18.672  56.057  37.839  1.00 38.85
ATOM   2620  N    ILE  342      16.449  55.824  37.600  1.00 39.61
ATOM   2621  CA   ILE  342      16.364  56.905  36.624  1.00 39.07
ATOM   2622  CB   ILE  342      14.920  57.110  36.130  1.00 39.24
ATOM   2623  CG2  ILE  342      14.880  58.226  35.107  1.00 39.19
ATOM   2624  CG1  ILE  342      14.392  55.817  35.501  1.00 39.87
ATOM   2625  CD1  ILE  342      12.945  55.902  35.070  1.00 40.76
ATOM   2626  C    ILE  342      16.832  58.185  37.301  1.00 38.43
ATOM   2627  O    ILE  342      17.704  58.892  36.795  1.00 37.48
ATOM   2628  N    TYR  343      16.240  58.466  38.456  1.00 38.93
ATOM   2629  CA   TYR  343      16.580  59.647  39.236  1.00 39.71
ATOM   2630  CB   TYR  343      15.813  59.656  40.567  1.00 40.97
ATOM   2631  CG   TYR  343      16.173  60.835  41.448  1.00 42.53
ATOM   2632  CD1  TYR  343      15.344  61.954  41.521  1.00 43.30
ATOM   2633  CE1  TYR  343      15.730  63.092  42.228  1.00 44.58
ATOM   2634  CD2  TYR  343      17.397  60.880  42.119  1.00 43.04
ATOM   2635  CE2  TYR  343      17.791  62.014  42.826  1.00 43.55
ATOM   2636  CZ   TYR  343      16.958  63.117  42.872  1.00 44.31
ATOM   2637  OH   TYR  343      17.369  64.260  43.523  1.00 45.74
ATOM   2638  C    TYR  343      18.070  59.635  39.532  1.00 39.93
ATOM   2639  O    TYR  343      18.789  60.598  39.262  1.00 40.28
ATOM   2640  N    ASN  344      18.525  58.529  40.098  1.00 40.14
ATOM   2641  CA   ASN  344      19.924  58.371  40.460  1.00 40.97
ATOM   2642  CB   ASN  344      20.146  56.958  40.989  1.00 42.94
ATOM   2643  CG   ASN  344      21.287  56.880  41.977  1.00 44.68
ATOM   2644  OD1  ASN  344      22.448  57.137  41.628  1.00 46.05
ATOM   2645  ND2  ASN  344      20.965  56.531  43.225  1.00 44.93
ATOM   2646  C    ASN  344      20.869  58.649  39.292  1.00 40.46
ATOM   2647  O    ASN  344      21.946  59.208  39.483  1.00 40.33
ATOM   2648  N    ILE  345      20.460  58.262  38.085  1.00 40.50
ATOM   2649  CA   ILE  345      21.280  58.467  36.890  1.00 39.89
ATOM   2650  CB   ILE  345      20.803  57.555  35.720  1.00 39.76
ATOM   2651  CG2  ILE  345      21.597  57.849  34.448  1.00 38.62
ATOM   2652  CG1  ILE  345      20.966  56.090  36.114  1.00 38.74
ATOM   2653  CD1  ILE  345      20.201  55.151  35.242  1.00 38.61
ATOM   2654  C    ILE  345      21.247  59.924  36.434  1.00 39.80
ATOM   2655  O    ILE  345      22.281  60.490  36.074  1.00 39.67
ATOM   2656  N    LEU  346      20.062  60.529  36.449  1.00 39.59
ATOM   2657  CA   LEU  346      19.912  61.923  36.029  1.00 39.58
ATOM   2658  CB   LEU  346      18.434  62.255  35.818  1.00 37.79
ATOM   2659  CG   LEU  346      17.809  61.528  34.625  1.00 36.58
ATOM   2660  CD1  LEU  346      16.277  61.599  34.684  1.00 35.18
ATOM   2661  CD2  LEU  346      18.363  62.145  33.337  1.00 35.05
ATOM   2662  C    LEU  346      20.519  62.892  37.034  1.00 40.82
ATOM   2663  O    LEU  346      21.177  63.857  36.654  1.00 41.02
ATOM   2664  N    SER  347      20.298  62.646  38.322  1.00 42.34
ATOM   2665  CA   SER  347      20.859  63.530  39.339  1.00 43.44
ATOM   2666  CB   SER  347      20.491  63.042  40.745  1.00 43.90
ATOM   2667  OG   SER  347      20.665  61.639  40.868  1.00 45.32
ATOM   2668  C    SER  347      22.368  63.556  39.156  1.00 43.44
ATOM   2669  O    SER  347      22.974  64.624  39.051  1.00 44.11
ATOM   2670  N    THR  348      22.969  62.374  39.096  1.00 43.10
ATOM   2671  CA   THR  348      24.407  62.285  38.909  1.00 42.97
ATOM   2672  CB   THR  348      24.853  60.830  38.700  1.00 42.31
ATOM   2673  OG1  THR  348      24.666  60.096  39.918  1.00 42.08
ATOM   2674  CG2  THR  348      26.322  60.780  38.282  1.00 40.85
ATOM   2675  C    THR  348      24.798  63.093  37.683  1.00 43.25
```

*FIG. 4UU*

| | | | | | | | | |
|---|---|---|---|---|---|---|---|---|
| ATOM | 2676 | O | THR | 348 | 25.796 | 63.813 | 37.680 | 1.00 43.52 |
| ATOM | 2677 | N | LEU | 349 | 23.990 | 62.982 | 36.640 | 1.00 43.57 |
| ATOM | 2678 | CA | LEU | 349 | 24.271 | 63.697 | 35.412 | 1.00 44.17 |
| ATOM | 2679 | CB | LEU | 349 | 23.343 | 63.180 | 34.311 | 1.00 44.43 |
| ATOM | 2680 | CG | LEU | 349 | 23.787 | 63.204 | 32.847 | 1.00 44.86 |
| ATOM | 2681 | CD1 | LEU | 349 | 25.198 | 62.658 | 32.688 | 1.00 44.59 |
| ATOM | 2682 | CD2 | LEU | 349 | 22.790 | 62.375 | 32.046 | 1.00 44.64 |
| ATOM | 2683 | C | LEU | 349 | 24.102 | 65.201 | 35.638 | 1.00 44.32 |
| ATOM | 2684 | O | LEU | 349 | 24.317 | 66.003 | 34.726 | 1.00 45.33 |
| ATOM | 2685 | N | GLY | 350 | 23.722 | 65.574 | 36.862 | 1.00 43.94 |
| ATOM | 2686 | CA | GLY | 350 | 23.559 | 66.981 | 37.210 | 1.00 43.15 |
| ATOM | 2687 | C | GLY | 350 | 22.167 | 67.570 | 37.038 | 1.00 42.49 |
| ATOM | 2688 | O | GLY | 350 | 22.024 | 68.752 | 36.703 | 1.00 41.70 |
| ATOM | 2689 | N | LEU | 351 | 21.143 | 66.758 | 37.288 | 1.00 41.97 |
| ATOM | 2690 | CA | LEU | 351 | 19.758 | 67.197 | 37.132 | 1.00 41.45 |
| ATOM | 2691 | CB | LEU | 351 | 19.194 | 66.676 | 35.812 | 1.00 40.99 |
| ATOM | 2692 | CG | LEU | 351 | 19.875 | 67.115 | 34.522 | 1.00 40.66 |
| ATOM | 2693 | CD1 | LEU | 351 | 19.516 | 66.144 | 33.416 | 1.00 41.63 |
| ATOM | 2694 | CD2 | LEU | 351 | 19.453 | 68.533 | 34.172 | 1.00 40.77 |
| ATOM | 2695 | C | LEU | 351 | 18.858 | 66.718 | 38.262 | 1.00 41.15 |
| ATOM | 2696 | O | LEU | 351 | 19.170 | 65.760 | 38.973 | 1.00 40.88 |
| ATOM | 2697 | N | ARG | 352 | 17.720 | 67.379 | 38.410 | 1.00 41.10 |
| ATOM | 2698 | CA | ARG | 352 | 16.782 | 67.007 | 39.457 | 1.00 41.25 |
| ATOM | 2699 | CB | ARG | 352 | 16.614 | 68.173 | 40.431 | 1.00 42.65 |
| ATOM | 2700 | CG | ARG | 352 | 17.929 | 68.581 | 41.070 | 1.00 43.68 |
| ATOM | 2701 | CD | ARG | 352 | 18.504 | 67.421 | 41.851 | 1.00 45.59 |
| ATOM | 2702 | NE | ARG | 352 | 19.960 | 67.478 | 41.917 | 1.00 47.73 |
| ATOM | 2703 | CZ | ARG | 352 | 20.715 | 66.567 | 42.521 | 1.00 48.77 |
| ATOM | 2704 | NH1 | ARG | 352 | 20.143 | 65.524 | 43.119 | 1.00 49.05 |
| ATOM | 2705 | NH2 | ARG | 352 | 22.038 | 66.700 | 42.519 | 1.00 49.14 |
| ATOM | 2706 | C | ARG | 352 | 15.458 | 66.621 | 38.827 | 1.00 39.59 |
| ATOM | 2707 | O | ARG | 352 | 14.512 | 67.399 | 38.793 | 1.00 40.34 |
| ATOM | 2708 | N | PRO | 353 | 15.378 | 65.388 | 38.324 | 1.00 38.06 |
| ATOM | 2709 | CD | PRO | 353 | 16.325 | 64.285 | 38.555 | 1.00 37.28 |
| ATOM | 2710 | CA | PRO | 353 | 14.159 | 64.901 | 37.683 | 1.00 37.45 |
| ATOM | 2711 | CB | PRO | 353 | 14.595 | 63.552 | 37.134 | 1.00 37.27 |
| ATOM | 2712 | CG | PRO | 353 | 15.491 | 63.064 | 38.232 | 1.00 36.92 |
| ATOM | 2713 | C | PRO | 353 | 12.998 | 64.763 | 38.650 | 1.00 36.35 |
| ATOM | 2714 | O | PRO | 353 | 13.180 | 64.360 | 39.791 | 1.00 36.28 |
| ATOM | 2715 | N | SER | 354 | 11.805 | 65.110 | 38.194 | 1.00 35.82 |
| ATOM | 2716 | CA | SER | 354 | 10.625 | 64.951 | 39.028 | 1.00 36.40 |
| ATOM | 2717 | CB | SER | 354 | 9.570 | 66.010 | 38.698 | 1.00 35.94 |
| ATOM | 2718 | OG | SER | 354 | 8.944 | 65.725 | 37.459 | 1.00 35.63 |
| ATOM | 2719 | C | SER | 354 | 10.091 | 63.570 | 38.653 | 1.00 36.41 |
| ATOM | 2720 | O | SER | 354 | 10.592 | 62.948 | 37.716 | 1.00 37.42 |
| ATOM | 2721 | N | THR | 355 | 9.087 | 63.091 | 39.375 | 1.00 36.02 |
| ATOM | 2722 | CA | THR | 355 | 8.493 | 61.790 | 39.099 | 1.00 35.68 |
| ATOM | 2723 | CB | THR | 355 | 7.200 | 61.615 | 39.923 | 1.00 36.38 |
| ATOM | 2724 | OG1 | THR | 355 | 7.525 | 61.645 | 41.316 | 1.00 37.75 |
| ATOM | 2725 | CG2 | THR | 355 | 6.510 | 60.293 | 39.598 | 1.00 36.44 |
| ATOM | 2726 | C | THR | 355 | 8.161 | 61.633 | 37.609 | 1.00 35.80 |
| ATOM | 2727 | O | THR | 355 | 8.319 | 60.548 | 37.029 | 1.00 34.73 |
| ATOM | 2728 | N | THR | 356 | 7.698 | 62.720 | 36.994 | 1.00 35.28 |
| ATOM | 2729 | CA | THR | 356 | 7.336 | 62.690 | 35.586 | 1.00 35.39 |
| ATOM | 2730 | CB | THR | 356 | 6.287 | 63.774 | 35.263 | 1.00 35.59 |
| ATOM | 2731 | OG1 | THR | 356 | 6.651 | 64.990 | 35.925 | 1.00 35.39 |
| ATOM | 2732 | CG2 | THR | 356 | 4.892 | 63.331 | 35.719 | 1.00 34.33 |

*FIG. 4VV*

| ATOM | 2733 | C | THR | 356 | 8.542 | 62.848 | 34.662 | 1.00 | 35.30 |
|------|------|------|-----|-----|--------|--------|--------|------|-------|
| ATOM | 2734 | O | THR | 356 | 8.560 | 62.285 | 33.559 | 1.00 | 34.91 |
| ATOM | 2735 | N | ASP | 357 | 9.537 | 63.624 | 35.089 | 1.00 | 35.07 |
| ATOM | 2736 | CA | ASP | 357 | 10.740 | 63.782 | 34.277 | 1.00 | 35.80 |
| ATOM | 2737 | CB | ASP | 357 | 11.804 | 64.598 | 35.012 | 1.00 | 36.76 |
| ATOM | 2738 | CG | ASP | 357 | 11.451 | 66.077 | 35.116 | 1.00 | 38.19 |
| ATOM | 2739 | OD1 | ASP | 357 | 11.475 | 66.778 | 34.071 | 1.00 | 37.60 |
| ATOM | 2740 | OD2 | ASP | 357 | 11.158 | 66.538 | 36.249 | 1.00 | 38.76 |
| ATOM | 2741 | C | ASP | 357 | 11.277 | 62.373 | 34.039 | 1.00 | 35.97 |
| ATOM | 2742 | O | ASP | 357 | 11.460 | 61.942 | 32.901 | 1.00 | 36.94 |
| ATOM | 2743 | N | CYS | 358 | 11.498 | 61.649 | 35.131 | 1.00 | 35.67 |
| ATOM | 2744 | CA | CYS | 358 | 12.013 | 60.293 | 35.057 | 1.00 | 35.44 |
| ATOM | 2745 | CB | CYS | 358 | 12.051 | 59.658 | 36.447 | 1.00 | 35.93 |
| ATOM | 2746 | SG | CYS | 358 | 13.247 | 60.410 | 37.575 | 1.00 | 35.81 |
| ATOM | 2747 | C | CYS | 358 | 11.177 | 59.433 | 34.138 | 1.00 | 34.88 |
| ATOM | 2748 | O | CYS | 358 | 11.711 | 58.698 | 33.308 | 1.00 | 35.87 |
| ATOM | 2749 | N | ASP | 359 | 9.863 | 59.517 | 34.290 | 1.00 | 34.10 |
| ATOM | 2750 | CA | ASP | 359 | 8.960 | 58.729 | 33.464 | 1.00 | 33.10 |
| ATOM | 2751 | CB | ASP | 359 | 7.519 | 58.964 | 33.910 | 1.00 | 35.03 |
| ATOM | 2752 | CG | ASP | 359 | 7.118 | 58.058 | 35.062 | 1.00 | 36.65 |
| ATOM | 2753 | OD1 | ASP | 359 | 7.950 | 57.850 | 35.975 | 1.00 | 38.15 |
| ATOM | 2754 | OD2 | ASP | 359 | 5.969 | 57.561 | 35.055 | 1.00 | 37.12 |
| ATOM | 2755 | C | ASP | 359 | 9.130 | 59.058 | 31.985 | 1.00 | 31.16 |
| ATOM | 2756 | O | ASP | 359 | 9.090 | 58.170 | 31.133 | 1.00 | 30.01 |
| ATOM | 2757 | N | ILE | 360 | 9.325 | 60.334 | 31.682 | 1.00 | 29.54 |
| ATOM | 2758 | CA | ILE | 360 | 9.524 | 60.741 | 30.300 | 1.00 | 28.61 |
| ATOM | 2759 | CB | ILE | 360 | 9.546 | 62.273 | 30.162 | 1.00 | 27.75 |
| ATOM | 2760 | CG2 | ILE | 360 | 10.255 | 62.668 | 28.874 | 1.00 | 27.01 |
| ATOM | 2761 | CG1 | ILE | 360 | 8.112 | 62.818 | 30.235 | 1.00 | 26.18 |
| ATOM | 2762 | CD1 | ILE | 360 | 8.024 | 64.322 | 30.190 | 1.00 | 23.23 |
| ATOM | 2763 | C | ILE | 360 | 10.857 | 60.176 | 29.825 | 1.00 | 29.21 |
| ATOM | 2764 | O | ILE | 360 | 10.919 | 59.480 | 28.805 | 1.00 | 29.88 |
| ATOM | 2765 | N | VAL | 361 | 11.923 | 60.466 | 30.569 | 1.00 | 28.39 |
| ATOM | 2766 | CA | VAL | 361 | 13.248 | 59.971 | 30.219 | 1.00 | 28.01 |
| ATOM | 2767 | CB | VAL | 361 | 14.258 | 60.256 | 31.342 | 1.00 | 27.73 |
| ATOM | 2768 | CG1 | VAL | 361 | 15.575 | 59.551 | 31.055 | 1.00 | 27.43 |
| ATOM | 2769 | CG2 | VAL | 361 | 14.492 | 61.759 | 31.453 | 1.00 | 27.76 |
| ATOM | 2770 | C | VAL | 361 | 13.245 | 58.464 | 29.919 | 1.00 | 27.74 |
| ATOM | 2771 | O | VAL | 361 | 14.055 | 57.982 | 29.107 | 1.00 | 27.40 |
| ATOM | 2772 | N | ARG | 362 | 12.341 | 57.719 | 30.556 | 1.00 | 27.72 |
| ATOM | 2773 | CA | ARG | 362 | 12.277 | 56.275 | 30.325 | 1.00 | 27.95 |
| ATOM | 2774 | CB | ARG | 362 | 11.523 | 55.571 | 31.455 | 1.00 | 29.48 |
| ATOM | 2775 | CG | ARG | 362 | 11.137 | 54.147 | 31.101 | 1.00 | 31.97 |
| ATOM | 2776 | CD | ARG | 362 | 10.900 | 53.266 | 32.308 | 1.00 | 33.93 |
| ATOM | 2777 | NE | ARG | 362 | 10.930 | 51.859 | 31.893 | 1.00 | 37.37 |
| ATOM | 2778 | CZ | ARG | 362 | 10.938 | 50.817 | 32.725 | 1.00 | 37.52 |
| ATOM | 2779 | NH1 | ARG | 362 | 10.920 | 51.010 | 34.043 | 1.00 | 38.72 |
| ATOM | 2780 | NH2 | ARG | 362 | 10.960 | 49.582 | 32.230 | 1.00 | 36.06 |
| ATOM | 2781 | C | ARG | 362 | 11.614 | 55.959 | 28.994 | 1.00 | 27.88 |
| ATOM | 2782 | O | ARG | 362 | 12.016 | 55.032 | 28.289 | 1.00 | 29.02 |
| ATOM | 2783 | N | ARG | 363 | 10.586 | 56.728 | 28.660 | 1.00 | 27.31 |
| ATOM | 2784 | CA | ARG | 363 | 9.866 | 56.564 | 27.400 | 1.00 | 25.77 |
| ATOM | 2785 | CB | ARG | 363 | 8.641 | 57.486 | 27.374 | 1.00 | 26.51 |
| ATOM | 2786 | CG | ARG | 363 | 7.530 | 57.084 | 28.318 | 1.00 | 26.30 |
| ATOM | 2787 | CD | ARG | 363 | 6.730 | 55.929 | 27.739 | 1.00 | 28.36 |
| ATOM | 2788 | NE | ARG | 363 | 6.259 | 56.216 | 26.380 | 1.00 | 30.91 |
| ATOM | 2789 | CZ | ARG | 363 | 6.872 | 55.826 | 25.260 | 1.00 | 31.55 |

*FIG. 4WW*

```
ATOM   2790  NH1 ARG   363       7.992  55.112  25.315  1.00 33.18
ATOM   2791  NH2 ARG   363       6.370  56.158  24.077  1.00 32.30
ATOM   2792  C   ARG   363      10.817  56.949  26.272  1.00 24.71
ATOM   2793  O   ARG   363      10.748  56.392  25.175  1.00 24.40
ATOM   2794  N   ALA   364      11.706  57.905  26.540  1.00 23.90
ATOM   2795  CA  ALA   364      12.653  58.339  25.507  1.00 24.48
ATOM   2796  CB  ALA   364      13.463  59.545  25.969  1.00 23.15
ATOM   2797  C   ALA   364      13.571  57.176  25.226  1.00 25.01
ATOM   2798  O   ALA   364      13.854  56.872  24.069  1.00 26.22
ATOM   2799  N   CYS   365      14.023  56.518  26.290  1.00 25.03
ATOM   2800  CA  CYS   365      14.902  55.370  26.157  1.00 24.77
ATOM   2801  CB  CYS   365      15.450  54.970  27.528  1.00 23.03
ATOM   2802  SG  CYS   365      16.728  56.114  28.173  1.00 21.60
ATOM   2803  C   CYS   365      14.140  54.206  25.514  1.00 26.44
ATOM   2804  O   CYS   365      14.661  53.535  24.617  1.00 27.49
ATOM   2805  N   GLU   366      12.906  53.956  25.944  1.00 26.87
ATOM   2806  CA  GLU   366      12.145  52.859  25.342  1.00 27.98
ATOM   2807  CB  GLU   366      10.757  52.743  25.988  1.00 28.74
ATOM   2808  CG  GLU   366      10.785  52.431  27.490  1.00 30.75
ATOM   2809  CD  GLU   366       9.427  51.981  28.041  1.00 32.09
ATOM   2810  OE1 GLU   366       8.444  52.757  27.970  1.00 32.39
ATOM   2811  OE2 GLU   366       9.342  50.841  28.547  1.00 33.30
ATOM   2812  C   GLU   366      12.005  53.056  23.815  1.00 28.15
ATOM   2813  O   GLU   366      12.117  52.104  23.029  1.00 27.63
ATOM   2814  N   SER   367      11.776  54.304  23.407  1.00 28.42
ATOM   2815  CA  SER   367      11.612  54.650  21.993  1.00 27.23
ATOM   2816  CB  SER   367      11.368  56.156  21.833  1.00 27.45
ATOM   2817  OG  SER   367      10.161  56.552  22.447  1.00 27.44
ATOM   2818  C   SER   367      12.824  54.276  21.165  1.00 26.52
ATOM   2819  O   SER   367      12.724  53.567  20.162  1.00 27.99
ATOM   2820  N   VAL   368      13.977  54.773  21.581  1.00 24.30
ATOM   2821  CA  VAL   368      15.194  54.499  20.849  1.00 22.45
ATOM   2822  CB  VAL   368      16.324  55.395  21.375  1.00 20.96
ATOM   2823  CG1 VAL   368      17.623  55.075  20.682  1.00 18.44
ATOM   2824  CG2 VAL   368      15.928  56.843  21.190  1.00 18.99
ATOM   2825  C   VAL   368      15.605  53.019  20.888  1.00 23.13
ATOM   2826  O   VAL   368      15.850  52.420  19.832  1.00 23.88
ATOM   2827  N   SER   369      15.660  52.405  22.071  1.00 22.54
ATOM   2828  CA  SER   369      16.071  51.003  22.106  1.00 21.93
ATOM   2829  CB  SER   369      16.248  50.476  23.542  1.00 23.39
ATOM   2830  OG  SER   369      15.011  50.251  24.197  1.00 25.91
ATOM   2831  C   SER   369      15.109  50.112  21.348  1.00 20.54
ATOM   2832  O   SER   369      15.526  49.063  20.850  1.00 20.31
ATOM   2833  N   THR   370      13.832  50.499  21.259  1.00 18.40
ATOM   2834  CA  THR   370      12.878  49.682  20.496  1.00 17.32
ATOM   2835  CB  THR   370      11.400  49.976  20.859  1.00 16.46
ATOM   2836  OG1 THR   370      11.053  49.298  22.073  1.00 15.81
ATOM   2837  CG2 THR   370      10.473  49.487  19.774  1.00 14.39
ATOM   2838  C   THR   370      13.076  49.936  19.001  1.00 17.03
ATOM   2839  O   THR   370      12.977  49.008  18.186  1.00 17.38
ATOM   2840  N   ARG   371      13.358  51.177  18.617  1.00 16.71
ATOM   2841  CA  ARG   371      13.562  51.423  17.201  1.00 16.54
ATOM   2842  CB  ARG   371      13.810  52.905  16.882  1.00 17.42
ATOM   2843  CG  ARG   371      14.013  53.123  15.374  1.00 17.76
ATOM   2844  CD  ARG   371      14.283  54.559  14.943  1.00 17.40
ATOM   2845  NE  ARG   371      15.567  55.076  15.412  1.00 18.85
ATOM   2846  CZ  ARG   371      16.159  56.154  14.896  1.00 18.99
```

FIG. 4XX

| | | | | | | | | |
|---|---|---|---|---|---|---|---|---|
| ATOM | 2847 | NH1 | ARG | 371 | 15.583 | 56.810 | 13.892 | 1.00 17.43 |
| ATOM | 2848 | NH2 | ARG | 371 | 17.303 | 56.605 | 15.406 | 1.00 19.19 |
| ATOM | 2849 | C | ARG | 371 | 14.763 | 50.607 | 16.759 | 1.00 15.91 |
| ATOM | 2850 | O | ARG | 371 | 14.689 | 49.929 | 15.748 | 1.00 17.14 |
| ATOM | 2851 | N | ALA | 372 | 15.856 | 50.644 | 17.519 | 1.00 15.40 |
| ATOM | 2852 | CA | ALA | 372 | 17.061 | 49.883 | 17.148 | 1.00 16.23 |
| ATOM | 2853 | CB | ALA | 372 | 18.152 | 50.046 | 18.197 | 1.00 15.66 |
| ATOM | 2854 | C | ALA | 372 | 16.775 | 48.407 | 16.957 | 1.00 16.83 |
| ATOM | 2855 | O | ALA | 372 | 17.125 | 47.838 | 15.923 | 1.00 18.06 |
| ATOM | 2856 | N | ALA | 373 | 16.149 | 47.790 | 17.955 | 1.00 16.86 |
| ATOM | 2857 | CA | ALA | 373 | 15.817 | 46.367 | 17.912 | 1.00 17.10 |
| ATOM | 2858 | CB | ALA | 373 | 15.027 | 45.976 | 19.156 | 1.00 16.66 |
| ATOM | 2859 | C | ALA | 373 | 15.024 | 46.018 | 16.665 | 1.00 18.79 |
| ATOM | 2860 | O | ALA | 373 | 15.301 | 45.004 | 16.018 | 1.00 20.02 |
| ATOM | 2861 | N | HIS | 374 | 14.037 | 46.841 | 16.316 | 1.00 19.22 |
| ATOM | 2862 | CA | HIS | 374 | 13.243 | 46.560 | 15.122 | 1.00 20.89 |
| ATOM | 2863 | CB | HIS | 374 | 12.025 | 47.489 | 15.052 | 1.00 20.93 |
| ATOM | 2864 | CG | HIS | 374 | 10.948 | 47.131 | 16.029 | 1.00 19.79 |
| ATOM | 2865 | CD2 | HIS | 374 | 10.813 | 46.065 | 16.855 | 1.00 19.53 |
| ATOM | 2866 | ND1 | HIS | 374 | 9.833 | 47.914 | 16.229 | 1.00 19.92 |
| ATOM | 2867 | CE1 | HIS | 374 | 9.057 | 47.347 | 17.137 | 1.00 18.78 |
| ATOM | 2868 | NE2 | HIS | 374 | 9.629 | 46.223 | 17.532 | 1.00 18.61 |
| ATOM | 2869 | C | HIS | 374 | 14.075 | 46.696 | 13.866 | 1.00 21.57 |
| ATOM | 2870 | O | HIS | 374 | 14.136 | 45.789 | 13.058 | 1.00 21.42 |
| ATOM | 2871 | N | MSE | 375 | 14.722 | 47.835 | 13.698 | 1.00 24.00 |
| ATOM | 2872 | CA | MSE | 375 | 15.561 | 48.027 | 12.528 | 1.00 26.05 |
| ATOM | 2873 | CB | MSE | 375 | 16.390 | 49.311 | 12.666 | 1.00 28.31 |
| ATOM | 2874 | CG | MSE | 375 | 15.671 | 50.558 | 12.197 | 1.00 31.46 |
| ATOM | 2875 | SE | MSE | 375 | 15.246 | 50.448 | 10.400 | 1.00 41.26 |
| ATOM | 2876 | CE | MSE | 375 | 16.340 | 51.745 | 9.680 | 1.00 36.51 |
| ATOM | 2877 | C | MSE | 375 | 16.476 | 46.810 | 12.390 | 1.00 25.84 |
| ATOM | 2878 | O | MSE | 375 | 16.501 | 46.159 | 11.351 | 1.00 26.84 |
| ATOM | 2879 | N | CYS | 376 | 17.200 | 46.489 | 13.455 | 1.00 25.61 |
| ATOM | 2880 | CA | CYS | 376 | 18.107 | 45.349 | 13.436 | 1.00 25.11 |
| ATOM | 2881 | CB | CYS | 376 | 18.693 | 45.117 | 14.831 | 1.00 26.04 |
| ATOM | 2882 | SG | CYS | 376 | 20.038 | 43.879 | 14.876 | 1.00 27.98 |
| ATOM | 2883 | C | CYS | 376 | 17.445 | 44.058 | 12.931 | 1.00 24.01 |
| ATOM | 2884 | O | CYS | 376 | 18.015 | 43.369 | 12.078 | 1.00 24.35 |
| ATOM | 2885 | N | SER | 377 | 16.251 | 43.741 | 13.443 | 1.00 22.14 |
| ATOM | 2886 | CA | SER | 377 | 15.519 | 42.531 | 13.038 | 1.00 20.58 |
| ATOM | 2887 | CB | SER | 377 | 14.203 | 42.399 | 13.811 | 1.00 20.36 |
| ATOM | 2888 | OG | SER | 377 | 13.233 | 43.325 | 13.339 | 1.00 20.95 |
| ATOM | 2889 | C | SER | 377 | 15.210 | 42.535 | 11.542 | 1.00 20.00 |
| ATOM | 2890 | O | SER | 377 | 15.154 | 41.484 | 10.900 | 1.00 19.23 |
| ATOM | 2891 | N | ALA | 378 | 14.995 | 43.715 | 10.980 | 1.00 19.64 |
| ATOM | 2892 | CA | ALA | 378 | 14.723 | 43.787 | 9.549 | 1.00 19.32 |
| ATOM | 2893 | CB | ALA | 378 | 14.521 | 45.243 | 9.119 | 1.00 18.02 |
| ATOM | 2894 | C | ALA | 378 | 15.958 | 43.186 | 8.874 | 1.00 19.40 |
| ATOM | 2895 | O | ALA | 378 | 15.860 | 42.230 | 8.093 | 1.00 18.55 |
| ATOM | 2896 | N | GLY | 379 | 17.123 | 43.740 | 9.222 | 1.00 20.18 |
| ATOM | 2897 | CA | GLY | 379 | 18.381 | 43.271 | 8.669 | 1.00 20.06 |
| ATOM | 2898 | C | GLY | 379 | 18.547 | 41.762 | 8.734 | 1.00 19.52 |
| ATOM | 2899 | O | GLY | 379 | 18.754 | 41.113 | 7.704 | 1.00 20.07 |
| ATOM | 2900 | N | LEU | 380 | 18.442 | 41.201 | 9.936 | 1.00 18.61 |
| ATOM | 2901 | CA | LEU | 380 | 18.596 | 39.763 | 10.110 | 1.00 18.74 |
| ATOM | 2902 | CB | LEU | 380 | 18.489 | 39.371 | 11.579 | 1.00 18.49 |
| ATOM | 2903 | CG | LEU | 380 | 18.774 | 37.881 | 11.816 | 1.00 17.82 |

FIG. 4YY

| | | | | | | | | |
|---|---|---|---|---|---|---|---|---|
| ATOM | 2904 | CD1 | LEU | 380 | 20.215 | 37.586 | 11.383 | 1.00 16.94 |
| ATOM | 2905 | CD2 | LEU | 380 | 18.557 | 37.512 | 13.285 | 1.00 16.34 |
| ATOM | 2906 | C | LEU | 380 | 17.580 | 38.938 | 9.341 | 1.00 19.56 |
| ATOM | 2907 | O | LEU | 380 | 17.895 | 37.833 | 8.892 | 1.00 20.67 |
| ATOM | 2908 | N | ALA | 381 | 16.354 | 39.447 | 9.211 | 1.00 19.83 |
| ATOM | 2909 | CA | ALA | 381 | 15.311 | 38.713 | 8.496 | 1.00 20.17 |
| ATOM | 2910 | CB | ALA | 381 | 13.961 | 39.327 | 8.759 | 1.00 19.87 |
| ATOM | 2911 | C | ALA | 381 | 15.638 | 38.746 | 7.009 | 1.00 21.06 |
| ATOM | 2912 | O | ALA | 381 | 15.421 | 37.773 | 6.269 | 1.00 21.05 |
| ATOM | 2913 | N | GLY | 382 | 16.174 | 39.874 | 6.567 | 1.00 21.33 |
| ATOM | 2914 | CA | GLY | 382 | 16.561 | 39.965 | 5.175 | 1.00 22.63 |
| ATOM | 2915 | C | GLY | 382 | 17.670 | 38.954 | 4.903 | 1.00 23.10 |
| ATOM | 2916 | O | GLY | 382 | 17.708 | 38.319 | 3.832 | 1.00 23.74 |
| ATOM | 2917 | N | VAL | 383 | 18.579 | 38.778 | 5.859 | 1.00 21.83 |
| ATOM | 2918 | CA | VAL | 383 | 19.642 | 37.828 | 5.615 | 1.00 22.47 |
| ATOM | 2919 | CB | VAL | 383 | 20.786 | 37.967 | 6.643 | 1.00 22.80 |
| ATOM | 2920 | CG1 | VAL | 383 | 21.737 | 36.777 | 6.525 | 1.00 21.04 |
| ATOM | 2921 | CG2 | VAL | 383 | 21.562 | 39.298 | 6.396 | 1.00 21.85 |
| ATOM | 2922 | C | VAL | 383 | 19.075 | 36.423 | 5.639 | 1.00 22.92 |
| ATOM | 2923 | O | VAL | 383 | 19.199 | 35.681 | 4.675 | 1.00 23.65 |
| ATOM | 2924 | N | ILE | 384 | 18.414 | 36.061 | 6.724 | 1.00 23.52 |
| ATOM | 2925 | CA | ILE | 384 | 17.853 | 34.721 | 6.835 | 1.00 24.64 |
| ATOM | 2926 | CB | ILE | 384 | 17.124 | 34.551 | 8.179 | 1.00 24.17 |
| ATOM | 2927 | CG2 | ILE | 384 | 16.533 | 33.143 | 8.283 | 1.00 22.50 |
| ATOM | 2928 | CG1 | ILE | 384 | 18.112 | 34.810 | 9.318 | 1.00 23.69 |
| ATOM | 2929 | CD1 | ILE | 384 | 17.476 | 34.861 | 10.661 | 1.00 24.39 |
| ATOM | 2930 | C | ILE | 384 | 16.910 | 34.324 | 5.691 | 1.00 26.04 |
| ATOM | 2931 | O | ILE | 384 | 17.029 | 33.233 | 5.144 | 1.00 26.98 |
| ATOM | 2932 | N | ASN | 385 | 15.974 | 35.182 | 5.310 | 1.00 26.88 |
| ATOM | 2933 | CA | ASN | 385 | 15.097 | 34.785 | 4.218 | 1.00 27.99 |
| ATOM | 2934 | CB | ASN | 385 | 13.984 | 35.819 | 3.998 | 1.00 25.92 |
| ATOM | 2935 | CG | ASN | 385 | 13.038 | 35.918 | 5.174 | 1.00 23.68 |
| ATOM | 2936 | OD1 | ASN | 385 | 12.721 | 34.921 | 5.820 | 1.00 21.60 |
| ATOM | 2937 | ND2 | ASN | 385 | 12.567 | 37.128 | 5.448 | 1.00 23.03 |
| ATOM | 2938 | C | ASN | 385 | 15.888 | 34.579 | 2.915 | 1.00 29.62 |
| ATOM | 2939 | O | ASN | 385 | 15.610 | 33.647 | 2.143 | 1.00 29.62 |
| ATOM | 2940 | N | ARG | 386 | 16.869 | 35.440 | 2.660 | 1.00 31.30 |
| ATOM | 2941 | CA | ARG | 386 | 17.660 | 35.301 | 1.442 | 1.00 33.07 |
| ATOM | 2942 | CB | ARG | 386 | 18.840 | 36.261 | 1.446 | 1.00 32.62 |
| ATOM | 2943 | CG | ARG | 386 | 19.697 | 36.147 | 0.214 | 1.00 33.28 |
| ATOM | 2944 | CD | ARG | 386 | 20.908 | 37.059 | 0.284 | 1.00 34.52 |
| ATOM | 2945 | NE | ARG | 386 | 21.923 | 36.698 | -0.704 | 1.00 35.29 |
| ATOM | 2946 | CZ | ARG | 386 | 21.812 | 36.910 | -2.014 | 1.00 36.32 |
| ATOM | 2947 | NH1 | ARG | 386 | 20.729 | 37.492 | -2.518 | 1.00 35.95 |
| ATOM | 2948 | NH2 | ARG | 386 | 22.782 | 36.525 | -2.832 | 1.00 37.07 |
| ATOM | 2949 | C | ARG | 386 | 18.178 | 33.875 | 1.362 | 1.00 34.69 |
| ATOM | 2950 | O | ARG | 386 | 18.077 | 33.232 | 0.320 | 1.00 35.70 |
| ATOM | 2951 | N | MSE | 387 | 18.710 | 33.383 | 2.480 | 1.00 35.94 |
| ATOM | 2952 | CA | MSE | 387 | 19.250 | 32.036 | 2.560 | 1.00 37.39 |
| ATOM | 2953 | CB | MSE | 387 | 19.903 | 31.828 | 3.927 | 1.00 39.78 |
| ATOM | 2954 | CG | MSE | 387 | 21.099 | 32.754 | 4.186 | 1.00 42.37 |
| ATOM | 2955 | SE | MSE | 387 | 21.873 | 32.552 | 5.859 | 1.00 49.18 |
| ATOM | 2956 | CE | MSE | 387 | 21.738 | 30.694 | 6.097 | 1.00 44.67 |
| ATOM | 2957 | C | MSE | 387 | 18.179 | 30.976 | 2.311 | 1.00 38.50 |
| ATOM | 2958 | O | MSE | 387 | 18.463 | 29.927 | 1.721 | 1.00 37.80 |
| ATOM | 2959 | N | ARG | 388 | 16.954 | 31.255 | 2.769 | 1.00 40.15 |
| ATOM | 2960 | CA | ARG | 388 | 15.808 | 30.352 | 2.586 | 1.00 41.28 |

*FIG. 4ZZ*

| ATOM | 2961 | CB | ARG | 388 | 14.554 | 30.941 | 3.245 | 1.00 | 42.50 |
| ATOM | 2962 | CG | ARG | 388 | 13.268 | 30.115 | 3.069 | 1.00 | 42.73 |
| ATOM | 2963 | CD | ARG | 388 | 12.266 | 30.443 | 4.178 | 1.00 | 43.15 |
| ATOM | 2964 | NE | ARG | 388 | 10.965 | 29.787 | 4.012 | 1.00 | 44.47 |
| ATOM | 2965 | CZ | ARG | 388 | 10.049 | 30.134 | 3.104 | 1.00 | 44.46 |
| ATOM | 2966 | NH1 | ARG | 388 | 10.283 | 31.139 | 2.269 | 1.00 | 44.11 |
| ATOM | 2967 | NH2 | ARG | 388 | 8.895 | 29.478 | 3.033 | 1.00 | 44.15 |
| ATOM | 2968 | C | ARG | 388 | 15.579 | 30.210 | 1.094 | 1.00 | 41.39 |
| ATOM | 2969 | O | ARG | 388 | 15.516 | 29.104 | 0.554 | 1.00 | 40.76 |
| ATOM | 2970 | N | GLU | 389 | 15.460 | 31.355 | 0.439 | 1.00 | 41.88 |
| ATOM | 2971 | CA | GLU | 389 | 15.275 | 31.405 | -0.997 | 1.00 | 43.37 |
| ATOM | 2972 | CB | GLU | 389 | 15.211 | 32.867 | -1.448 | 1.00 | 45.21 |
| ATOM | 2973 | CG | GLU | 389 | 15.227 | 33.079 | -2.957 | 1.00 | 48.22 |
| ATOM | 2974 | CD | GLU | 389 | 13.894 | 32.754 | -3.632 | 1.00 | 50.35 |
| ATOM | 2975 | OE1 | GLU | 389 | 13.850 | 32.799 | -4.891 | 1.00 | 51.00 |
| ATOM | 2976 | OE2 | GLU | 389 | 12.900 | 32.464 | -2.912 | 1.00 | 50.86 |
| ATOM | 2977 | C | GLU | 389 | 16.476 | 30.713 | -1.635 | 1.00 | 43.77 |
| ATOM | 2978 | O | GLU | 389 | 16.325 | 29.726 | -2.355 | 1.00 | 43.53 |
| ATOM | 2979 | N | SER | 390 | 17.671 | 31.227 | -1.335 | 1.00 | 43.84 |
| ATOM | 2980 | CA | SER | 390 | 18.925 | 30.697 | -1.878 | 1.00 | 43.61 |
| ATOM | 2981 | CB | SER | 390 | 20.112 | 31.549 | -1.425 | 1.00 | 43.41 |
| ATOM | 2982 | OG | SER | 390 | 20.229 | 32.703 | -2.241 | 1.00 | 43.45 |
| ATOM | 2983 | C | SER | 390 | 19.243 | 29.234 | -1.607 | 1.00 | 43.62 |
| ATOM | 2984 | O | SER | 390 | 20.126 | 28.671 | -2.251 | 1.00 | 44.11 |
| ATOM | 2985 | N | ARG | 391 | 18.555 | 28.614 | -0.660 | 1.00 | 43.22 |
| ATOM | 2986 | CA | ARG | 391 | 18.815 | 27.213 | -0.396 | 1.00 | 43.67 |
| ATOM | 2987 | CB | ARG | 391 | 19.174 | 26.994 | 1.078 | 1.00 | 42.72 |
| ATOM | 2988 | CG | ARG | 391 | 20.440 | 27.699 | 1.512 | 1.00 | 41.51 |
| ATOM | 2989 | CD | ARG | 391 | 20.907 | 27.245 | 2.892 | 1.00 | 39.51 |
| ATOM | 2990 | NE | ARG | 391 | 22.183 | 27.864 | 3.231 | 1.00 | 37.99 |
| ATOM | 2991 | CZ | ARG | 391 | 22.940 | 27.512 | 4.266 | 1.00 | 37.81 |
| ATOM | 2992 | NH1 | ARG | 391 | 22.545 | 26.540 | 5.070 | 1.00 | 36.05 |
| ATOM | 2993 | NH2 | ARG | 391 | 24.105 | 28.121 | 4.482 | 1.00 | 37.12 |
| ATOM | 2994 | C | ARG | 391 | 17.578 | 26.404 | -0.756 | 1.00 | 44.95 |
| ATOM | 2995 | O | ARG | 391 | 17.458 | 25.241 | -0.372 | 1.00 | 45.05 |
| ATOM | 2996 | N | SER | 392 | 16.666 | 27.023 | -1.502 | 1.00 | 46.71 |
| ATOM | 2997 | CA | SER | 392 | 15.420 | 26.367 | -1.895 | 1.00 | 48.25 |
| ATOM | 2998 | CB | SER | 392 | 15.631 | 25.468 | -3.121 | 1.00 | 48.10 |
| ATOM | 2999 | OG | SER | 392 | 15.610 | 26.216 | -4.326 | 1.00 | 48.60 |
| ATOM | 3000 | C | SER | 392 | 14.880 | 25.536 | -0.737 | 1.00 | 49.61 |
| ATOM | 3001 | O | SER | 392 | 14.601 | 24.344 | -0.882 | 1.00 | 49.37 |
| ATOM | 3002 | N | GLU | 393 | 14.749 | 26.175 | 0.420 | 1.00 | 51.58 |
| ATOM | 3003 | CA | GLU | 393 | 14.237 | 25.510 | 1.617 | 1.00 | 53.54 |
| ATOM | 3004 | CB | GLU | 393 | 15.085 | 25.897 | 2.842 | 1.00 | 54.33 |
| ATOM | 3005 | CG | GLU | 393 | 16.586 | 25.655 | 2.701 | 1.00 | 54.92 |
| ATOM | 3006 | CD | GLU | 393 | 17.057 | 24.420 | 3.450 | 1.00 | 55.87 |
| ATOM | 3007 | OE1 | GLU | 393 | 16.845 | 24.347 | 4.683 | 1.00 | 55.29 |
| ATOM | 3008 | OE2 | GLU | 393 | 17.646 | 23.523 | 2.806 | 1.00 | 56.69 |
| ATOM | 3009 | C | GLU | 393 | 12.793 | 25.961 | 1.838 | 1.00 | 54.20 |
| ATOM | 3010 | O | GLU | 393 | 12.482 | 27.151 | 1.693 | 1.00 | 53.70 |
| ATOM | 3011 | N | ASP | 394 | 11.907 | 25.026 | 2.173 | 1.00 | 55.42 |
| ATOM | 3012 | CA | ASP | 394 | 10.519 | 25.404 | 2.419 | 1.00 | 56.88 |
| ATOM | 3013 | CB | ASP | 394 | 9.585 | 24.194 | 2.400 | 1.00 | 58.69 |
| ATOM | 3014 | CG | ASP | 394 | 8.111 | 24.602 | 2.415 | 1.00 | 61.23 |
| ATOM | 3015 | OD1 | ASP | 394 | 7.691 | 25.298 | 3.376 | 1.00 | 62.29 |
| ATOM | 3016 | OD2 | ASP | 394 | 7.374 | 24.237 | 1.466 | 1.00 | 62.03 |
| ATOM | 3017 | C | ASP | 394 | 10.489 | 26.041 | 3.795 | 1.00 | 56.57 |

FIG. 4AAA

| | | | | | | | | |
|---|---|---|---|---|---|---|---|---|
| ATOM | 3018 | O | ASP | 394 | 10.023 | 27.164 | 3.959 | 1.00 56.22 |
| ATOM | 3019 | N | VAL | 395 | 10.994 | 25.298 | 4.773 | 1.00 56.79 |
| ATOM | 3020 | CA | VAL | 395 | 11.086 | 25.756 | 6.153 | 1.00 57.23 |
| ATOM | 3021 | CB | VAL | 395 | 10.166 | 24.949 | 7.093 | 1.00 57.72 |
| ATOM | 3022 | CG1 | VAL | 395 | 10.444 | 25.320 | 8.548 | 1.00 57.64 |
| ATOM | 3023 | CG2 | VAL | 395 | 8.708 | 25.221 | 6.749 | 1.00 58.46 |
| ATOM | 3024 | C | VAL | 395 | 12.534 | 25.538 | 6.575 | 1.00 57.01 |
| ATOM | 3025 | O | VAL | 395 | 12.968 | 24.407 | 6.793 | 1.00 56.90 |
| ATOM | 3026 | N | MSE | 396 | 13.280 | 26.626 | 6.690 | 1.00 56.80 |
| ATOM | 3027 | CA | MSE | 396 | 14.682 | 26.536 | 7.058 | 1.00 56.12 |
| ATOM | 3028 | CB | MSE | 396 | 15.463 | 27.645 | 6.375 | 1.00 57.66 |
| ATOM | 3029 | CG | MSE | 396 | 16.932 | 27.623 | 6.690 | 1.00 60.51 |
| ATOM | 3030 | SE | MSE | 396 | 17.716 | 29.077 | 6.002 | 1.00 65.26 |
| ATOM | 3031 | CE | MSE | 396 | 17.988 | 28.564 | 4.293 | 1.00 64.74 |
| ATOM | 3032 | C | MSE | 396 | 14.964 | 26.600 | 8.545 | 1.00 54.59 |
| ATOM | 3033 | O | MSE | 396 | 14.487 | 27.491 | 9.245 | 1.00 54.08 |
| ATOM | 3034 | N | ARG | 397 | 15.740 | 25.637 | 9.025 | 1.00 53.05 |
| ATOM | 3035 | CA | ARG | 397 | 16.134 | 25.613 | 10.426 | 1.00 51.13 |
| ATOM | 3036 | CB | ARG | 397 | 16.226 | 24.181 | 10.951 | 1.00 52.77 |
| ATOM | 3037 | CG | ARG | 397 | 14.888 | 23.520 | 11.244 | 1.00 55.36 |
| ATOM | 3038 | CD | ARG | 397 | 15.132 | 22.079 | 11.671 | 1.00 58.69 |
| ATOM | 3039 | NE | ARG | 397 | 13.985 | 21.448 | 12.326 | 1.00 61.28 |
| ATOM | 3040 | CZ | ARG | 397 | 14.056 | 20.294 | 12.990 | 1.00 62.10 |
| ATOM | 3041 | NH1 | ARG | 397 | 15.215 | 19.651 | 13.078 | 1.00 62.57 |
| ATOM | 3042 | NH2 | ARG | 397 | 12.978 | 19.793 | 13.583 | 1.00 62.49 |
| ATOM | 3043 | C | ARG | 397 | 17.509 | 26.252 | 10.397 | 1.00 48.33 |
| ATOM | 3044 | O | ARG | 397 | 18.273 | 26.029 | 9.466 | 1.00 47.77 |
| ATOM | 3045 | N | ILE | 398 | 17.825 | 27.064 | 11.395 | 1.00 45.82 |
| ATOM | 3046 | CA | ILE | 398 | 19.120 | 27.721 | 11.396 | 1.00 43.01 |
| ATOM | 3047 | CB | ILE | 398 | 19.202 | 28.791 | 10.293 | 1.00 43.25 |
| ATOM | 3048 | CG2 | ILE | 398 | 18.161 | 29.864 | 10.532 | 1.00 43.18 |
| ATOM | 3049 | CG1 | ILE | 398 | 20.594 | 29.417 | 10.279 | 1.00 43.75 |
| ATOM | 3050 | CD1 | ILE | 398 | 20.768 | 30.466 | 9.206 | 1.00 44.64 |
| ATOM | 3051 | C | ILE | 398 | 19.441 | 28.381 | 12.717 | 1.00 40.64 |
| ATOM | 3052 | O | ILE | 398 | 18.557 | 28.890 | 13.404 | 1.00 40.10 |
| ATOM | 3053 | N | THR | 399 | 20.722 | 28.360 | 13.060 | 1.00 37.78 |
| ATOM | 3054 | CA | THR | 399 | 21.185 | 28.954 | 14.290 | 1.00 35.36 |
| ATOM | 3055 | CB | THR | 399 | 22.052 | 27.988 | 15.079 | 1.00 35.02 |
| ATOM | 3056 | OG1 | THR | 399 | 21.280 | 26.832 | 15.425 | 1.00 34.92 |
| ATOM | 3057 | CG2 | THR | 399 | 22.570 | 28.666 | 16.345 | 1.00 34.73 |
| ATOM | 3058 | C | THR | 399 | 22.001 | 30.197 | 13.994 | 1.00 34.71 |
| ATOM | 3059 | O | THR | 399 | 22.736 | 30.254 | 13.005 | 1.00 35.10 |
| ATOM | 3060 | N | VAL | 400 | 21.858 | 31.184 | 14.871 | 1.00 32.96 |
| ATOM | 3061 | CA | VAL | 400 | 22.539 | 32.457 | 14.759 | 1.00 31.07 |
| ATOM | 3062 | CB | VAL | 400 | 21.514 | 33.593 | 14.592 | 1.00 31.21 |
| ATOM | 3063 | CG1 | VAL | 400 | 22.211 | 34.934 | 14.415 | 1.00 31.76 |
| ATOM | 3064 | CG2 | VAL | 400 | 20.628 | 33.298 | 13.405 | 1.00 31.47 |
| ATOM | 3065 | C | VAL | 400 | 23.336 | 32.685 | 16.039 | 1.00 30.19 |
| ATOM | 3066 | O | VAL | 400 | 22.779 | 32.640 | 17.144 | 1.00 30.96 |
| ATOM | 3067 | N | GLY | 401 | 24.641 | 32.905 | 15.888 | 1.00 28.35 |
| ATOM | 3068 | CA | GLY | 401 | 25.482 | 33.150 | 17.041 | 1.00 24.47 |
| ATOM | 3069 | C | GLY | 401 | 25.487 | 34.641 | 17.235 | 1.00 23.04 |
| ATOM | 3070 | O | GLY | 401 | 25.595 | 35.388 | 16.260 | 1.00 20.38 |
| ATOM | 3071 | N | VAL | 402 | 25.367 | 35.086 | 18.482 | 1.00 23.36 |
| ATOM | 3072 | CA | VAL | 402 | 25.338 | 36.514 | 18.751 | 1.00 23.38 |
| ATOM | 3073 | CB | VAL | 402 | 23.927 | 36.960 | 19.124 | 1.00 22.79 |
| ATOM | 3074 | CG1 | VAL | 402 | 23.790 | 38.458 | 18.909 | 1.00 22.85 |

FIG. 4BBB

| ATOM | 3075 | CG2 | VAL | 402 | 22.895 | 36.176 | 18.320 | 1.00 | 22.42 |
| --- | --- | --- | --- | --- | --- | --- | --- | --- | --- |
| ATOM | 3076 | C | VAL | 402 | 26.252 | 36.899 | 19.893 | 1.00 | 24.25 |
| ATOM | 3077 | O | VAL | 402 | 26.484 | 36.098 | 20.794 | 1.00 | 25.20 |
| ATOM | 3078 | N | ASP | 403 | 26.770 | 38.124 | 19.848 | 1.00 | 24.83 |
| ATOM | 3079 | CA | ASP | 403 | 27.637 | 38.649 | 20.894 | 1.00 | 27.11 |
| ATOM | 3080 | CB | ASP | 403 | 29.078 | 38.212 | 20.691 | 1.00 | 30.98 |
| ATOM | 3081 | CG | ASP | 403 | 30.003 | 38.739 | 21.787 | 1.00 | 34.48 |
| ATOM | 3082 | OD1 | ASP | 403 | 29.887 | 39.938 | 22.122 | 1.00 | 36.02 |
| ATOM | 3083 | OD2 | ASP | 403 | 30.842 | 37.960 | 22.311 | 1.00 | 36.05 |
| ATOM | 3084 | C | ASP | 403 | 27.562 | 40.154 | 20.763 | 1.00 | 27.24 |
| ATOM | 3085 | O | ASP | 403 | 27.550 | 40.667 | 19.645 | 1.00 | 29.15 |
| ATOM | 3086 | N | GLY | 404 | 27.519 | 40.863 | 21.888 | 1.00 | 26.60 |
| ATOM | 3087 | CA | GLY | 404 | 27.410 | 42.316 | 21.863 | 1.00 | 26.50 |
| ATOM | 3088 | C | GLY | 404 | 26.750 | 42.829 | 23.137 | 1.00 | 27.10 |
| ATOM | 3089 | O | GLY | 404 | 25.810 | 42.193 | 23.665 | 1.00 | 26.90 |
| ATOM | 3090 | N | SER | 405 | 27.209 | 43.972 | 23.644 | 1.00 | 26.72 |
| ATOM | 3091 | CA | SER | 405 | 26.638 | 44.496 | 24.887 | 1.00 | 27.96 |
| ATOM | 3092 | CB | SER | 405 | 27.409 | 45.722 | 25.371 | 1.00 | 28.04 |
| ATOM | 3093 | OG | SER | 405 | 27.164 | 46.828 | 24.521 | 1.00 | 30.53 |
| ATOM | 3094 | C | SER | 405 | 25.168 | 44.857 | 24.738 | 1.00 | 28.25 |
| ATOM | 3095 | O | SER | 405 | 24.341 | 44.473 | 25.573 | 1.00 | 27.96 |
| ATOM | 3096 | N | VAL | 406 | 24.844 | 45.591 | 23.675 | 1.00 | 27.79 |
| ATOM | 3097 | CA | VAL | 406 | 23.465 | 45.992 | 23.445 | 1.00 | 28.13 |
| ATOM | 3098 | CB | VAL | 406 | 23.281 | 46.667 | 22.074 | 1.00 | 28.02 |
| ATOM | 3099 | CG1 | VAL | 406 | 21.814 | 47.063 | 21.908 | 1.00 | 27.91 |
| ATOM | 3100 | CG2 | VAL | 406 | 24.197 | 47.877 | 21.940 | 1.00 | 26.07 |
| ATOM | 3101 | C | VAL | 406 | 22.535 | 44.789 | 23.488 | 1.00 | 28.35 |
| ATOM | 3102 | O | VAL | 406 | 21.484 | 44.826 | 24.120 | 1.00 | 28.48 |
| ATOM | 3103 | N | TYR | 407 | 22.934 | 43.718 | 22.811 | 1.00 | 28.72 |
| ATOM | 3104 | CA | TYR | 407 | 22.130 | 42.493 | 22.736 | 1.00 | 28.45 |
| ATOM | 3105 | CB | TYR | 407 | 22.613 | 41.643 | 21.558 | 1.00 | 26.86 |
| ATOM | 3106 | CG | TYR | 407 | 21.831 | 40.373 | 21.341 | 1.00 | 25.29 |
| ATOM | 3107 | CD1 | TYR | 407 | 20.700 | 40.358 | 20.535 | 1.00 | 25.44 |
| ATOM | 3108 | CE1 | TYR | 407 | 19.964 | 39.189 | 20.346 | 1.00 | 25.93 |
| ATOM | 3109 | CD2 | TYR | 407 | 22.213 | 39.192 | 21.955 | 1.00 | 24.93 |
| ATOM | 3110 | CE2 | TYR | 407 | 21.488 | 38.021 | 21.780 | 1.00 | 25.18 |
| ATOM | 3111 | CZ | TYR | 407 | 20.362 | 38.024 | 20.974 | 1.00 | 26.03 |
| ATOM | 3112 | OH | TYR | 407 | 19.626 | 36.868 | 20.822 | 1.00 | 25.67 |
| ATOM | 3113 | C | TYR | 407 | 22.175 | 41.651 | 24.014 | 1.00 | 28.83 |
| ATOM | 3114 | O | TYR | 407 | 21.202 | 40.988 | 24.369 | 1.00 | 28.62 |
| ATOM | 3115 | N | LYS | 408 | 23.306 | 41.674 | 24.705 | 1.00 | 29.64 |
| ATOM | 3116 | CA | LYS | 408 | 23.440 | 40.881 | 25.916 | 1.00 | 30.07 |
| ATOM | 3117 | CB | LYS | 408 | 24.904 | 40.477 | 26.118 | 1.00 | 30.08 |
| ATOM | 3118 | CG | LYS | 408 | 25.442 | 39.556 | 25.030 | 1.00 | 30.61 |
| ATOM | 3119 | CD | LYS | 408 | 26.597 | 38.698 | 25.529 | 1.00 | 30.05 |
| ATOM | 3120 | CE | LYS | 408 | 26.799 | 37.515 | 24.601 | 1.00 | 30.22 |
| ATOM | 3121 | NZ | LYS | 408 | 27.828 | 36.573 | 25.097 | 1.00 | 30.20 |
| ATOM | 3122 | C | LYS | 408 | 22.940 | 41.551 | 27.185 | 1.00 | 30.82 |
| ATOM | 3123 | O | LYS | 408 | 22.327 | 40.901 | 28.038 | 1.00 | 31.98 |
| ATOM | 3124 | N | LEU | 409 | 23.176 | 42.853 | 27.296 | 1.00 | 30.97 |
| ATOM | 3125 | CA | LEU | 409 | 22.823 | 43.598 | 28.501 | 1.00 | 31.11 |
| ATOM | 3126 | CB | LEU | 409 | 24.006 | 44.482 | 28.875 | 1.00 | 30.54 |
| ATOM | 3127 | CG | LEU | 409 | 25.305 | 43.700 | 28.962 | 1.00 | 29.31 |
| ATOM | 3128 | CD1 | LEU | 409 | 26.372 | 44.591 | 29.597 | 1.00 | 29.41 |
| ATOM | 3129 | CD2 | LEU | 409 | 25.067 | 42.423 | 29.785 | 1.00 | 28.16 |
| ATOM | 3130 | C | LEU | 409 | 21.548 | 44.441 | 28.611 | 1.00 | 31.44 |
| ATOM | 3131 | O | LEU | 409 | 20.978 | 44.542 | 29.708 | 1.00 | 31.86 |

*FIG. 4CCC*

| | | | | | | | | | |
|---|---|---|---|---|---|---|---|---|---|
| ATOM | 3132 | N | HIS | 410 | 21.122 | 45.077 | 27.519 | 1.00 | 31.34 |
| ATOM | 3133 | CA | HIS | 410 | 19.929 | 45.912 | 27.572 | 1.00 | 30.80 |
| ATOM | 3134 | CB | HIS | 410 | 19.732 | 46.635 | 26.247 | 1.00 | 30.36 |
| ATOM | 3135 | CG | HIS | 410 | 18.703 | 47.717 | 26.303 | 1.00 | 29.89 |
| ATOM | 3136 | CD2 | HIS | 410 | 18.815 | 49.060 | 26.179 | 1.00 | 29.29 |
| ATOM | 3137 | ND1 | HIS | 410 | 17.362 | 47.457 | 26.508 | 1.00 | 30.79 |
| ATOM | 3138 | CE1 | HIS | 410 | 16.691 | 48.595 | 26.505 | 1.00 | 29.88 |
| ATOM | 3139 | NE2 | HIS | 410 | 17.548 | 49.583 | 26.309 | 1.00 | 30.87 |
| ATOM | 3140 | C | HIS | 410 | 18.728 | 45.031 | 27.900 | 1.00 | 31.41 |
| ATOM | 3141 | O | HIS | 410 | 18.467 | 44.055 | 27.207 | 1.00 | 31.97 |
| ATOM | 3142 | N | PRO | 411 | 17.985 | 45.376 | 28.969 | 1.00 | 31.63 |
| ATOM | 3143 | CD | PRO | 411 | 18.173 | 46.690 | 29.610 | 1.00 | 31.32 |
| ATOM | 3144 | CA | PRO | 411 | 16.798 | 44.708 | 29.518 | 1.00 | 31.33 |
| ATOM | 3145 | CB | PRO | 411 | 16.111 | 45.815 | 30.299 | 1.00 | 31.27 |
| ATOM | 3146 | CG | PRO | 411 | 17.257 | 46.599 | 30.822 | 1.00 | 32.32 |
| ATOM | 3147 | C | PRO | 411 | 15.827 | 44.037 | 28.571 | 1.00 | 32.09 |
| ATOM | 3148 | O | PRO | 411 | 15.362 | 42.920 | 28.838 | 1.00 | 32.76 |
| ATOM | 3149 | N | SER | 412 | 15.519 | 44.684 | 27.457 | 1.00 | 31.73 |
| ATOM | 3150 | CA | SER | 412 | 14.527 | 44.094 | 26.573 | 1.00 | 31.92 |
| ATOM | 3151 | CB | SER | 412 | 13.210 | 44.834 | 26.771 | 1.00 | 32.51 |
| ATOM | 3152 | CG | SER | 412 | 13.368 | 46.200 | 26.390 | 1.00 | 33.27 |
| ATOM | 3153 | C | SER | 412 | 14.838 | 44.047 | 25.082 | 1.00 | 31.91 |
| ATOM | 3154 | O | SER | 412 | 14.039 | 43.520 | 24.304 | 1.00 | 32.59 |
| ATOM | 3155 | N | PHE | 413 | 15.974 | 44.601 | 24.679 | 1.00 | 30.72 |
| ATOM | 3156 | CA | PHE | 413 | 16.348 | 44.615 | 23.271 | 1.00 | 30.13 |
| ATOM | 3157 | CB | PHE | 413 | 17.778 | 45.105 | 23.130 | 1.00 | 28.18 |
| ATOM | 3158 | CG | PHE | 413 | 18.213 | 45.285 | 21.716 | 1.00 | 25.96 |
| ATOM | 3159 | CD1 | PHE | 413 | 18.085 | 46.522 | 21.094 | 1.00 | 25.70 |
| ATOM | 3160 | CD2 | PHE | 413 | 18.772 | 44.233 | 21.015 | 1.00 | 24.47 |
| ATOM | 3161 | CE1 | PHE | 413 | 18.517 | 46.711 | 19.787 | 1.00 | 25.13 |
| ATOM | 3162 | CE2 | PHE | 413 | 19.208 | 44.408 | 19.707 | 1.00 | 24.84 |
| ATOM | 3163 | CZ | PHE | 413 | 19.082 | 45.652 | 19.092 | 1.00 | 24.48 |
| ATOM | 3164 | C | PHE | 413 | 16.232 | 43.228 | 22.645 | 1.00 | 31.20 |
| ATOM | 3165 | O | PHE | 413 | 15.571 | 43.026 | 21.612 | 1.00 | 31.56 |
| ATOM | 3166 | N | LYS | 414 | 16.888 | 42.268 | 23.275 | 1.00 | 31.75 |
| ATOM | 3167 | CA | LYS | 414 | 16.851 | 40.906 | 22.790 | 1.00 | 32.75 |
| ATOM | 3168 | CB | LYS | 414 | 17.626 | 39.999 | 23.755 | 1.00 | 33.66 |
| ATOM | 3169 | CG | LYS | 414 | 17.570 | 38.526 | 23.429 | 1.00 | 34.45 |
| ATOM | 3170 | CD | LYS | 414 | 18.732 | 37.744 | 24.049 | 1.00 | 36.05 |
| ATOM | 3171 | CE | LYS | 414 | 18.845 | 37.909 | 25.558 | 1.00 | 35.80 |
| ATOM | 3172 | NZ | LYS | 414 | 19.972 | 38.817 | 25.920 | 1.00 | 36.66 |
| ATOM | 3173 | C | LYS | 414 | 15.412 | 40.411 | 22.600 | 1.00 | 33.19 |
| ATOM | 3174 | O | LYS | 414 | 15.054 | 39.927 | 21.518 | 1.00 | 33.30 |
| ATOM | 3175 | N | GLU | 415 | 14.577 | 40.542 | 23.627 | 1.00 | 33.81 |
| ATOM | 3176 | CA | GLU | 415 | 13.193 | 40.071 | 23.513 | 1.00 | 34.53 |
| ATOM | 3177 | CB | GLU | 415 | 12.462 | 40.251 | 24.838 | 1.00 | 37.66 |
| ATOM | 3178 | CG | GLU | 415 | 13.062 | 39.497 | 26.002 | 1.00 | 42.83 |
| ATOM | 3179 | CD | GLU | 415 | 14.376 | 40.090 | 26.520 | 1.00 | 45.68 |
| ATOM | 3180 | OE1 | GLU | 415 | 14.523 | 41.339 | 26.526 | 1.00 | 47.31 |
| ATOM | 3181 | OE2 | GLU | 415 | 15.245 | 39.293 | 26.956 | 1.00 | 47.44 |
| ATOM | 3182 | C | GLU | 415 | 12.409 | 40.776 | 22.401 | 1.00 | 33.23 |
| ATOM | 3183 | O | GLU | 415 | 11.676 | 40.137 | 21.649 | 1.00 | 33.06 |
| ATOM | 3184 | N | ARG | 416 | 12.551 | 42.092 | 22.299 | 1.00 | 31.77 |
| ATOM | 3185 | CA | ARG | 416 | 11.841 | 42.825 | 21.264 | 1.00 | 30.32 |
| ATOM | 3186 | CB | ARG | 416 | 12.066 | 44.328 | 21.427 | 1.00 | 31.27 |
| ATOM | 3187 | CG | ARG | 416 | 11.645 | 44.875 | 22.796 | 1.00 | 33.92 |
| ATOM | 3188 | CD | ARG | 416 | 11.783 | 46.393 | 22.901 | 1.00 | 35.48 |

FIG. 4DDD

| | | | | | | | | |
|---|---|---|---|---|---|---|---|---|
| ATOM | 3189 | NE | ARG | 416 | 11.545 | 46.866 | 24.267 | 1.00 38.24 |
| ATOM | 3190 | CZ | ARG | 416 | 11.982 | 48.030 | 24.746 | 1.00 39.11 |
| ATOM | 3191 | NH1 | ARG | 416 | 12.676 | 48.850 | 23.967 | 1.00 39.89 |
| ATOM | 3192 | NH2 | ARG | 416 | 11.754 | 48.365 | 26.009 | 1.00 38.52 |
| ATOM | 3193 | C | ARG | 416 | 12.379 | 42.354 | 19.916 | 1.00 29.08 |
| ATOM | 3194 | O | ARG | 416 | 11.620 | 42.159 | 18.964 | 1.00 28.85 |
| ATOM | 3195 | N | PHE | 417 | 13.694 | 42.144 | 19.862 | 1.00 27.59 |
| ATOM | 3196 | CA | PHE | 417 | 14.377 | 41.707 | 18.648 | 1.00 25.70 |
| ATOM | 3197 | CB | PHE | 417 | 15.886 | 41.687 | 18.890 | 1.00 23.64 |
| ATOM | 3198 | CG | PHE | 417 | 16.687 | 41.310 | 17.680 | 1.00 20.59 |
| ATOM | 3199 | CD1 | PHE | 417 | 16.910 | 42.230 | 16.671 | 1.00 18.99 |
| ATOM | 3200 | CD2 | PHE | 417 | 17.183 | 40.018 | 17.540 | 1.00 19.41 |
| ATOM | 3201 | CE1 | PHE | 417 | 17.610 | 41.870 | 15.540 | 1.00 19.87 |
| ATOM | 3202 | CE2 | PHE | 417 | 17.884 | 39.641 | 16.413 | 1.00 18.04 |
| ATOM | 3203 | CZ | PHE | 417 | 18.100 | 40.563 | 15.409 | 1.00 20.04 |
| ATOM | 3204 | C | PHE | 417 | 13.943 | 40.342 | 18.099 | 1.00 25.74 |
| ATOM | 3205 | O | PHE | 417 | 13.568 | 40.225 | 16.927 | 1.00 25.24 |
| ATOM | 3206 | N | HIS | 418 | 14.012 | 39.301 | 18.922 | 1.00 26.11 |
| ATOM | 3207 | CA | HIS | 418 | 13.612 | 37.962 | 18.459 | 1.00 26.79 |
| ATOM | 3208 | CB | HIS | 418 | 13.638 | 36.973 | 19.615 | 1.00 28.01 |
| ATOM | 3209 | CG | HIS | 418 | 14.973 | 36.854 | 20.279 | 1.00 28.81 |
| ATOM | 3210 | CD2 | HIS | 418 | 16.168 | 37.425 | 19.989 | 1.00 29.42 |
| ATOM | 3211 | ND1 | HIS | 418 | 15.182 | 36.067 | 21.389 | 1.00 28.15 |
| ATOM | 3212 | CE1 | HIS | 418 | 16.446 | 36.157 | 21.755 | 1.00 29.43 |
| ATOM | 3213 | NE2 | HIS | 418 | 17.067 | 36.974 | 20.924 | 1.00 29.74 |
| ATOM | 3214 | C | HIS | 418 | 12.209 | 37.985 | 17.876 | 1.00 26.41 |
| ATOM | 3215 | O | HIS | 418 | 11.976 | 37.565 | 16.733 | 1.00 26.40 |
| ATOM | 3216 | N | ALA | 419 | 11.284 | 38.487 | 18.688 | 1.00 25.83 |
| ATOM | 3217 | CA | ALA | 419 | 9.885 | 38.603 | 18.328 | 1.00 25.05 |
| ATOM | 3218 | CB | ALA | 419 | 9.182 | 39.454 | 19.352 | 1.00 24.80 |
| ATOM | 3219 | C | ALA | 419 | 9.731 | 39.215 | 16.943 | 1.00 25.35 |
| ATOM | 3220 | O | ALA | 419 | 9.146 | 38.601 | 16.029 | 1.00 25.99 |
| ATOM | 3221 | N | SER | 420 | 10.249 | 40.425 | 16.777 | 1.00 25.26 |
| ATOM | 3222 | CA | SER | 420 | 10.159 | 41.078 | 15.481 | 1.00 25.31 |
| ATOM | 3223 | CB | SER | 420 | 10.897 | 42.405 | 15.515 | 1.00 23.85 |
| ATOM | 3224 | OG | SER | 420 | 10.692 | 43.089 | 14.303 | 1.00 23.43 |
| ATOM | 3225 | C | SER | 420 | 10.751 | 40.170 | 14.391 | 1.00 26.14 |
| ATOM | 3226 | O | SER | 420 | 10.145 | 39.976 | 13.331 | 1.00 25.95 |
| ATOM | 3227 | N | VAL | 421 | 11.926 | 39.602 | 14.670 | 1.00 27.34 |
| ATOM | 3228 | CA | VAL | 421 | 12.602 | 38.699 | 13.733 | 1.00 28.41 |
| ATOM | 3229 | CB | VAL | 421 | 13.919 | 38.127 | 14.346 | 1.00 27.63 |
| ATOM | 3230 | CG1 | VAL | 421 | 14.479 | 37.020 | 13.475 | 1.00 26.36 |
| ATOM | 3231 | CG2 | VAL | 421 | 14.953 | 39.232 | 14.469 | 1.00 28.22 |
| ATOM | 3232 | C | VAL | 421 | 11.689 | 37.535 | 13.325 | 1.00 29.65 |
| ATOM | 3233 | O | VAL | 421 | 11.557 | 37.227 | 12.130 | 1.00 28.72 |
| ATOM | 3234 | N | ARG | 422 | 11.069 | 36.886 | 14.310 | 1.00 30.74 |
| ATOM | 3235 | CA | ARG | 422 | 10.165 | 35.775 | 14.014 | 1.00 32.79 |
| ATOM | 3236 | CB | ARG | 422 | 9.419 | 35.328 | 15.265 | 1.00 33.29 |
| ATOM | 3237 | CG | ARG | 422 | 10.259 | 35.197 | 16.512 | 1.00 34.47 |
| ATOM | 3238 | CD | ARG | 422 | 11.081 | 33.927 | 16.558 | 1.00 34.54 |
| ATOM | 3239 | NE | ARG | 422 | 11.862 | 33.905 | 17.795 | 1.00 35.75 |
| ATOM | 3240 | CZ | ARG | 422 | 12.824 | 33.028 | 18.066 | 1.00 35.45 |
| ATOM | 3241 | NH1 | ARG | 422 | 13.127 | 32.085 | 17.180 | 1.00 35.35 |
| ATOM | 3242 | NH2 | ARG | 422 | 13.490 | 33.108 | 19.215 | 1.00 33.55 |
| ATOM | 3243 | C | ARG | 422 | 9.123 | 36.277 | 13.019 | 1.00 33.41 |
| ATOM | 3244 | O | ARG | 422 | 8.949 | 35.728 | 11.929 | 1.00 33.68 |
| ATOM | 3245 | N | ARG | 423 | 8.446 | 37.348 | 13.417 | 1.00 34.00 |

*FIG. 4EEE*

```
ATOM  3246  CA   ARG  423   7.394  37.946  12.622  1.00  34.13
ATOM  3247  CB   ARG  423   7.022  39.301  13.207  1.00  35.16
ATOM  3248  CG   ARG  423   5.538  39.584  13.202  1.00  36.10
ATOM  3249  CD   ARG  423   5.212  40.831  14.012  1.00  37.57
ATOM  3250  NE   ARG  423   5.482  40.682  15.441  1.00  38.90
ATOM  3251  CZ   ARG  423   6.274  41.503  16.133  1.00  40.51
ATOM  3252  NH1  ARG  423   6.874  42.523  15.513  1.00  41.42
ATOM  3253  NH2  ARG  423   6.461  41.324  17.440  1.00  38.76
ATOM  3254  C    ARG  423   7.754  38.100  11.165  1.00  33.94
ATOM  3255  O    ARG  423   6.919  37.849  10.295  1.00  35.59
ATOM  3256  N    LEU  424   8.993  38.494  10.884  1.00  32.85
ATOM  3257  CA   LEU  424   9.418  38.699   9.497  1.00  31.57
ATOM  3258  CB   LEU  424  10.474  39.788   9.450  1.00  28.75
ATOM  3259  CG   LEU  424  10.030  41.129  10.003  1.00  27.64
ATOM  3260  CD1  LEU  424  11.220  42.080  10.066  1.00  26.47
ATOM  3261  CD2  LEU  424   8.942  41.686   9.115  1.00  27.23
ATOM  3262  C    LEU  424   9.950  37.479   8.747  1.00  32.00
ATOM  3263  O    LEU  424  10.232  37.562   7.551  1.00  31.15
ATOM  3264  N    THR  425  10.065  36.343   9.424  1.00  33.88
ATOM  3265  CA   THR  425  10.615  35.153   8.778  1.00  35.30
ATOM  3266  CB   THR  425  11.886  34.722   9.495  1.00  35.17
ATOM  3267  OG1  THR  425  11.580  34.463  10.874  1.00  35.24
ATOM  3268  CG2  THR  425  12.939  35.817   9.399  1.00  35.16
ATOM  3269  C    THR  425   9.711  33.923   8.675  1.00  37.00
ATOM  3270  O    THR  425  10.059  32.854   9.182  1.00  37.54
ATOM  3271  N    PRO  426   8.562  34.040   7.982  1.00  38.04
ATOM  3272  CD   PRO  426   8.144  35.123   7.073  1.00  38.49
ATOM  3273  CA   PRO  426   7.663  32.890   7.856  1.00  38.85
ATOM  3274  CB   PRO  426   6.745  33.295   6.700  1.00  38.23
ATOM  3275  CG   PRO  426   6.699  34.772   6.802  1.00  38.07
ATOM  3276  C    PRO  426   8.445  31.615   7.527  1.00  39.83
ATOM  3277  O    PRO  426   9.378  31.641   6.728  1.00  40.28
ATOM  3278  N    SER  427   8.073  30.510   8.158  1.00  40.72
ATOM  3279  CA   SER  427   8.713  29.232   7.892  1.00  41.82
ATOM  3280  CB   SER  427   8.358  28.785   6.474  1.00  42.86
ATOM  3281  CG   SER  427   6.954  28.802   6.287  1.00  44.69
ATOM  3282  C    SER  427  10.234  29.228   8.068  1.00  42.10
ATOM  3283  O    SER  427  10.981  28.899   7.140  1.00  41.85
ATOM  3284  N    CYS  428  10.679  29.586   9.267  1.00  42.60
ATOM  3285  CA   CYS  428  12.096  29.608   9.601  1.00  42.43
ATOM  3286  CB   CYS  428  12.724  30.960   9.258  1.00  42.59
ATOM  3287  SG   CYS  428  12.860  31.327   7.492  1.00  44.02
ATOM  3288  C    CYS  428  12.195  29.381  11.096  1.00  42.45
ATOM  3289  O    CYS  428  11.671  30.169  11.879  1.00  43.76
ATOM  3290  N    GLU  429  12.846  28.296  11.494  1.00  42.34
ATOM  3291  CA   GLU  429  13.014  27.995  12.909  1.00  41.23
ATOM  3292  CB   GLU  429  13.030  26.486  13.146  1.00  42.97
ATOM  3293  CG   GLU  429  11.699  25.796  12.933  1.00  45.48
ATOM  3294  CD   GLU  429  11.847  24.282  12.925  1.00  47.43
ATOM  3295  OE1  GLU  429  12.518  23.756  13.847  1.00  48.77
ATOM  3296  OE2  GLU  429  11.298  23.623  12.005  1.00  48.07
ATOM  3297  C    GLU  429  14.341  28.587  13.346  1.00  39.77
ATOM  3298  O    GLU  429  15.370  27.902  13.352  1.00  39.92
ATOM  3299  N    ILE  430  14.315  29.864  13.708  1.00  38.09
ATOM  3300  CA   ILE  430  15.514  30.560  14.142  1.00  36.48
ATOM  3301  CB   ILE  430  15.341  32.070  13.998  1.00  35.17
ATOM  3302  CG2  ILE  430  16.659  32.770  14.280  1.00  34.48
```

*FIG. 4FFF*

| ATOM | 3303 | CG1 | ILE | 430 | 14.839 | 32.390 | 12.589 | 1.00 | 35.30 |
| --- | --- | --- | --- | --- | --- | --- | --- | --- | --- |
| ATOM | 3304 | CD1 | ILE | 430 | 14.669 | 33.866 | 12.310 | 1.00 | 34.88 |
| ATOM | 3305 | C | ILE | 430 | 15.872 | 30.254 | 15.591 | 1.00 | 37.06 |
| ATOM | 3306 | O | ILE | 430 | 15.044 | 30.399 | 16.495 | 1.00 | 38.13 |
| ATOM | 3307 | N | THR | 431 | 17.109 | 29.823 | 15.808 | 1.00 | 36.61 |
| ATOM | 3308 | CA | THR | 431 | 17.600 | 29.520 | 17.146 | 1.00 | 36.17 |
| ATOM | 3309 | CB | THR | 431 | 18.067 | 28.053 | 17.240 | 1.00 | 36.58 |
| ATOM | 3310 | OG1 | THR | 431 | 16.950 | 27.180 | 17.031 | 1.00 | 36.34 |
| ATOM | 3311 | CG2 | THR | 431 | 18.692 | 27.774 | 18.604 | 1.00 | 36.38 |
| ATOM | 3312 | C | THR | 431 | 18.796 | 30.441 | 17.396 | 1.00 | 36.13 |
| ATOM | 3313 | O | THR | 431 | 19.705 | 30.513 | 16.569 | 1.00 | 36.10 |
| ATOM | 3314 | N | PHE | 432 | 18.804 | 31.157 | 18.514 | 1.00 | 35.79 |
| ATOM | 3315 | CA | PHE | 432 | 19.926 | 32.054 | 18.794 | 1.00 | 35.93 |
| ATOM | 3316 | CB | PHE | 432 | 19.443 | 33.450 | 19.232 | 1.00 | 34.31 |
| ATOM | 3317 | CG | PHE | 432 | 18.643 | 34.194 | 18.188 | 1.00 | 32.53 |
| ATOM | 3318 | CD1 | PHE | 432 | 17.271 | 33.977 | 18.048 | 1.00 | 31.59 |
| ATOM | 3319 | CD2 | PHE | 432 | 19.262 | 35.124 | 17.353 | 1.00 | 31.00 |
| ATOM | 3320 | CE1 | PHE | 432 | 16.527 | 34.676 | 17.092 | 1.00 | 30.53 |
| ATOM | 3321 | CE2 | PHE | 432 | 18.525 | 35.826 | 16.395 | 1.00 | 30.25 |
| ATOM | 3322 | CZ | PHE | 432 | 17.154 | 35.600 | 16.266 | 1.00 | 30.11 |
| ATOM | 3323 | C | PHE | 432 | 20.767 | 31.483 | 19.917 | 1.00 | 37.08 |
| ATOM | 3324 | O | PHE | 432 | 20.248 | 30.772 | 20.779 | 1.00 | 38.85 |
| ATOM | 3325 | N | ILE | 433 | 22.063 | 31.774 | 19.906 | 1.00 | 37.32 |
| ATOM | 3326 | CA | ILE | 433 | 22.933 | 31.321 | 20.983 | 1.00 | 38.46 |
| ATOM | 3327 | CB | ILE | 433 | 23.526 | 29.890 | 20.722 | 1.00 | 39.06 |
| ATOM | 3328 | CG2 | ILE | 433 | 22.398 | 28.863 | 20.624 | 1.00 | 38.62 |
| ATOM | 3329 | CG1 | ILE | 433 | 24.367 | 29.861 | 19.449 | 1.00 | 39.03 |
| ATOM | 3330 | CD1 | ILE | 433 | 25.028 | 28.520 | 19.227 | 1.00 | 38.32 |
| ATOM | 3331 | C | ILE | 433 | 24.039 | 32.358 | 21.161 | 1.00 | 39.33 |
| ATOM | 3332 | O | ILE | 433 | 24.429 | 33.034 | 20.201 | 1.00 | 39.15 |
| ATOM | 3333 | N | GLU | 434 | 24.527 | 32.505 | 22.388 | 1.00 | 40.58 |
| ATOM | 3334 | CA | GLU | 434 | 25.559 | 33.498 | 22.669 | 1.00 | 42.92 |
| ATOM | 3335 | CB | GLU | 434 | 25.152 | 34.312 | 23.885 | 1.00 | 43.91 |
| ATOM | 3336 | CG | GLU | 434 | 23.769 | 34.883 | 23.744 | 1.00 | 45.53 |
| ATOM | 3337 | CD | GLU | 434 | 23.342 | 35.640 | 24.965 | 1.00 | 46.68 |
| ATOM | 3338 | CE1 | GLU | 434 | 23.436 | 35.072 | 26.074 | 1.00 | 47.18 |
| ATOM | 3339 | OE2 | GLU | 434 | 22.910 | 36.802 | 24.816 | 1.00 | 48.77 |
| ATOM | 3340 | C | GLU | 434 | 26.965 | 32.950 | 22.865 | 1.00 | 44.01 |
| ATOM | 3341 | O | GLU | 434 | 27.206 | 32.058 | 23.680 | 1.00 | 44.48 |
| ATOM | 3342 | N | SER | 435 | 27.901 | 33.518 | 22.119 | 1.00 | 45.00 |
| ATOM | 3343 | CA | SER | 435 | 29.284 | 33.075 | 22.167 | 1.00 | 46.11 |
| ATOM | 3344 | CB | SER | 435 | 30.077 | 33.779 | 21.057 | 1.00 | 46.95 |
| ATOM | 3345 | OG | SER | 435 | 29.839 | 35.186 | 21.053 | 1.00 | 47.94 |
| ATOM | 3346 | C | SER | 435 | 29.984 | 33.274 | 23.507 | 1.00 | 46.36 |
| ATOM | 3347 | O | SER | 435 | 30.043 | 34.395 | 24.022 | 1.00 | 46.31 |
| ATOM | 3348 | N | GLU | 436 | 30.505 | 32.180 | 24.069 | 1.00 | 46.22 |
| ATOM | 3349 | CA | GLU | 436 | 31.248 | 32.250 | 25.330 | 1.00 | 46.33 |
| ATOM | 3350 | CB | GLU | 436 | 31.322 | 30.884 | 26.020 | 1.00 | 47.64 |
| ATOM | 3351 | CG | GLU | 436 | 32.144 | 30.908 | 27.317 | 1.00 | 50.83 |
| ATOM | 3352 | CD | GLU | 436 | 32.726 | 29.541 | 27.711 | 1.00 | 52.03 |
| ATOM | 3353 | OE1 | GLU | 436 | 31.951 | 28.585 | 27.970 | 1.00 | 52.84 |
| ATOM | 3354 | OE2 | GLU | 436 | 33.972 | 29.428 | 27.765 | 1.00 | 52.07 |
| ATOM | 3355 | C | GLU | 436 | 32.650 | 32.671 | 24.912 | 1.00 | 45.58 |
| ATOM | 3356 | O | GLU | 436 | 33.446 | 31.843 | 24.463 | 1.00 | 45.50 |
| ATOM | 3357 | N | GLU | 437 | 32.950 | 33.956 | 25.051 | 1.00 | 44.67 |
| ATOM | 3358 | CA | GLU | 437 | 34.252 | 34.462 | 24.643 | 1.00 | 44.13 |
| ATOM | 3359 | CB | GLU | 437 | 35.328 | 34.050 | 25.652 | 1.00 | 43.61 |

*FIG. 4GGG*

| ATOM | 3360 | CG | GLU | 437 | 36.745 | 34.334 | 25.190 | 1.00 | 43.39 |
| ATOM | 3361 | CD | GLU | 437 | 36.931 | 35.752 | 24.678 | 1.00 | 43.50 |
| ATOM | 3362 | OE1 | GLU | 437 | 36.976 | 36.680 | 25.514 | 1.00 | 44.49 |
| ATOM | 3363 | OE2 | GLU | 437 | 37.025 | 35.940 | 23.441 | 1.00 | 42.17 |
| ATOM | 3364 | C | GLU | 437 | 34.569 | 33.880 | 23.264 | 1.00 | 43.56 |
| ATOM | 3365 | O | GLU | 437 | 35.530 | 33.131 | 23.108 | 1.00 | 45.30 |
| ATOM | 3366 | N | GLY | 438 | 33.757 | 34.225 | 22.266 | 1.00 | 41.68 |
| ATOM | 3367 | CA | GLY | 438 | 33.958 | 33.700 | 20.926 | 1.00 | 39.44 |
| ATOM | 3368 | C | GLY | 438 | 34.748 | 34.538 | 19.934 | 1.00 | 38.11 |
| ATOM | 3369 | O | GLY | 438 | 34.932 | 34.130 | 18.791 | 1.00 | 37.45 |
| ATOM | 3370 | N | SER | 439 | 35.213 | 35.713 | 20.329 | 1.00 | 37.14 |
| ATOM | 3371 | CA | SER | 439 | 35.980 | 36.502 | 19.386 | 1.00 | 36.86 |
| ATOM | 3372 | CB | SER | 439 | 35.916 | 37.983 | 19.714 | 1.00 | 36.81 |
| ATOM | 3373 | OG | SER | 439 | 36.825 | 38.678 | 18.878 | 1.00 | 35.32 |
| ATOM | 3374 | C | SER | 439 | 37.420 | 36.053 | 19.444 | 1.00 | 36.74 |
| ATOM | 3375 | O | SER | 439 | 38.192 | 36.265 | 18.513 | 1.00 | 36.37 |
| ATOM | 3376 | N | GLY | 440 | 37.774 | 35.439 | 20.562 | 1.00 | 36.58 |
| ATOM | 3377 | CA | GLY | 440 | 39.126 | 34.957 | 20.746 | 1.00 | 36.42 |
| ATOM | 3378 | C | GLY | 440 | 39.207 | 33.518 | 20.302 | 1.00 | 36.28 |
| ATOM | 3379 | O | GLY | 440 | 40.146 | 33.140 | 19.613 | 1.00 | 36.20 |
| ATOM | 3380 | N | ARG | 441 | 38.224 | 32.714 | 20.699 | 1.00 | 36.09 |
| ATOM | 3381 | CA | ARG | 441 | 38.190 | 31.309 | 20.312 | 1.00 | 37.16 |
| ATOM | 3382 | CB | ARG | 441 | 37.151 | 30.562 | 21.138 | 1.00 | 37.34 |
| ATOM | 3383 | CG | ARG | 441 | 37.312 | 30.717 | 22.632 | 1.00 | 39.57 |
| ATOM | 3384 | CD | ARG | 441 | 36.334 | 29.806 | 23.375 | 1.00 | 42.28 |
| ATOM | 3385 | NE | ARG | 441 | 35.270 | 29.339 | 22.488 | 1.00 | 44.36 |
| ATOM | 3386 | CZ | ARG | 441 | 34.240 | 28.585 | 22.862 | 1.00 | 45.80 |
| ATOM | 3387 | NH1 | ARG | 441 | 34.103 | 28.192 | 24.127 | 1.00 | 45.87 |
| ATOM | 3388 | NH2 | ARG | 441 | 33.346 | 28.214 | 21.955 | 1.00 | 47.26 |
| ATOM | 3389 | C | ARG | 441 | 37.848 | 31.179 | 18.821 | 1.00 | 37.42 |
| ATOM | 3390 | O | ARG | 441 | 38.103 | 30.151 | 18.189 | 1.00 | 37.52 |
| ATOM | 3391 | N | GLY | 442 | 37.270 | 32.234 | 18.262 | 1.00 | 37.34 |
| ATOM | 3392 | CA | GLY | 442 | 36.906 | 32.204 | 16.863 | 1.00 | 37.39 |
| ATOM | 3393 | C | GLY | 442 | 38.165 | 32.308 | 16.048 | 1.00 | 37.47 |
| ATOM | 3394 | O | GLY | 442 | 38.483 | 31.410 | 15.278 | 1.00 | 37.51 |
| ATOM | 3395 | N | ALA | 443 | 38.887 | 33.408 | 16.241 | 1.00 | 38.17 |
| ATOM | 3396 | CA | ALA | 443 | 40.134 | 33.660 | 15.526 | 1.00 | 38.50 |
| ATOM | 3397 | CB | ALA | 443 | 40.739 | 34.999 | 15.967 | 1.00 | 36.50 |
| ATOM | 3398 | C | ALA | 443 | 41.127 | 32.521 | 15.759 | 1.00 | 39.03 |
| ATOM | 3399 | O | ALA | 443 | 42.015 | 32.297 | 14.941 | 1.00 | 39.36 |
| ATOM | 3400 | N | ALA | 444 | 40.977 | 31.807 | 16.875 | 1.00 | 39.93 |
| ATOM | 3401 | CA | ALA | 444 | 41.864 | 30.685 | 17.172 | 1.00 | 40.31 |
| ATOM | 3402 | CB | ALA | 444 | 41.724 | 30.242 | 18.623 | 1.00 | 39.25 |
| ATOM | 3403 | C | ALA | 444 | 41.427 | 29.569 | 16.246 | 1.00 | 40.97 |
| ATOM | 3404 | O | ALA | 444 | 42.146 | 29.210 | 15.312 | 1.00 | 41.31 |
| ATOM | 3405 | N | LEU | 445 | 40.233 | 29.038 | 16.501 | 1.00 | 41.41 |
| ATOM | 3406 | CA | LEU | 445 | 39.678 | 27.960 | 15.690 | 1.00 | 41.97 |
| ATOM | 3407 | CB | LEU | 445 | 38.195 | 27.776 | 16.024 | 1.00 | 40.09 |
| ATOM | 3408 | CG | LEU | 445 | 37.954 | 26.806 | 17.182 | 1.00 | 39.14 |
| ATOM | 3409 | CD1 | LEU | 445 | 36.750 | 27.233 | 17.982 | 1.00 | 39.27 |
| ATOM | 3410 | CD2 | LEU | 445 | 37.781 | 25.399 | 16.647 | 1.00 | 37.36 |
| ATOM | 3411 | C | LEU | 445 | 39.860 | 28.156 | 14.176 | 1.00 | 43.29 |
| ATOM | 3412 | O | LEU | 445 | 39.918 | 27.179 | 13.427 | 1.00 | 43.28 |
| ATOM | 3413 | N | VAL | 446 | 39.955 | 29.406 | 13.729 | 1.00 | 44.66 |
| ATOM | 3414 | CA | VAL | 446 | 40.136 | 29.684 | 12.307 | 1.00 | 46.32 |
| ATOM | 3415 | CB | VAL | 446 | 39.687 | 31.120 | 11.948 | 1.00 | 46.15 |
| ATOM | 3416 | CG1 | VAL | 446 | 40.356 | 31.578 | 10.653 | 1.00 | 46.15 |

*FIG. 4HHH*

| | | | | | | | |
|---|---|---|---|---|---|---|---|
| ATOM | 3417 | CG2 VAL | 446 | 38.164 | 31.160 | 11.793 | 1.00 45.75 |
| ATOM | 3418 | C   VAL | 446 | 41.597 | 29.503 | 11.944 | 1.00 48.03 |
| ATOM | 3419 | O   VAL | 446 | 41.929 | 29.105 | 10.825 | 1.00 48.75 |
| ATOM | 3420 | N   SER | 447 | 42.465 | 29.802 | 12.904 | 1.00 49.63 |
| ATOM | 3421 | CA  SER | 447 | 43.902 | 29.657 | 12.725 | 1.00 50.76 |
| ATOM | 3422 | CB  SER | 447 | 44.635 | 30.267 | 13.918 | 1.00 50.76 |
| ATOM | 3423 | OG  SER | 447 | 44.377 | 31.659 | 14.021 | 1.00 50.83 |
| ATOM | 3424 | C   SER | 447 | 44.259 | 28.173 | 12.612 | 1.00 52.07 |
| ATOM | 3425 | O   SER | 447 | 44.923 | 27.753 | 11.662 | 1.00 52.17 |
| ATOM | 3426 | N   ALA | 448 | 43.804 | 27.387 | 13.584 | 1.00 53.51 |
| ATOM | 3427 | CA  ALA | 448 | 44.071 | 25.953 | 13.621 | 1.00 55.46 |
| ATOM | 3428 | CB  ALA | 448 | 43.273 | 25.306 | 14.745 | 1.00 55.02 |
| ATOM | 3429 | C   ALA | 448 | 43.751 | 25.263 | 12.300 | 1.00 57.02 |
| ATOM | 3430 | O   ALA | 448 | 44.599 | 24.564 | 11.726 | 1.00 57.18 |
| ATOM | 3431 | N   VAL | 449 | 42.523 | 25.457 | 11.825 | 1.00 58.39 |
| ATOM | 3432 | CA  VAL | 449 | 42.093 | 24.841 | 10.579 | 1.00 59.69 |
| ATOM | 3433 | CB  VAL | 449 | 40.571 | 24.977 | 10.382 | 1.00 59.67 |
| ATOM | 3434 | CG1 VAL | 449 | 40.152 | 24.262 | 9.112  | 1.00 60.28 |
| ATOM | 3435 | CG2 VAL | 449 | 39.833 | 24.384 | 11.577 | 1.00 59.48 |
| ATOM | 3436 | C   VAL | 449 | 42.821 | 25.482 | 9.403  | 1.00 60.70 |
| ATOM | 3437 | O   VAL | 449 | 42.903 | 24.898 | 8.321  | 1.00 61.00 |
| ATOM | 3438 | N   ALA | 450 | 43.361 | 26.677 | 9.627  | 1.00 61.41 |
| ATOM | 3439 | CA  ALA | 450 | 44.093 | 27.392 | 8.591  | 1.00 62.12 |
| ATOM | 3440 | CB  ALA | 450 | 43.981 | 28.889 | 8.814  | 1.00 62.32 |
| ATOM | 3441 | C   ALA | 450 | 45.558 | 26.973 | 8.606  | 1.00 63.02 |
| ATOM | 3442 | O   ALA | 450 | 46.437 | 27.748 | 8.217  | 1.00 62.75 |
| ATOM | 3443 | N   CYS | 451 | 45.807 | 25.744 | 9.061  | 1.00 64.03 |
| ATOM | 3444 | CA  CYS | 451 | 47.160 | 25.183 | 9.148  | 1.00 65.19 |
| ATOM | 3445 | CB  CYS | 451 | 47.530 | 24.440 | 7.850  | 1.00 65.75 |
| ATOM | 3446 | SG  CYS | 451 | 46.901 | 22.720 | 7.723  | 1.00 66.86 |
| ATOM | 3447 | C   CYS | 451 | 48.239 | 26.217 | 9.474  | 1.00 65.22 |
| ATOM | 3448 | O   CYS | 451 | 47.929 | 27.230 | 10.144 | 1.00 65.18 |
| ATOM | 3449 | OXT CYS | 451 | 49.398 | 25.979 | 9.073  | 1.00 65.50 |
| ATOM | 3450 | C1  HEX | 1   | 31.023 | 47.521 | 12.611 | 1.00 25.83 |
| ATOM | 3451 | C2  HEX | 1   | 32.239 | 47.182 | 11.801 | 1.00 25.25 |
| ATOM | 3452 | C3  HEX | 1   | 32.203 | 45.697 | 11.565 | 1.00 25.11 |
| ATOM | 3453 | C4  HEX | 1   | 32.071 | 44.939 | 12.862 | 1.00 24.99 |
| ATOM | 3454 | C5  HEX | 1   | 31.030 | 45.591 | 13.785 | 1.00 25.34 |
| ATOM | 3455 | C6  HEX | 1   | 30.772 | 44.921 | 15.126 | 1.00 25.58 |
| ATOM | 3456 | O1  HEX | 1   | 30.750 | 48.942 | 12.579 | 1.00 27.04 |
| ATOM | 3457 | O2  HEX | 1   | 32.183 | 47.912 | 10.609 | 1.00 24.71 |
| ATOM | 3458 | O3  HEX | 1   | 33.337 | 45.251 | 10.836 | 1.00 25.99 |
| ATOM | 3459 | O4  HEX | 1   | 31.699 | 43.621 | 12.545 | 1.00 25.85 |
| ATOM | 3460 | O5  HEX | 1   | 31.267 | 46.968 | 13.935 | 1.00 25.37 |
| ATOM | 3461 | O6  HEX | 1   | 31.835 | 45.222 | 16.009 | 1.00 27.23 |
| ATOM | 3462 | C1  LIG | 1   | 30.034 | 26.620 | 8.669  | 1.00 35.87 |
| ATOM | 3463 | C2  LIG | 1   | 29.909 | 27.259 | 10.064 | 1.00 34.82 |
| ATOM | 3464 | C3  LIG | 1   | 31.308 | 27.852 | 10.344 | 1.00 35.54 |
| ATOM | 3465 | C4  LIG | 1   | 32.212 | 27.447 | 9.148  | 1.00 35.52 |
| ATOM | 3466 | C5  LIG | 1   | 31.520 | 26.207 | 8.584  | 1.00 35.20 |
| ATOM | 3467 | C6  LIG | 1   | 33.670 | 27.245 | 9.637  | 1.00 36.33 |
| ATOM | 3468 | C7  LIG | 1   | 34.562 | 26.321 | 8.758  | 1.00 37.11 |
| ATOM | 3469 | C8  LIG | 1   | 35.946 | 26.832 | 8.778  | 1.00 36.91 |
| ATOM | 3470 | N9  LIG | 1   | 36.382 | 27.317 | 7.570  | 1.00 36.92 |
| ATOM | 3471 | C10 LIG | 1   | 37.668 | 27.907 | 7.331  | 1.00 36.42 |
| ATOM | 3472 | N11 LIG | 1   | 38.035 | 28.336 | 6.087  | 1.00 37.39 |
| ATOM | 3473 | C12 LIG | 1   | 39.058 | 28.930 | 6.462  | 1.00 36.99 |

*FIG. 4III*

| ATOM | 3474 | C13 | LIG | 1 | 39.426 | 29.003 | 7.575 | 1.00 | 37.10 |
| ATOM | 3475 | S14 | LIG | 1 | 38.681 | 28.342 | 8.700 | 1.00 | 37.86 |
| ATOM | 3476 | O15 | LIG | 1 | 36.640 | 26.843 | 9.817 | 1.00 | 38.32 |
| ATOM | 3477 | C16 | LIG | 1 | 34.538 | 24.890 | 9.296 | 1.00 | 37.59 |
| ATOM | 3478 | C17 | LIG | 1 | 34.906 | 24.620 | 10.610 | 1.00 | 37.22 |
| ATOM | 3479 | C18 | LIG | 1 | 34.658 | 23.346 | 11.130 | 1.00 | 38.09 |
| ATOM | 3480 | N19 | LIG | 1 | 34.084 | 22.371 | 10.404 | 1.00 | 38.80 |
| ATOM | 3481 | C20 | LIG | 1 | 33.729 | 22.598 | 9.128 | 1.00 | 38.90 |
| ATOM | 3482 | C21 | LIG | 1 | 33.942 | 23.860 | 8.546 | 1.00 | 38.73 |
| ATOM | 3483 | K1 | K | 1 | 32.471 | 32.037 | -7.104 | 1.00 | 46.91 |

*FIG. 4JJJ*

SEQUENCE LISTING

```
<160> NUMBER OF SEQ ID NOS: 1

<210> SEQ ID NO 1
<211> LENGTH: 692
<212> TYPE: PRT
<213> ORGANISM: Escherichia coli

<400> SEQUENCE: 1

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95
```

```
Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
            130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
                180                 185                 190

Leu Lys Ser Ser Lys Tyr Ile Ala Trp Pro Leu Gln Gly Trp Gln Ala
                195                 200                 205

Thr Phe Gly Gly Gly Asp His Pro Pro Lys Ser Asp Leu Ile Glu Gly
            210                 215                 220

Arg Gly Ile His Met Pro Arg Pro Arg Ser Gln Leu Pro Gln Pro Asn
225                 230                 235                 240

Ser Gln Val Glu Gln Ile Leu Ala Glu Phe Gln Leu Gln Glu Glu Asp
                245                 250                 255

Leu Lys Lys Val Met Arg Arg Met Gln Lys Glu Met Asp Arg Gly Leu
                260                 265                 270

Arg Leu Glu Thr His Glu Glu Ala Ser Val Lys Met Leu Pro Thr Tyr
            275                 280                 285

Val Arg Ser Thr Pro Glu Gly Ser Glu Val Gly Asp Phe Leu Ser Leu
            290                 295                 300

Asp Leu Gly Gly Thr Asn Phe Arg Val Met Leu Val Lys Val Gly Glu
305                 310                 315                 320

Gly Glu Glu Gly Gln Trp Ser Val Lys Thr Lys His Gln Met Tyr Ser
                325                 330                 335

Ile Pro Glu Asp Ala Met Thr Gly Thr Ala Glu Met Leu Phe Asp Tyr
            340                 345                 350

Ile Ser Glu Cys Ile Ser Asp Phe Leu Asp Lys His Gln Met Lys His
            355                 360                 365

Lys Lys Leu Pro Leu Gly Phe Thr Phe Ser Phe Pro Val Arg His Glu
            370                 375                 380

Asp Ile Asp Lys Gly Ile Leu Leu Asn Trp Thr Lys Gly Phe Lys Ala
385                 390                 395                 400

Ser Gly Ala Glu Gly Asn Asn Val Val Gly Leu Leu Arg Asp Ala Ile
                405                 410                 415

Lys Arg Arg Gly Asp Phe Glu Met Asp Val Val Ala Met Val Asn Asp
                420                 425                 430

Thr Val Ala Thr Met Ile Ser Cys Tyr Tyr Glu Asp His Gln Cys Glu
            435                 440                 445

Val Gly Met Ile Val Gly Thr Gly Cys Asn Ala Cys Tyr Met Glu Glu
            450                 455                 460

Met Gln Asn Val Glu Leu Val Glu Gly Asp Glu Gly Arg Met Cys Val
465                 470                 475                 480

Asn Thr Glu Trp Gly Ala Phe Gly Asp Ser Gly Glu Leu Asp Glu Phe
                485                 490                 495

Leu Leu Glu Tyr Asp Arg Leu Val Asp Glu Ser Ser Ala Asn Pro Gly
            500                 505                 510
```

-continued

```
Gln Gln Leu Tyr Glu Lys Leu Ile Gly Gly Lys Tyr Met Gly Glu Leu
        515                 520                 525

Val Arg Leu Val Leu Leu Arg Leu Val Asp Glu Asn Leu Leu Phe His
    530                 535                 540

Gly Glu Ala Ser Glu Gln Leu Arg Thr Arg Gly Ala Phe Glu Thr Arg
545                 550                 555                 560

Phe Val Ser Gln Val Glu Ser Asp Thr Gly Asp Arg Lys Gln Ile Tyr
                565                 570                 575

Asn Ile Leu Ser Thr Leu Gly Leu Arg Pro Ser Thr Thr Asp Cys Asp
                580                 585                 590

Ile Val Arg Arg Ala Cys Glu Ser Val Ser Thr Arg Ala Ala His Met
        595                 600                 605

Cys Ser Ala Gly Leu Ala Gly Val Ile Asn Arg Met Arg Glu Ser Arg
    610                 615                 620

Ser Glu Asp Val Met Arg Ile Thr Val Gly Val Asp Gly Ser Val Tyr
625                 630                 635                 640

Lys Leu His Pro Ser Phe Lys Glu Arg Phe His Ala Ser Val Arg Arg
                645                 650                 655

Leu Thr Pro Ser Cys Glu Ile Thr Phe Ile Glu Ser Glu Glu Gly Ser
                660                 665                 670

Gly Arg Gly Ala Ala Leu Val Ser Ala Val Ala Cys Lys Lys Ala Cys
        675                 680                 685

Met Leu Gly Gln
        690
```

CRYSTALS OF GLUCOKINASE AND METHODS OF GROWING THEM

PRIORITY TO RELATED APPLICATIONS

This application is a Divisional of Ser. No. 10/318,308, filed Dec. 12, 2002, which is now pending. This application claims the benefit of U.S. Provisional Application(s) Ser. No. 60/341,988, filed Dec. 19, 2001.

FIELD OF THE INVENTION

The invention relates to crystalline forms of Gluckokinase of sufficient size and quality to obtain structural data by X-ray crystallography and to methods of growing such crystals.

BACKGROUND OF THE INVENTION

Glucokinase (GK) is one of four hexokinases found in mammals [Colowick, S. P., in The Enzymes, Vol. 9 (P. Boyer, ed.) Academic Press, New York, N.Y., pages 1-48, 1973]. The hexokinases catalyze the first step in the metabolism of glucose, i.e., the conversion of glucose to glucose-6-phosphate. Glucokinase has a limited cellular distribution, being found principally in pancreatic β-cells and liver parenchymal cells. In addition, GK is a rate-controlling enzyme for glucose metabolism in these two cell types that are known to play critical roles in whole-body glucose homeostasis [Chipkin, S. R., Kelly, K. L., and Ruderman, N. B. in *Joslin's Diabetes* (C. R. Khan and G. C. Wier, eds.), Lea and Febiger, Philadelphia, Pa., pages 97-115, 1994]. The concentration of glucose at which GK demonstrates half-maximal activity is approximately 8 mM. The other three hexokinases are saturated with glucose at much lower concentrations (<1 mM). Therefore, the flux of glucose through the GK pathway rises as the concentration of glucose in the blood increases from fasting (5 mM) to postprandial ($\approx$10-15 mM) levels following a carbohydrate-containing meal [Printz, R. G., Magnuson, M. A., and Granner, D. K. in *Ann. Rev. Nutrition* Vol. 13 (R. E. Olson, D. M. Bier, and D. B. McCormick, eds.), Annual Review, Inc., Palo Alto, Calif., pages 463-496, 1993]. These findings contributed over a decade ago to the hypothesis that GK functions as a glucose sensor in β-cells and hepatocytes (Meglasson, M. D. and Matschinsky, F. M. *Amer. J. Physiol.* 246, E1-E13, 1984). In recent years, studies in transgenic animals have confirmed that GK does indeed play a critical role in whole-body glucose homeostasis. Animals that do not express GK die within days of birth with severe diabetes while animals overexpressing GK have improved glucose tolerance (Grupe, A., Hultgren, B., Ryan, A. et al., *Cell* 83, 69-78, 1995; Ferrie, T., Riu, E., Bosch, F. et al., *FASEB J,* 10, 1213-1218, 1996). An increase in glucose exposure is coupled through GK in β-cells to increased insulin secretion and in hepatocytes to increased glycogen deposition and perhaps decreased glucose production.

The finding that type II maturity-onset diabetes of the young (MODY-2) is caused by loss of function mutations in the GK gene suggests that GK also functions as a glucose sensor in humans (Liang, Y., Kesavan, P., Wang, L. et al., *Biochem. J.* 309, 167-173, 1995). Additional evidence supporting an important role for GK in the regulation of glucose metabolism in humans was provided by the identification of patients that express a mutant form of GK with increased enzymatic activity. These patients exhibit a fasting hypoglycemia associated with an inappropriately elevated level of plasma insulin (Glaser, B., Kesavan, P., Heyman, M. et al., *New England J. Med.* 338, 226-230, 1998). While mutations of the GK gene are not found in the majority of patients with type II diabetes, compounds that activate GK and, thereby, increase the sensitivity of the GK sensor system will still be useful in the treatment of the hyperglycemia characteristic of all type II diabetes. Glucokinase activators will increase the flux of glucose metabolism in β-cells and hepatocytes, which will be coupled to increased insulin secretion. Such agents would be useful for treating type II diabetes.

In an effort to elucidate the mechanisms underlying kinase activation, the crystal structure of such proteins is often sought to be determined. The crystal structures of several hexokinases have been reported. See, e.g. A. E. Aleshin, C. Zeng, G. P. Bourenkov, H. D. Bartunik, H. J. Fromm & R. B. Honzatko 'The mechanism of regulation of hexokinase: new insights from the crystal structure of recombinant human brain hexokinase complexed with glucose and glucose-6-phosphate' Structure 6, 39-50 (1998); W. S. Bennett, Jr. & T. A. Steitz 'Structure of a complex between yeast hexokinase A and glucose I. Structure determination and refinement at 3.5 Å resolution' *J. Mol. Biol.* 140, 183-209 (1978); and S. Ito, S. Fushinobu, I. Yoshioka, S. Koga, H. Matsuzawa & T. Wakagi 'Structural Basis for the ADP-Specificity of a Novel Glucokinase from a Hyperthermophilic Archaeon' Structure 9, 205-214 (2001). Despite these reports, researchers armed with the knowledge of how to obtain crystals of related hexokinases have attempted to obtain crystals of any mammalian Glucokinase without success.

SUMMARY OF THE INVENTION

Applicants have discovered protocols which allow crystallization of mammalian Glucokinase with or without a bound allosteric ligand. The crystal structure has been solved by X-ray crystallography to a resolution of 2.7 Å. See FIGS. 3 and 4. Thus the invention relates to a crystalline form of Gluckokinase and a crystalline form of a complex of Glucokinase and an allosteric ligand. The invention further relates to a method of forming crystals of Glucokinase, with or without a bound allosteric ligand.

BRIEF DESCRIPTION OF THE FIGURES

FIG. 2 shows the amino acid sequence (SEQ ID NO: 1) of an expressed Glucokinase used for crystallization.

FIG. 4 shows the atomic structure coordinates for Glucokinase bound to 3-Cyclopentyl-2-pyridin-4-yl-N-thiazol-2-yl-propionamide. Polypeptide is disclosed as SEQ ID NO: 2.

DETAILED DESCRIPTION OF THE INVENTION

Figure 1:
FIG. 1 shows Glucokinase co-crystals having P6(5)22 symmetry.

The present invention relates to crystalline forms of mammalian Glucokinase, with or without a ligand bound in the allosteric site, where the crystals are of sufficient quality and size to allow for the determination of the three-dimensional X-ray diffraction structure to a resolution of about 2.0 Å to about 3.5 Å. The invention also relates to methods for preparing and crystallizing the Glucokinase. The crystalline forms of Glucokinase, as well as information derived from their crystal structures can be used to analyze and modify glucokinase activity as well as to identify compounds that interact with the allosteric site.

The crystals of the invention include apo crystals and co-crystals. The apo crystals of the invention generally comprise substantially pure Glucokinase. The co-crystals generally comprise substantially pure Glucokinase with a ligand bound to the allosteric site.

It is to be understood that the crystalline Glucokinases of the invention are not limited to naturally occurring or native Glucokinases. Indeed, the crystals of the invention include mutants of the native Glucokinases. Mutants of native Glucokinases are obtained by replacing at lest one amino acid residue in a native Glucokinase domain with a different amino acid residue, or by adding or deleting amino acid residues within the native polypeptide or at the N- or C-terminus of the native polypeptide, and have substantially the same three-dimensional structure as the native Glucokinase from which the mutant is derived.

By having substantially the same three-dimensional structure is meant having a set of atomic structure coordinates from an apo- or co-crystal that have a root mean square deviation of less than or equal to about 2 Å when superimposed with the atomic structure coordinates of the native Glucokinase from which the mutant is derived when at least about 50% to about 100% of the alpha carbon atoms of the native Glucokinase are included in the superposition.

In some instances, it may be particularly advantageous or convenient to substitute, delete and/or add amino acid residues to a native Glucokinase domain in order to provide convenient cloning sites in cDNA encoding the polypeptide, to aid in purification of the polypeptide, etc. Such substitutions, deleteions and/or additions which do not substantially alter the three dimensional structure of the native Glucokinase will be apparent to those having skills in the art.

It should be noted that the mutants contemplated herein need not exhibit glucokinase activity. Indeed, amino acid substitutions, additions or deletions that interfere with the kinase activity of the glucokinase but which do not significantly alter the three-dimensional structure of the domain are specifically contemplated by the invention. Such crystalline polypeptides, or the atomic structure coordinates obtained therefrom, can be used to identify compounds that bind to the native domain. These compounds may affect the activity or the native domain.

The derivative crystals of the invention generally comprise a crystalline glucokinase polypeptide in covalent association with one or more heavy metal atoms. The polypeptide may correspond to a native or a mutated Glucokinase. Heavy metal atoms useful for providing derivative crystals include, by way of example and not limitation, gold and mercury. Alternatively, derivative crystals can be formed from proteins which have heavy atoms incorporated into one or more amino acids, such as seleno-methionine substitutions for methionine.

The co-crystals of the invention generally comprise a crystalline Glucokinase polypeptide in association with one or more compounds at an allosteric site of the polypeptide. The association may be covalent or non-covalent.

Production of Polypeptides

The native and mutated glucokinase polypeptides described herein may be isolated from natural sources or produced by methods well known to those skilled in the art of molecular biology. Expression vectors to be used may contain a native or mutated Glucokinase polypeptide coding sequence and appropriate transcriptional and/or translational control signals. These methods include in vitro recombinant DNA techniques, synthetic techniques and in vivo recombination/genetic recombination. See, for example, the techniques described in Maniatis et al., 1989, *Molecular Cloning: A Laboratory Manual*, Cold Spring Harbor Laboratory, NY; and Ausubel et al., 1989, *Current Protocols in Molecular Biology*, Greene Publishing Associates and Wiley Interscience, NY.

A variety of host-expression vector systems may be utilized to express the Glucokinase coding sequence. These include but are not limited to microorganisms such as bacteria transformed with recombinant bacteriophage DNA, plasmid DNA or cosmid DNA expression vectors containing the Glucokinase coding sequence; yeast transformed with recombinant yeast expression vectors containing the Glucokinase coding sequence; insect cell systems infected with recombinant virus expression vectors (e.g. baculovirus) containing the Glucokinase coding sequence; plant cell systems infected with recombinant virus expression vectors (e.g., cauliflower mosaic virus, CaMV; tobacco mosiac virus, TMV) or transformed with recombinant plasmid expression vectors (e.g., Ti plasmid) containing the glucokinase coding sequence; or animal cell systems. The expression elements of these systems vary in their strength and specificities. Depending on the host/vector system utilized, any of a number of suitable transcription and translation elements, including constitutive and inducible promotors such as pL of bacteriophage μ, plac, ptrp, ptac (ptrp-lac hybrid promoter) and the like may be used; when cloning in insect cell systems, promoters such as the baculovirus polyhedrin promoter may be used; when cloingin in plant cell systems, promoters derived from the genome of plant cells (e.g., heat shock promoters; the promoter for the small subunit of RUBISCO; the promoter for the chlorophyll a/b binding protein) or from plant viruses (e.g., the 35 S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5K promoter) may be used; when generating cell lines that contain multiple copies of the glucokinase coding sequence, SV40-, BPV- and EBV-based vectors may be used with an appropriate selectable marker.

Crystallization of Polypeptides and Characterization of Crystal Structure

The apo, derivative and co-crystals of the invention can be obtained by techniques well-known in the art of protein crystallography, including batch, liquid bridge, dialysis, vapor diffusion and hanging drop methods (see e.g. McPherson, 1982, *Preparation and Analysis of Protein Crystals*, John Wiley, NY; McPherson, 1990, *Eur. J. Biochem.* 189:1-23; Webber, 1991, *Adv. Protein Chem.* 41:1-36; Crystallization of Nucleic Acids and Proteins, Edited by Arnaud Ducruix and Richard Giege, Oxford University Press; Protein Crystallization Techniques, Strategies, and Tips, Edited by Terese Bergfors, International University Line, 1999). Generally, the apo- or co-crystals of the invention are grown by placing a substantially pure Glucokinase polypeptide in an aqueous buffer containing a precipitant at a concentration just below that necessary to precipitate the protein. Water is then removed from the solution by controlled evaporation to produce crystallizing conditions, which are maintained until crystal growth ceases.

In a preferred embodiment of the invention, apo or co-crystals are grown by vapor diffusion. In this method, the polypeptide/precipitant solution is allowed to equilibrate in a closed container with a larger aqueous reservoir having a precipitant concentration optimal for producing crystals. Generally, less than about 10 μL of subtantially pure polypeptide solution is mixed with an equal volume of reservoir solution, giving a precipitant concentration about half that required for crystallization. This solution is suspended as a droplet underneath a coverslip, which is sealed onto the top of a reservoir. The sealed container is allowed to stand, from one day to one year, usually for about 2-6 weeks, until crystals grow.

For crystals of the invention, it has been found that hanging drops containing about 2-5 µl of Glucokinase (9-22 mg/ml in 20 mM tris pH 7.1 measured at room temperature, 50 mM NaCl, 50 mM glucose, 10 mM DTT and optionally 0.2 mM EDTA) and an equal amount of reservoir solution (16-25% w/v polyethylene glycol with an average molecular weight from about 8000 to about 10000 Daltons, 0.1-0.2 M tris or bistris or Hepes or ammonium phosphate buffer, pH 6.9-7.5, 8-10 mM DTT, 0-30% saturated glucose) suspended over 0.5 to 1.0 mL reservoir buffer for about 3-4 weeks at 4-6° C. provided crystals suitable for high resolution X-ray structure determination. Particularly preferred conditions were: about 2-5 µl of Glucokinase (10 mg/ml in 20 mM tris pH 7.1 measured at room temperature, 50 mM NaCl, 50 mM glucose, 10 mM DTT and optionally 0.2 mM EDTA) and an equal amount of reservoir solution (22.5% w/v polyethylene glycol with an average molecular weight of about 10000 Daltons, 0.1 M tris pH 7.08, 10 mM DTT, 20% glucose) were suspended over 0.5 to 1.0 mL reservoir buffer for about 3-4 weeks at 4-6° C.

The optimum procedure for growing crystals large enough to collect data from involved first streaking 3-4 µl of protein solution on the coverslip, followed by streaking 3-4 µl of well solution across the elongated droplet of protein, forming a droplet shaped like the letter 'X'. Before discovering this crossed droplet technique, most droplets yielded showers of small crystals which were not large enough for data collection purposes. The crossed droplets allow gradients of protein and precipitating agent to form as the two solutions slowly mix, and the resulting kinetics of crystal nucleation and growth are optimal for the growth of a small number of large crystals in each crossed droplet. Simply mixing the protein and precipitant solutions together in a single round droplet often produced an overabundance of nuclei which grew to a final size too small for data collection purposes. Crystals usually appeared within 5 days of setup. The crystals grow in the form of hexagonal bipyramids, reaching dimensions of 0.2×0.2× 0.4 mm typically, although larger crystals are often observed. FIG. 1 shows grown crystals.

Crystals may be frozen prior to data collection. The crystals were cryo-protected with either (a) 20-30% saturated glucose present in the crystallization setup, (b) ethanol added to 15-20%, (c) ethylene glycol added to 10-20% and PEG10,000 brought up to 25%, or (d) glycerol added to 15%. The crystals were either briefly immersed in the cryo-protectant or soaked in the cryo-protectant for periods as long as a day. Freezing was accomplished by immersing the crystal in a bath of liquid nitrogen or by placing the crystal in a stream of nitrogen gas at 100 K.

The mosaic spread of the frozen crystals could sometimes be reduced by annealing, wherein the stream of cold nitrogen gas is briefly blocked, allowing the frozen crystal to thaw momentarily before re-freezing in the nitrogen gas stream. Another technique which was sometimes helpful in data collection was to center one of the ends of the hexagonal bipyramid in the x-ray beam, rather than the mid portion of the crystal. The mosaic spread could sometimes be reduced by this technique.

Figure 3:
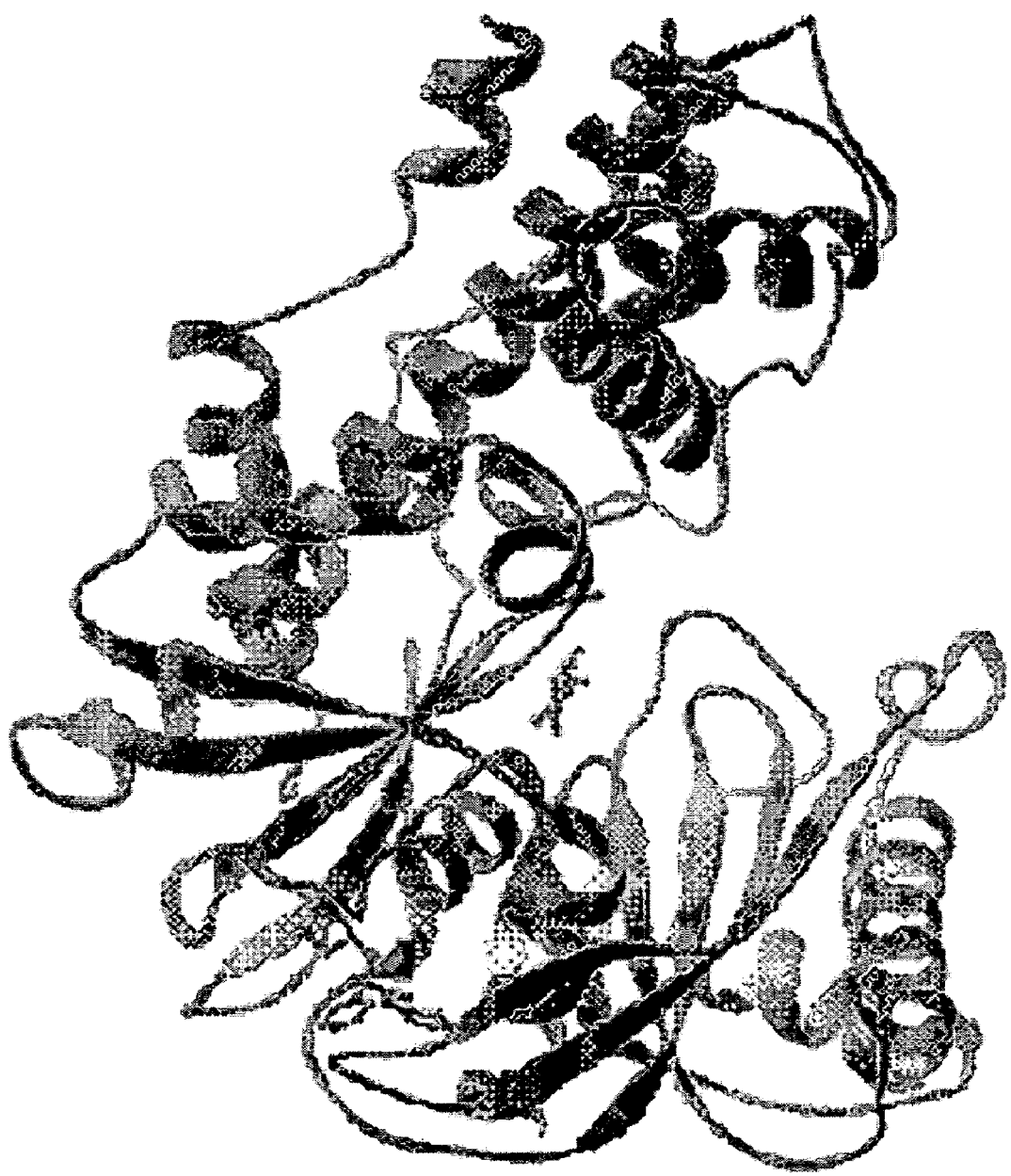
FIG. 3 shows a ribbon diagram of the structure of Glucokinase colored according to secondary structure. Light blue represents α-helix, dark blue represents $3_{10}$-helix, green represents β-sheet and orange is coil.

Diffraction data typically extending to 2.7 Å was collected from the frozen crystals at the synchrotron beamline X8C of the National Synchrotron Light Source in Brookhaven, N.Y. Under optimum conditions, data extending to 2.2 Å was recorded. See FIGS. 3 and 4 for solution. The space group of the crystals was determined to be P6(5)22 during the course of the solution of the crystal structure. The crystals have unit cell dimensions a=b=79.62+/−0.60 Å, c=321.73+/−3.70 Å, $\alpha=\beta=90°$, $\gamma=120°$. The crystals are in a hexagonal system with P6(5)22 symmetry.

Of course, those having skill in the art will recognize that the above-described crystallization conditions can be varied. Such variations may be used alone or in combination, and include polypeptide solutions containing polypeptide concentrations between 1 mg/mL and 60 mg/mL, any commercially available buffer systems which can maintain pH from about 6.5 to about 7.6, Tris-HCl concentrations between 10 mM and 200 mM, dithiothreitol concentrations between 0 mM and 20 mM, substitution of dithiothreitol with beta mercapto ethanol or other art-recognized equivalents, or substitution of glucose with other sugars known to bind to Glucokinase; and reservoir solutions containing polyethylene glycol concentrations between about 10% and about 30%, polyethylene glycol average molecular weights between about 1000 and about 20,000 daltons, any commercially available buffer systems which can maintain pH from about 6.5 to about 7.6, dithiothreitol concentrations between 0 mM and 20 mM, substitution of dithiothreitol with beta mercapto ethanol or other art-recognized —SH group containing equivalents, or substitution of glucose with other sugars known to bind to Glucokinase, and temperature ranges between 4 and 20° C.

Derivative crystals of the invention can be obtained by soaking apo or co-crystals in mother liquor containing salts of heavy metal atoms, according to procedures known to those of skill in the art of X-ray crystallography.

Co-crystals of the invention can be obtained by soaking an apo crystal in mother liquor containing a ligand that binds to the allosteric site, or can be obtained by co-crystallizing the Glucokinase polypeptide in the presence of one or more ligands that bind to the allosteric site. Preferably, co-crystals are formed with a glucokinase activator disclosed in U.S. Pat. No. 6,320,050; U.S. patent application Ser. No. 09/532,506 filed Mar. 21, 2000; U.S. patent application Ser. No. 09/675,781 filed Sep. 28, 2000; U.S. patent application Ser. No. 09/727,624, filed Dec. 1, 2000; U.S. patent application Ser. No. 09/841,983, filed Apr. 25, 2001; U.S. patent application Ser. No. 09/843,466, filed Apr. 26, 2001; U.S. patent application Ser. No. 09/846,820, filed May 1, 2001; U.S. patent application Ser. No. 09/846,821, filed May 1, 2001; U.S. patent application Ser. No. 09/905,152, filed Jul. 13, 2001; U.S. patent application Ser. No. 09/924,247, filed Aug. 8, 2001; U.S. Provisional Pat. Appl. 60/251,637, filed Dec. 6, 2000; or U.S. Provisional Pat. Appl. 60/318,715, filed Sep. 13, 2001, each of which is incorporated herein by reference.

Methods for obtaining the three-dimensional structure of the crystalline glucokinases described herein, as well as the atomic structure coordinates, are well-known in the art (see, e.g., D. E. McRee, Practical Protein Crystallography, published by Academic Press, San Diego (1993), and references cited therein).

Uses of the Crystals and Atomic Structure Coordinates

The crystals of the invention, and particularly the atomic structure coordinates obtained therefrom, have a wide variety of uses. For example, the crystals and structure coordinates described herein are particularly useful for identifying compounds that activate Glucokinases as an approach towards developing new therapeutic agents.

The structure coordinates described herein can be used as phasing models in determining the crystal structures of additional native or mutated glucokinases, as well as the structures of co-crystals of such glucokinases with allosteric inhibitors or activators bound. The structure coordinates, as well as models of the three-dimensional structures obtained therefrom, can also be used to aid the elucidation of solution-based structures of native or mutated glucokinases, such as those obtained via NMR. Thus, the crystals and atomic structure coordinates of the invention provide a convenient means for elucidating the structures and functions of glucokinases.

For purposes of clarity and discussion, the crystals of the invention will be described by reference to specific Glucokinase exemplary apo crystals and co-crystals. Those skilled in the art will appreciate that the principles described herein are generally applicable to crystals of any mammalian Glucokinase, including, but not limited to the Glucokinase of FIG. 2.

Definitions

As used herein, "allosteric site" refers in general to any ligand binding site on a mammalian Glucokinase other than the active site of the enzyme.

As used herein, "apo crystal" refers to crystals of mammalian Glucokinase formed without a bound allosteric ligand.

As used herein, "allosteric ligand" refers to any molecule which specifically binds an allosteric site on a mammalian Glucokinase.

EXAMPLES

Example 1

Expression and Purification of Glucokinase

Expression of GK

Glucokinase (GK) was expressed as a glutathione S-transferase (GST) fusion protein in *Escherichia coli*. The amino-acid sequence of the fusion protein is given in FIG. 2. The expression construct is based on the pGEX-3x vector from Pharmacia, as described in Y. Liang, P. Kesavan, L. Wang, K. Niswender, Y. Tanizawa, M. A. Permutt, M. A. Magnuson, F. M. Matschinsky, *Biochem. J.* 309, 167 (1995). The construct codes for one of the two liver isozymes of human GK. The GST tag is at the N-terminus of the construct, and is separated from the coding sequence for GK by a Factor Xa cleavage site. After purification of the GST fusion protein, the GST fusion tag was removed with Factor Xa protease, which also removes five residues from the N-terminus of GK.

Purification of GK

E. coli cells expressing GST-GK were suspended in lysis buffer (50 mM tris, 200 mM NaCl, 5 mM EDTA, 5 mM DTT, 1% NP-40, pH 7.7) in the presence of protease inhibitors, incubated with lysozyme at 200 µ/ml for 30 minutes at room temperature, and sonicated 4×30 sec. at 4° C. After centrifugation to remove insoluble material, the supernatant was loaded onto glutathione-Sepharose, washed with lysis buffer and then with lysis buffer minus NP-40. GST-GK was eluted with lysis buffer (minus NP-40) containing 50 mM D-glucose and 20 mM glutathione. The eluted protein was concentrated and dialyzed into 20 mM tris, 100 mM NaCl, 0.2 mM EDTA, 50 mM D-glucose, 1 mM DTT, pH 7.7. Factor Xa was added at a protein ratio of 1:100 GST-GK followed by the addition of $CaCl_2$ to 1 mM, and the sample was incubated at 4° C. for 48 hours. The sample was added to glutathione Sepharose and the unbound fraction collected and concentrated. The sample was then incubated with benzamidine Sepharose to remove Factor Xa, and the unbound fraction was collected and loaded on a Q Sepharose column equilibrated with 25 mM bis-tris propane, 50 mM NaCl, 5 mM DTT, 50 mM D-glucose and 5% glycerol (pH 7.0). The protein was eluted with a NaCl gradient from 50-400 mM. Fractions containing purified GK were pooled and concentrated and filtered.

Example 2

Formation of apo Crystal

4 µl of glucokinase and 4 µl of precipitant were mixed and equilibrated against the precipitant solution at 4° C. The glucokinase solution consisted of 22 mg/ml glucokinase prepared in Example 1 in 20 mM hepes pH 7.5, 50 mM NaCl, 10 mM DTT, and 50 mM glucose. The precipitant consisted of 22.5% PEG10000, 0.1 M tris pH 7.08, 10 mM DTT, 20% glucose; the precipitant solution contained seed crystals in order to microseed the droplets. Crystals appeared in the droplets after leaving the crystallization plates at 4° C.

Example 3

Formation of Co-crystal with 3-Cyclopentyl-2-pyridin-4-yl-N-thiazol-2-yl-propionamide 3(a):

4 µl of glucokinase and 4 µl of precipitant were mixed and equilibrated against the precipitant solution at 4° C. The glucokinase solution consisted of 13 mg/ml glucokinase prepared in Example 1 in 20 mM tris pH 7.0, 50 mM NaCl, 10 mM DTT, 50 mM glucose, and the glucokinase activator 3-Cyclopentyl-2-pyridin-4-yl-N-thiazol-2-yl-propionamide at a concentration 5 times that of the protein. The precipitant consisted of 22.5% PEG10000, 0.1 M tris pH 7.08, 10 mM DTT, 20% glucose. Crystals appeared in the droplets after leaving the crystallization plates at 4° C.

3(b):

Alternatively, crystals were grown as in Example 3(a) with the following changes: instead of 4 µl glucokinase and 4 µl precipitant, 2 µl of each were used; the glucokinase solution contained 11 mg/ml glucokinase in tris buffer at pH 7.08 instead of 7.0; the glucokinase solution included 0.2 mM EDTA; in place of 22.5% PEG10000 as precipitant 18% PEG8000 was used; the precipitant solution contained seed crystals in order to microseed the droplets.

3(c):

In another alternative, crystals were grown as in Example 3(a) with the following changes: instead of 4 µl glucokinase and 4 µl precipitant, 2 µl of each were used; the glucokinase solution contained 11 mg/ml glucokinase in tris buffer at pH 7.08 instead of 7.0; the glucokinase solution included 0.2 mM EDTA; in place of 22.5% PEG10000 as precipitant 20% PEG8000 was used; the precipitant solution contained seed crystals in order to microseed the droplets.

3(d):

In yet another alternative, crystals were grown as in Example 3(a) with the following changes: instead of 4 µl glucokinase and 4 µl precipitant, 2 µl of each were used; the glucokinase solution contained 12 mg/ml glucokinase in tris buffer at pH 7.08 instead of 7.0; the glucokinase solution included 0.2 mM EDTA; in place of 22.5% PEG10000 as precipitant 16% PEG10000 was used; glucose was not present as a component of the precipitant; the precipitant solution contained seed crystals in order to microseed the droplets.

3(e):

In still another alternative, crystals were grown as in Example 3(a) with the following changes: the glucokinase solution contained 11 mg/ml glucokinase in tris buffer at pH 7.1 instead of 7.0; the glucokinase solution included 0.2 mM EDTA; in place of 22.5% PEG10000 as precipitant 25% PEG10000 was used.

3(f):

In still another alternative, crystals were grown as in Example 3(a) with the following changes: the glucokinase solution contained 11 mg/ml glucokinase in tris buffer at pH 7.1 instead of 7.0; the glucokinase solution included 0.2 mM EDTA; in place of 22.5% PEG10000 as precipitant 21.25% PEG10000 was used; in place of tris buffered at pH 7.08 in the precipitant tris buffered at pH 7.52 was used.

3(g):

In still another alternative, crystals were grown as in Example 3(a) with the following changes: the glucokinase solution contained 12 mg/ml glucokinase in tris buffer at pH 7.08 instead of 7.0; the glucokinase solution included 0.2 mM EDTA; in place of tris buffered at pH 7.08 in the precipitant, hepes buffered at pH 6.89 was used; in place of 20% glucose in the precipitant, 200 mM glucose was used.

3(h):

In still another alternative, crystals were grown as in Example 3(a) with the following changes: the glucokinase solution contained 12 mg/ml glucokinase in tris buffer at pH 7.08 instead of 7.0; the glucokinase solution included 0.2 mM EDTA; in place of 0.1 M tris buffered at pH 7.08 in the precipitant, 0.2 M ammonium phosphate buffered at pH 7.03 was used; in place of 20% glucose in the precipitant, 200 mM glucose was used.

3(i):

In still another alternative, crystals were grown as in Example 3(a) with the following changes: the glucokinase solution contained 10 mg/ml glucokinase in tris buffer at pH 7.08 instead of 7.0; the glucokinase solution included 0.2 mM EDTA; in place of 22.5% PEG10000 as precipitant, 20% PEG10000 was used; in place of tris buffered at pH 7.08 in the precipitant, tris buffered at pH 7.05 was used; in place of 10 mM DTT in the precipitant, 8 mM DTT was used; glucose was not present as a component of the precipitant.

3(j):

In still another alternative, crystals were grown as in Example 3(a) with the following changes: the glucokinase solution contained 12 mg/ml glucokinase in tris buffer at pH 7.08 instead of 7.0; the glucokinase solution included 0.2 mM EDTA; in place of 22.5% PEG10000 as precipitant, 22% PEG8000 was used; glucose was not present as a component of the precipitant; the precipitant solution contained seed crystals in order to microseed the droplets.

3(k):

In still another alternative, crystals were grown as in Example 3(a) with the following changes: the glucokinase solution contained 11 mg/ml glucokinase in tris buffer at pH 7.1 instead of 7.0; the glucokinase solution included 0.2 mM EDTA; in place of 20% glucose in the precipitant, 30% glucose was used.

Example 4

Formation of Co-crystal with N-(5-Bromo-pyridin-2-yl)-2-(3-chloro-4-methanesulfonyl-phenyl)-3-cyclopentyl-propionamide Crystals were grown as in Example 3(a) with the following changes: the glucokinase solution contained 9 mg/ml glucokinase in tris buffer at pH 7.1 instead of 7.0; the glucokinase solution included 0.2 mM EDTA; in place of the glucokinase activator of Example 3(a), the glucokinase solution contained the glucokinase activator N-(5-Bromo-pyridin-2-yl)-2-(3-chloro-4-methanesulfonyl-phenyl)-3-cyclopentyl-propionamide; in place of 20% glucose in the precipitant, 200 mM glucose was used.

Example 5

Formation of Co-crystal with 2-(3-Chloro-4-methanesulfonyl-phenyl)-3-cyclopentyl-N-(5-trifluoromethyl-pyridin-2-yl)-propionamide Crystals were grown as in Example 3(a) with the following changes: the glucokinase solution contained 10 mg/ml glucokinase in tris buffer at pH 7.1 instead of 7.0; the glucokinase solution included 0.2 mM EDTA; in place of the glucokinase activator of Example 3(a), the glucokinase solution contained the glucokinase activator 2-(3-Chloro-4-methanesulfonyl-phenyl)-3-cyclopentyl-N-(5-trifluoromethyl-pyridin-2-yl)-propionamide; in place of 22.5% PEG10000 as precipitant, 21.25% PEG10000 was used.

Example 6

Formation of Co-crystal with (2S)-2-[3-Cyclopentyl-2-(3,4-dichlorophenyl)-propionylamino]-thiazole-4-carboxylic acid methyl ester Crystals were grown as in Example 3(a) with the following changes: the glucokinase solution contained 10 mg/ml glucokinase in tris buffer at pH 7.1 instead of 7.0; the glucokinase solution included 0.2 mM EDTA; in place of the glucokinase activator of Example 3(a), the glucokinase solution contained the glucokinase activator (2S)-2-[3-Cyclopentyl-2-(3,4-dichloro-phenyl)-propionylamino]-thiazole-4-carboxylic acid methyl ester; in place of 22.5% PEG10000 as precipitant, 21.25% PEG10000 was used; in place of tris buffered at pH 7.08 in the precipitant, bistris buffered at pH 7.0 was used.

Example 7

Formation of Co-crystal with (2S)-{2-[3-Cyclopentyl-2-(3,4-dichlorophenyl)-propionylamino]-thiazol-5-yl}-oxo-acetic acid ethyl ester Crystals were grown as in Example 3(a) with the following changes: the glucokinase solution contained 10 mg/ml glucokinase in tris buffer at pH 7.1 instead of 7.0; the glucokinase solution included 0.2 mM EDTA; in place of the glucokinase activator of Example 3(a), the glucokinase solution contained the glucokinase activator (2S)-{2-[3-Cyclopentyl-2-(3,4-dichloro-phenyl)-propionylamino]-thiazol-5-yl}-oxo-acetic acid ethyl ester; in place of 22.5% PEG10000 as precipitant, 21.25% PEG10000 was used.

Example 8

Formation of Co-crystal with (2S)-{3-[3-Cyclopentyl-2-(3,4-dichloro-phenyl)-propionyl]-ureido}-acetic acid methylester Crystals were grown as in Example 3(a) with the following changes: the glucokinase solution contained 9 mg/ml glucokinase in tris buffer at pH 7.08 instead of 7.0; the glucokinase solution included 0.2 mM EDTA; in place of the glucokinase activator of Example 3(a), the glucokinase solution contained the glucokinase activator (2S)-{3-[3-Cyclopentyl-2-(3,4-dichloro-phenyl)-propionyl]-ureido}-acetic acid methylester; in place of 20% glucose in the precipitant, 200 mM glucose was used.

Example 9

Formation of Co-crystal with (2S)-1-[3-Cyclopentyl-2-(3,4-dichloro-phenyl)-propionyl]-3-(3-hydroxy-propyl)-urea Crystals were grown as in Example 3(a) with the following changes: the glucokinase solution contained 14 mg/ml glucokinase in tris buffer at pH 7.08 instead of 7.0; the glucokinase solution included 0.2 mM EDTA; in place of the glucokinase activator of Example 3(a), the glucokinase solution contained the glucokinase activator (2S)-1-[3-Cyclopentyl-2-(3,4-dichloro-phenyl)-propionyl]-3-(3-hydroxy-propyl)-urea; in place of 20% glucose in the precipitant, 200 mM glucose was used.

Example 10

Formation of Co-crystal with (2S)-{3-[3-Cyclopentyl-2-(3,4-dichloro-phenyl)-propionyl]-ureido}-acetic acid ethyl ester Crystals were grown as in Example 3(a) with the following changes: the glucokinase solution contained 14 mg/ml glucokinase in tris buffer at pH 7.08 instead of 7.0; the glucokinase solution included 0.2 mM EDTA; in place of the glucokinase activator of Example 3(a), the glucokinase solution contained the glucokinase activator (2S)-{3-[3-Cyclopentyl-2-(3,4-dichloro-phenyl)-propionyl]-ureido}-acetic acid ethyl ester; in place of tris buffered at pH 7.08 in the precipitant, tris buffered at pH 7.05 was used.

Example 11

Synthesis of 3-Cyclopentyl-2-pyridin-4-yl-N-thiazol-2-yl-propionamide

3-Cyclopentyl-2-pyridin-4-yl-N-thiazol-2-yl-propionamide can be prepared using well-known organic synthesis techniques according to the following reaction scheme:

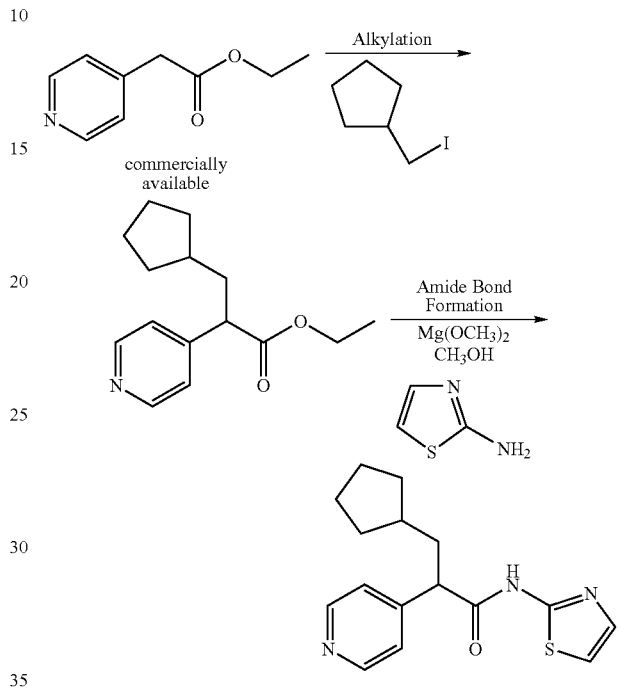

3-Cyclopentyl-2-pyridin-4-yl-N-thiazol-2-yl-propionamide is useful as an allosteric activator of Glucokinase and to assist the formation of co-crystals of Glucokinase.

We claim:

1. A co-crystal of mammalian Glucokinase (SEQ ID NO:1) and a ligand bound to an allosteric site of the Glucokinase, wherein
   the co-crystal has unit cell dimensions of:
   a and b are from about 79 Å to about 80.2 Å;
   c is from about 318 Å to about 325 Å;
   α and β are 90°; and
   γ is 120°;
   and the co-crystal has P6(5)22 symmetry, wherein further the ligand is selected from the group consisting of 3-Cyclopentyl-2-pyridin-4-yl-N-thiazol-2-yl-propionamide, N-(5-Bromo-pyridin-2-yl)-2-(3-chloro-4-methanesulfonyl-phenyl)-3-cyclopentyl-propionamide, 2-(3-Chloro-4-methanesulfonyl-phenyl)-3-cyclopentyl-N-(5-trifluoromethyl-pyridin-2-yl)- propionamide, (2S)-2-[3-Cyclopentyl-2-(3,4-dichloro-phenyl)-propionylaminol]-thiazole-4- carboxylic acid methyl ester, (2S)-{2-[3-Cyclopentyl-2-(3,4-dichloro-phenyl) -propionylaminol]-thiazol-5-yl}-oxo-acetic acid ethyl ester, (2S)-{3-[3-Cyclopentyl-2-(3,4- dichloro-pheny)-propionyl]-ureidol}-acetic acid methylester, (2S)-1-[3-Cyclopentyl-2- (3,4-dichloro-phenyl)-propionyl]-3-(3-hydroxy-propyl)-urea, and (2S)-{3-[3-Cyclopentyl- 2-(3,4-dichloro-phenyl)-propionyl]-ureido}-acetic acid ethyl ester.

2. A crystal of mammalian Glucokinase, (SEQ ID NO:1), wherein
   the crystal has unit cell dimensions of:
   a and b are from about 79 Å to about 80.2 Å;
   c is from about 318 Å to about 325 Å;
   α and β are 90°; and
   γ is 120°;
   and the crystal has P6(5)22 symmetry.

3. A process for co-crystalizing mammalian Glucokinase (SEQ ID NO:1) and an allosteric ligand of Glucokinase, the process comprising:

providing a buffered, aqueous solution of 9 to 22mg/ml of the mammalian Glucokinase (SEQ ID NO:1);

adding a molar excess of the allosteric ligand to the aqueous solution of mammalian Glucokinase; and growing crystals by vapor diffusion using a buffered reservoir solution of 16% to 25% PEG, 0% w/v to 30% w/v glucose and 8 to 10 mM DTT, wherein the PEG has an average molecular weight of about 8,000 to about 10,000 Daltons, wherein further the ligand is selected from the group consisting of 3-Cyclopentyl-2-pyridin-4-yl-N-thiazol-2-yl -propionamide, N-(5-Bromo-pyridin-2-yl)-2-(3-chloro-4-methanesulfonyl-phenyl)-3-cyclopentyl-propionamide, 2-(3-Chloro-4-methanesulfonyl-phenyl)-3-cyclopentyl-N-(5-trifluoromethyl-pyridin-2-yl)-propionamide, (2S)-2-[3-Cyclopentyl-2-(3,4-dichloro-phenyl) - propionylamino]-thiazole-4-carboxylic acid methyl ester, (2S)-{2-[3-Cyclopentyl-2-(3,4-dichloro-phenyl)-propionylamino]-thiazol-5-yl}-oxo-acetic acid ethyl ester, (2S)-{3-[3-Cyclopentyl-2-(3,4-dichloro-phenyl)-propionyl]-ureido}-acetic acid methylester, (2S)-1-[3-Cyclopentyl-2-(3,4-dichloro-phenyl)-propionyl]-3-(3-hydroxy-propyl)-urea, and (2S)-{3-[3-Cyclopentyl-2-(3,4-dichloro-phenyl)-propionyl]-ureido}-acetic acid ethyl ester.

4. The process of claim 3, wherein the step of growing crystals by vapor diffusion comprises:

streaking the buffered, aqueous solution of mammalian Glucokinase (SEQ ID NO:1) with added allosteric ligand on a surface to form an elongated droplet of protein solution, and streaking about an equal amount of the buffered reservoir solution across the elongated droplet of protein solution, forming a combined droplet shaped like the letter 'X'.

* * * * *

UNITED STATES PATENT AND TRADEMARK OFFICE
CERTIFICATE OF CORRECTION

PATENT NO. : 7,534,593 B2  
APPLICATION NO. : 10/816708  
DATED : May 19, 2009  
INVENTOR(S) : Wendy Lea Corbett et al.

Page 1 of 1

It is certified that error appears in the above-identified patent and that said Letters Patent is hereby corrected as shown below:

Title page, item (75), Inventors - please delete -

"Pete William Dunten, Mountainview, PA"

And Insert:

--Pete William Dunten, Mountainview, CA--

Signed and Sealed this

Fourth Day of August, 2009

JOHN DOLL  
*Acting Director of the United States Patent and Trademark Office*